US009464076B2

(12) United States Patent
Inoue et al.

(10) Patent No.: US 9,464,076 B2
(45) Date of Patent: Oct. 11, 2016

(54) BENZOTHIOPHENE DERIVATIVE

(71) Applicant: Daiichi Sankyo Company, Limited, Chou-ku, Tokyo (JP)

(72) Inventors: Hidekazu Inoue, Tokyo (JP); Yoshito Kawamoto, Tokyo (JP); Katsuhide Kamei, Osaka (JP); Kenichi Hiramatsu, Tokyo (JP); Minako Tomino, Tokyo (JP)

(73) Assignee: Daiichi Sankyo Company, Limited, Chuo-ku (JP)

( * ) Notice: Subject to any disclaimer, the term of this patent is extended or adjusted under 35 U.S.C. 154(b) by 0 days.

(21) Appl. No.: 14/775,390

(22) PCT Filed: Mar. 14, 2014

(86) PCT No.: PCT/JP2014/056978
§ 371 (c)(1),
(2) Date: Sep. 11, 2015

(87) PCT Pub. No.: WO2014/142322
PCT Pub. Date: Sep. 18, 2014

(65) Prior Publication Data
US 2016/0024060 A1 Jan. 28, 2016

(30) Foreign Application Priority Data
Mar. 15, 2013 (JP) .................................. 2013-052704

(51) Int. Cl.
| C07D 409/12 | (2006.01) |
| C07D 409/14 | (2006.01) |
| C07C 309/04 | (2006.01) |
| C07C 309/05 | (2006.01) |
| C07C 309/29 | (2006.01) |
| C07C 309/30 | (2006.01) |
| C07F 9/6558 | (2006.01) |

(52) U.S. Cl.
CPC ........... *C07D 409/12* (2013.01); *C07C 309/04* (2013.01); *C07C 309/05* (2013.01); *C07C 309/29* (2013.01); *C07C 309/30* (2013.01); *C07D 409/14* (2013.01); *C07F 9/65586* (2013.01)

(58) Field of Classification Search
None
See application file for complete search history.

(56) References Cited

U.S. PATENT DOCUMENTS

| 9,029,388 B2 | 5/2015 | Taniguchi |
| 2006/0111368 A1 | 5/2006 | Osakada |
| 2007/0265256 A1 | 11/2007 | Arrington |
| 2009/0176829 A1 | 7/2009 | Verhoest |

FOREIGN PATENT DOCUMENTS

| JP | 2009-527560 A | 7/2009 |
| JP | 2009-535394 A | 10/2009 |
| WO | 2004/002484 A1 | 1/2004 |
| WO | 2006/034491 A2 | 3/2006 |
| WO | 2006/034512 A2 | 3/2006 |
| WO | 2006/072828 A2 | 7/2006 |
| WO | 2007/077490 A2 | 7/2007 |
| WO | 2007/129183 A2 | 11/2007 |
| WO | 2008/001182 A1 | 1/2008 |
| WO | 2008/004117 A1 | 1/2008 |
| WO | 2008/084299 A1 | 7/2008 |
| WO | 2009/158393 A1 | 12/2009 |
| WO | 2009/158473 A1 | 12/2009 |
| WO | 2010/057121 A1 | 5/2010 |
| WO | 2010/057126 A1 | 5/2010 |
| WO | 2010/090737 A1 | 8/2010 |
| WO | 2011/089132 A1 | 7/2011 |
| WO | 2011/150156 A2 | 12/2011 |
| WO | 2012/124782 A1 | 9/2012 |
| WO | 2012/133607 A1 | 10/2012 |

OTHER PUBLICATIONS

International Search Report mailed May 20, 2014, issued in International Application No. PCT/JP2014/056978, filed Mar. 14, 2014, 4 pages.

Giampà, C., et al., "Inhibition of the Striatal Specific Phosphodiesterase PDE10A Ameliorates Striatal and Cortical Pathology in R6/2 Mouse Model of Huntington's Disease," PLoS ONE 5(10):e13417, Oct. 2010, 14 pages.

Giampà, C., et al., "Phosphodiesterase 10 Inhibition Reduces Striatal Excitotoxicity in the Quinolinic Acid Model of Huntington's Disease," Neurobiology of Disease 34(3):450-456, Jun. 2009.

Grauer, S.M., "Phosphodiesterase 10A Inhibitor Activity in Preclinical Models of the Positive, Cognitive, and Negative Symptoms of Schizophrenia," Journal of Pharmacology and Experimental Therapeutics 331(2):574-590, Nov. 2009.

Malamas, M.S., et al., "Highly Potent, Selective, and Orally Active Phosphodiesterase 10A Inhibitors," Journal of Medicinal Chemistry 54(21):7621-7638, Nov. 2011.

Rodefer, J.S., et al., "PDE10A Inhibition Reverses Subchronic PCP-Induced Deficits in Attentional Set-Shifting in Rats," European Journal of Neuroscience 21(4):1070-1076, Feb. 2005.

Sano, H., et al., "Increased Social Interaction in Mice Deficient of the Striatal Medium Spiny Neuron-Specific Phosphodiesterase 10A2," Journal of Neurochemistry 105(2):546-556, Apr. 2008.

Schmidt, C.J., et al., "Preclinical Characterization of Selective Phosphodiesterase 10A Inhibitors: A New Therapeutic Approach to the Treatment of Schizophrenia," Journal of Pharmacology and Experimental Therapeutics 325(2):681-690, May 2008.

(Continued)

Primary Examiner — Yevegeny Valenrod
(74) Attorney, Agent, or Firm — Christensen O'Connor Johnson Kindness PLLC

(57) ABSTRACT

Compounds having PDE10A inhibitory activity and having general formula (I), or an isotope thereof or a pharmaceutically acceptable salt thereof, and a pharmaceutical composition comprising the same as an active ingredient.

41 Claims, No Drawings

(56) References Cited

OTHER PUBLICATIONS

Siuciak, J.A., et al., "Behavioral Characterization of Mice Deficient in the Phosphodiesterase-10A (PDE10A) Enzyme on a C57/B16N Congenic Background," Neuropharmacology 54(2):417-427, Feb. 2008.

Siuciak, J.A., et al., "Genetic Deletion of the Striatum-Enriched Phosphodiesterase PDE10A: Evidence for Altered Striatal Function," Neuropharmacology 51(2):374-385, Aug. 2006.

Smith, S.M., et al., "The Novel Phosphodiesterase 10A Inhibitor THPP-1 Has Antipsychotic-Like Effects in Rat and Improves Cognition in Rat and Rhesus Monkey," Neuropharmacology 64:215-223, Jan. 2013.

Verhoest, P.R., et al., "Discovery of a Novel Class of Phosphodiesterase 10A Inhibitors and Identification of Clinical Candidate 2-[4-(1-Methyl-4-pyridin-4-yl-1H-pyrazol-3-yl)-phenoxymethyl]-quinoline (PF-2545920) for the Treatment of Schizophrenia," Journal of Medicinal Chemistry 52(16)5188-5196, Aug. 2009.

Ellenbroek, B.A., "Psychopharmacological Treatment of Schizophrenia: What Do We Have, and What Could We Get?" Neuropharmacology 62(3):1371-1380, Mar. 2012.

"ZINC00044149," PubChem Compound Summary for Database Accession No. CID 679716, created Jul. 7, 2005, modified Jun. 20, 2016, <https://pubchem.ncbi.nlm.nih.gov/compound/679716 . . . > [retrieved Jun. 23, 2016], 12 pages.

Extended European Search Report mailed Jul. 13, 2016, issued in corresponding Application No. EP 14 76 5144, filed Mar. 14, 2014, 7 pages.

BENZOTHIOPHENE DERIVATIVE

TECHNICAL FIELD

The present invention relates to benzothiophene derivatives having phosphodiesterase (hereinafter, also referred to as PDE) 10A inhibitory activity or pharmaceutically acceptable salts thereof, and pharmaceutical compositions comprising the same as active ingredients.

BACKGROUND ART

Schizophrenia affects approximately 24 million people worldwide. This disorder, however, is treatable, and treatment at the initial stage thereof is effective. Nonetheless, more than 50% of people with schizophrenia have not undergone appropriate treatment.

Examples of currently commercially available therapeutic agents for schizophrenia include chlorpromazine, haloperidol, clozapine, risperidone, olanzapine, quetiapine, ziprasidone, aripiprazole, amisulpride, and paliperidone.

It is known that positive symptoms, negative symptoms, and/or cognitive impairment of schizophrenia can be improved by inhibition of PDE10A, and it is further known that schizophrenia can also be treated by inhibition of PDE10A (e.g., Patent Literatures 1 to 15 and Non-patent Literatures 1, 3 to 5, and 9 to 12).

In addition, studies have also been made on PDE10A knockout mice (e.g., Non-patent Literature 7) and the treatment of Huntington's disease, mental illness, or the like by inhibition of PDE10A (e.g., Non-patent Literatures 2, 6, and 8).

CITATION LIST

Patent Literature

Patent Literature 1: WO2004/002484
Patent Literature 2: WO2006/034491
Patent Literature 3: WO2006/072828
Patent Literature 4: WO2007/077490
Patent Literature 5: WO2007/129183
Patent Literature 6: WO2008/001182
Patent Literature 7: WO2008/004117
Patent Literature 8: WO2008/084299
Patent Literature 9: WO2009/158393
Patent Literature 10: WO2009/158473
Patent Literature 11: WO2010/057121
Patent Literature 12: WO2010/057126
Patent Literature 13: WO2010/090737
Patent Literature 14: WO2012/124782
Patent Literature 15: WO2012/133607

Non-Patent Literature

Non-patent Literature 1: Journal of Medicinal Chemistry, 2009, 52, 5188-5196
Non-patent Literature 2: Neurobiology of disease, 34 (2009) 450-456
Non-patent Literature 3: The Journal of Pharmacology and Experimental Therapeutics, Vol. 325, No. 2, 681-690, 2008
Non-patent Literature 4: European Journal of Neuroscience, Vol. 21, pp. 1070-1076, 2005
Non-patent Literature 5: Journal of Neurochemistry, 2008, 105, 546-556
Non-patent Literature 6: Neuropharmacology, 51, (2006), 374-385
Non-patent Literature 7: Neuropharmacology, 54, (2008), 417-427
Non-patent Literature 8: PLoS ONE, October 2010, Volume 5, Issue 10, e13417, 1-14
Non-patent Literature 9: The Journal of Pharmacology and Experimental Therapeutics, Vol. 331, No. 2, 574-590, 2009
Non-patent Literature 10: Journal of Medicinal Chemistry, 2011, 54, 7621-7638
Non-patent Literature 11: Neuropharmacology 2012, 62:1371-1380
Non-patent Literature 12: Neuropharmacology 2013, 64:215-223

SUMMARY OF INVENTION

Technical Problem

None of Patent Literatures and Non-patent Literatures described above specifically describe the compound of the present invention. Thus, an object of the present invention is to provide a compound having PDE10A inhibitory activity and having a novel structure or a pharmaceutically acceptable salt thereof, and a pharmaceutical composition comprising the same as an active ingredient.

Solution to Problem

The present invention provides
(1) a compound represented by the general formula (I):

[Formula 1]

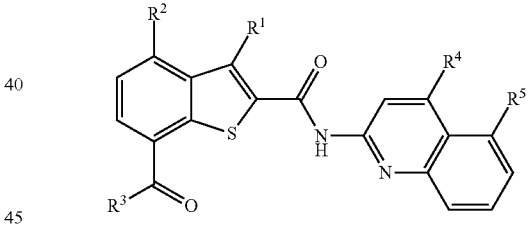

(I)

wherein
$R^1$ represents a hydrogen atom or a C1-C3 alkyl group;
$R^2$ represents a hydrogen atom, a C1-C3 alkylcarbonyl group, a hydroxy-C1-C3 alkyl group, or a C1-C3 alkoxy-C1-C3 alkyl group;
$R^3$ represents a C1-C6 alkyl group or a C3-C6 cycloalkyl group;
$R^4$ and $R^5$ each independently represent a hydrogen atom, a C1-C6 alkyl group optionally substituted by one substituent selected from substituent group α, or an (azetidin-1-yl)carbonyl group optionally substituted by one substituent selected from substituent group α; and
substituent group α is the group consisting of a hydroxy group, a C1-C6 alkoxy group, a methylsulfonyl group, a hydroxypyrrolidine group, and a hydroxypiperidine group, provided that
at least one of $R^4$ and $R^5$ is a hydrogen atom or a pharmaceutically acceptable salt thereof;
(2) the compound or a pharmaceutically acceptable salt thereof according to (1), wherein $R^1$ is a hydrogen atom, a methyl group, or an ethyl group;

(3) the compound or a pharmaceutically acceptable salt thereof according to (1) or (2), wherein $R^2$ is a hydrogen atom, an acetyl group, a propionyl group, a hydroxymethyl group, a 1-hydroxyethyl group, a 1-methoxyethyl group, a methoxymethyl group, an ethoxymethyl group, a propoxymethyl group, or an isopropoxymethyl group;

(4) the compound or a pharmaceutically acceptable salt thereof according to any one of (1) to (3), wherein $R^3$ is a methyl group, an ethyl group, a propyl group, an isopropyl group, a butyl group, an isobutyl group, a 1-ethylpropyl group, a tert-butyl group, a cyclopropyl group, a cyclobutyl group, or a cyclopentyl group;

(5) the compound or a pharmaceutically acceptable salt thereof according to any one of (1) to (3), wherein $R^3$ is a methyl group;

(6) the compound or a pharmaceutically acceptable salt thereof according to any one of (1) to (5), wherein $R^4$ is a hydrogen atom, and $R^5$ is a methyl group, a hydroxymethyl group, a 1-hydroxyethyl group, a 2-hydroxypropan-2-yl group, a methoxymethyl group, an ethoxymethyl group, a methylsulfonylmethyl group, a (3-hydroxypyrrolidin-1-yl)methyl group, a (3-hydroxyazetidin-1-yl)carbonyl group, or a (3-methoxyazetidin-1-yl)carbonyl group;

(7) the compound or a pharmaceutically acceptable salt thereof according to any one of (1) to (5), wherein $R^5$ is a hydrogen atom, and $R^4$ is a methyl group, a hydroxymethyl group, a 1-hydroxyethyl group, a 2-hydroxypropan-2-yl group, a (3-hydroxypyrrolidin-1-yl)methyl group, a (3-hydroxypiperidin-1-yl)methyl group, or a (4-hydroxypiperidin-1-yl)methyl group;

(8) a compound selected from the group consisting of the following:

7-acetyl-N-(4-((4-hydroxypiperidin-1-yl)methyl)quinolin-2-yl)-4-(methoxymethyl)-3-methylbenzo[b]thiophene-2-carboxamide;

7-acetyl-N-(4-((3-hydroxypyrrolidin-1-yl)methyl)quinolin-2-yl)-4-(methoxymethyl)-3-methylbenzo[b]thiophene-2-carboxamide;

(S)-7-acetyl-N-(4-((3-hydroxypyrrolidin-1-yl)methyl)quinolin-2-yl)-4-(methoxymethyl)-3-methylbenzo[b]thiophene-2-carboxamide;

(R)-7-acetyl-N-(4-((3-hydroxypyrrolidin-1-yl)methyl)quinolin-2-yl)-4-(methoxymethyl)-3-methylbenzo[b]thiophene-2-carboxamide;

(R)-7-acetyl-N-(4-((3-hydroxypyrrolidin-1-yl)methyl)quinolin-2-yl)-4-(methoxymethyl)-3-methylbenzo[b]thiophene-2-carboxamide hydrochloride;

(R)-7-acetyl-N-(4-((3-hydroxypyrrolidin-1-yl)methyl)quinolin-2-yl)-4-(methoxymethyl)-3-methylbenzo[b]thiophene-2-carboxamide p-toluenesulfonate;

7-acetyl-N-(5-((3-methoxyazetidin-1-yl)carbonyl)quinolin-2-yl)-4-(methoxymethyl)-3-methylbenzo[b]thiophene-2-carboxamide;

7-acetyl-N-(5-((3-methoxyazetidin-1-yl)carbonyl)quinolin-2-yl)-4-(methoxymethyl)-3-methylbenzo[b]thiophene-2-carboxamide hydrochloride;

7-acetyl-N-(5-((3-methoxyazetidin-1-yl)carbonyl)quinolin-2-yl)-4-(methoxymethyl)-3-methylbenzo[b]thiophene-2-carboxamide benzenesulfonate;

7-acetyl-N-(5-((3-methoxyazetidin-1-yl)carbonyl)quinolin-2-yl)-4-(methoxymethyl)-3-methylbenzo[b]thiophene-2-carboxamide methanesulfonate;

7-acetyl-N-(5-((3-methoxyazetidin-1-yl)carbonyl)quinolin-2-yl)-4-(methoxymethyl)-3-methylbenzo[b]thiophene-2-carboxamide p-toluenesulfonate;

7-acetyl-N-(5-((3-methoxyazetidin-1-yl)carbonyl)quinolin-2-yl)-4-(methoxymethyl)-3-methylbenzo[b]thiophene-2-carboxamide hydrobromide;

7-acetyl-4-(methoxymethyl)-3-methyl-N-(5-((methylsulfonyl)methyl)quinolin-2-yl)benzo[b]thiophene-2-carboxamide;

7-acetyl-4-(methoxymethyl)-3-methyl-N-(5-((methylsulfonyl)methyl)quinolin-2-yl)benzo[b]thiophene-2-carboxamide hydrochloride;

7-acetyl-4-(methoxymethyl)-3-methyl-N-(5-((methylsulfonyl)methyl)quinolin-2-yl)benzo[b]thiophene-2-carboxamide methanesulfonate;

7-acetyl-4-(methoxymethyl)-3-methyl-N-(5-((methylsulfonyl)methyl)quinolin-2-yl)benzo[b]thiophene-2-carboxamide hydrobromide;

7-acetyl-4-(methoxymethyl)-N-(5-(methoxymethyl)quinolin-2-yl)-3-methylbenzo[b]thiophene-2-carboxamide;

7-acetyl-4-(methoxymethyl)-N-(5-(methoxymethyl)quinolin-2-yl)-3-methylbenzo[b]thiophene-2-carboxamide hydrochloride;

7-acetyl-4-(methoxymethyl)-N-(5-(methoxymethyl)quinolin-2-yl)-3-methylbenzo[b]thiophene-2-carboxamide methanesulfonate;

7-acetyl-N-(5-(hydroxymethyl)quinolin-2-yl)-4-(methoxymethyl)-3-methylbenzo[b]thiophene-2-carboxamide;

7-acetyl-N-(5-(hydroxymethyl)quinolin-2-yl)-4-(methoxymethyl)-3-methylbenzo[b]thiophene-2-carboxamide hydrochloride;

7-acetyl-N-(5-(hydroxymethyl)quinolin-2-yl)-4-(methoxymethyl)-3-methylbenzo[b]thiophene-2-carboxamide methanesulfonate;

7-acetyl-N-(5-(hydroxymethyl)quinolin-2-yl)-4-(methoxymethyl)-3-methylbenzo[b]thiophene-2-carboxamide hydrobromide;

7-acetyl-N-(5-(hydroxymethyl)quinolin-2-yl)-4-(methoxymethyl)-3-methylbenzo[b]thiophene-2-carboxamide p-toluenesulfonate;

7-acetyl-N-(5-(hydroxymethyl)quinolin-2-yl)-4-(methoxymethyl)-3-methylbenzo[b]thiophene-2-carboxamide semi-ethane-1,2-disulfonate;

7-acetyl-N-(4-(2-hydroxypropan-2-yl)quinolin-2-yl)-4-(methoxymethyl)-3-methylbenzo[b]thiophene-2-carboxamide;

7-acetyl-N-(4-(2-hydroxypropan-2-yl)quinolin-2-yl)-4-(methoxymethyl)-3-methylbenzo[b]thiophene-2-carboxamide hydrochloride; and 7-acetyl-N-(4-(2-hydroxypropan-2-yl)quinolin-2-yl)-4-(methoxymethyl)-3-methylbenzo[b]thiophene-2-carboxamide hydrobromide;

(9) 7-Acetyl-N-(4-((4-hydroxypiperidin-1-yl)methyl)quinolin-2-yl)-4-(methoxymethyl)-3-methylbenzo[b]thiophene-2-carboxamide or a pharmaceutically acceptable salt thereof;

(10) 7-Acetyl-N-(4-((3-hydroxypyrrolidin-1-yl)methyl)quinolin-2-yl)-4-(methoxymethyl)-3-methylbenzo[b]thiophene-2-carboxamide or a pharmaceutically acceptable salt thereof;

(11) (S)-7-Acetyl-N-(4-((3-hydroxypyrrolidin-1-yl)methyl)quinolin-2-yl)-4-(methoxymethyl)-3-methylbenzo[b]thiophene-2-carboxamide or a pharmaceutically acceptable salt thereof;

(12) (R)-7-Acetyl-N-(4-((3-hydroxypyrrolidin-1-yl)methyl)quinolin-2-yl)-4-(methoxymethyl)-3-methylbenzo[b]thiophene-2-carboxamide or a pharmaceutically acceptable salt thereof;

(13) (R)-7-Acetyl-N-(4-((3-hydroxypyrrolidin-1-yl)methyl)quinolin-2-yl)-4-(methoxymethyl)-3-methylbenzo[b]thiophene-2-carboxamide hydrochloride;
(14) (R)-7-Acetyl-N-(4-((3-hydroxypyrrolidin-1-yl)methyl)quinolin-2-yl)-4-(methoxymethyl)-3-methylbenzo[b]thiophene-2-carboxamide p-toluenesulfonate;
(15) 7-Acetyl-N-(5-((3-methoxyazetidin-1-yl)carbonyl)quinolin-2-yl)-4-(methoxymethyl)-3-methylbenzo[b]thiophene-2-carboxamide or a pharmaceutically acceptable salt thereof;
(16) 7-Acetyl-N-(5-((3-methoxyazetidin-1-yl)carbonyl)quinolin-2-yl)-4-(methoxymethyl)-3-methylbenzo[b]thiophene-2-carboxamide hydrochloride;
(17) 7-Acetyl-N-(5-((3-methoxyazetidin-1-yl)carbonyl)quinolin-2-yl)-4-(methoxymethyl)-3-methylbenzo[b]thiophene-2-carboxamide benzenesulfonate;
(18) 7-Acetyl-N-(5-((3-methoxyazetidin-1-yl)carbonyl)quinolin-2-yl)-4-(methoxymethyl)-3-methylbenzo[b]thiophene-2-carboxamide methanesulfonate;
(19) 7-Acetyl-N-(5-((3-methoxyazetidin-1-yl)carbonyl)quinolin-2-yl)-4-(methoxymethyl)-3-methylbenzo[b]thiophene-2-carboxamide p-toluenesulfonate;
(20) 7-Acetyl-N-(5-((3-methoxyazetidin-1-yl)carbonyl)quinolin-2-yl)-4-(methoxymethyl)-3-methylbenzo[b]thiophene-2-carboxamide hydrobromide;
(21) 7-Acetyl-4-(methoxymethyl)-3-methyl-N-(5-((methylsulfonyl)methyl)quinolin-2-yl)benzo[b]thiophene-2-carboxamide or a pharmaceutically acceptable salt thereof;
(22) 7-Acetyl-4-(methoxymethyl)-3-methyl-N-(5-((methylsulfonyl)methyl)quinolin-2-yl)benzo[b]thiophene-2-carboxamide hydrochloride;
(23) 7-Acetyl-4-(methoxymethyl)-3-methyl-N-(5-((methylsulfonyl)methyl)quinolin-2-yl)benzo[b]thiophene-2-carboxamide methanesulfonate;
(24) 7-Acetyl-4-(methoxymethyl)-3-methyl-N-(5-((methylsulfonyl)methyl)quinolin-2-yl)benzo[b]thiophene-2-carboxamide hydrobromide;
(25) 7-Acetyl-4-(methoxymethyl)-N-(5-(methoxymethyl)quinolin-2-yl)-3-methylbenzo[b]thiophene-2-carboxamide or a pharmaceutically acceptable salt thereof;
(26) 7-Acetyl-4-(methoxymethyl)-N-(5-(methoxymethyl)quinolin-2-yl)-3-methylbenzo[b]thiophene-2-carboxamide hydrochloride;
(27) 7-Acetyl-4-(methoxymethyl)-N-(5-(methoxymethyl)quinolin-2-yl)-3-methylbenzo[b]thiophene-2-carboxamide methanesulfonate;
(28) 7-Acetyl-N-(5-(hydroxymethyl)quinolin-2-yl)-4-(methoxymethyl)-3-methylbenzo[b]thiophene-2-carboxamide or a pharmaceutically acceptable salt thereof;
(29) 7-Acetyl-N-(5-(hydroxymethyl)quinolin-2-yl)-4-(methoxymethyl)-3-methylbenzo[b]thiophene-2-carboxamide hydrochloride;
(30) 7-Acetyl-N-(5-(hydroxymethyl)quinolin-2-yl)-4-(methoxymethyl)-3-methylbenzo[b]thiophene-2-carboxamide methanesulfonate;
(31) 7-Acetyl-N-(5-(hydroxymethyl)quinolin-2-yl)-4-(methoxymethyl)-3-methylbenzo[b]thiophene-2-carboxamide hydrobromide;
(32) 7-Acetyl-N-(5-(hydroxymethyl)quinolin-2-yl)-4-(methoxymethyl)-3-methylbenzo[b]thiophene-2-carboxamide p-toluenesulfonate;
(33) 7-Acetyl-N-(5-(hydroxymethyl)quinolin-2-yl)-4-(methoxymethyl)-3-methylbenzo[b]thiophene-2-carboxamide semi-ethane-1,2-disulfonate;
(34) 7-Acetyl-N-(4-(2-hydroxypropan-2-yl)quinolin-2-yl)-4-(methoxymethyl)-3-methylbenzo[b]thiophene-2-carboxamide or a pharmaceutically acceptable salt thereof;
(35) 7-Acetyl-N-(4-(2-hydroxypropan-2-yl)quinolin-2-yl)-4-(methoxymethyl)-3-methylbenzo[b]thiophene-2-carboxamide hydrochloride;
(36) 7-Acetyl-N-(4-(2-hydroxypropan-2-yl)quinolin-2-yl)-4-(methoxymethyl)-3-methylbenzo[b]thiophene-2-carboxamide hydrobromide;
(37) a pharmaceutical composition comprising a compound or a pharmaceutically acceptable salt thereof according to any one of (1) to (36) as an active ingredient;
(38) the pharmaceutical composition according to (37), wherein the pharmaceutical composition is intended for the treatment of schizophrenia;
(39) the pharmaceutical composition according to (37), wherein the pharmaceutical composition is intended for the improvement of positive symptoms, negative symptoms, and/or cognitive impairment of schizophrenia;
(40) the pharmaceutical composition according to (37), wherein the pharmaceutical composition is intended for the treatment of Huntington's disease;
(41) use of a compound or a pharmaceutically acceptable salt thereof according to any one of (1) to (36) for the production of a pharmaceutical composition;
(42) the use according to (41), wherein the pharmaceutical composition is a pharmaceutical composition for the treatment of schizophrenia;
(43) the use according to (41), wherein the pharmaceutical composition is a pharmaceutical composition for the improvement of positive symptoms, negative symptoms, and/or cognitive impairment of schizophrenia;
(44) the use according to (41), wherein the pharmaceutical composition is a pharmaceutical composition for the treatment of Huntington's disease;
(45) a method for treating a disease or improving a symptom, comprising administering a therapeutically effective amount of a compound or a pharmaceutically acceptable salt thereof according to any one of (1) to (36) to a mammal;
(46) the method according to (45), wherein the disease is schizophrenia or Huntington's disease, and the symptom is a positive symptom, negative symptom, and/or cognitive impairment of schizophrenia; and
(47) the method according to (45) or (46), wherein the mammal is a human.

Advantageous Effects of Invention

The compound of the present invention or a pharmaceutically acceptable salt thereof has excellent PDE10A inhibitory activity. The compound of the present invention or the pharmaceutically acceptable salt thereof also improves positive symptoms, negative symptoms, and/or cognitive impairment, etc., of schizophrenia in vivo. The compound of the present invention or the pharmaceutically acceptable salt thereof further exhibits the effect of being less likely to cause hyperprolactinemia. In addition, the pharmaceutical composition of the present invention exhibits the effect of being able to treat schizophrenia or the like in a mammal, particularly, a human.

DESCRIPTION OF EMBODIMENTS

In the present specification, the "C1-Cn alkyl group" refers to a linear or branched alkyl group having 1 to n carbon atoms. Examples of the C1-C3 alkyl group include a methyl group, an ethyl group, a propyl group, and an isopropyl group. Examples of the C1-C6 alkyl group include the C1-C3 alkyl group as well as a butyl group, an isobutyl group, a tert-butyl group, a pentyl group, a 1-ethylpropyl group, and a hexyl group.

In the present specification, the "C1-C3 alkylcarbonyl group" refers to a carbonyl group bonded by the aforementioned "C1-C3 alkyl group". Examples of the C1-C3 alkylcarbonyl group include an acetyl group, a propionyl group, and a propylcarbonyl group.

In the present specification, the "hydroxy-C1-C3 alkyl group" refers to a group in which at least one hydrogen atom of the aforementioned "C1-C3 alkyl group" is replaced by a hydroxy group. Examples of the hydroxy-C1-C3 alkyl group include a hydroxymethyl group, a 1-hydroxyethyl group, a 2-hydroxyethyl group, and a 1-hydroxypropyl group.

In the present specification, the "C1 to Cn alkoxy group" refers to a group in which the aforementioned "C1 to Cn alkyl group" is bonded to an oxygen atom. Examples of the C1 to C3 alkoxy group include a methoxy group, an ethoxy group, a propoxy group, and an isopropoxy group. Examples of the C1-C6 alkoxy group include the C1 to C3 alkoxy group as well as a butyloxy group and a hexyloxy group.

In the present specification, the "C1-C3 alkoxy-C1-C3 alkyl group" refers to a group in which at least one hydrogen atom of the aforementioned "C1-C3 alkyl group" is replaced by the aforementioned "C1 to C3 alkoxy group". Examples of the C1-C3 alkoxy-C1-C3 alkyl group include a methoxymethyl group, an ethoxymethyl group, a propoxymethyl group, and a 1-methoxyethyl group.

In the present specification, the "C3-C6 cycloalkyl group" refers to a saturated cyclic hydrocarbon group having 3 to 6 carbon atoms. Examples of the C3-C6 cycloalkyl group include a cyclopropyl group, a cyclobutyl group, a cyclopentyl group, and a cyclohexyl group.

In the present specification, the "C1 to Cn alkyl group optionally substituted by one substituent" refers to a group in which one hydrogen atom of the aforementioned "C1 to Cn alkyl group" may be replaced by the substituent.

In the present specification, the "(azetidin-1-yl)carbonyl group optionally substituted by one substituent" refers to a group in which one hydrogen atom of the azetidine ring may be replaced by the substituent.

In the present specification, the "pharmaceutically acceptable salt" refers to a salt formed through the reaction of the compound of the present invention with an acid or a base.

Examples of salts include: hydrohalides such as hydrofluoride, hydrochloride, hydrobromide, and hydroiodide; inorganic acid salts such as nitrate, perchlorate, sulfate, and phosphate; lower alkanesulfonates such as methanesulfonate, trifluoromethanesulfonate, and ethanesulfonate; arylsulfonates such as benzenesulfonate and p-toluenesulfonate; organic acid salts such as acetate, malate, fumarate, succinate, citrate, ascorbate, tartrate, oxalate, and maleate; alkali metal salts such as sodium salt, potassium salt, and lithium salt; alkaline earth metal salts such as calcium salt and magnesium salt; metal salts such as aluminum salt and iron salt; inorganic salts such as ammonium salts; amine salts including organic salts such as t-octylamine salt, dibenzylamine salt, morpholine salt, glucosamine salt, phenylglycine alkyl ester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzylphenethylamine salt, piperazine salt, tetramethylammonium salt, and tris(hydroxymethyl)aminomethane salt; and amino acid salts such as glycine salt, lysine salt, arginine salt, ornithine salt, glutamate, and aspartate.

The compound of the present invention, for example, when left in air, may absorb moisture to have absorbed water so as to form a hydrate. Such hydrates are also included in the salts of the present invention.

Since the compound of the present invention may have asymmetric carbon atoms in its molecule, there may exist stereoisomers. All of these stereoisomers and mixtures of the stereoisomers are represented by a single formula, i.e., the general formula (I). Thus, the present invention also encompasses all of these stereoisomers and mixtures of these stereoisomers at arbitrary ratios. A stereoisomer is as defined in "1996 IUPAC, Pure and Applied Chemistry 68, 2193-2222".

The present invention may also encompass compounds in which one or more atoms constituting the compound of the present invention are replaced by isotopes of the atoms. The isotopes are classified into two types: radioisotopes and stable isotopes. Examples of the isotopes include hydrogen isotopes ($^2$H and $^3$H), carbon isotopes ($^{11}$C, $^{13}$C, and $^{14}$C), nitrogen isotopes ($^{13}$N and $^{15}$N), oxygen isotopes ($^{15}$O, $^{17}$O, and $^{18}$O), and a fluorine isotope ($^{18}$F). A composition containing such an isotope-labeled compound is useful as, for example, a therapeutic agent, a preventive agent, a research reagent, an assay reagent, a diagnostic agent, and an in vivo image diagnostic agent. Isotope-labeled compounds are also included in the compound of the present invention. All of mixtures of such isotope-labeled compounds are also included in the compound of the present invention. The isotope-labeled compound of the present invention can be produced by a method known in the art, for example, by use of an isotope-labeled starting material instead of a starting material in the production method of the present invention mentioned later.

The present invention may also encompass a prodrug of the compound of the present invention. The prodrug is a derivative of the compound of the present invention and refers to a compound that is converted enzymatically or chemically to the compound of the present invention in vivo. Examples of prodrugs of the compound of the present invention include compounds in which a hydroxy group is acylated, alkylated, or phosphorylated (see e.g., Povl Krogsgaard-Larsen et al., "Text Book of Drug Design and Development", the 4th edition, CRC Press, 2009, p. 135-149). Such prodrugs can be produced from the compound of the present invention by methods known in the art.

$R^1$ is preferably a hydrogen atom, a methyl group, or an ethyl group, more preferably a methyl group or an ethyl group, further preferably a methyl group.

$R^2$ is preferably a hydrogen atom, an acetyl group, a propionyl group, a hydroxymethyl group, a 1-hydroxyethyl group, a 1-methoxyethyl group, a methoxymethyl group, an ethoxymethyl group, a propoxymethyl group, or an isopropoxymethyl group, more preferably a methoxymethyl group.

$R^3$ is preferably a C1-C3 alkyl group or a C3-C6 cycloalkyl group, more preferably a methyl group, an ethyl group, a propyl group, an isopropyl group, a cyclopropyl group, a cyclobutyl group, or a cyclopentyl group, further preferably a methyl group.

$R^4$ is preferably a hydrogen atom, a C1-C3 alkyl group optionally substituted by one substituent selected from substituent group α, or an (azetidin-1-yl)carbonyl group optionally substituted by one substituent selected from substituent group α, more preferably a hydrogen atom, a methyl group, a hydroxymethyl group, a 1-hydroxyethyl group, a 2-hydroxypropan-2-yl group, a (3-hydroxypyrrolidin-1-yl)methyl group, a (3-hydroxypiperidin-1-yl)methyl group, or a (4-hydroxypiperidin-1-yl)methyl group, further preferably a hydrogen atom, a 2-hydroxypropan-2-yl group, a (3-hydroxypyrrolidin-1-yl)methyl group, or a (4-hydroxypiperidin-1-yl)methyl group.

$R^5$ is preferably a hydrogen atom, a C1-C3 alkyl group optionally substituted by one substituent selected from substituent group α, or an (azetidin-1-yl)carbonyl group optionally substituted by one substituent selected from substituent group α, more preferably a hydrogen atom, a methyl group, a hydroxymethyl group, a 1-hydroxyethyl group, a 2-hydroxypropan-2-yl group, a methoxymethyl group, an ethoxymethyl group, a methylsulfonylmethyl group, a (3-hydroxypyrrolidin-1-yl)methyl group, a (3-hydroxyazetidin-1-yl)carbonyl group, or a (3-methoxyazetidin-1-yl)carbonyl group, further preferably a hydrogen atom, a hydroxymethyl group, a methoxymethyl group, a methylsulfonylmethyl group, or a (3-methoxyazetidin-1-yl)carbonyl group.

Substituent α is preferably the group consisting of a hydroxy group, a C1-C3 alkoxy group, a methylsulfonyl group, a hydroxypyrrolidine group, and a hydroxypiperidine group, more preferably the group consisting of a hydroxy group, a methoxy group, an ethoxy group, a methylsulfonyl group, a 3-hydroxypyrrolidine group, a 3-hydroxypiperidine group, and a 4-hydroxypiperidine group.

A preferred combination of $R^1$, $R^2$, $R^3$, $R^4$, and $R^5$ is the combination in which $R^1$ is a hydrogen atom, a methyl group, or an ethyl group, $R^2$ is a hydrogen atom, an acetyl group, a propionyl group, a hydroxymethyl group, a 1-hydroxyethyl group, a 1-methoxyethyl group, a methoxymethyl group, an ethoxymethyl group, a propoxymethyl group, or an isopropoxymethyl group, $R^3$ is a C1-C3 alkyl group or a C3-C6 cycloalkyl group, $R^4$ is a hydrogen atom, a C1-C3 alkyl group optionally substituted by one substituent selected from substituent group α, or an (azetidin-1-yl)carbonyl group optionally substituted by one substituent selected from substituent group α, $R^5$ is a hydrogen atom, a C1-C3 alkyl group optionally substituted by one substituent selected from substituent group α, or an (azetidin-1-yl)carbonyl group optionally substituted by one substituent selected from substituent group α, and at least one of $R^4$ and $R^5$ is a hydrogen atom.

A more preferred combination of $R^1$, $R^2$, $R^3$, $R^4$, and $R^5$ is the combination in which $R^1$ is a hydrogen atom, a methyl group, or an ethyl group, $R^2$ is a hydrogen atom, an acetyl group, a propionyl group, a hydroxymethyl group, a 1-hydroxyethyl group, a 1-methoxyethyl group, a methoxymethyl group, an ethoxymethyl group, a propoxymethyl group, or an isopropoxymethyl group, $R^3$ is a methyl group, an ethyl group, a propyl group, an isopropyl group, a butyl group, an isobutyl group, a 1-ethylpropyl group, a tert-butyl group, a cyclopropyl group, a cyclobutyl group, or a cyclopentyl group, $R^4$ is a hydrogen atom, a methyl group, a hydroxymethyl group, a 1-hydroxyethyl group, a 2-hydroxypropan-2-yl group, a (3-hydroxypyrrolidin-1-yl)methyl group, a (3-hydroxypiperidin-1-yl)methyl group, or a (4-hydroxypiperidin-1-yl)methyl group, $R^5$ is a hydrogen atom, a methyl group, a hydroxymethyl group, a 1-hydroxyethyl group, a 2-hydroxypropan-2-yl group, a methoxymethyl group, an ethoxymethyl group, a methylsulfonylmethyl group, a (3-hydroxypyrrolidin-1-yl)methyl group, a (3-hydroxyazetidin-1-yl)carbonyl group, or a (3-methoxyazetidin-1-yl)carbonyl group, and at least one of $R^4$ and $R^5$ is a hydrogen atom.

A further preferred combination of $R^1$, $R^2$, $R^3$, $R^4$, and $R^5$ is the combination in which $R^1$ is a methyl group, $R^2$ is a methoxymethyl group, $R^3$ is a methyl group, $R^4$ is a hydrogen atom, a 2-hydroxypropan-2-yl group, a (3-hydroxypyrrolidin-1-yl)methyl group, or a (4-hydroxypiperidin-1-yl)methyl group, $R^5$ is a hydrogen atom, a hydroxymethyl group, a methoxymethyl group, a methylsulfonylmethyl group, or a (3-methoxyazetidin-1-yl)carbonyl group, and at least one of $R^4$ and $R^5$ is a hydrogen atom.

A particularly preferred combination of $R^1$, $R^2$, $R^3$, $R^4$, and $R^5$ is the combination in which $R^1$ is a methyl group, $R^2$ is a methoxymethyl group, $R^3$ is a methyl group, $R^4$ is a hydrogen atom, and $R^5$ is a hydroxymethyl group, a methoxymethyl group, a methylsulfonylmethyl group, or a (3-methoxyazetidin-1-yl)carbonyl group.

The compound of the present invention can be produced by, for example, methods described below.

In the production methods described below, depending on the type of functional group, substitution of a functional group with an appropriate protective group (a group that can easily be converted to the functional group) at a stage from a starting material to an intermediate may be effective for production technology. Examples of such functional groups include an amino group, a hydroxy group, a formyl group, and a carboxy group. Protective groups for these groups are not particularly limited as long as the protective groups are usually used. Examples thereof include protective groups described in, for example, Theodora W. Greene and Peter G. M. Wuts, Greene's Protective Groups in Organic Synthesis. Fourth Edition, John Wiley & Sons, Inc. Reactions for the introduction of these protective groups and reactions for the removal of the protective groups can be carried out according to routine methods such as methods described in the aforementioned literature.

The compound of the present invention can be produced according to, for example, the following method:

[Formula 2]

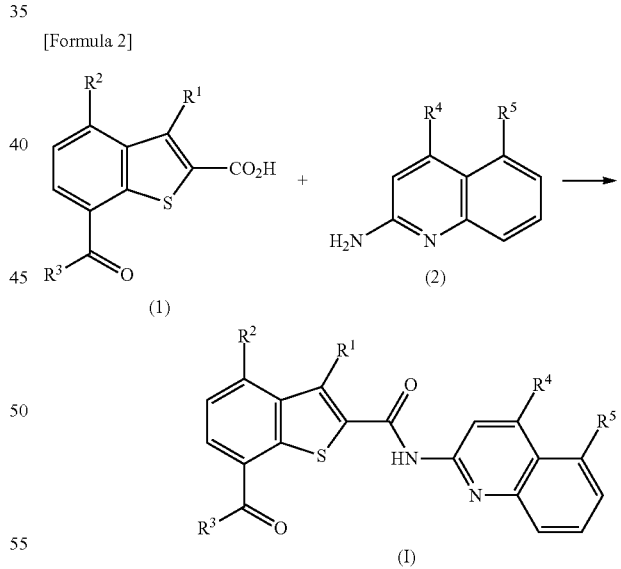

In the formula, $R^1$, $R^2$, $R^3$, $R^4$, and $R^5$ are as defined above.

This reaction is carried out using compound (1) and compound (2) at equivalents or either of them in excess by stirring at room temperature to 80° C. usually for 1 hour to 7 days in the presence of a condensing agent in a solvent inert to the reaction. This reaction may be carried out in the presence of a base. Examples of the solvent include, but are not particularly limited to, dichloromethane, chloroform, 1,2-dichloroethane, N,N-dimethylformamide (hereinafter, also referred to as "DMF"), and N,N-dimethylacetamide. The condensing agent is not particularly limited as long as the condensing agent is used in amidation reactions. Examples thereof include: carbodiimides such as 1-ethyl-3-(3-dimethylaminopropyl)carbodiimide hydrochloride; carbodiimides combined with N-hydroxy compounds such as 1-hydroxy-7-azabenzotriazole; carbodiimides combined with N,N-dimethyl-4-aminopyridine; phosphoniums such as 1H-benzotriazol-1-yloxytripyrrolidinophosphonium hexafluorophosphate (hereinafter, also referred to as "PyBOP"); and uroniums such as O-(1H-benzotriazol-1-yl)-N,N,N',N'-tetramethyluronium hexafluorophosphate (hereinafter, also referred to as "HBTU"). Examples of the base include triethylamine, N,N-diisopropylethylamine, and potassium carbonate.

The compound (2) may be commercially available, or a compound known in the art may be used. Alternatively, the compound can be produced by use of a method described later in the Reference Examples and Examples, a method known in the art, or a modification thereof. The compound (1) can be produced by use of, for example, a method described below, a method described later in Reference Examples and Examples, a method known in the art, or a modification thereof.

The compound (1) can be produced according to, for example, the following method:

"THF"). Examples of the base include lithium diisopropylamide and lithium tetramethylpiperidide. Lithium diisopropylamide can be prepared by mixing N,N-diisopropylamine with n-butyllithium. Lithium tetramethylpiperidide can be prepared by mixing 2,2,6,6-tetramethylpiperidine with n-butyllithium.

Step 2 is the step of producing compound (5) from compound (4). This step is carried out using compound (4) and an alkylating agent at equivalents or either of them in excess by stirring at −80° C. to room temperature usually for 10 minutes to 24 hours in a solvent inert to the reaction. Examples of the solvent include, but are not particularly limited to, THF and toluene. Examples of the alkylating agent include C1-C3 alkyl magnesium halides (e.g., methyl magnesium bromide and ethyl magnesium bromide) and di-C1-C3 alkylzincs (e.g., diethylzinc).

Step 3 is the step of producing compound (6) from compound (5). This step can be carried out by Method A or Method B.

(Method A)

This method is carried out using compound (5) and N-methylmorpholine-N-oxide at equivalents or either of them in excess by stirring at 0 to 50° C. usually for 10 minutes to 3 hours in the presence of tetrapropylammonium perruthenate in a solvent inert to the reaction. Examples of the solvent include, but are not particularly limited to, acetonitrile.

[Formula 3]

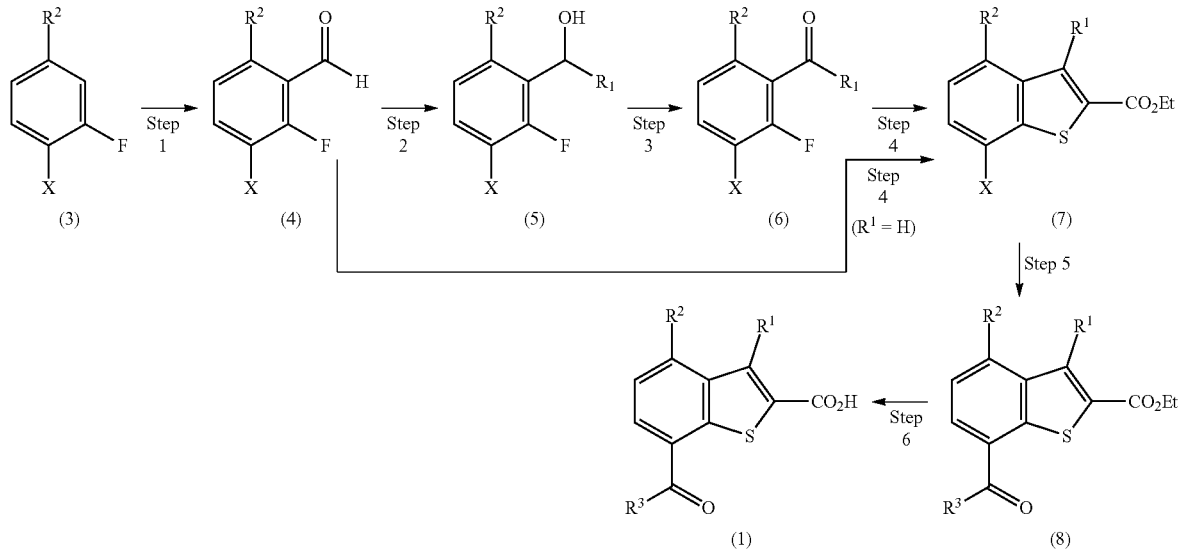

In the formula, X represents a halogen atom, and $R^1$, $R^2$, and $R^3$ are as defined above. The compound (3) may be commercially available, or a compound known in the art may be used. Alternatively, the compound can be produced by use of a method described later in the Reference Examples and Examples, a method known in the art, or a modification thereof.

Step 1 is the step of producing compound (4) from compound (3). This step is carried out using compound (3) and a base at equivalents or either of them in excess by stirring at −78 to −40° C. usually for 10 minutes to 5 hours in a solvent inert to the reaction followed by the addition of DMF and stirring usually for 10 minutes to 5 hours. Examples of the solvent include, but are not particularly limited to, tetrahydrofuran (hereinafter, also referred to as (Method B)

This method is carried out using compound (5) and sodium hypochlorite at equivalents or either of them in excess by stirring at −20° C. to room temperature usually for 30 minutes to 6 hours in the presence of 2-azaadamantane-N-oxyl, potassium bromide, tetrabutylammonium bromide, and a saturated aqueous solution of sodium bicarbonate in a solvent inert to the reaction. Examples of the solvent include, but are not particularly limited to, dichloromethane.

Step 4 is the step of producing compound (7) from compound (4) or compound (6). This step is carried out using compound (4) or compound (6) and ethyl thioglycolate at equivalents or either of them in excess by stirring at 0 to 50° C. usually for 1 to 24 hours in the presence of a base in a solvent inert to the reaction. Examples of the solvent include, but are not particularly limited to, DMF. Examples of the base include potassium carbonate and 1,8-diazabicyclo[5.4.0]-7-undecene.

Step 5 is the step of producing compound (8) from compound (7). This step can be carried out by Method C, Method D, or Method E.

(Method C)

This method can be carried out by step A and step B.

(Step A)

This step is carried out using compound (7) and (1-ethoxyvinyl)tributyltin at equivalents or either of them in excess by stirring at 60 to 150° C. usually for 1 to 48 hours in the presence of a catalyst in a solvent inert to the reaction. This step is preferably carried out under an inert gas atmosphere. Examples of the solvent include, but are not particularly limited to, toluene. Examples of the catalyst include dichlorobis(triphenylphosphine)palladium(II). Examples of the inert gas include argon and nitrogen.

(Step B)

This step is carried out using the compound obtained in step A and hydrochloric acid at equivalents or either of them in excess by stirring at 0 to 50° C. usually for 1 to 48 hours in a solvent inert to the reaction. Examples of the solvent include, but are not particularly limited to, toluene, ethanol, and THF.

(Method D)

This method can be carried out by step C and step D.

(Step C)

This step is carried out using compound (7) and trimethylsilylacetylene at equivalents or either of them in excess by stirring at 50 to 120° C. usually for 1 to 48 hours in the presence of a catalyst in a solvent inert to the reaction. This step is preferably carried out under an inert gas atmosphere. Examples of the solvent include, but are not particularly limited to, triethylamine and a mixed solvent of triethylamine and THF. Examples of the catalyst include copper(I) iodide, copper(I) bromide, dichlorobis(triphenylphosphine)palladium(II), and tetrakis(triphenylphosphine)palladium(0). Examples of the inert gas include argon and nitrogen.

(Step D)

This step is carried out using the compound obtained in step C and p-toluenesulfonic acid monohydrate at equivalents or either of them in excess by stirring at 50 to 120° C. usually for 1 to 48 hours in a solvent inert to the reaction. Examples of the solvent include, but are not particularly limited to, acetic acid and chloroform.

(Method E)

This method is carried out using compound (7) and isopropyl magnesium chloride at equivalents or either of them in excess by stirring at −78 to −40° C. usually for 10 minutes to 3 hours in a solvent inert to the reaction, the addition of copper(I) iodide and lithium chloride, and stirring usually for 10 minutes to 3 hours followed by the addition of $C_1$-$C_6$ alkylcarbonyl halide or $C_3$-$C_6$ cycloalkylcarbonyl halide and stirring usually for 30 minutes to 6 hours. Examples of the solvent include, but are not particularly limited to, THF.

Step 6 is the step of producing compound (1) from compound (8). This step is carried out using compound (8) and a base at equivalents or either of them in excess by stirring at 0 to 80° C. usually for 1 to 24 hours in a solvent inert to the reaction followed by the addition of an acid. Examples of the solvent include, but are not particularly limited to, single solvents such as water, ethanol, methanol, THF, and 1,4-dioxane, and mixed solvents thereof. Examples of the base include sodium hydroxide and lithium hydroxide. Examples of the acid include hydrochloric acid.

The compound of the present invention can be produced using the aforementioned method or can be easily produced from a compound known in the art according to the Reference Examples and Examples mentioned later.

The compound of the present invention obtained by the aforementioned method or a pharmaceutically acceptable salt thereof has excellent PDE10A inhibitory activity and as such, can be used as an active ingredient in a pharmaceutical composition for the treatment or improvement of, for example, schizophrenia (positive symptoms, negative symptoms, cognitive impairment, etc.) (which can be tested for positive symptoms using a method described in, for example, the Test Examples, for negative symptoms using a method described in, for example, NeuroReport 2001, 12: 11-15 and Physiology Behav 2011, 104: 880-885, or for cognitive impairment using a method described in, for example, Eur J Pharmacol 2005, 519: 114-117, Neuropsychopharmacology 2001, 24: 451-460, and Physiology Behav 2011, 104: 880-885), Huntington's disease, Alzheimer-type dementia, type I bipolar disorder, type II bipolar disorder, anxiety disorders (e.g., obsessive-compulsive disorder, social phobia, generalized anxiety disorder, panic disorder, agoraphobia, specific phobias, post-traumatic stress disorder, acute stress disorder, substance-induced anxiety disorder, and unidentifiable anxiety disorder), major depressive disorder, at risk mental state, substance use disorders (caused by, for example, alcohols, amphetamine, *cannabis*, cocaine, hallucinogen, inhalants, nicotine, opiums, phencyclidine, sedatives, hypnotics, antianxiety drugs, and multiple substances), attention deficit hyperactivity disorder, Parkinson's disease, autism, Tourette's disorder, adiposity, learning disabilities (e.g., dyslexia, dyscalculia, dysgraphia, and unidentifiable learning disabilities), post-stroke depression, substance-induced psychotic disorders (caused by, for example, alcohols, amphetamine, *cannabis*, cocaine, hallucinogen, inhalants, opiums, phencyclidine, sedatives, hypnotics, and antianxiety drugs), schizophreniform disorder, schizoaffective disorder, delusional disorder, brief psychotic disorder, shared psychotic disorder, unidentifiable psychotic disorders, motor skills disorders, unidentifiable depressive disorder, major depressive episode, manic episode, mixed episode, hypomanic episode, major depressive episode with atypical features, major depressive episode with melancholic features, mood episode with catatonic features, postpartum-onset mood episode, dysthymic disorder, dementia of Huntington's disease, delirium, amnestic disorder, mental retardation, cyclothymic disorder, paranoid personality disorder, schizoid personality disorder, and schizotypal personality disorder.

When a pharmaceutical composition comprising the compound of the present invention or the pharmaceutically acceptable salt thereof as an active ingredient is administered to a mammal (e.g., a human, a horse, cattle, or a pig, preferably a human), the pharmaceutical composition can be administered orally or parenterally and systemically or locally.

The pharmaceutical composition of the present invention can be prepared in an appropriate form selected according to the administration method by a method for preparing each preparation usually used.

Examples of oral forms of the pharmaceutical composition include tablets, pills, powders, granules, capsules, solutions, suspensions, emulsions, syrups, and elixirs. The pharmaceutical composition in such forms can be produced according to routine methods using, if necessary, appropriately selected additives usually used, such as excipients, binders, disintegrants, lubricants, swelling agents, swelling aids, coating agents, plasticizers, stabilizers, antiseptics, antioxidants, colorants, solubilizers, suspending agents, emulsifying agents, sweeteners, preservatives, buffers, diluents, and wetting agents.

Examples of parenteral forms of the pharmaceutical composition include injections, ointments, gels, creams, poultices, patches, aerosols, inhalants, sprays, eye drops, nasal drops, suppositories, and inhalants. The pharmaceutical composition in such forms can be produced according to routine methods using, if necessary, appropriately selected additives usually used, such as stabilizers, antiseptics, solubilizers, moisturizers, preservatives, antioxidants, flavors, gelling agents, neutralizing agents, buffers, tonicity agents, surfactants, colorants, buffering agents, thickeners, wetting agents, fillers, absorption promoters, suspending agents, and binders.

The dose of the compound of the present invention or the pharmaceutically acceptable salt thereof differs depending on symptoms, age, body weight, etc. For oral administration, the dose is 0.01 to 1000 mg, preferably 0.1 to 500 mg, in terms of the amount of the compound per dose for one adult, which can be administered once to several times a day. For parenteral administration, the dose is 0.005 to 500 mg, preferably 0.05 to 250 mg, in terms of the amount of the compound per dose for one adult, which can be administered once to several times a day.

Hereinafter, the present invention will be described in more detail with reference to the Reference Examples, Examples, Formulation Example, and Test Examples. However, the scope of the present invention is not intended to be limited by these.

EXAMPLES

In the Reference Examples and Examples, a fraction containing each compound of interest was detected by TLC (thin-layer chromatography) observation or LC/MS (liquid chromatography/mass spectrometry) analysis. In the Reference Examples and Examples, "room temperature" usually represents approximately 10° C. to approximately 35° C. Regarding the data as to indeterminable broad spectra of OH, NH protons, etc., proton NMR spectra were not described.

In the description below, the following abbreviations are used:
DMSO: Dimethyl sulfoxide
TIPS: Triisopropylsilyl
TBS: tert-Butyldimethylsilyl
Boc: tert-Butoxycarbonyl
ESI: Electron spray ionization
FAB: Fast atom bombardment ionization
[M+H]+: Molecular ion peak Reference Example 1

1-(3,6-Dibromo-2-fluorophenyl) ethanol

[Formula 4]

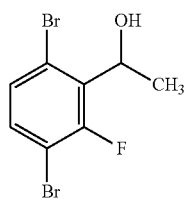

A solution of 3,6-dibromo-2-fluorobenzaldehyde (34.56 g) in THF (400 mL) was cooled to −78° C. under a nitrogen stream. Methyl magnesium bromide (0.97 M solution in THF, 190 mL) was added dropwise thereto, and the mixture was stirred at the same temperature as above for 10 minutes and then stirred at room temperature for 1 hour. The reaction mixture was cooled to 0° C., and a saturated aqueous solution of ammonium chloride (105 mL) and water (63 mL) were added thereto, followed by extraction with ethyl acetate. The organic layer was washed with saturated aqueous sodium chloride, then dried over anhydrous magnesium sulfate, and concentrated to obtain the title compound (36.77 g).

$^1$H NMR (CDCl$_3$, 400 MHz): δ (ppm) 7.22-7.37 (m, 2H), 5.29-5.41 (m, 1H), 2.42 (m, 1H), 1.62 (dd, J=6.9, 1.2 Hz, 3H)

Reference Example 2

1-(3,6-Dibromo-2-fluorophenyl)ethanone

[Formula 5]

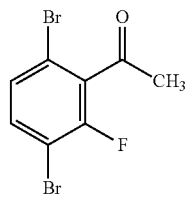

To a solution of the compound (36.77 g) obtained in Reference Example 1 in acetonitrile (700 mL), N-methylmorpholine-N-oxide (21.69 g) and tetrapropylammonium perruthenate (4.34 g) were added at room temperature, and the mixture was stirred at the same temperature as above for 20 minutes. The reaction mixture was concentrated, and the residue was purified by silica gel column chromatography (hexane:ethyl acetate=100:0-90:10) to obtain the title compound (35.49 g).

$^1$H NMR (CDCl$_3$, 400 MHz): δ (ppm) 7.46 (dd, J=8.5, 6.9 Hz, 1H), 7.27-7.31 (m, 1H), 2.59 (d, J=1.2 Hz, 3H)

Reference Example 3

Ethyl 4,7-dibromo-3-methylbenzo[b]thiophene-2-carboxylate

[Formula 6]

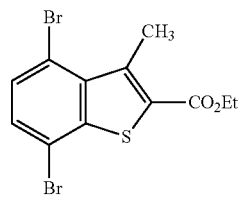

To a suspension of the compound (30.49 g) obtained in Reference Example 2 and potassium carbonate (42.72 g) in DMF (670 mL), ethyl thioglycolate (5.65 mL) was added at room temperature, and the mixture was stirred at the same temperature as above for 2 hours. To the reaction mixture, ethyl thioglycolate (5.65 mL) was added at room temperature, and the mixture was stirred at the same temperature as above for 6 hours. To the reaction mixture, ethyl thioglycolate (1.13 mL) was added at room temperature, and the mixture was stirred at the same temperature as above for 16 hours. To the reaction mixture, ethyl iodide (16.5 mL) was added at room temperature, and the mixture was stirred at the same temperature as above for 23 hours. The reaction mixture was cooled to 0° C. Water (760 mL) was added dropwise thereto, and the mixture was stirred at the same temperature as above for 2 hours. The precipitated solid was collected by filtration and washed with a DMF-water mixed solution, water, and hexane in this order to obtain the title compound (35.15 g).

$^1$H NMR (CDCl$_3$, 400 MHz): δ (ppm) 7.47-7.51 (m, 1H), 7.35-7.41 (m, 1H), 4.41 (q, J=6.9 Hz, 2H), 3.11 (s, 3H), 1.43 (t, J=7.1 Hz, 3H)

Reference Example 4

Ethyl 4,7-diacetyl-3-methylbenzo[b]thiophene-2-carboxylate

[Formula 7]

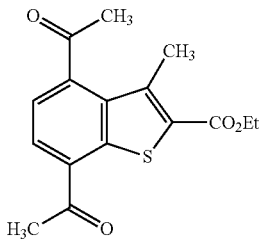

To a solution of the compound (11.19 g) obtained in Reference Example 3 and dichlorobis(triphenylphosphine)palladium(II) (2.08 g) in toluene (500 mL), a solution of (1-ethoxyvinyl)tributyltin (26.73 g) in toluene (82 mL) was added, and the mixture was stirred at 110° C. for 28 hours under an argon atmosphere. The reaction mixture was cooled to room temperature and then filtered, and the filtrate was concentrated. To the residue, ethanol (100 mL) and 2 N hydrochloric acid (33 mL) were added, and the mixture was stirred at room temperature for 3.5 hours. To the reaction mixture, saturated aqueous sodium chloride (224 mL) was added, followed by extraction with ethyl acetate (560 mL). The organic layer was washed with saturated aqueous sodium chloride, a saturated aqueous solution of sodium bicarbonate, and saturated aqueous sodium chloride in this order, then dried over anhydrous magnesium sulfate, and concentrated. The residue was purified by silica gel column chromatography (hexane-chloroform (1:1) mixed solution: ethyl acetate=100:0-80:20), and the obtained solid was washed with hexane to obtain the title compound (8.256 g).

$^1$H NMR (CDCl$_3$, 400 MHz): δ (ppm) 8.12 (d, J=7.7 Hz, 1H), 7.43 (d, J=7.3 Hz, 1H), 4.42 (q, J=6.9 Hz, 2H), 2.79 (s, 3H), 2.73 (s, 3H), 2.69 (s, 3H), 1.44 (t, J=7.1 Hz, 3H)

Reference Example 5

4,7-Diacetyl-3-methylbenzo[b]thiophene-2-carboxylic acid

[Formula 8]

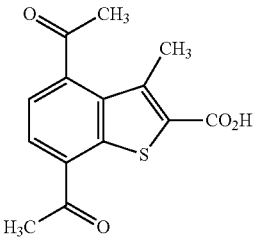

To a suspension of the compound (8.255 g) obtained in Reference Example 4 in methanol (40 mL), a 2 N aqueous sodium hydroxide solution (27.1 mL) was added, and the mixture was stirred at 40° C. for 3 hours and 20 minutes. The reaction mixture was cooled to room temperature. Then, 2 N hydrochloric acid (29.8 mL) was added dropwise thereto, and the mixture was cooled to 0° C. The precipitated solid was collected by filtration and washed with a methanol-water (1:2) mixed solution to obtain the title compound (7.457 g).

$^1$H NMR (DMSO, 400 MHz): δ (ppm) 13.58 (s, 1H), 8.41 (d, J=7.7 Hz, 1H), 7.77 (d, J=7.7 Hz, 1H), 2.78 (s, 3H), 2.77 (s, 3H), 2.55 (s, 3H)

Reference Example 6

2-(2-Chloroquinolin-4-yl)propan-2-ol

[Formula 9]

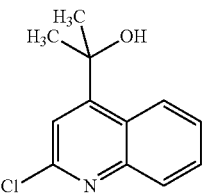

Methyl magnesium bromide (a mixture of a 0.97 M solution in THF (100 mL) and a 0.93 M solution in THF (800 mL)) was cooled to 0° C. A solution of methyl 2-chloroquinoline-4-carboxylate (46.60 g) in THF (383 mL) was added dropwise thereto, and the mixture was stirred at the same temperature as above for 2.5 hours. To the reaction mixture, a saturated aqueous solution of ammonium chloride (433 mL) and water (260 mL) were added, followed by extraction with ethyl acetate. The organic layer was washed with saturated aqueous sodium chloride, dried over anhydrous magnesium sulfate, and concentrated. To the residue, ethyl acetate (39 mL) was added, and the mixture was heated to 75° C. Hexane (89 mL) was added thereto, and the mixture was then cooled to 0° C. The precipitated solid was collected by filtration and washed with a hexane-ethyl acetate (5:1) mixed solution to obtain the title compound (34.79 g).

¹H NMR (CDCl₃, 400 MHz): δ (ppm) 8.65 (dd, J=8.7, 1.0 Hz, 1H), 8.05 (dd, J=8.3, 1.4 Hz, 1H), 7.71 (ddd, J=8.3, 6.9, 1.4 Hz, 1H), 7.53-7.61 (m, 1H), 7.50 (s, 1H), 2.05 (s, 1H), 1.86 (s, 6H)

Reference Example 7

2-(2-((4-Methoxybenzyl)amino)quinolin-4-yl)propan-2-ol

[Formula 10]

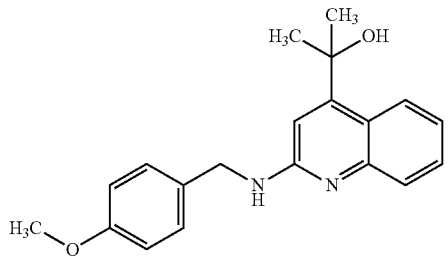

The compound (34.79 g) obtained in Reference Example 6 and 4-methoxybenzylamine (86.15 g) were stirred at 120° C. for 33 hours. The reaction mixture was cooled to room temperature. Then, ethyl acetate (410 mL) and water (690 mL) were added thereto, and carbon dioxide was blown into the mixture. The organic layer was washed with saturated aqueous sodium chloride, dried over anhydrous magnesium sulfate, and concentrated. To the residue, diisopropyl ether was added, and the precipitated solid was collected by filtration and washed with diisopropyl ether to obtain the title compound (46.65 g).

¹H NMR (CDCl₃, 400 MHz): δ (ppm) 8.36 (dd, J=8.5, 1.2 Hz, 1H), 7.76 (dd, J=8.1, 1.2 Hz, 1H), 7.52 (ddd, J=8.3, 6.9, 1.4 Hz, 1H), 7.31-7.39 (m, 2H), 7.23 (ddd, J=8.4, 6.8, 1.4 Hz, 1H), 6.84-6.92 (m, 2H), 6.75 (s, 1H), 4.89 (br. s., 1H), 4.66 (d, J=5.3 Hz, 2H), 3.81 (s, 3H), 1.98 (s, 1H), 1.78 (s, 6H)

Reference Example 8

2-(2-Aminoquinolin-4-yl)propan-2-ol

[Formula 11]

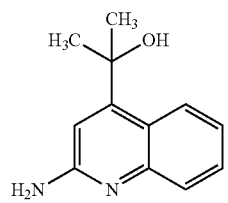

To a solution of the compound (10.00 g) obtained in Reference Example 7 in dichloromethane (21.1 mL), trifluoroacetic acid (hereinafter, also referred to as "TFA") (21.0 mL) was added, and the mixture was stirred at room temperature for 86 hours. The reaction mixture was concentrated. To the residue, chloroform (50 mL) and an 8 N aqueous sodium hydroxide solution (13 mL) were added, and then, hexane (79 mL) and chloroform (23 mL) were added. The organic layer was dried over anhydrous magnesium sulfate and concentrated. To the residue, chloroform (73 mL) was added, and the mixture was heated to 60° C. Hexane (29 mL) was added thereto, and the mixture was then cooled to 0° C. The precipitated solid was collected by filtration and washed with a hexane-chloroform (1:1) mixed solution to obtain the title compound (6.344 g).

¹H NMR (CDCl₃, 400 MHz): δ (ppm) 8.40 (d, J=8.5 Hz, 1H), 7.72 (dd, J=8.5, 1.2 Hz, 1H), 7.56 (ddd, J=8.4, 7.0, 1.2 Hz, 1H), 7.30 (ddd, J=8.5, 6.9, 1.6 Hz, 1H), 6.91 (s, 1H), 5.19 (br. s., 2H), 2.07 (br. s., 1H), 1.83 (s, 6H)

Reference Example 9

1-(3,6-Dibromo-2-fluorophenyl)propan-1-ol

[Formula 12]

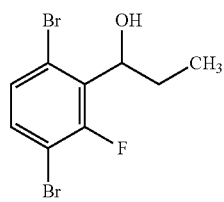

A solution of 3,6-dibromo-2-fluorobenzaldehyde (282 mg) and tetraisopropyl titanate (6.4 µL) in toluene (1 mL) was cooled to 0° C. Diethylzinc (0.99 M solution in hexane, 1.22 mL) was added thereto, and the mixture was stirred at room temperature for 23 hours. To the reaction mixture, 1 N hydrochloric acid was added, followed by extraction with ethyl acetate. The organic layer was washed with saturated aqueous sodium chloride, then dried over anhydrous sodium sulfate, and concentrated. The residue was purified by silica gel column chromatography (hexane:ethyl acetate=100:0-60:40) to obtain the title compound (119 mg).

¹H NMR (CDCl₃, 400 MHz): δ (ppm) 7.31-7.36 (m, 1H), 7.23-7.26 (m, 1H), 5.05-5.12 (m, 1H), 2.34-2.41 (m, 1H), 1.86-2.04 (m, 2H), 1.00 (t, J=7.3 Hz, 3H)

Reference Example 10

1-(3,6-Dibromo-2-fluorophenyl)propan-1-one

[Formula 13]

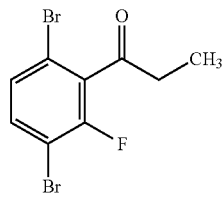

The title compound (54.0 mg) was obtained in the same way as in Reference Example 2 using the compound (62.4 mg) obtained in Reference Example 9, acetonitrile (1 mL), N-methylmorpholine-N-oxide (35.1 mg), and tetrapropylammonium perruthenate (7.0 mg).

¹H NMR (CDCl₃, 400 MHz): δ (ppm) 7.42-7.48 (m, 1H), 7.25-7.29 (m, 1H), 2.81-2.89 (m, 2H), 1.23 (t, J=7.3 Hz, 3H)

MS (ESI⁺) m/z: 311 [M+H]⁺

Reference Example 11

Ethyl 4,7-dibromo-3-ethylbenzo[b]thiophene-2-carboxylate

[Formula 14]

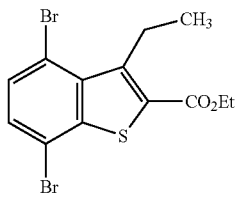

To a suspension of the compound (810 mg) obtained in Reference Example 10 and potassium carbonate (721 mg) in DMF (10 mL), ethyl thioglycolate (0.371 mL) was added at 0° C., and the mixture was stirred at the same temperature as above for 1 hour, stirred at room temperature for 18 hours, stirred at 40° C. for 5 hours, and stirred at 50° C. for 3 hours. To the reaction mixture, water was added, followed by extraction with ethyl acetate. The organic layer was washed with water and saturated aqueous sodium chloride in this order, then dried over anhydrous sodium sulfate, and concentrated. The residue was purified by silica gel column chromatography (hexane:ethyl acetate=100:0-80:20) to obtain the title compound (842 mg).

$^1$H NMR (CDCl$_3$, 400 MHz): δ (ppm) 7.49-7.51 (m, 1H), 7.39 (d, J=8.1 Hz, 1H), 4.41 (q, J=7.2 Hz, 2H), 3.65 (q, J=7.4 Hz, 2H), 1.43 (t, J=7.1 Hz, 3H), 1.32 (t, J=7.5 Hz, 3H)

Reference Example 12

Ethyl 4,7-diacetyl-3-ethylbenzo[b]thiophene-2-carboxylate

[Formula 15]

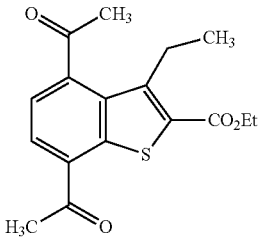

To a solution of the compound (800 mg) obtained in Reference Example 11 and dichlorobis(triphenylphosphine)palladium(II) (344 mg) in toluene (10 mL), (1-ethoxyvinyl)tributyltin (4.13 mL) was added, and the mixture was stirred at 110° C. for 22 hours under a nitrogen atmosphere. The reaction mixture was cooled to room temperature and then filtered, and the filtrate was concentrated. To the residue, THF (15 mL) and 6 N hydrochloric acid (5 mL) were added, and the mixture was stirred at room temperature for 60 hours. To the reaction mixture, water was added, followed by extraction with ethyl acetate. The organic layer was dried over anhydrous sodium sulfate and concentrated. The residue was purified by silica gel column chromatography (hexane:ethyl acetate=90:10-50:50) and basic silica gel column chromatography (hexane:ethyl acetate=70:30-30:70) in this order to obtain the title compound (505 mg).

$^1$H NMR (CDCl$_3$, 400 MHz): δ (ppm) 8.11 (d, J=7.7 Hz, 1H), 7.38 (d, J=7.7 Hz, 1H), 4.41 (q, J=7.2 Hz, 2H), 3.18 (q, J=7.3 Hz, 2H), 2.78 (s, 3H), 2.74 (s, 3H), 1.43 (t, J=7.3 Hz, 3H), 1.17 (t, J=7.3 Hz, 3H)

MS (ESI$^+$) m/z: 319 [M+H]$^+$

Reference Example 13

4,7-Diacetyl-3-ethylbenzo[b]thiophene-2-carboxylic acid

[Formula 16]

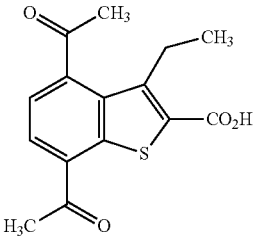

To the compound (500 mg) obtained in Reference Example 12, a methanol-THF (1:1) mixed solution (15 mL) and a 2 N aqueous sodium hydroxide solution (15 mL) were added, and the mixture was stirred at room temperature for 22 hours. To the reaction mixture, 6 N hydrochloric acid was added, followed by extraction with dichloromethane. The organic layer was dried over anhydrous sodium sulfate and concentrated to obtain the title compound (451 mg).

$^1$H NMR (DMSO, 400 MHz): δ (ppm) 13.52 (br. s., 1H), 8.40 (d, J=7.5 Hz, 1H), 7.73 (d, J=7.5 Hz, 1H), 3.08 (q, J=7.4 Hz, 2H), 2.78 (s, 3H), 2.77 (s, 3H), 1.06 (t, J=7.4 Hz, 3H)

MS (ESI$^+$) m/z: 291[M+H]$^+$

Reference Example 14

Ethyl 4,7-dibromobenzo[b]thiophene-2-carboxylate

[Formula 17]

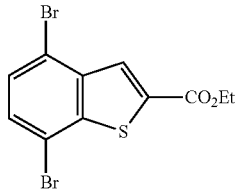

To a suspension of sodium hydride (60% oil suspension, 300 mg) in DMSO (20 mL), ethyl thioglycolate (600 μL) was added, and the mixture was stirred at room temperature for 15 minutes. To the reaction mixture, a solution of 3,6-dibromo-2-fluorobenzaldehyde (1.4 g) in DMSO was added, and the mixture was stirred at room temperature for 1 hour and then stirred at 80° C. for 3 hours. To the reaction mixture, ethyl acetate and water were added, and the obtained organic layer was dried over anhydrous sodium sulfate and concentrated. The residue was purified by silica gel column chromatography (hexane:dichloromethane=90:10-80:20) to obtain the title compound (1000 mg).

$^1$H NMR (CDCl$_3$, 400 MHz): δ (ppm) 8.25 (s, 1H), 7.43-7.49 (m, 2H), 4.44 (q, J=6.9 Hz, 2H), 1.44 (t, J=7.1 Hz, 3H)

Reference Example 15

Ethyl 4,7-diacetylbenzo[b]thiophene-2-carboxylate

[Formula 18]

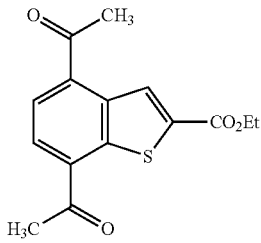

The title compound (700 mg) was obtained in the same way as in Reference Example 12 using the compound (1000 mg) obtained in Reference Example 14, dichlorobis(triphenylphosphine)palladium(II) (450 mg), toluene (50 mL), and (1-ethoxyvinyl)tributyltin (5.57 mL).

$^1$H NMR (CDCl$_3$, 400 MHz): δ (ppm) 8.91 (s, 1H), 8.17 (d, J=7.7 Hz, 1H), 8.03 (d, J=7.7 Hz, 1H), 4.44 (q, J=7.3 Hz, 2H), 2.82 (s, 3H), 2.78 (s, 3H), 1.41-1.47 (m, 3H)

MS (ESI$^+$) m/z: 291[M+H]$^+$

Reference Example 16

4,7-Diacetylbenzo[b]thiophene-2-carboxylic acid

[Formula 19]

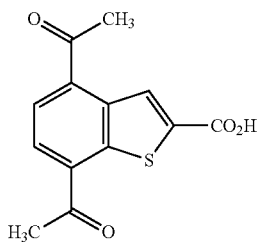

To a solution of the compound (700 mg) obtained in Reference Example 15 in methanol (50 mL), a 2 N aqueous sodium hydroxide solution (50 mL) was added, and the mixture was stirred at room temperature for 2 hours. The reaction mixture was rendered acidic by the addition of hydrochloric acid, followed by extraction with ethyl acetate. The organic layer was dried over anhydrous sodium sulfate and concentrated to obtain the title compound (250 mg).

Reference Example 17

1-Bromo-4-(dimethoxymethyl)-2-fluorobenzene

[Formula 20]

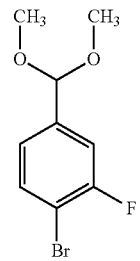

To a solution of 4-bromo-3-fluorobenzaldehyde (7.540 g) and trimethyl orthoformate (5.3 mL) in methanol (14 mL), concentrated sulfuric acid (41 μL) was added, and the mixture was stirred at 80° C. for 3.5 hours. To the reaction mixture, trimethyl orthoformate (2.3 mL) was added, and the mixture was stirred at 80° C. for 20 hours. The reaction mixture was cooled to 0° C. Sodium methoxide (28% solution in methanol, 840 μL) was added thereto, and the mixture was then concentrated. The residue was purified by basic silica gel column chromatography (hexane:ethyl acetate=1:0-12:1) to obtain the title compound (9.190 g).

$^1$H NMR (CDCl$_3$, 400 MHz): δ (ppm) 7.54 (dd, J=8.3, 7.1 Hz, 1H), 7.23-7.26 (m, 1H), 7.12 (dd, J=8.1, 2.0 Hz, 1H), 5.36 (s, 1H), 3.31 (s, 6H)

Reference Example 18

3-Bromo-6-(dimethoxymethyl)-2-fluorobenzaldehyde

[Formula 21]

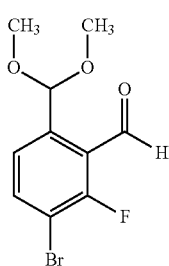

A solution of lithium diisopropylamide (1.1 M solution in THF/ethylbenzene/heptane, 96 mL) in THF (300 mL) was cooled to −78° C. A solution of the compound (25.0 g) obtained in Reference Example 17 in THF (100 mL) was added dropwise thereto under an argon atmosphere, and the mixture was stirred at −78° C. for 1 hour. To the reaction mixture, a solution of DMF (8.2 mL) in THF (20 mL) was added dropwise, and the mixture was stirred at the same temperature as above for 30 minutes. To the reaction mixture, acetic acid (20 mL) was added, and the temperature of the mixture was raised to 0° C. Then, water added thereto, followed by extraction with ethyl acetate. The organic layer was washed with a saturated aqueous solution of sodium bicarbonate and saturated aqueous sodium chloride in this order, dried over anhydrous magnesium sulfate, and concentrated. The residue was purified by silica gel column chromatography (hexane:ethyl acetate=100:0-70:30) to obtain the title compound (25.1 g).

¹H NMR (CDCl₃, 400 MHz): δ (ppm) 10.47 (s, 1H), 7.76 (dd, J=8.4, 6.7 Hz, 1H), 7.43-7.47 (m, 1H), 5.92 (s, 1H), 3.41 (s, 6H)

Reference Example 19

1-(3-Bromo-6-(dimethoxymethyl)-2-fluorophenyl) ethanol

[Formula 22]

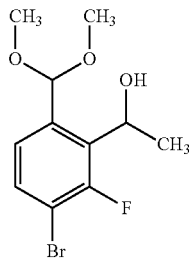

A solution of the compound (23.5 g) obtained in Reference Example 18 in THF (300 mL) was cooled to 0° C. under an argon stream. Methyl magnesium bromide (0.97 M solution in THF, 130 mL) was added dropwise thereto, and the mixture was stirred at the same temperature as above for 3 hours. To the reaction mixture, saturated aqueous sodium chloride (100 mL) was added, followed by extraction with ethyl acetate. The organic layer was washed with water and a saturated aqueous solution of sodium chloride in this order, then dried over anhydrous sodium sulfate, and concentrated. The residue was purified by silica gel column chromatography (hexane:ethyl acetate=100:0-70:30) to obtain the title compound (15.4 g).

¹H NMR (CDCl₃, 400 MHz): δ (ppm) 7.45 (dd, J=8.3, 6.8 Hz, 1H), 7.25-7.28 (m, 1H), 5.59 (s, 1H), 3.37 (s, 3H), 3.28 (s, 3H), 2.64 (dd, J=8.2, 3.9 Hz, 1H), 1.59 (dd, J=6.8, 1.5 Hz, 3H)

Reference Example 20

1-(3-Bromo-6-(dimethoxymethyl)-2-fluorophenyl) ethanone

[Formula 23]

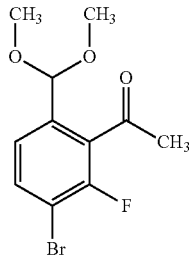

The title compound (13.2 g) was obtained in the same way as in Reference Example 2 using the compound (15.1 g) obtained in Reference Example 19, acetonitrile (300 mL), N-methylmorpholine-N-oxide (9.0 g), and tetrapropylammonium perruthenate (1.8 g).

¹H NMR (CDCl₃, 400 MHz): δ (ppm) 7.56 (dd, J=8.3, 7.0 Hz, 1H), 7.24-7.26 (m, 1H), 5.48 (s, 1H), 3.34 (s, 6H), 2.54 (d, J=1.8 Hz, 3H)

Reference Example 21

Ethyl 7-bromo-4-(dimethoxymethyl)-3-methylbenzo [b]thiophene-2-carboxylate

[Formula 24]

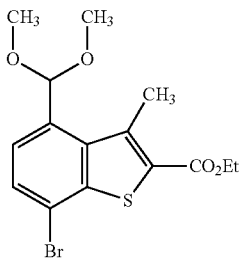

To a solution of the compound (12.1 g) obtained in Reference Example 20 in DMF (300 mL), ethyl thioglycolate (10.0 g) and potassium carbonate (22.8 g) were added, and the mixture was stirred at 85° C. for 8 hours. The reaction mixture was cooled to 0° C., and saturated aqueous sodium chloride (300 mL) was added thereto, followed by extraction with ethyl acetate. The organic layer was washed with water and saturated aqueous sodium chloride in this order, then dried over anhydrous sodium sulfate, and concentrated. The residue was purified by silica gel column chromatography (hexane:ethyl acetate=100:0-70:30) to obtain the title compound (6.97 g).

¹H NMR (CDCl₃, 400 MHz): δ (ppm) 7.63-7.66 (m, 1H), 7.58-7.61 (m, 1H), 6.07 (s, 1H), 4.40 (q, J=7.0 Hz, 2H), 3.35 (s, 6H), 3.04 (s, 3H), 1.42 (t, J=7.2 Hz, 3H)

Reference Example 22

Ethyl 7-bromo-4-formyl-3-methylbenzo[b]thiophene-2-carboxylate

[Formula 25]

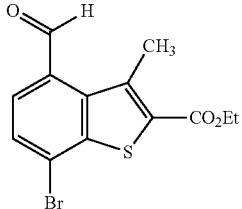

To a solution of the compound (1.61 g) obtained in Reference Example 21 in THF (30 mL) 1 N hydrochloric acid (30 mL) was added, and the mixture was stirred at room temperature for 2 hours. To the reaction mixture, water was added, followed by extraction with ethyl acetate. The organic layer was dried over anhydrous sodium sulfate and then concentrated to obtain the title compound (1.35 g).

MS (FAB⁺) m/z: 327 [M+H]⁺

Reference Example 23

Ethyl 7-bromo-4-(1-hydroxyethyl)-3-methylbenzo[b]thiophene-2-carboxylate

[Formula 26]

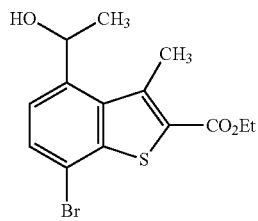

A solution of the compound (255 mg) obtained in Reference Example 22 in THF (30 mL) was cooled to −78° C. Methyl magnesium bromide (0.96 M solution in THF, 974 μL) was added dropwise thereto under a nitrogen atmosphere, and the mixture was stirred at the same temperature as above for 15 minutes and stirred at room temperature for 10 hours. To the reaction mixture, a saturated aqueous solution of ammonium chloride was added, followed by extraction with dichloromethane. The organic layer was dried over anhydrous sodium sulfate and concentrated. The residue was purified by basic silica gel column chromatography (hexane:ethyl acetate=80:20-10:90) to obtain the title compound (270 mg).

$^1$H NMR (CDCl$_3$, 400 MHz): δ (ppm) 7.58-7.63 (m, 2H), 5.87-5.94 (m, 1H), 4.40 (q, J=7.0 Hz, 2H), 3.01 (s, 3H), 1.90 (d, J=3.7 Hz, 1H), 1.59 (d, J=6.5 Hz, 3H), 1.41-1.45 (m, 3H)

Reference Example 24

7-Acetyl-4-(1-hydroxyethyl)-3-methylbenzo[b]thiophene-2-carboxylic acid

[Formula 27]

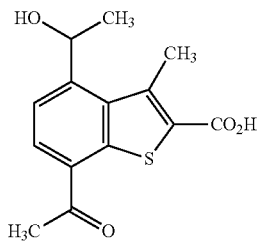

A solution of the compound (700 mg) obtained in Reference Example 23, dichlorobis(triphenylphosphine)palladium(II) (168 mg), and (1-ethoxyvinyl)tributyltin (2 mL) in toluene (100 mL) was stirred at 110° C. for 10 hours under a nitrogen atmosphere. The reaction mixture was cooled to room temperature. Then, 2 N hydrochloric acid was added thereto, and the mixture was stirred for 1 hour. To the reaction mixture, water was added, followed by extraction with ethyl acetate. The organic layer was dried over anhydrous sodium sulfate and concentrated. The residue was purified by silica gel column chromatography (hexane:ethyl acetate=70:30-0:100) and basic silica gel column chromatography (ethyl acetate) in this order to obtain ethyl 7-acetyl-4-(1-hydroxyethyl)-3-methylbenzo[b]thiophene-2-carboxylate.

To a solution of ethyl 7-acetyl-4-(1-hydroxyethyl)-3-methylbenzo[b]thiophene-2-carboxylate thus obtained in methanol (20 mL), a 2 N aqueous sodium hydroxide solution (20 mL) was added, and the mixture was stirred at room temperature for 3 hours. The reaction mixture was rendered acidic by the addition of hydrochloric acid, followed by extraction with ethyl acetate. The organic layer was dried over anhydrous sodium sulfate and then concentrated to obtain the title compound (450 mg).

Reference Example 25

Ethyl 7-bromo-4-(1-hydroxypropyl)-3-methylbenzo[b]thiophene-2-carboxylate

[Formula 28]

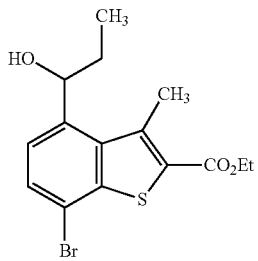

The title compound (380 mg) was obtained in the same way as in Reference Example 23 using the compound (700 mg) obtained in Reference Example 22, THF (100 mL), and ethyl magnesium bromide (1 M solution in THF, 2.8 mL).

$^1$H NMR (CDCl$_3$, 400 MHz): δ (ppm) 7.54-7.64 (m, 2H), 5.62-5.69 (m, 1H), 4.40 (q, J=7.3 Hz, 2H), 2.99 (s, 3H), 1.84-1.95 (m, 2H), 1.71-1.80 (m, 1H), 1.42 (t, J=7.1 Hz, 3H), 1.08 (t, J=7.3 Hz, 3H)

Reference Example 26

Ethyl 7-acetyl-4-(1-hydroxypropyl)-3-methylbenzo[b]thiophene-2-carboxylate

[Formula 29]

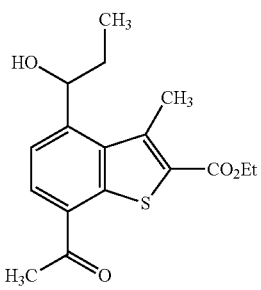

A solution of the compound (380 mg) obtained in Reference Example 25, dichlorobis(triphenylphosphine)palladium(II) (100 mg), and (1-ethoxyvinyl)tributyltin (1.2 mL) in toluene (30 mL) was stirred at 110° C. for 10 hours under a nitrogen atmosphere. The reaction mixture was cooled to room temperature. Then, 2 N hydrochloric acid was added thereto, and the mixture was stirred for 2 hours. To the reaction mixture, water was added, followed by extraction with ethyl acetate. The organic layer was dried over anhydrous sodium sulfate and concentrated. The residue was purified by basic silica gel column chromatography (hexane:ethyl acetate=80:20-20:80) and silica gel column chromatography (hexane:ethyl acetate=80:20-40:60) in this order to obtain the title compound (260 mg).

Reference Example 27

Ethyl 7-acetyl-3-methyl-4-propionylbenzo[b]thiophene-2-carboxylate

[Formula 30]

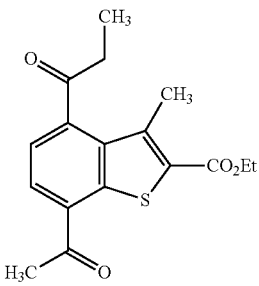

The title compound (120 mg) was obtained in the same way as in Reference Example 2 using the compound (130 mg) obtained in Reference Example 26, acetonitrile (25 mL), N-methylmorpholine-N-oxide (71 mg), and tetrapropylammonium perruthenate (15 mg).

$^1$H NMR (CDCl$_3$, 400 MHz): δ (ppm) 8.10 (d, J=7.7 Hz, 1H), 7.35 (d, J=7.7 Hz, 1H), 4.41 (q, J=7.3 Hz, 2H), 2.98 (q, J=7.3 Hz, 2H), 2.78 (s, 3H), 2.64 (s, 3H), 1.43 (t, J=7.1 Hz, 3H), 1.30 (t, J=7.3 Hz, 3H)

Reference Example 28

7-Acetyl-3-methyl-4-propionylbenzo[b]thiophene-2-carboxylic acid

[Formula 31]

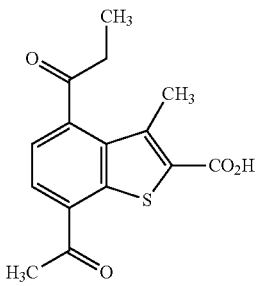

To a solution of the compound (120 mg) obtained in Reference Example 27 in methanol (10 mL), a 2 N aqueous sodium hydroxide solution (10 mL) was added, and the mixture was stirred at room temperature for 1 hour. The reaction mixture was rendered acidic by the addition of hydrochloric acid, followed by extraction with ethyl acetate. The organic layer was dried over anhydrous sodium sulfate and then concentrated to obtain the title compound.

Reference Example 29

4-Methoxyquinolin-2-amine

[Formula 32]

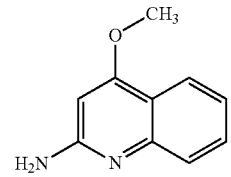

A suspension of 2-aminoquinolin-4-ol (500 mg), methyl iodide (214 μL), and potassium carbonate (648 mg) in DMF (20 mL) was stirred at room temperature for 24 hours. The reaction mixture was concentrated, and the residue was purified by basic silica gel column chromatography (dichloromethane:methanol=100:0-85:15) to obtain the title compound (160 mg).

$^1$H NMR (CDCl$_3$, 400 MHz): δ (ppm) 7.98 (dd, J=8.3, 1.4 Hz, 1H), 7.60-7.64 (m, 1H), 7.53-7.59 (m, 1H), 7.22-7.28 (m, 1H), 6.12 (s, 1H), 5.27 (br. s., 2H), 4.00 (s, 3H)

Reference Example 30

N-Benzyl-2-(benzylamino)quinoline-4-carboxamide

[Formula 33]

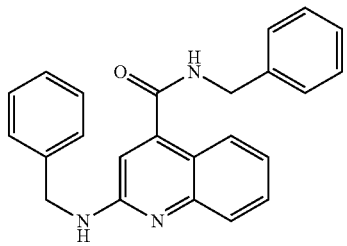

A mixture of methyl 2-chloroquinoline-4-carboxylate (20.000 g) and benzylamine (48.247 g) was stirred at 135° C. for 2.5 hours. The reaction mixture was cooled to 70° C. Chloroform (100 mL) was added thereto, and the mixture was cooled to room temperature. Water (100 mL) was added thereto, and the mixture was then cooled to 0° C. The precipitated solid was collected by filtration and washed with a hexane-chloroform (1:1) mixed solution and water in this order to obtain the title compound (21.253 g).

Reference Example 31

Methyl 2-aminoquinoline-4-carboxylate

[Formula 34]

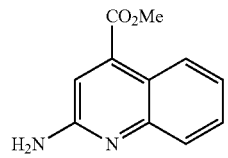

To the compound (178.400 g) obtained in Reference Example 30, 47% hydrobromic acid (1020 mL) and acetic acid (1020 mL) were added, and the mixture was stirred at 125° C. for 37.5 hours. The reaction mixture was concentrated. To the residue, water (580 mL) was added, and the mixture was cooled to 0° C. To the reaction mixture, a 4 N aqueous sodium hydroxide solution (650 mL), 6 N hydrochloric acid (10 mL), water (100 mL), and ethyl acetate (380 mL) were added, and the temperature of the mixture was raised to room temperature. The precipitated solid was collected by filtration and washed with water and ethyl acetate in this order. A solution of the obtained solid (115.15 g) in methanol (920 mL) was cooled to 0° C. Concentrated sulfuric acid (55.6 mL) was added thereto, and the mixture was stirred at 90° C. for 45 hours. The reaction mixture was cooled to room temperature and concentrated, and the residue was washed with methanol (100 mL). To the obtained solid, water (700 mL) and a saturated aqueous solution of sodium bicarbonate (475 mL) were added, and the precipitated solid was collected by filtration and washed with water to obtain the title compound (94.32 g).

$^1$H NMR (CDCl$_3$, 400 MHz): δ (ppm) 8.49 (dd, J=8.5, 0.8 Hz, 1H), 7.72 (dd, J=8.5, 0.8 Hz, 1H), 7.58-7.65 (m, 1H), 7.33-7.40 (m, 1H), 7.28 (s, 1H), 5.00 (br. s., 2H), 4.02 (s, 3H)

Reference Example 32

Methyl 2-((tert-butoxycarbonyl)amino)quinoline-4-carboxylate

[Formula 35]

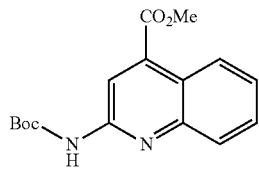

To a solution of the compound (20.0 g) obtained in Reference Example 31 in DMF (100 mL), a solution of di-tert-butyl dicarbonate (138 mL) in dichloromethane (100 mL) was added, and the mixture was cooled to 0° C.

To the reaction mixture, triethylamine (55.1 mL) was added dropwise, and the mixture was stirred at room temperature for 7 hours. The reaction mixture was concentrated, and the residue was purified by silica gel column chromatography (hexane:ethyl acetate=1:0-5:1) to obtain the title compound (22.4 g).

$^1$H NMR (CDCl$_3$, 400 MHz): δ (ppm) 8.70 (s, 1H), 8.62 (dd, J=8.5, 1.2 Hz, 1H), 7.84 (dd, J=8.5, 0.8 Hz, 1H), 7.65-7.73 (m, 2H), 7.48-7.54 (m, 1H), 4.03 (s, 3H), 1.55 (s, 9H)

Reference Example 33

2-((tert-Butoxycarbonyl)amino)quinoline-4-carboxylic acid

[Formula 36]

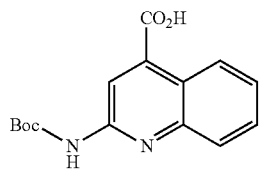

A mixture of the compound (1 g) obtained in Reference Example 32, a 1 N aqueous sodium hydroxide solution (9.9 mL), and ethanol (9.9 mL) was stirred at room temperature for 2 hours. To the reaction mixture, 1 N hydrochloric acid (9.9 mL) was added, and the precipitated solid was collected by filtration and dried to obtain the title compound (965 mg).

$^1$H NMR (DMSO, 400 MHz): δ (ppm) 10.33 (s, 1H), 8.57 (d, J=7.7 Hz, 1H), 8.53 (s, 1H), 7.81-7.85 (m, 1H), 7.73 (ddd, J=8.3, 6.9, 1.4 Hz, 1H), 7.54 (ddd, J=8.3, 6.9, 1.4 Hz, 1H), 1.50 (s, 9H)

Reference Example 34 tert-Butyl(4-(methoxy(methyl)carbamoyl)quinolin-2-yl)carbamate

[Formula 37]

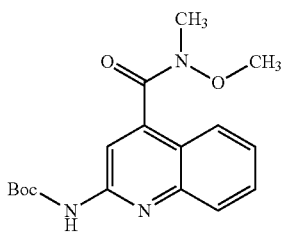

A mixture of the compound (200 mg) obtained in Reference Example 33, N,O-dimethylhydroxylamine hydrochloride (74 mg), 1-ethyl-3-(3-dimethylaminopropyl)carbodiimide hydrochloride (146 mg), 1-hydroxy-7-azabenzotriazole (103 mg), N,N-diisopropylethylamine (98 mg), and DMF (3 mL) was stirred at room temperature for 2 hours. To the reaction mixture, water was added, followed by extraction with ethyl acetate. The organic layer was dried over anhydrous sodium sulfate and concentrated. The residue was purified by basic silica gel column chromatography (hexane:ethyl acetate=3:1-2:1) to obtain the title compound (202 mg).

$^1$H NMR (CDCl$_3$, 400 MHz): δ (ppm) 8.26 (s, 1H), 7.82 (d, J=8.5 Hz, 1H), 7.76 (d, J=8.1 Hz, 1H), 7.63-7.70 (m, 1H), 7.61 (s, 1H), 7.41-7.48 (m, 1H), 3.48 (s, 3H), 2.96 (s, 3H), 1.54 (s, 9H)

Reference Example 35 tert-Butyl(4-acetylquinolin-2-yl)carbamate

[Formula 38]

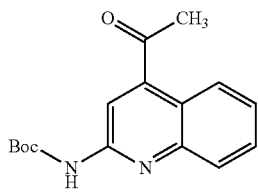

A solution of the compound (202 mg) obtained in Reference Example 34 in THF (2.5 mL) was cooled to −78° C. Methyl magnesium bromide (1 M solution in THF, 730 μL) was added dropwise thereto, and the mixture was stirred at the same temperature as above for 2 hours and then stirred overnight at room temperature. The reaction mixture was cooled to 0° C. Methyl magnesium bromide (1 M solution in THF, 6 mL) was added dropwise thereto, and the mixture was stirred. The reaction mixture was poured into ice water, and a saturated aqueous solution of ammonium chloride was added to the mixture, followed by extraction with dichloromethane. The organic layer was dried over anhydrous sodium sulfate and concentrated. The residue was purified by basic silica gel column chromatography (hexane:ethyl acetate=3:1) to obtain the title compound (144 mg).

$^1$H NMR (CDCl$_3$, 400 MHz): δ (ppm) 8.53 (s, 1H), 8.31-8.35 (m, 1H), 7.80-7.84 (m, 1H), 7.67 (ddd, J=8.4, 7.0, 1.2 Hz, 1H), 7.56 (br. s., 1H), 7.48 (ddd, J=8.4, 6.8, 1.4 Hz, 1H), 2.77 (s, 3H), 1.56 (s, 9H)

Reference Example 36

1-(2-Aminoquinolin-4-yl)ethanone

[Formula 39]

A mixture of the compound (634 mg) obtained in Reference Example 35, dichloromethane (1 mL), and TFA (1 mL) was stirred overnight at room temperature. The reaction mixture was concentrated, and the residue was purified by basic silica gel column chromatography (dichloromethane:methanol=100:0-96:4) to obtain the title compound (302 mg).

$^1$H NMR (CDCl$_3$, 400 MHz): δ (ppm) 8.12 (dd, J=8.1, 1.2 Hz, 1H), 7.71 (dd, J=8.5, 0.8 Hz, 1H), 7.57-7.63 (m, 1H), 7.33 (ddd, J=8.3, 6.9, 1.4 Hz, 1H), 6.92 (s, 1H), 4.85 (br. s., 2H), 2.69 (s, 3H)

Reference Example 37

1-(2-Aminoquinolin-4-yl)ethanol

[Formula 40]

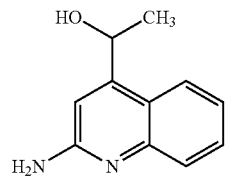

A mixture of the compound (302 mg) obtained in Reference Example 36, methanol (8.6 mL), and sodium borohydride (92 mg) was stirred at room temperature. The reaction mixture was concentrated, and the residue was purified by basic silica gel column chromatography (dichloromethane:methanol=99:1-95:5) to obtain the title compound (281 mg).

$^1$H NMR (CDCl$_3$, 400 MHz): δ (ppm) 7.76 (dd, J=8.1, 1.2 Hz, 1H), 7.68 (dd, J=8.5, 0.8 Hz, 1H), 7.52-7.57 (m, 1H), 7.23-7.29 (m, 1H), 6.93 (s, 1H), 5.52 (q, J=6.4 Hz, 1H), 4.75 (br. s., 2H), 3.49 (s, 1H), 1.61 (d, J=6.5 Hz, 3H)

Reference Example 38 tert-Butyl(4-(hydroxymethyl)quinolin-2-yl)carbamate

[Formula 41]

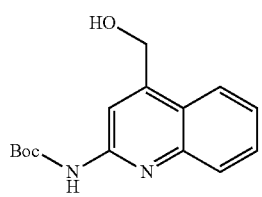

A mixture of the compound (500 mg) obtained in Reference Example 32, ethanol (30 mL), and sodium borohydride (180 mg) was stirred at 80° C. for 6 hours. The reaction mixture was concentrated, and the residue was purified by basic silica gel column chromatography (hexane:ethyl acetate=100:0-50:50) to obtain the title compound (320 mg).

MS (ESI$^+$) m/z: 275 [M+H]$^+$

Reference Example 39

(2-Aminoquinolin-4-yl)methanol

[Formula 42]

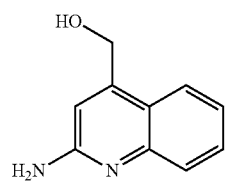

A mixture of the compound (320 mg) obtained in Reference Example 38, dichloromethane (5 mL), and TFA (5 mL) was stirred at room temperature for 2 hours. The reaction mixture was concentrated, and the residue was purified by basic silica gel column chromatography (dichloromethane:methanol=100:0-90:10) to obtain the title compound (62 mg).

MS (ESI$^+$) m/z: 175 [M+H]$^+$

Reference Example 40

N-((2-Aminoquinolin-4-yl)methyl)-N-methylacetamide

[Formula 43]

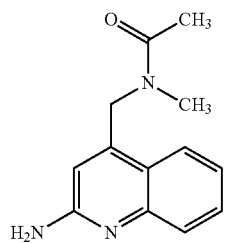

A mixture of the compound (600 mg) obtained in Reference Example 38, 1,2-dichloroethane (10 mL), triethylamine (365 μL), and methanesulfonyl chloride (203 μL) was stirred at room temperature for 2 hours. To the reaction mixture, a saturated aqueous solution of sodium bicarbonate was added, followed by extraction with dichloromethane. The organic layer was dried over anhydrous sodium sulfate and concentrated. To the residue, methylamine (2 M solution in THF, 20 mL) was added, and the mixture was stirred at room temperature for 2 hours. Then, the reaction mixture was concentrated. To the residue, THF (10 mL), triethylamine (446 μL), and acetyl chloride (220 μL) were added, and the mixture was stirred at room temperature for 10 minutes. To the reaction mixture, a saturated aqueous solution of sodium bicarbonate was added, followed by extraction with dichloromethane. The organic layer was dried over anhydrous sodium sulfate and concentrated. To the residue, dichloromethane (5 mL) and TFA (5 mL) were added, and the mixture was stirred at room temperature for 20 hours. The reaction mixture was concentrated, and the residue was purified by basic silica gel column chromatography (dichloromethane:methanol=100:0-92:8) to obtain the title compound (320 mg).

MS (ESI$^+$) m/z: 230 [M+H]$^+$

Reference Example 41

2-Fluoro-3-iodobenzaldehyde

[Formula 44]

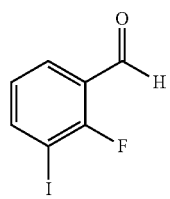

A solution of N,N-diisopropylamine (14.2 mL) in THF (180 mL) was cooled to 0° C. n-Butyllithium (1.59 M solution in hexane, 75.5 mL) was added thereto, and the mixture was stirred for 10 minutes. The reaction mixture was cooled to −78° C. 1-Fluoro-2-iodobenzene (11.77 mL) was added dropwise thereto, and the mixture was stirred for 1 hour. To the reaction mixture, DMF (20.4 mL) was added, and the mixture was stirred for 5 minutes. Then, acetic acid (9 mL) and water were added thereto in this order, followed by extraction with ethyl acetate. The organic layer was dried over anhydrous sodium sulfate and concentrated. The residue was purified by silica gel column chromatography (hexane:ethyl acetate=100:0-80:20) to obtain the title compound (10.7 g).

Reference Example 42

1-(2-Fluoro-3-iodophenyl)ethanol

[Formula 45]

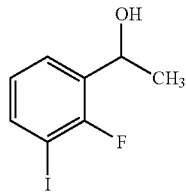

The title compound (10.0 g) was obtained in the same way as in Reference Example 1 using the compound (10.6 g) obtained in Reference Example 41, THF (70 mL), and methyl magnesium bromide (0.9 M solution in THF, 71 mL).

$^1$H NMR (CDCl$_3$, 400 MHz): δ (ppm) 7.65 (ddd, J=7.7, 6.1, 1.6 Hz, 1H), 7.45-7.50 (m, 1H), 6.92 (t, J=7.7 Hz, 1H), 5.15-5.23 (m, 1H), 1.50 (d, J=6.5 Hz, 3H)

Reference Example 43

1-(2-Fluoro-3-iodophenyl)ethanone

[Formula 46]

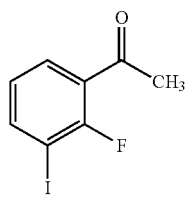

The title compound (4.26 g) was obtained in the same way as in Reference Example 2 using the compound (5.00 g) obtained in Reference Example 42, acetonitrile (100 mL), N-methylmorpholine-N-oxide (3.30 g), and tetrapropylammonium perruthenate (661 mg).

$^1$H NMR (CDCl$_3$, 400 MHz): δ (ppm) 7.93 (ddd, J=7.7, 5.9, 1.8 Hz, 1H), 7.79-7.84 (m, 1H), 7.00 (t, J=7.7 Hz, 1H), 2.65 (d, J=4.9 Hz, 3H)

MS (ESI$^+$) m/z: 265 [M+H]$^+$

Reference Example 44

Ethyl 7-iodo-3-methylbenzo[b]thiophene-2-carboxylate

[Formula 47]

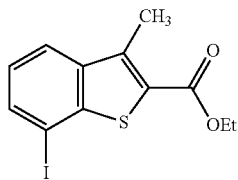

To a suspension of the compound (2.90 g) obtained in Reference Example 43 and potassium carbonate (4.56 g) in acetonitrile (20 mL), ethyl thioglycolate (1.81 mL) was added, and the mixture was stirred at 80° C. for 4 hours. To the reaction mixture, water was added, followed by extraction with ethyl acetate. The organic layer was dried over anhydrous sodium sulfate and concentrated. The residue was purified by silica gel column chromatography (hexane:ethyl acetate=100:0-80:20) to obtain the title compound (2.70 g).

$^1$H NMR (CDCl$_3$, 400 MHz): δ (ppm) 7.79-7.84 (m, 2H), 7.12-7.17 (m, 1H), 4.40 (q, J=6.9 Hz, 2H), 2.73 (s, 3H), 1.43 (t, J=7.1 Hz, 3H)

MS (ESI$^+$) m/z: 347 [M+H]$^+$

Reference Example 45

Ethyl 3-methyl-7-propionylbenzo[b]thiophene-2-carboxylate

[Formula 48]

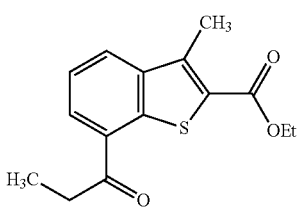

A mixture of the compound (346 mg) obtained in Reference Example 44, propionic anhydride (386 μL), tris(dibenzylideneacetone)dipalladium(0) (23 mg), N,N-diisopropylethylamine (344 μL), lithium chloride (297 mg), and DMF (6 mL) was stirred at 140° C. for 3.5 hours under a nitrogen atmosphere. The reaction mixture was cooled to room temperature, and water was added thereto, followed by extraction with ethyl acetate. The organic layer was dried over anhydrous sodium sulfate and concentrated. The residue was purified by silica gel column chromatography (hexane:ethyl acetate=100:0-80:20) to obtain the title compound (75 mg).

$^1$H NMR (CDCl$_3$, 400 MHz): δ (ppm) 8.14-8.17 (m, 1H), 8.06-8.09 (m, 1H), 7.52-7.57 (m, 1H), 4.40 (q, J=7.0 Hz, 2H), 3.18 (q, J=7.3 Hz, 2H), 2.80 (s, 3H), 1.42 (t, J=7.1 Hz, 3H), 1.32 (t, J=7.3 Hz, 3H)

MS (ESI$^+$) m/z: 277 [M+H]$^+$

Reference Example 46

3-Methyl-7-propionylbenzo[b]thiophene-2-carboxylic acid

[Formula 49]

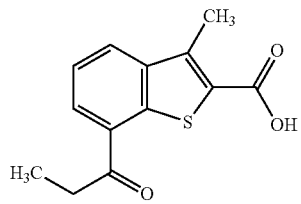

A mixture of the compound (70 mg) obtained in Reference Example 45, THF (4 mL), methanol (4 mL), and a 2 N aqueous sodium hydroxide solution (4 mL) was stirred at room temperature for 60 hours. To the reaction mixture, 6 N hydrochloric acid was added, followed by extraction with ethyl acetate. The organic layer was dried over anhydrous sodium sulfate and concentrated to obtain the title compound (80 mg).

$^1$H NMR (DMSO, 400 MHz): δ (ppm) 8.39 (dd, J=7.4, 0.9 Hz, 1H), 8.27 (dd, J=8.0, 1.0 Hz, 1H), 7.66-7.71 (m, 1H), 3.24 (q, J=7.3 Hz, 2H), 2.75 (s, 3H), 1.17 (t, J=7.2 Hz, 3H)

MS (ESI$^+$) m/z: 249 [M+H]$^+$

Reference Example 47

Ethyl 7-butyryl-3-methylbenzo[b]thiophene-2-carboxylate

[Formula 50]

A solution of the compound (346 mg) obtained in Reference Example 44 in THF (4 mL) was cooled to −78° C. Isopropyl magnesium chloride (2.0 M solution in THF, 0.7 mL) was added thereto, and the mixture was stirred for 30 minutes. To the reaction mixture, copper(I) iodide (229 mg) and lithium chloride (102 mg) were added, and the mixture was stirred for 20 minutes. Then, butyryl chloride (345 μL) was added thereto, and the mixture was stirred at room temperature for 2 hours. To the reaction mixture, a saturated aqueous solution of ammonium chloride was added, followed by extraction with ethyl acetate. The organic layer was dried over anhydrous sodium sulfate and concentrated. The residue was purified by silica gel column chromatography (hexane:ethyl acetate=100:0-80:20) to obtain the title compound (166 mg).

$^1$H NMR (CDCl$_3$, 400 MHz): δ (ppm) 8.14-8.18 (m, 1H), 8.06-8.10 (m, 1H), 7.53-7.58 (m, 1H), 4.40 (q, J=7.0 Hz, 2H), 3.12 (t, J=7.3 Hz, 2H), 2.81 (s, 3H), 1.82-1.92 (m, 2H), 1.40-1.45 (m, 3H), 1.05 (t, J=7.5 Hz, 3H)

MS (ESI+) m/z: 291 [M+H]+

Reference Example 48

7-Butyryl-3-methylbenzo[b]thiophene-2-carboxylic acid

[Formula 51]

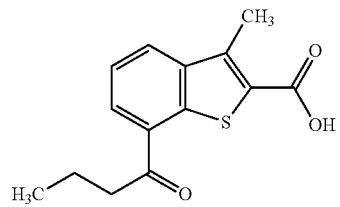

A mixture of the compound (150 mg) obtained in Reference Example 47, a methanol-THF (1:1) mixed solution (5 mL), and a 2 N aqueous sodium hydroxide solution (5 mL) was stirred at room temperature for 2.5 days. To the reaction mixture, 6 N hydrochloric acid was added, followed by extraction with dichloromethane. The organic layer was dried over anhydrous sodium sulfate and concentrated to obtain the title compound (132 mg).

$^1$H NMR (DMSO, 400 MHz): δ (ppm) 13.36 (br. s., 1H), 8.40 (dd, J=7.5, 1.0 Hz, 1H), 8.27 (dd, J=8.0, 1.0 Hz, 1H), 7.65-7.70 (m, 1H), 3.18 (t, J=7.3 Hz, 2H), 2.74 (s, 3H), 1.67-1.77 (m, 2H), 0.97 (t, J=7.4 Hz, 3H)

MS (ESI+) m/z: 263 [M+H]+

Reference Example 49

Ethyl 7-isobutyryl-3-methylbenzo[b]thiophene-2-carboxylate

[Formula 52]

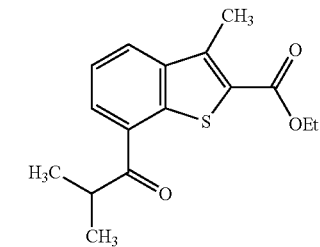

The title compound (137 mg) was obtained in the same way as in Reference Example 47 using the compound (346 mg) obtained in Reference Example 44, THF (4 mL), isopropyl magnesium chloride (2.0 M solution in THF, 0.7 mL), copper(I) iodide (229 mg), lithium chloride (102 mg), and isobutyryl chloride (346 μL).

$^1$H NMR (CDCl$_3$, 400 MHz): δ (ppm) 8.16-8.19 (m, 1H), 8.07-8.10 (m, 1H), 7.54-7.59 (m, 1H), 4.40 (q, J=7.3 Hz, 2H), 3.70-3.82 (m, 1H), 2.81 (s, 3H), 1.42 (t, J=7.1 Hz, 3H), 1.31 (d, J=6.9 Hz, 6H)

MS (ESI+) m/z: 291 [M+H]+

Reference Example 50

7-Isobutyryl-3-methylbenzo[b]thiophene-2-carboxylic acid

[Formula 53]

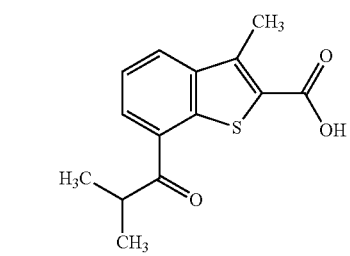

A mixture of the compound (125 mg) obtained in Reference Example 49, a methanol-THF (1:1) mixed solution (5 mL), and a 2 N aqueous sodium hydroxide solution (5 mL) was stirred at room temperature for 20 hours. To the reaction mixture, 6 N hydrochloric acid was added, followed by extraction with dichloromethane. The organic layer was dried over anhydrous sodium sulfate and concentrated to obtain the title compound (120 mg).

Reference Example 51

Ethyl 7-(cyclopropylcarbonyl)-3-methylbenzo[b]thiophene-2-carboxylate

[Formula 54]

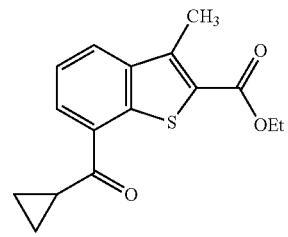

The title compound (130 mg) was obtained in the same way as in Reference Example 47 using the compound (346 mg) obtained in Reference Example 44, THF (4 mL), isopropyl magnesium chloride (2.0 M solution in THF, 0.7 mL), copper(I) iodide (229 mg), lithium chloride (102 mg), and cyclopropanecarbonyl chloride (299 μL).

$^1$H NMR (CDCl$_3$, 400 MHz): δ (ppm) 8.33-8.36 (m, 1H), 8.08-8.11 (m, 1H), 7.57-7.62 (m, 1H), 4.39 (q, J=7.3 Hz, 2H), 2.82-2.89 (m, 1H), 1.41 (t, J=7.2 Hz, 3H), 1.35-1.39 (m, 2H), 1.10-1.15 (m, 2H)

MS (ESI+) m/z: 289 [M+H]+

Reference Example 52

7-(Cyclopropylcarbonyl)-3-methylbenzo[b]thiophene-2-carboxylic acid

[Formula 55]

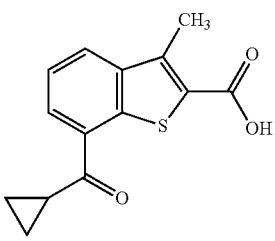

A mixture of the compound (120 mg) obtained in Reference Example 51, a methanol-THF (1:1) mixed solution (5 mL), and a 2 N aqueous sodium hydroxide solution (5 mL) was stirred at room temperature for 15 hours. To the reaction mixture, 6 N hydrochloric acid was added, followed by extraction with dichloromethane. The organic layer was dried over anhydrous sodium sulfate and concentrated to obtain the title compound (108 mg).

Reference Example 53

Ethyl 3-methyl-7-pentanoylbenzo[b]thiophene-2-carboxylate

[Formula 56]

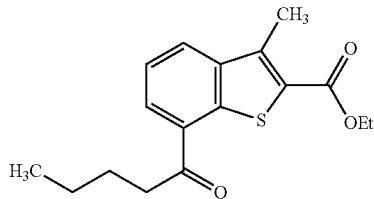

The title compound (265 mg) was obtained in the same way as in Reference Example 47 using the compound (346 mg) obtained in Reference Example 44, THF (4 mL), isopropyl magnesium chloride (2.0 M solution in THF, 0.7 mL), copper(I) iodide (229 mg), lithium chloride (102 mg), and valeryl chloride (392 µL).

$^1$H NMR (CDCl$_3$, 400 MHz): δ (ppm) 8.15-8.18 (m, 1H), 8.07-8.10 (m, 1H), 7.53-7.58 (m, 1H), 4.40 (q, J=7.3 Hz, 2H), 3.14 (t, J=7.3 Hz, 2H), 2.81 (s, 3H), 1.77-1.87 (m, 2H), 1.40-1.51 (m, 5H), 0.98 (t, J=7.3 Hz, 3H)

MS (ESI$^+$) m/z: 305 [M+H]$^+$

Reference Example 54

3-Methyl-7-pentanoylbenzo[b]thiophene-2-carboxylic acid

[Formula 57]

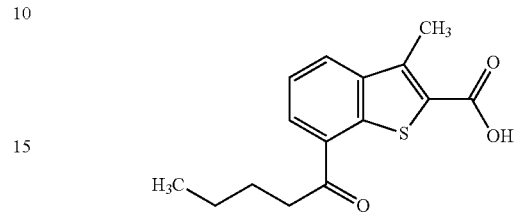

The title compound (222 mg) was obtained in the same way as in Reference Example 52 using the compound (120 mg) obtained in Reference Example 53, a methanol-THF (1:1) mixed solution (5 mL), and a 2 N aqueous sodium hydroxide solution (5 mL).

$^1$H NMR (DMSO, 400 MHz): δ (ppm) 13.32 (br. s., 1H), 8.40 (dd, J=7.5, 0.8 Hz, 1H), 8.26 (dd, J=8.0, 1.0 Hz, 1H), 7.65-7.70 (m, 1H), 3.20 (t, J=7.4 Hz, 2H), 2.74 (s, 3H), 1.63-1.72 (m, 2H), 1.33-1.44 (m, 2H), 0.93 (t, J=7.4 Hz, 3H)

MS (ESI$^+$) m/z: 277 [M+H]$^+$

Reference Example 55

Ethyl 7-(cyclobutylcarbonyl)-3-methylbenzo[b]thiophene-2-carboxylate

[Formula 58]

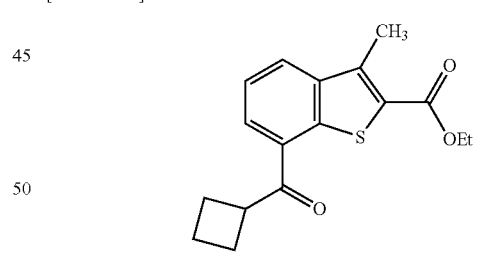

The title compound (300 mg) was obtained in the same way as in Reference Example 47 using the compound (346 mg) obtained in Reference Example 44, THF (4 mL), isopropyl magnesium chloride (2.0 M solution in THF, 0.7 mL), copper(I) iodide (229 mg), lithium chloride (102 mg), and cyclobutanecarbonyl chloride (377 µL).

$^1$H NMR (MeOD, 400 MHz): δ (ppm) 8.02-8.05 (m, 1H), 7.95-7.98 (m, 1H), 7.48-7.53 (m, 1H), 4.40 (q, J=7.2 Hz, 2H), 4.11-4.21 (m, 1H), 2.79 (s, 3H), 2.47-2.58 (m, 2H), 2.31-2.42 (m, 2H), 2.07-2.20 (m, 1H), 1.91-2.02 (m, 1H), 1.43 (t, J=7.1 Hz, 3H)

MS (ESI$^+$) m/z: 303 [M+H]$^+$

Reference Example 56

7-(Cyclobutylcarbonyl)-3-methylbenzo[b]thiophene-2-carboxylic acid

[Formula 59]

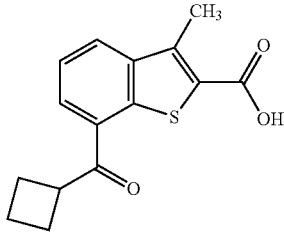

The title compound (320 mg) was obtained in the same way as in Reference Example 52 using the compound (390 mg) obtained in Reference Example 55, a methanol-THF (1:1) mixed solution (5 mL), and a 2 N aqueous sodium hydroxide solution (5 mL).

$^1$H NMR (DMSO, 400 MHz): δ (ppm) 13.35 (br. s., 1H), 8.26 (dd, J=8.0, 1.0 Hz, 1H), 8.20 (dd, J=7.5, 0.8 Hz, 1H), 7.63-7.68 (m, 1H), 4.29-4.38 (m, 1H), 2.74 (s, 3H), 2.29-2.38 (m, 4H), 2.02-2.15 (m, 1H), 1.79-1.89 (m, 1H)

MS (ESI$^+$) m/z: 275 [M+H]$^+$

Reference Example 57

Ethyl 3-methyl-7-pivaloylbenzo[b]thiophene-2-carboxylate

[Formula 60]

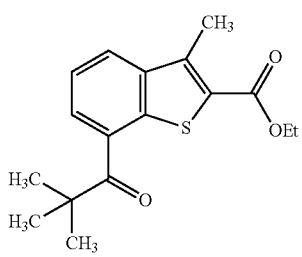

lp;1p

The title compound (166 mg) was obtained in the same way as in Reference Example 47 using the compound (346 mg) obtained in Reference Example 44, THF (4 mL), isopropyl magnesium chloride (2.0 M solution in THF, 0.7 mL), copper(I) iodide (229 mg), lithium chloride (102 mg), and pivaloyl chloride (406 μL).

$^1$H NMR (CDCl$_3$, 400 MHz): δ(ppm) 8.28-8.32 (m, 1H), 8.02-8.05 (m, 1H), 7.49-7.54 (m, 1H), 4.39 (q, J=7.3 Hz, 2H), 2.80 (s, 3H), 1.51 (s, 9H), 1.42 (t, J=7.1 Hz, 3H)

MS (ESI$^+$) m/z: 305 [M+H]$^+$

Reference Example 58

3-Methyl-7-pivaloylbenzo[b]thiophene-2-carboxylic acid

[Formula 61]

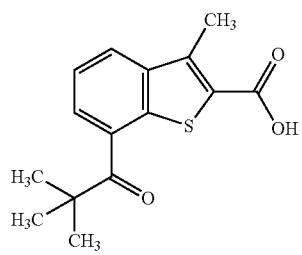

A mixture of the compound (160 mg) obtained in Reference Example 57, a methanol-THF (1:1) mixed solution (5 mL), and a 2 N aqueous sodium hydroxide solution (5 mL) was stirred at room temperature for 36 hours. To the reaction mixture, 6 N hydrochloric acid was added, followed by extraction with dichloromethane. The organic layer was dried over anhydrous sodium sulfate and concentrated to obtain the title compound (144 mg).

$^1$H NMR (DMSO, 400 MHz): δ (ppm) 13.34 (br. s., 1H), 8.47 (dd, J=7.7, 0.9 Hz, 1H), 8.22 (dd, J=8.0, 1.0 Hz, 1H), 7.62-7.67 (m, 1H), 2.74 (s, 3H), 1.43 (s, 9H)

MS (ESI$^+$) m/z: 277 [M+H]$^+$

Reference Example 59

Ethyl 3-methyl-7-(3-methylbutanoyl)benzo[b]thiophene-2-carboxylate

[Formula 62]

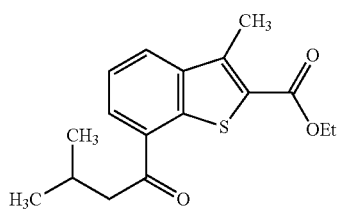

The title compound (188 mg) was obtained in the same way as in Reference Example 47 using the compound (346 mg) obtained in Reference Example 44, THF (4 mL), isopropyl magnesium chloride (2.0 M solution in THF, 0.7 mL), copper(I) iodide (229 mg), lithium chloride (102 mg), and isovaleryl chloride (402 μL).

$^1$H NMR (CDCl$_3$, 400 MHz): δ(ppm) 8.13-8.16 (m, 1H), 8.07-8.10 (m, 1H), 7.53-7.58 (m, 1H), 4.40 (q, J=7.3 Hz, 2H), 3.00 (d, J=6.9 Hz, 2H), 2.81 (s, 3H), 2.35-2.46 (m, 1H), 1.43 (t, J=7.1 Hz, 3H), 1.04 (d, J=6.9 Hz, 6H)

MS (ESI$^+$) m/z: 305 [M+H]$^+$

Reference Example 60

3-Methyl-7-(3-methylbutanoyl)benzo[b]thiophene-2-carboxylic acid

[Formula 63]

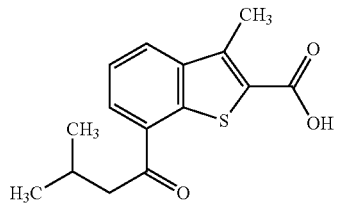

A mixture of the compound (180 mg) obtained in Reference Example 59, a methanol-THF (1:1) mixed solution (5 mL), and a 2 N aqueous sodium hydroxide solution (5 mL) was stirred at room temperature for 36 hours. To the reaction mixture, 6 N hydrochloric acid was added, followed by extraction with dichloromethane. The organic layer was dried over anhydrous sodium sulfate and concentrated to obtain the title compound (166 mg).

$^1$H NMR (DMSO, 400 MHz): δ (ppm) 13.36 (br. s., 1H), 8.40 (dd, J=7.5, 0.8 Hz, 1H), 8.27 (dd, J=8.0, 1.0 Hz, 1H), 7.65-7.70 (m, 1H), 3.07 (d, J=7.0 Hz, 2H), 2.74 (s, 3H), 2.18-2.29 (m, 1H), 0.97 (d, J=6.8 Hz, 6H)

MS (ESI$^+$) m/z: 277 [M+H]$^+$

Reference Example 61

Ethyl 7-(2-ethylbutanoyl)-3-methylbenzo[b]thiophene-2-carboxylate

[Formula 64]

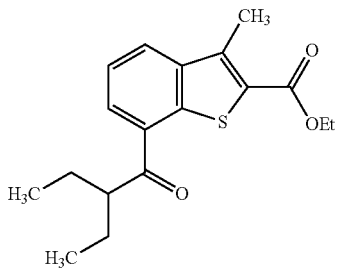

The title compound (271 mg) was obtained in the same way as in Reference Example 47 using the compound (346 mg) obtained in Reference Example 44, THF (4 mL), isopropyl magnesium chloride (2.0 M solution in THF, 0.7 mL), copper(I) iodide (229 mg), lithium chloride (102 mg), and 2-ethylbutyryl chloride (452 μL).

$^1$H NMR (CDCl$_3$, 400 MHz): δ (ppm) 8.16-8.20 (m, 1H), 8.08-8.12 (m, 1H), 7.55-7.60 (m, 1H), 4.40 (q, J=7.0 Hz, 2H), 3.43-3.53 (m, 1H), 2.82 (s, 3H), 1.83-1.95 (m, 2H), 1.60-1.72 (m, 2H), 1.42 (t, J=7.5 Hz, 3H), 0.89 (t, J=7.5 Hz, 6H)

MS (ESI$^+$) m/z: 319 [M+H]$^+$

Reference Example 62

7-(2-Ethylbutanoyl)-3-methylbenzo[b]thiophene-2-carboxylic acid

[Formula 65]

A mixture of the compound (250 mg) obtained in Reference Example 61, a methanol-THF (1:1) mixed solution (5 mL), and a 2 N aqueous sodium hydroxide solution (5 mL) was stirred at room temperature for 36 hours. To the reaction mixture, 6 N hydrochloric acid was added, followed by extraction with dichloromethane. The organic layer was dried over anhydrous sodium sulfate and concentrated to obtain the title compound (215 mg).

$^1$H NMR (DMSO, 400 MHz): δ (ppm) 13.36 (br. s., 1H), 8.46 (d, J=7.0 Hz, 1H), 8.29 (dd, J=7.9, 0.9 Hz, 1H), 7.68-7.72 (m, 1H), 3.63-3.71 (m, 1H), 2.75 (s, 3H), 1.68-1.80 (m, 2H), 1.51-1.62 (m, 2H), 0.81 (t, J=7.4 Hz, 6H)

MS (ESI$^+$) m/z: 291 [M+H]$^+$

Reference Example 63

Ethyl 7-(cyclopentylcarbonyl)-3-methylbenzo[b]thiophene-2-carboxylate

[Formula 66]

The title compound (180 mg) was obtained in the same way as in Reference Example 47 using the compound (346 mg) obtained in Reference Example 44, THF (4 mL), isopropyl magnesium chloride (2.0 M solution in THF, 0.7 mL), copper(I) iodide (229 mg), lithium chloride (102 mg), and cyclopentanecarbonyl chloride (401 μL).

$^1$H NMR (CDCl$_3$, 400 MHz): δ(ppm) 8.17-8.20 (m, 1H), 8.06-8.09 (m, 1H), 7.54-7.59 (m, 1H), 4.39 (q, J=7.3 Hz, 2H), 3.86-3.95 (m, 1H), 2.81 (s, 3H), 1.98-2.06 (m, 4H), 1.65-1.85 (m, 4H), 1.42 (t, J=7.1 Hz, 3H)

MS (ESI$^+$) m/z: 317 [M+H]$^+$

Reference Example 64

7-(Cyclopentylcarbonyl)-3-methylbenzo[b]thiophene-2-carboxylic acid

[Formula 67]

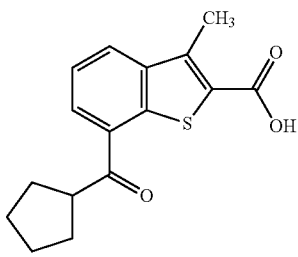

The title compound (155 mg) was obtained in the same way as in Reference Example 62 using the compound (170 mg) obtained in Reference Example 63, a methanol-THF (1:1) mixed solution (5 mL), and a 2 N aqueous sodium hydroxide solution (5 mL).

$^1$H NMR (DMSO, 400 MHz): δ (ppm) 13.35 (br. s., 1H), 8.43 (d, J=7.0 Hz, 1H), 8.27 (dd, J=8.0, 1.0 Hz, 1H), 7.66-7.71 (m, 1H), 4.00-4.09 (m, 1H), 2.75 (s, 3H), 1.93-2.03 (m, 2H), 1.76-1.87 (m, 2H), 1.62-1.70 (m, 4H)

MS (ESI$^+$) m/z: 289 [M+H]$^+$

Reference Example 65

(4-Bromo-3-fluorophenyl)methanol

[Formula 68]

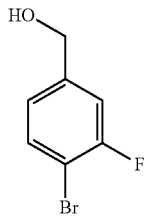

A solution of 4-bromo-3-fluorobenzoic acid (39.422 g) in THF (240 mL) was cooled to 0° C. under a nitrogen atmosphere. A borane-tetrahydrofuran complex (0.9 M solution in THF, 400 mL) was added dropwise thereto, and the mixture was stirred for 2 hours and then stirred at room temperature for 20 hours. The reaction mixture was cooled to 0° C., and water (40 mL) was added dropwise thereto. The reaction mixture was concentrated, and water (200 mL), ethyl acetate (100 mL), and a saturated aqueous solution of sodium bicarbonate (100 mL) were added to the residue in this order, followed by extraction with ethyl acetate. The organic layer was washed with an aqueous sodium bicarbonate solution and saturated aqueous sodium chloride in this order, dried over anhydrous magnesium sulfate, and then concentrated to obtain the title compound (36.71 g).

$^1$H NMR (CDCl$_3$, 400 MHz): δ (ppm) 7.53 (dd, J=8.1, 7.3 Hz, 1H), 7.14-7.19 (m, 1H), 7.00-7.06 (m, 1H), 4.68 (d, J=5.7 Hz, 2H), 1.75 (t, J=5.9 Hz, 1H)

Reference Example 66

4-Bromo-3-fluorobenzyl methanesulfonate

[Formula 69]

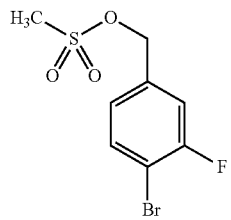

A solution of the compound (30.0 g) obtained in Reference Example 65 and triethylamine (22.4 mL) in dichloromethane (300 mL) was cooled to 0° C. Methanesulfonyl chloride (12.5 mL) was added dropwise thereto, and the mixture was stirred at the same temperature as above for 1.5 hours. The reaction mixture was washed with a mixed solution of a saturated aqueous solution of sodium bicarbonate and water (1:3) (300 mL) and saturated aqueous sodium chloride (300 mL), dried over anhydrous sodium sulfate, and then concentrated to obtain the title compound (40.7 g).

$^1$H NMR (CDCl$_3$, 400 MHz): δ (ppm) 7.57-7.62 (m, 1H), 7.18-7.22 (m, 1H), 7.07-7.11 (m, 1H), 5.18 (s, 2H), 3.00 (s, 3H)

Reference Example 67

1-Bromo-2-fluoro-4-(methoxymethyl)benzene

[Formula 70]

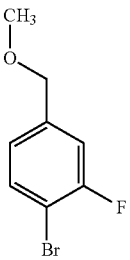

To a solution of the compound (40.7 g) obtained in Reference Example 66 in methanol (150 mL), sodium methoxide (5.0 M solution in methanol, 150 mL) was added dropwise, and the mixture was stirred at room temperature for 1 hour. To the reaction mixture, a saturated aqueous solution of ammonium chloride (150 mL) and water (150 mL) were added, followed by extraction with dichloromethane. The organic layer was washed with saturated aqueous sodium chloride, dried over anhydrous sodium sulfate, and then concentrated to obtain the title compound (31.0 g).

$^1$H NMR (CDCl$_3$, 400 MHz): δ (ppm) 7.48-7.53 (m, 1H), 7.10-7.14 (m, 1H), 6.97-7.01 (m, 1H), 4.41 (s, 2H), 3.39 (s, 3H)

Reference Example 68

3-Bromo-2-fluoro-6-(methoxymethyl)benzaldehyde

[Formula 71]

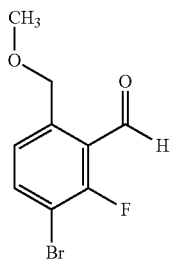

A solution of 2,2,6,6-tetramethylpiperidine (232.70 g) in THF (2543 mL) was cooled to −72° C. under an argon stream. n-Butyllithium (1.5 M solution in hexane, 925 mL) was added dropwise thereto, and the mixture was stirred at the same temperature as above for 1 hour. To the reaction mixture, a solution of the compound (305.15 g) obtained in Reference Example 67 in THF (1272 mL) was added dropwise, and the mixture was stirred at the same temperature as above for 1 hour. To the reaction mixture, a solution of DMF (117.6 mL) in THF (255 mL) was added dropwise, and the mixture was stirred at the same temperature as above for 1 hour. To the reaction mixture, acetic acid (255 mL) was added, and the temperature of the mixture was raised to room temperature. Water (3360 mL) was added thereto, followed by extraction with ethyl acetate (1850 mL). The organic layer was washed with a saturated aqueous solution of sodium bicarbonate (1540 mL) and saturated aqueous sodium chloride (1540 mL) in this order, then dried over anhydrous magnesium sulfate, and concentrated. To the residue, hexane (2000 mL) was added, and the mixture was stirred at room temperature for 16 hours and then cooled to 0° C., followed by collection by filtration. The obtained solid was washed with hexane (100 mL) to obtain the title compound (231.4 g).

$^1$H NMR (CDCl$_3$, 400 MHz): δ (ppm) 10.48 (d, J=0.8 Hz, 1H), 7.78 (dd, J=8.3, 7.0 Hz, 1H), 7.42-7.47 (m, 1H), 4.79 (s, 2H), 3.49 (s, 3H)

Reference Example 69

1-(3-Bromo-2-fluoro-6-(methoxymethyl)phenyl)ethanol

[Formula 72]

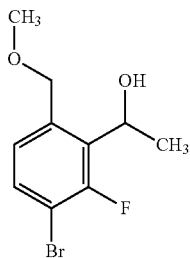

A solution of methyl magnesium bromide (a mixture of a 0.99 M solution in THF (3500 mL) and a 1.12 M solution in THF (800 mL)) in THF (1100 mL) was cooled to 0° C. under a nitrogen stream. A solution of the compound (652.99 g) obtained in Reference Example 68 in THF (4570 mL) was added dropwise thereto, and the mixture was stirred at 10° C. for 1.5 hours. To the reaction mixture, a saturated aqueous solution of ammonium chloride (3450 mL) was added dropwise, and water (3450 mL) was added, followed by extraction with ethyl acetate (6900 mL). The organic layer was washed with a water-saturated aqueous sodium chloride (1:1) mixed solution (4400 mL), dried over anhydrous magnesium sulfate, and then concentrated to obtain the title compound (703.00 g).

$^1$H NMR (CDCl$_3$, 400 MHz): δ (ppm) 7.42 (dd, J=8.3, 6.8 Hz, 1H), 6.99 (dd, J=8.2, 1.1 Hz, 1H), 5.19-5.28 (m, 1H), 4.49-4.63 (m, 2H), 3.39 (s, 3H), 2.92 (dd, J=7.8, 3.0 Hz, 1H), 1.58-1.61 (m, 3H)

Reference Example 70

1-(3-Bromo-2-fluoro-6-(methoxymethyl)phenyl)ethanone

[Formula 73]

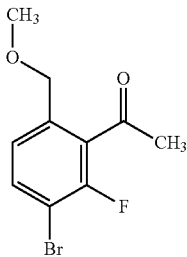

To a solution of the compound (800 g) obtained in Reference Example 69 in dichloromethane (8000 mL), 2-azaadamantane-n-oxyl (0.463 g) was added, then a mixture of potassium bromide (36.18 g), tetrabutylammonium bromide (49.01 g), and a saturated aqueous solution of sodium bicarbonate (4165 mL) was added, and the mixture was cooled to 0° C. and stirred. To the reaction mixture, a mixture of an aqueous sodium hypochlorite solution (manufactured by Nacalai Tesque, Inc., 8.5 to 13.5% available chlorine, 2880 mL) and a saturated aqueous solution of sodium bicarbonate (4000 mL) was added dropwise, and the mixture was stirred at the same temperature as above for 2 hours. To the reaction mixture, hexane (8800 mL) was added, and the temperature of the mixture was raised to room temperature. The organic layer was washed with a mixture of sodium thiosulfate (239 g), water (2280 mL), and saturated aqueous sodium chloride (2280 mL), then washed with water and saturated aqueous sodium chloride in this order, and concentrated to obtain the title compound (783 g).

$^1$H NMR (CDCl$_3$, 400 MHz): δ (ppm) 7.56 (dd, J=8.2, 6.9 Hz, 1H), 7.11 (dd, J=8.3, 1.0 Hz, 1H), 4.43 (s, 2H), 3.35 (s, 3H), 2.57 (d, J=2.8 Hz, 3H)

Reference Example 71

Ethyl 7-bromo-4-(methoxymethyl)-3-methylbenzo[b]thiophene-2-carboxylate

[Formula 74]

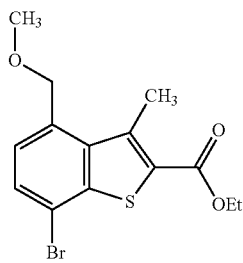

To a solution of the compound (1000 g) obtained in Reference Example 70 in DMF (11.00 L), 1,8-diazabicyclo[5.4.0]-7-undecene (1720 mL) was added, and the mixture was cooled to 10° C. To the reaction mixture, a solution of ethyl thioglycolate (440 mL) in DMF (390 mL) was added dropwise, and the mixture was stirred at room temperature for 22 hours. The reaction mixture was cooled to 0° C. Water (11.72 L) was added dropwise thereto, and the precipitated solid was collected by filtration, then washed with water, and dried to obtain the title compound (1103 g).

$^1$H NMR (CDCl$_3$, 400 MHz): δ (ppm) 7.55 (d, J=7.8 Hz, 1H), 7.26 (d, J=7.8 Hz, 1H), 4.82 (s, 2H), 4.40 (q, J=7.0 Hz, 2H), 3.45 (s, 3H), 3.01 (s, 3H), 1.42 (t, J=7.2 Hz, 3H)

Reference Example 72

Ethyl 4-(methoxymethyl)-3-methyl-7-((trimethylsilyl)ethynyl)benzo[b]thiophene-2-carboxylate

[Formula 75]

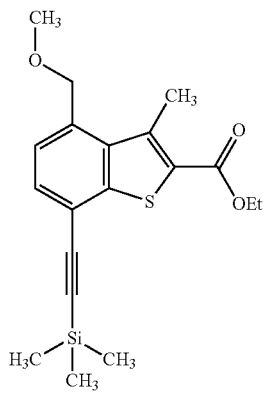

A mixture of the compound (100.00 g) obtained in Reference Example 71, copper(I) iodide (1.110 g), dichlorobis(triphenylphosphine)palladium(II) (4.090 g), trimethylsilylacetylene (66.7 mL), and triethylamine (1000 mL) was stirred at 70° C. for 29.5 hours under an argon atmosphere. The reaction mixture was cooled to room temperature and concentrated. The residue was purified by silica gel column chromatography (hexane:chloroform=1:1). To the obtained solid, ethanol (525 mL) was added, and the mixture was heated to 75° C. and then cooled to 0° C. The precipitated solid was collected by filtration and washed with ethanol to obtain the title compound (97.60 g).

$^1$H NMR (CDCl$_3$, 400 MHz): δ (ppm) 7.50 (d, J=7.5 Hz, 1H), 7.33 (d, J=7.5 Hz, 1H), 4.85 (s, 2H), 4.41 (q, J=7.1 Hz, 2H), 3.44 (s, 3H), 3.01 (s, 3H), 1.43 (t, J=7.2 Hz, 3H), 0.32 (s, 9H)

Reference Example 73

Ethyl 7-acetyl-4-(methoxymethyl)-3-methylbenzo[b]thiophene-2-carboxylate

[Formula 76]

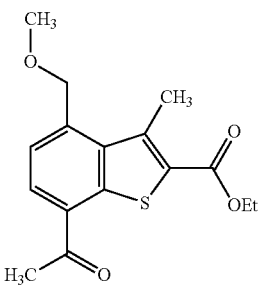

A mixture of the compound (25.00 g) obtained in Reference Example 72, p-toluenesulfonic acid monohydrate (32.97 g), and acetic acid (250 mL) was stirred at 65° C. for 6 hours. The reaction mixture was cooled to room temperature. Water (250 mL) was added dropwise thereto, and the mixture was then cooled to 0° C. The precipitated solid was collected by filtration and washed with a water-ethanol (1:2) mixed solution. The obtained solid was purified by silica gel column chromatography (chloroform). To the obtained solid, toluene (102 mL) was added, and the mixture was heated to 75° C. and then cooled to 0° C. The precipitated solid was collected by filtration and washed with a hexane-toluene (1:1) mixed solution to obtain the title compound (18.01 g).

$^1$H NMR (CDCl$_3$, 400 MHz): δ (ppm) 8.07 (d, J=7.5 Hz, 1H), 7.58 (d, J=7.5 Hz, 1H), 4.99 (s, 2H), 4.40 (q, J=7.0 Hz, 2H), 3.51 (s, 3H), 3.03 (s, 3H), 2.75 (s, 3H), 1.43 (t, J=7.2 Hz, 3H)

Reference Example 74

7-Acetyl-4-(methoxymethyl)-3-methylbenzo[b]thiophene-2-carboxylic acid

[Formula 77]

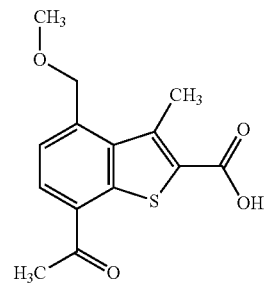

A mixture of the compound (18.01 g) obtained in Reference Example 73, a 4 N aqueous sodium hydroxide solution (29.4 mL), and ethanol (201 mL) was stirred at 60° C. for 3 hours. The reaction mixture was cooled to room temperature. Water (96.7 mL) and 2 N hydrochloric acid (64.7 mL) were added thereto, and the mixture was cooled to 0° C. The precipitated solid was collected by filtration and washed with an ethanol-water (2:1) mixed solution to obtain the title compound (16.037 g).

$^1$H NMR (DMSO, 400 MHz): δ (ppm) 13.36 (br. s., 1H), 8.31 (d, J=7.8 Hz, 1H), 7.65 (d, J=7.8 Hz, 1H), 5.00 (s, 2H), 3.40 (s, 3H), 2.96 (s, 3H), 2.74 (s, 3H)

MS (ESI$^+$) m/z: 279 [M+H]$^+$

Reference Example 75

Ethyl 7-acetyl-4-(dimethoxymethyl)-3-methylbenzo[b]thiophene-2-carboxylate

[Formula 78]

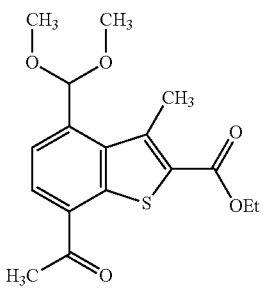

A solution of the compound (11.680 g) obtained in Reference Example 21, dichlorobis(triphenylphosphine)palladium(II) (1.779 g), and (1-ethoxyvinyl)tributyltin (31.1 mL) in toluene (350 mL) was stirred at 100° C. for 18 hours under an argon atmosphere. The reaction mixture was cooled to room temperature. Then, 2 N hydrochloric acid (175 mL) was added thereto, and the mixture was stirred for 8 hours. The reaction mixture was filtered through Hyflo Super Cel (manufactured by Nacalai Tesque, Inc.). The Hyflo Super Cel was washed with toluene (150 mL), and the organic layer was obtained from the filtrate. The obtained organic layer was washed with water, a saturated aqueous solution of sodium bicarbonate, and saturated aqueous sodium chloride in this order, dried over anhydrous magnesium sulfate, and concentrated. The residue was purified by basic silica gel column chromatography (hexane:ethyl acetate=1:0 to 4:1) to obtain a solid containing the title compound. To the obtained solid, hexane (300 mL) was added, and the mixture was heated to 70° C. and then cooled to 0° C. The precipitated solid was collected by filtration. The obtained solid was washed with hexane to obtain the title compound (7.787 g).

$^1$H NMR (CDCl$_3$, 400 MHz): δ (ppm) 8.11 (d, J=8.1 Hz, 1H), 7.91 (d, J=7.7 Hz, 1H), 6.20 (s, 1H), 4.41 (q, J=7.3 Hz, 2H), 3.38 (s, 6H), 3.08 (s, 3H), 2.77 (s, 3H), 1.43 (t, J=7.3 Hz, 3H)

Reference Example 76

Ethyl 7-acetyl-4-formyl-3-methylbenzo[b]thiophene-2-carboxylate

[Formula 79]

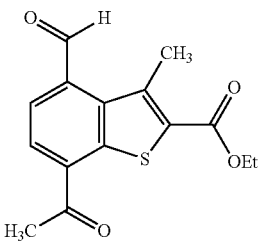

To a solution of the compound (4.0 g) obtained in Reference Example 75 in THF (60 mL), 2 N hydrochloric acid (30 mL) was added, and the mixture was stirred at room temperature for 3 hours. To the reaction mixture, water was added, followed by extraction with dichloromethane. The organic layer was dried over anhydrous sodium sulfate and concentrated to obtain the title compound (3.5 g).

$^1$H NMR (CDCl$_3$, 400 MHz): δ (ppm) 11.05 (s, 1H), 8.18 (d, J=7.8 Hz, 1H), 8.05 (d, J=7.8 Hz, 1H), 4.44 (q, J=7.0 Hz, 2H), 3.05 (s, 3H), 2.81 (s, 3H), 1.45 (t, J=7.2 Hz, 3H)

Reference Example 77

Ethyl 7-acetyl-4-(hydroxymethyl)-3-methylbenzo[b]thiophene-2-carboxylate

[Formula 80]

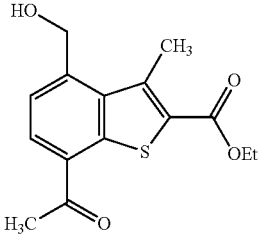

To a solution of the compound (3.0 g) obtained in Reference Example 76 in dichloromethane (100 mL), sodium triacetoxyborohydride (10.9 g) was added, then acetic acid (2.4 mL) was added, and the mixture was stirred at 40° C. for 4 days. To the reaction mixture, a saturated aqueous solution of ammonium chloride (70 mL) and water (70 mL) were added, followed by extraction with dichloromethane. The organic layer was dried over anhydrous sodium sulfate and concentrated to obtain the title compound (3.0 g).

$^1$H NMR (CDCl$_3$, 400 MHz): δ (ppm) 8.09 (d, J=7.5 Hz, 1H), 7.65 (d, J=7.5 Hz, 1H), 5.31 (d, J=5.8 Hz, 2H), 4.40 (q, J=7.0 Hz, 2H), 3.05 (s, 3H), 2.76 (s, 3H), 1.92 (t, J=5.8 Hz, 1H), 1.43 (t, J=7.2 Hz, 3H)

Reference Example 78

7-Acetyl-4-(ethoxymethyl)-3-methylbenzo[b]thiophene-2-carboxylic acid

[Formula 81]

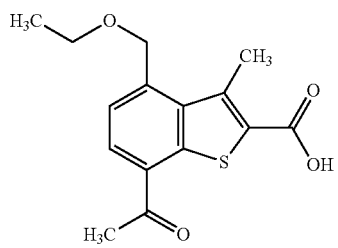

To a suspension of the compound (146 mg) obtained in Reference Example 77 in ethanol (10 mL), concentrated sulfuric acid (5 mL) was added dropwise at room temperature, and the mixture was stirred at 60° C. for 22 hours. To the reaction mixture, water was added, followed by extraction with dichloromethane. The organic layer was washed with saturated aqueous sodium chloride, dried over anhydrous sodium sulfate, and concentrated. The obtained residue was dissolved in a THF-methanol (2:1) mixed solution (7.5 mL). To the solution, a 4 N aqueous sodium hydroxide solution (2.5 mL) was added, and the mixture was stirred at room temperature for 4 hours.

The reaction mixture was rendered acidic by the addition of 6 N hydrochloric acid, followed by extraction with dichloromethane. The organic layer was dried over anhydrous sodium sulfate and concentrated to obtain the title compound.

MS (ESI$^+$) m/z: 293 [M+H]$^+$

Reference Example 79

7-Acetyl-3-methyl-4-(propoxymethyl)benzo[b]thiophene-2-carboxylic acid

[Formula 82]

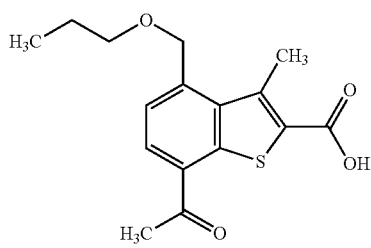

To a suspension of the compound (146 mg) obtained in Reference Example 77 in 1-propanol (10 mL), concentrated sulfuric acid (5 mL) was added dropwise at room temperature, and the mixture was stirred at 60° C. for 3 days. To the reaction mixture, water was added, followed by extraction with dichloromethane. The organic layer was washed with saturated aqueous sodium chloride, dried over anhydrous sodium sulfate, and concentrated. The obtained residue was dissolved in a THF-methanol (2:1) mixed solution (7.5 mL). To the solution, a 4 N aqueous sodium hydroxide solution (2.5 mL) was added, and the mixture was stirred at room temperature for 20 hours. The reaction mixture was rendered acidic by the addition of 6 N hydrochloric acid, followed by extraction with dichloromethane. The organic layer was dried over anhydrous sodium sulfate and concentrated to obtain the title compound.

MS (ESI$^+$) m/z: 307 [M+H]$^+$

Reference Example 80

7-Acetyl-4-(isopropoxymethyl)-3-methylbenzo[b]thiophene-2-carboxylic acid

[Formula 83]

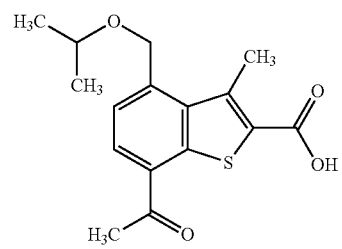

To a suspension of the compound (146 mg) obtained in Reference Example 77 in 2-propanol (10 mL), concentrated sulfuric acid (5 mL) was added dropwise at room temperature, and the mixture was stirred at 60° C. for 3 days. To the reaction mixture, water was added, followed by extraction with dichloromethane. The organic layer was washed with saturated aqueous sodium chloride, dried over anhydrous sodium sulfate, and concentrated. The obtained residue was dissolved in a THF-methanol (2:1) mixed solution (7.5 mL). To the solution, a 4 N aqueous sodium hydroxide solution (2.5 mL) was added, and the mixture was stirred at room temperature for 20 hours. The reaction mixture was rendered acidic by the addition of 6 N hydrochloric acid, followed by extraction with dichloromethane. The organic layer was dried over anhydrous sodium sulfate and concentrated to obtain the title compound.

MS (ESI$^+$) m/z: 307 [M+H]$^+$

Reference Example 81

Ethyl 7-acetyl-4-(1-hydroxyethyl)-3-methylbenzo[b]thiophene-2-carboxylate

[Formula 84]

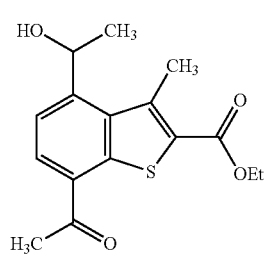

A solution of the compound (350 mg) obtained in Reference Example 76 in THF (20 mL) was cooled to −78° C. under a nitrogen atmosphere. Methyl magnesium bromide (0.96 M solution in THF, 2.5 mL) was added dropwise thereto, and the mixture was stirred at room temperature for 6 hours. To the reaction mixture, a saturated aqueous solution of ammonium chloride was added, followed by extraction with ethyl acetate. The organic layer was dried over anhydrous sodium sulfate and concentrated. The residue was purified by silica gel column chromatography (hexane:ethyl acetate=85:15-50:50) to obtain the title compound (230 mg).

$^1$H NMR (MeOD, 400 MHz): δ (ppm) 8.22 (d, J=8.1 Hz, 1H), 7.93 (d, J=7.7 Hz, 1H), 5.95-6.02 (m, 1H), 4.37-4.45 (m, 2H), 3.03 (s, 3H), 2.77 (s, 3H), 1.57 (d, J=5.7 Hz, 3H), 1.44 (t, J=7.1 Hz, 3H)

MS (ESI$^+$) m/z: 307 [M+H]$^+$

Reference Example 82

Ethyl 7-acetyl-4-(1-methoxyethyl)-3-methylbenzo[b]thiophene-2-carboxylate

[Formula 85]

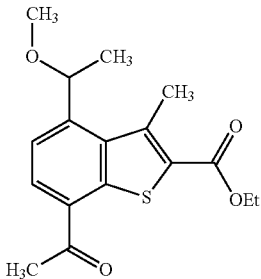

A mixture of the compound (90 mg) obtained in Reference Example 81, p-toluenesulfonic acid (14 mg), and methanol (25 mL) was stirred at 70° C. for 2 days. The reaction mixture was concentrated, and the residue was purified by silica gel column chromatography (hexane:ethyl acetate=90:10-60:40) to obtain the title compound (100 mg).

$^1$H NMR (CDCl$_3$, 400 MHz): δ (ppm) 8.14 (d, J=7.7 Hz, 1H), 7.79 (d, J=7.7 Hz, 1H), 5.42-5.52 (m, 1H), 4.41 (q, J=6.9 Hz, 2H), 3.31 (s, 3H), 3.28-3.36 (m, 3H), 3.03 (s, 3H), 2.76 (s, 3H), 1.54 (d, J=6.5 Hz, 3H), 1.38-1.47 (m, 3H)

Reference Example 83

7-Acetyl-4-(1-methoxyethyl)-3-methylbenzo[b]thiophene-2-carboxylic acid

[Formula 86]

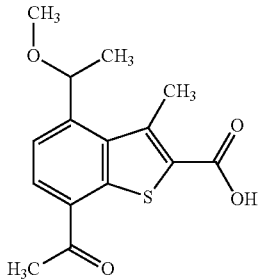

A mixture of the compound (100 mg) obtained in Reference Example 82, methanol (10 mL), and a 2 N aqueous sodium hydroxide solution (10 mL) was stirred at room temperature for 3 hours. The reaction mixture was rendered acidic by the addition of hydrochloric acid, followed by extraction with ethyl acetate. The organic layer was dried over anhydrous sodium sulfate and concentrated to obtain the title compound (60 mg).

MS (ESI$^+$) m/z: 293 [M+H]$^+$

Reference Example 84

(2-((tert-Butoxycarbonyl)amino)quinolin-4-yl)methyl methanesulfonate

[Formula 87]

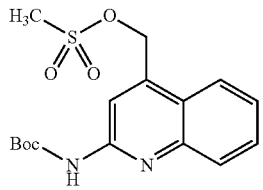

A solution of the compound (3.00 g) obtained in Reference Example 38 and triethylamine (1.68 mL) in dichloromethane (50 mL) was cooled to 0° C. Methanesulfonyl chloride (929 μL) was added thereto, and the mixture was stirred at the same temperature as above for 1 hour. To the reaction mixture, a mixed solution of a saturated aqueous solution of sodium bicarbonate and water (1:3) was added, followed by extraction with dichloromethane. The organic layer was dried over anhydrous sodium sulfate and concentrated to obtain the title compound (3.90 g).

MS (ESI$^+$) m/z: 353 [M+H]$^+$

Reference Example 85

2-(((2-Aminoquinolin-4-yl)methyl)(methyl)amino)ethanol

[Formula 88]

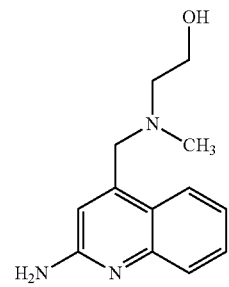

A mixture of the compound (2.71 g) obtained in Reference Example 84, 2-(methylamino)ethanol (693 mg), N,N-diisopropylethylamine (1.49 g), and DMF (8 mL) was stirred at room temperature for 1 hour. To the reaction mixture, water was added, followed by extraction with ethyl acetate. The organic layer was dried over anhydrous sodium sulfate and concentrated. The residue was dissolved in dichloromethane (4.86 mL). To the solution, TFA (4.86 mL) was added, and the mixture was stirred at room temperature for 17 hours. The reaction mixture was concentrated, and the residue was purified by basic silica gel column chromatography (dichloromethane:methanol=98:2 to 92:8) to obtain the title compound (1.29 g).

$^1$H NMR (CDCl$_3$, 400 MHz): δ (ppm) 7.91-7.95 (m, 1H), 7.68-7.72 (m, 1H), 7.54-7.59 (m, 1H), 7.27-7.32 (m, 1H), 6.79 (s, 1H), 5.00 (br. s., 2H), 3.89 (s, 2H), 3.65-3.70 (m, 2H), 2.68-2.73 (m, 2H), 2.32 (s, 3H)

Reference Example 86

1-((2-Aminoquinolin-4-yl)methyl) pyrrolidin-3-ol

[Formula 89]

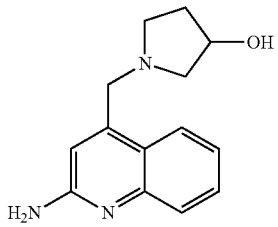

To a solution of the compound (700 mg) obtained in Reference Example 38 and triethylamine (426 μL) in 1,2-dichloroethane (15 mL), methanesulfonyl chloride (237 μL) was added, and the mixture was stirred at room temperature for 2 hours. To the reaction mixture, an aqueous sodium bicarbonate solution was added, followed by extraction with dichloromethane. The organic layer was dried over anhydrous sodium sulfate and concentrated. To the residue, THF (15 mL) and DL-3-pyrrolidinol (1 mL) were added, and the mixture was stirred for 24 hours. The reaction mixture was concentrated, and the residue was purified by silica gel column chromatography (dichloromethane:methanol=100:0-80:20) to obtain tert-butyl (4-((3-hydroxypyrrolidin-1-yl)methyl)quinolin-2-yl)carbamate. To the obtained compound, dichloromethane (10 mL) and TFA (6 mL) were added, and the mixture was stirred at room temperature for 1 hour. The reaction mixture was concentrated, and the residue was purified by silica gel column chromatography (dichloromethane:methanol=100:0-90:10) to obtain the title compound (500 mg).

MS (ESI$^+$) m/z: 244 [M+H]$^+$

Reference Example 87

1-((2-Aminoquinolin-4-yl)methyl)piperidin-4-ol

[Formula 90]

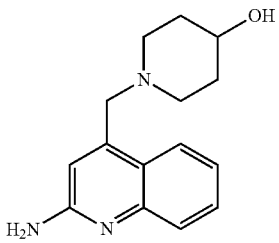

A mixture of the compound (282 mg) obtained in Reference Example 84, 4-hydroxypiperidine (243 mg), and THF (4 mL) was stirred at 50° C. for 3 hours. To the reaction mixture, water was added, followed by extraction with dichloromethane. The organic layer was dried over anhydrous sodium sulfate and concentrated. To the residue, dichloromethane (5 mL) and TFA (1 mL) were added, and the mixture was stirred at room temperature for 14 hours. To the reaction mixture, a 2 N aqueous sodium hydroxide solution was added, followed by extraction with dichloromethane. The organic layer was dried over anhydrous sodium sulfate and concentrated. The residue was purified by basic silica gel column chromatography (dichloromethane:methanol=100:0-90:10) to obtain the title compound (183 mg).

$^1$H NMR (CDCl$_3$, 400 MHz): δ (ppm) 7.96-8.00 (m, 1H), 7.66-7.69 (m, 1H), 7.53-7.58 (m, 1H), 7.27-7.29 (m, 1H), 7.24-7.26 (m, 1H), 6.82 (s, 1H), 4.74 (br. s., 2H), 3.81 (s, 2H), 3.72-3.80 (m, 1H), 2.79-2.88 (m, 2H), 2.23-2.32 (m, 2H), 1.88-1.96 (m, 2H), 1.58-1.68 (m, 2H)

MS (ESI$^+$) m/z: 258 [M+H]$^+$

Reference Example 88

1-((2-Aminoquinolin-4-yl)methyl)piperidin-3-ol

[Formula 91]

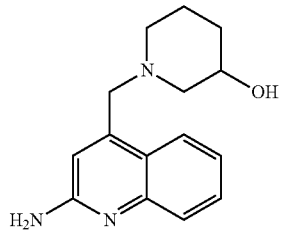

A mixture of the compound (282 mg) obtained in Reference Example 84, 3-hydroxypiperidine (243 mg), and THF (4 mL) was stirred at 50° C. for 5.5 hours. To the reaction mixture, water was added, followed by extraction with dichloromethane. The organic layer was dried over anhydrous sodium sulfate and concentrated. To the residue, dichloromethane (5 mL) and TFA (1 mL) were added, and the mixture was stirred at room temperature for 18 hours. To the reaction mixture, a 2 N aqueous sodium hydroxide solution was added, followed by extraction with dichloromethane. The organic layer was dried over anhydrous sodium sulfate and concentrated. The residue was purified by basic silica gel column chromatography (dichloromethane:methanol=100:0-85:15) to obtain the title compound (178 mg).

$^1$H NMR (CDCl$_3$, 400 MHz): δ (ppm) 7.94-7.97 (m, 1H), 7.66-7.69 (m, 1H), 7.53-7.58 (m, 1H), 7.25-7.29 (m, 1H), 6.75 (s, 1H), 4.73 (br. s., 2H), 3.78-3.89 (m, 3H), 2.27-2.71 (m, 5H), 1.48-1.92 (m, 3H)

MS (ESI$^+$) m/z: 258 [M+H]$^+$

Reference Example 89

(S)-1-((2-Aminoquinolin-4-yl)methyl)pyrrolidin-3-ol

[Formula 92]

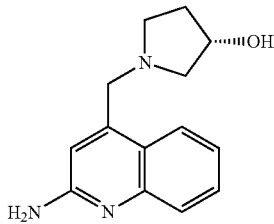

A mixture of the compound (160 mg) obtained in Reference Example 84, (S)-3-pyrrolidinol (110 μL), and THF (2 mL) was stirred at 50° C. for 6 hours. To the reaction mixture, water was added, followed by extraction with dichloromethane. The organic layer was dried over anhydrous sodium sulfate and concentrated. To the residue, dichloromethane (5 mL) and TFA (1 mL) were added, and the mixture was stirred at room temperature for 18 hours. To the reaction mixture, a 2 N aqueous sodium hydroxide solution was added, followed by extraction with dichloromethane. The organic layer was dried over anhydrous sodium sulfate and concentrated. The residue was purified by basic silica gel column chromatography (dichloromethane:methanol=100:0-90:10) to obtain the title compound (102 mg).

$^1$H NMR (CDCl$_3$, 400 MHz): δ (ppm) 7.94 (dd, J=8.5, 1.2 Hz, 1H), 7.68 (dd, J=8.7, 1.0 Hz, 1H), 7.52-7.58 (m, 1H), 7.25-7.29 (m, 1H), 6.81 (s, 1H), 4.75 (br. s., 2H), 4.35-4.41 (m, 1H), 3.96 (s, 2H), 2.94-3.02 (m, 1H), 2.76-2.83 (m, 1H), 2.58-2.65 (m, 1H), 2.37-2.46 (m, 1H), 2.17-2.28 (m, 1H), 1.75-1.85 (m, 1H)

MS (ESI$^+$) m/z: 244 [M+H]$^+$

Reference Example 90

(R)-1-((2-Aminoquinolin-4-yl)methyl)pyrrolidin-3-ol

[Formula 93]

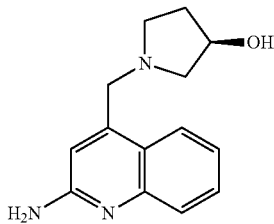

A mixture of the compound (160 mg) obtained in Reference Example 84, (R)-3-pyrrolidinol (110 μL), and THF (2 mL) was stirred at 50° C. for 7 hours. To the reaction mixture, water was added, followed by extraction with dichloromethane. The organic layer was dried over anhydrous sodium sulfate and concentrated. To the residue, dichloromethane (5 mL) and TFA (1 mL) were added, and the mixture was stirred at room temperature for 18 hours. To the reaction mixture, a 2 N aqueous sodium hydroxide solution was added, followed by extraction with dichloromethane. The organic layer was dried over anhydrous sodium sulfate and concentrated. The residue was purified by basic silica gel column chromatography (dichloromethane:methanol=100:0-90:10) to obtain the title compound (103 mg).

$^1$H NMR (CDCl$_3$, 400 MHz): δ (ppm) 7.94 (dd, J=8.3, 1.4 Hz, 1H), 7.68 (dd, J=8.5, 1.2 Hz, 1H), 7.53-7.58 (m, 1H), 7.25-7.30 (m, 1H), 6.81 (s, 1H), 4.74 (br. s., 2H), 4.35-4.42 (m, 1H), 3.97 (s, 2H), 2.94-3.02 (m, 1H), 2.77-2.82 (m, 1H), 2.59-2.66 (m, 1H), 2.37-2.45 (m, 1H), 2.17-2.29 (m, 1H), 1.76-1.84 (m, 1H)

MS (ESI$^+$) m/z: 244 [M+H]$^+$

Reference Example 91

1-(3-Bromo-2-fluoro-6-(methoxymethyl)phenyl)propan-1-ol

[Formula 94]

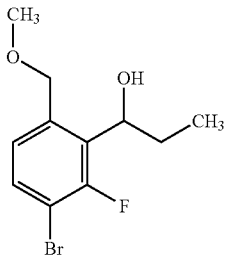

Ethyl magnesium bromide (1 M solution in THF, 76 mL) was cooled to 0° C. A solution of the compound (12.6 g) obtained in Reference Example 68 in THF (200 mL) was added dropwise thereto, and the mixture was stirred at room temperature for 3 hours. To the reaction mixture, a saturated aqueous solution of ammonium chloride and water were added, followed by extraction with ethyl acetate. The organic layer was washed with saturated aqueous sodium chloride, dried over anhydrous sodium sulfate, and concentrated. The residue was purified by silica gel column chromatography (hexane:ethyl acetate=50:1-1:1) to obtain the title compound (10.1 g).

$^1$H NMR (CDCl$_3$, 400 MHz): δ (ppm) 7.41 (dd, J=8.1, 6.9 Hz, 1H), 6.99-7.03 (m, 1H), 4.92 (dd, J=8.1, 6.1 Hz, 1H), 4.55-4.60 (m, 1H), 4.46-4.51 (m, 1H), 3.38 (s, 3H), 1.77-1.99 (m, 2H), 0.97 (t, J=7.5 Hz, 3H)

Reference Example 92

1-(3-Bromo-2-fluoro-6-(methoxymethyl)phenyl) propan-1-one

[Formula 95]

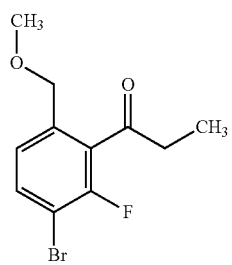

To a solution of the compound (10.1 g) obtained in Reference Example 91 in acetonitrile (100 mL), N-methyl-morpholine-N-oxide (6.40 g) and tetrapropylammonium perruthenate (1.281 g) were added, and the mixture was stirred at room temperature for 10 hours. To the reaction mixture, water was added, followed by extraction with ethyl acetate. The organic layer was dried over anhydrous sodium sulfate and concentrated. The residue was purified by silica gel column chromatography (hexane:ethyl acetate=100:0-3:1) to obtain the title compound (7.2 g).

$^1$H NMR (CDCl$_3$, 400 MHz): δ (ppm) 7.51-7.56 (m, 1H), 7.05-7.09 (m, 1H), 4.39 (s, 2H), 3.32-3.34 (m, 3H), 2.82-2.90 (m, 2H), 1.17-1.22 (m, 3H)

Reference Example 93

Ethyl 7-bromo-3-ethyl-4-(methoxymethyl)benzo[b] thiophene-2-carboxylate

[Formula 96]

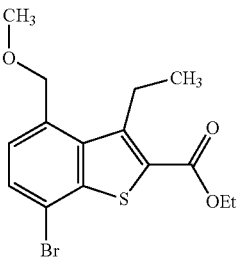

To a solution of the compound (7.2 g) obtained in Reference Example 92 in DMF (100 mL), 1,8-diazabicyclo [5.4.0]-7-undecene (11.83 mL) and ethyl thioglycolate (3.16 mL) were added, and the mixture was stirred at room temperature for 8 hours. To the reaction mixture, water was added, followed by extraction with ethyl acetate. The organic layer was dried over anhydrous sodium sulfate and concentrated. The residue was purified by silica gel column chromatography (hexane:ethyl acetate=100:0-80:20) to obtain the title compound (7.3 g).

$^1$H NMR (CDCl$_3$, 400 MHz): δ (ppm) 7.57 (d, J=7.7 Hz, 1H), 7.30 (d, J=7.7 Hz, 1H), 4.82 (s, 2H), 4.39-4.44 (m, 2H), 3.44 (s, 3H), 3.41-3.48 (m, 2H), 1.43 (t, J=7.1 Hz, 3H), 1.28-1.35 (m, 3H)

Reference Example 94

Ethyl 3-ethyl-4-(methoxymethyl)-7-((trimethylsilyl) ethynyl)benzo[b]thiophene-2-carboxylate

[Formula 97]

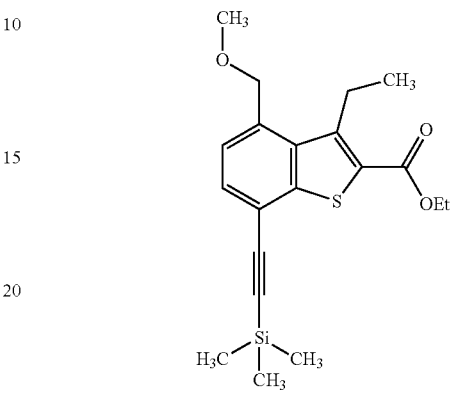

To a solution of the compound (4.33 g) obtained in Reference Example 93 in THF (100 mL), trimethylsilylacetylene (2.89 mL), tetrakis(triphenylphosphine)palladium(0) (0.420 g), copper(I) bromide (0.174 g), and triethylamine (3.38 mL) were added, and the mixture was stirred at 80° C. for 12 hours under an argon atmosphere. The reaction mixture was cooled to room temperature and filtered, and the filtrate was then concentrated. The residue was purified by silica gel column chromatography (hexane:ethyl acetate=100:0-1:1) to obtain the title compound (3.70 g).

$^1$H NMR (CDCl$_3$, 400 MHz): δ (ppm) 7.51 (d, J=7.7 Hz, 1H), 7.37 (d, J=7.7 Hz, 1H), 4.84 (s, 2H), 4.41 (q, J=7.0 Hz, 2H), 3.42-3.49 (m, 2H), 3.44 (s, 3H), 1.43 (t, J=7.1 Hz, 3H), 1.27-1.34 (m, 3H), 0.32 (s, 9H)

Reference Example 95

Ethyl 7-acetyl-3-ethyl-4-(methoxymethyl)benzo[b] thiophene-2-carboxylate

[Formula 98]

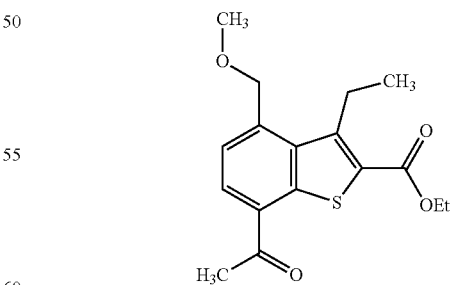

A mixture of the compound (3.70 g) obtained in Reference Example 94, p-toluenesulfonic acid monohydrate (15.03 g), and chloroform (10 mL) was stirred at 80° C. for 10 hours. To the reaction mixture, a saturated aqueous solution of sodium bicarbonate was added, followed by extraction with chloroform. The organic layer was dried over anhydrous sodium sulfate and concentrated. The residue was purified by silica gel column chromatography (hexane:ethyl acetate=10:1-1:1) to obtain the title compound (1.80 g).

$^1$H NMR (CDCl$_3$, 400 MHz): δ (ppm) 8.08 (d, J=7.7 Hz, 1H), 7.62 (d, J=7.7 Hz, 1H), 4.98 (s, 2H), 4.40 (q, J=6.9 Hz, 2H), 3.51 (s, 3H), 3.47 (q, J=7.4 Hz, 2H), 2.76 (s, 3H), 1.43 (t, J=7.1 Hz, 3H), 1.32 (t, J=7.5 Hz, 3H)

Reference Example 96

7-Acetyl-3-ethyl-4-(methoxymethyl)benzo[b]thiophene-2-carboxylic acid

[Formula 99]

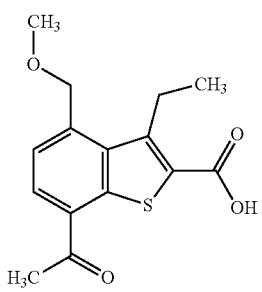

To a solution of the compound (1.80 g) obtained in Reference Example 95 in methanol (50 mL), a 2 N aqueous sodium hydroxide solution (28.1 mL) was added dropwise, and the mixture was stirred at room temperature for 12 hours. To the reaction mixture, 4 N hydrochloric acid was added, followed by extraction with ethyl acetate. The organic layer was dried over anhydrous sodium sulfate and concentrated to obtain the title compound (1.64 g).

Reference Example 97

4-(Pyrrolidin-1-ylmethyl)quinolin-2-amine

[Formula 100]

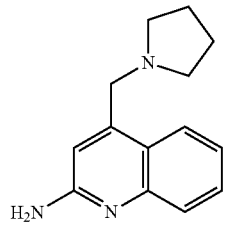

To a solution of 4-(bromomethyl)-2-chloroquinoline (1.03 g) and triethylamine (669 μL) in acetonitrile (10 mL), pyrrolidine (334 μL) was added, and the mixture was stirred at room temperature for 3 hours. To the reaction mixture, a saturated aqueous solution of sodium bicarbonate was added, followed by extraction with dichloromethane. The organic layer was dried over anhydrous sodium sulfate and concentrated. To the residue, 4-methoxybenzylamine (2.61 mL) was added, and the mixture was stirred at 110° C. for 18 hours under an argon atmosphere. The reaction mixture was dissolved in dichloromethane. To the solution, dry ice was added. The precipitated solid was collected by filtration, and the filtrate was concentrated. To the residue, toluene (1.30 mL) and methanesulfonic acid (1.30 mL) were added, and the mixture was stirred at 80° C. for 16 hours. To the reaction mixture, 4 N sodium hydroxide was added, followed by extraction with dichloromethane. The organic layer was dried over anhydrous sodium sulfate and concentrated. The residue was purified by basic silica gel column chromatography (dichloromethane:methanol=100:0-90:10), and the obtained solid was washed with an ethyl acetate-hexane (1:3) mixed solution to obtain the title compound (432 mg).

$^1$H NMR (CDCl$_3$, 400 MHz): δ (ppm) 7.95 (dd, J=8.5, 1.2 Hz, 1H), 7.67 (dd, J=8.7, 1.0 Hz, 1H), 7.51-7.57 (m, 1H), 7.24-7.29 (m, 1H), 6.84 (s, 1H), 4.74 (br. s., 2H), 3.95 (d, J=1.2 Hz, 2H), 2.59-2.65 (m, 4H), 1.79-1.87 (m, 4H)

MS (ESI$^+$) m/z: 228 [M+H]$^+$

Reference Example 98

4-(Morpholinomethyl)quinolin-2-amine

[Formula 101]

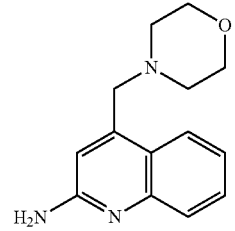

To a solution of 4-(bromomethyl)-2-chloroquinoline (1.03 g) and triethylamine (669 μL) in acetonitrile (10 mL), morpholine (350 μL) was added, and the mixture was stirred at room temperature for 3 hours. To the reaction mixture, a saturated aqueous solution of sodium bicarbonate was added, followed by extraction with dichloromethane. The organic layer was dried over anhydrous sodium sulfate and concentrated. To the residue, 4-methoxybenzylamine (2.61 mL) was added, and the mixture was stirred at 110° C. for 18 hours under an argon atmosphere. The reaction mixture was dissolved in dichloromethane. To the solution, dry ice was added. The precipitated solid was collected by filtration, and the filtrate was concentrated. To the residue, toluene (1.30 mL) and methanesulfonic acid (1.30 mL) were added, and the mixture was stirred at 80° C. for 16 hours. To the reaction mixture, 4 N sodium hydroxide was added, followed by extraction with dichloromethane. The organic layer was dried over anhydrous sodium sulfate and concentrated. The residue was purified by basic silica gel column chromatography (dichloromethane:methanol=100:0-90:10), and the obtained solid was washed with an ethyl acetate-hexane (1:3) mixed solution to obtain the title compound (348 mg).

$^1$H NMR (CDCl$_3$, 400 MHz): δ (ppm) 8.00 (dd, J=8.3, 1.0 Hz, 1H), 7.68 (dd, J=8.7, 1.0 Hz, 1H), 7.53-7.58 (m, 1H), 7.25-7.30 (m, 1H), 6.81 (s, 1H), 4.76 (br. s., 2H), 3.80 (d, J=0.8 Hz, 2H), 3.71-3.75 (m, 4H), 2.51-2.56 (m, 4H)

MS (ESI$^+$) m/z: 244 [M+H]$^+$

Reference Example 99

(R)-4-((3-Fluoropyrrolidin-1-yl)methyl)quinolin-2-amine

[Formula 102]

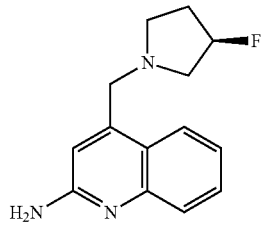

A suspension of 4-(bromomethyl)-2-chloroquinoline (1.946 g), potassium carbonate (2.306 g), and sodium iodide (3.87 g) in DMF (30 mL) was stirred for 30 minutes. (R)-3-Fluoropyrrolidine hydrochloride (1.00 g) was added thereto, and the mixture was stirred at room temperature for 4 hours. To the reaction mixture, water was added, followed by extraction with ethyl acetate. The organic layer was washed with water, dried over anhydrous sodium sulfate, and concentrated. To the residue, 2,4-dimethoxybenzylamine (0.990 mL) was added, and the mixture was stirred at 120° C. for 12 hours. The reaction mixture was concentrated, and the residue was purified by silica gel column chromatography (dichloromethane:methanol=100:0-90:10) to obtain (R)—N-(2,4-dimethoxybenzyl)-4-((3-fluoropyrrolidin-1-yl)methyl)quinolin-2-amine. To the obtained compound, dichloromethane (10 mL) and TFA (1.752 mL) were added, and the mixture was stirred at 50° C. for 1 hour. The reaction mixture was cooled to room temperature and concentrated, and the residue was purified by silica gel column chromatography (dichloromethane:methanol=100:0-70:30) to obtain the title compound (1.20 g).

$^1$H NMR (CDCl$_3$, 400 MHz): δ (ppm) 7.93 (dd, J=8.1, 1.2 Hz, 1H), 7.70 (dd, J=8.5, 0.8 Hz, 1H), 7.57 (ddd, J=8.4, 7.0, 1.6 Hz, 1H), 7.29 (ddd, J=8.4, 7.0, 1.2 Hz, 1H), 6.88 (s, 1H), 5.09-5.30 (m, 3H), 3.99-4.03 (m, 2H), 2.79-3.04 (m, 3H), 2.55-2.62 (m, 1H), 2.04-2.27 (m, 2H)

MS (ESI$^+$) m/z: 246 [M+H]+

Reference Example 100

4-((4-Fluoropiperidin-1-yl)methyl)quinolin-2-amine

[Formula 103]

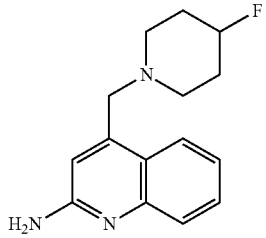

A mixture of 4-(bromomethyl)-2-chloroquinoline (436 mg), triethylamine (1 mL), water (0.5 mL), acetonitrile (2 mL), and 4-fluoropiperidine hydrochloride (237 mg) was stirred at room temperature for 1.5 hours. To the reaction mixture, a saturated aqueous solution of sodium bicarbonate was added, followed by extraction with dichloromethane. The organic layer was dried over anhydrous sodium sulfate and concentrated. To the residue, 4-methoxybenzylamine (2.2 mL) was added, and the mixture was stirred overnight at 100° C. The reaction mixture was dissolved in dichloromethane. To the solution, dry ice was added. The precipitated solid was collected by filtration, and the filtrate was concentrated. To the residue, toluene (1.1 mL) and methanesulfonic acid (1.1 mL) were added, and the mixture was stirred at 100° C. for 3 hours. To the reaction mixture, 4 N sodium hydroxide was added, followed by extraction with dichloromethane. The organic layer was dried over anhydrous sodium sulfate and concentrated. The residue was purified by basic silica gel column chromatography (dichloromethane:methanol=100:0-90:10) to obtain the title compound (104 mg).

MS (ESI$^+$) m/z: 260 [M+H]$^+$

Reference Example 101

1-((2-Aminoquinolin-4-yl)methyl)azetidin-3-ol

[Formula 104]

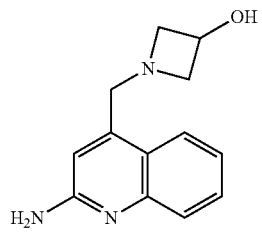

A mixture of 4-(bromomethyl)-2-chloroquinoline (1.28 g), triethylamine (2 mL), water (1 mL), acetonitrile (4 mL), and 3-hydroxyazetidine hydrochloride (548 mg) was stirred at room temperature for 1.5 hours. To the reaction mixture, a saturated aqueous solution of sodium bicarbonate was added, followed by extraction with dichloromethane. The organic layer was dried over anhydrous sodium sulfate and concentrated. To the residue, 4-methoxybenzylamine (3.27 mL) was added, and the mixture was stirred at 75° C. for 15 hours. The reaction mixture was dissolved in dichloromethane. To the solution, dry ice was added. The precipitated solid was collected by filtration, and the filtrate was concentrated. To the residue, toluene (1.6 mL) and methanesulfonic acid (1.6 mL) were added, and the mixture was stirred at 60° C. for 15 hours. To the reaction mixture, a 4 N aqueous sodium hydroxide solution was added, followed by extraction with dichloromethane. The organic layer was dried over anhydrous sodium sulfate and concentrated. The residue was purified by basic silica gel column chromatography (dichloromethane:methanol=100:0-90:10) to obtain the title compound (23 mg).

MS (ESI$^+$) m/z: 230 [M+H]$^+$

Reference Example 102

7-Acetyl-4-(methoxymethyl)-3-methylbenzo[b]thiophene-2-carboxamide

[Formula 105]

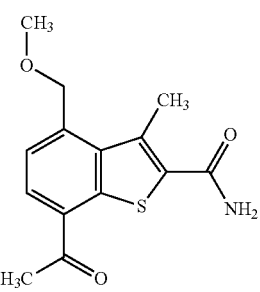

To a solution of the compound (2.00 g) obtained in Reference Example 74 in N,N-dimethylacetamide (20 mL), HBTU (3.27 g) and N,N-diisopropylethylamine (1.11 g) were added under a nitrogen atmosphere, and the mixture was stirred for 30 minutes. To the reaction mixture, a mixture of ammonium acetate (1.66 g) and N,N-diisopropylethylamine (2.78 g) was added, and the mixture was stirred at room temperature for 3 hours. The reaction mixture was diluted with ethyl acetate, washed with water, 0.05 N hydrochloric acid, a saturated aqueous solution of sodium bicarbonate, and saturated aqueous sodium chloride in this order, then dried over anhydrous magnesium sulfate, and concentrated. The residue was washed with an ethyl acetate-heptane mixed solution to obtain the title compound (1.36 g).

$^1$H NMR (DMSO, 400 MHz): δ (ppm) 8.26 (d, J=7.6 Hz, 1H), 7.90 (brs, 1H), 7.67 (brs, 1H), 7.63 (d, J=7.6 Hz, 1H), 4.97 (s, 2H), 3.39 (s, 3H), 2.77 (s, 3H), 2.74 (s, 3H)

Reference Example 103

2-Chloro-4-((3,3-difluoropyrrolidin-1-yl)methyl)quinoline

[Formula 106]

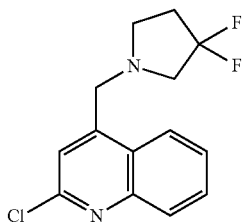

A suspension of 4-(bromomethyl)-2-chloroquinoline (447 mg), potassium carbonate (505 mg), and sodium iodide (861 mg) in DMF (10 mL) was stirred at room temperature for 30 minutes. 3,3-Difluoropyrrolidine hydrochloride (250 mg) was added thereto, and the mixture was stirred at room temperature for 5 hours. To the reaction mixture, water was added, followed by extraction with dichloromethane. The organic layer was dried over anhydrous sodium sulfate and concentrated to obtain the title compound (480 mg).

Reference Example 104

(R)-(2-Chloroquinolin-4-yl)(3-hydroxypyrrolidin-1-yl)methanone

[Formula 107]

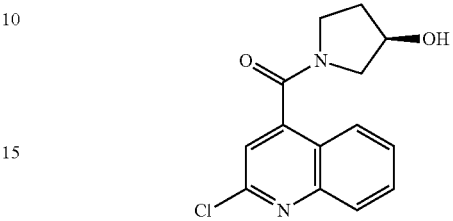

A mixture of 2-chloroquinoline-4-carboxylic acid (623 mg), thionyl chloride (2.19 mL), and chloroform (10 mL) was refluxed overnight, and the reaction mixture was concentrated. To the residue, triethylamine (502 μL) and chloroform (8 mL) were added, and the mixture was cooled to 0° C. A solution of (R)-pyrrolidinol in chloroform (2 mL) was added dropwise thereto, and the mixture was stirred at the same temperature as above for 1 hour. To the reaction mixture, water and a saturated aqueous solution of sodium bicarbonate were added, followed by extraction with dichloromethane. The organic layer was dried over anhydrous sodium sulfate and concentrated. The residue was washed with a dichloromethane-hexane (1:3) mixed solution to obtain the title compound (720 mg).

$^1$H NMR (CDCl$_3$, 400 MHz): δ (ppm) 8.04-8.09 (m, 1H), 7.82-7.86 (m, 1H), 7.75-7.81 (m, 1H), 7.58-7.63 (m, 1H), 7.37 (d, J=7.7 Hz, 1H), 4.43-4.70 (m, 1H), 3.79-3.98 (m, 2H), 3.10-3.50 (m, 2H), 1.94-2.20 (m, 2H)

MS (ESI$^+$) m/z: 277 [M+H]$^+$

Reference Example 105

(R)-(2-Aminoquinolin-4-yl)(3-hydroxypyrrolidin-1-yl)methanone

[Formula 108]

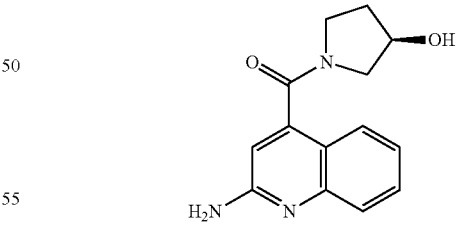

A mixture of the compound (166 mg) obtained in Reference Example 104 and 4-methoxybenzylamine (785 mg) was stirred overnight at 80° C. The reaction mixture was dissolved in dichloromethane. To the solution, dry ice was added. The precipitated solid was collected by filtration, and the filtrate was concentrated. To the residue, toluene (0.4 mL) and methanesulfonic acid (0.389 mL) were added, and the mixture was stirred overnight at 60° C. To the reaction mixture, a 4 N aqueous sodium hydroxide solution was added, followed by extraction with dichloromethane. The organic layer was dried over anhydrous sodium sulfate and concentrated. The residue was purified by basic silica gel column chromatography (dichloromethane:methanol=100:0-85:15) to obtain the title compound (26 mg).

MS (ESI+) m/z: 258 [M+H]+

Reference Example 106

N4,N4-Dimethylquinoline-2,4-diamine

[Formula 109]

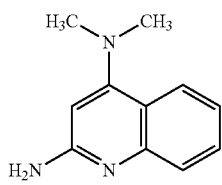

A mixture of 2-amino-4-chloroquinoline (43 mg) and a 50% aqueous dimethylamine solution (2 mL) was stirred at 150° C. for 30 minutes. To the reaction mixture, water was added, followed by extraction with ethyl acetate. The organic layer was washed with saturated aqueous sodium chloride, dried over anhydrous magnesium sulfate, and concentrated to obtain the title compound (43 mg).

$^1$H NMR (CDCl$_3$, 400 MHz): δ (ppm) 7.88 (dd, J=8.4, 1.3 Hz, 1H), 7.62 (dd, J=8.6, 1.0 Hz, 1H), 7.46-7.52 (m, 1H), 7.18-7.23 (m, 1H), 6.10 (s, 1H), 4.69 (brs, 2H), 2.97 (s, 6H)

Reference Example 107

7-Acetyl-4-(methoxymethyl)-3-methylbenzo[b]thiophene-2-carboxylic acid 2,4,6-trimethylbenzoic anhydride

[Formula 110]

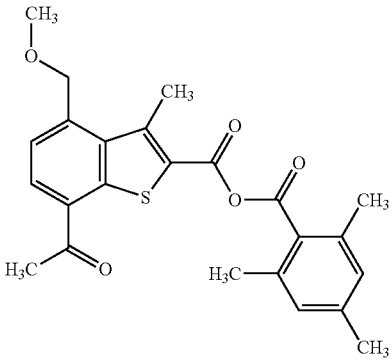

To a solution of the compound (27.8 g) obtained in Reference Example 74 and triethylamine (19.0 mL) in chloroform (300 mL), 2,4,6-trimethylbenzoyl chloride (21.6 mL) was added dropwise, and the mixture was stirred at room temperature for 3 hours. The reaction mixture was concentrated, and water and a saturated aqueous solution of ammonium chloride were added to the residue, followed by extraction with toluene. The organic layer was washed with a mixed solution of a saturated aqueous solution of ammonium chloride and water (1:1), dried over anhydrous sodium sulfate, and concentrated. The residue was washed with diisopropyl ether to obtain the title compound (39.0 g).

$^1$H NMR (CDCl$_3$, 400 MHz): δ (ppm) 8.12 (d, J=7.7 Hz, 1H), 7.62 (d, J=7.7 Hz, 1H), 6.93 (s, 2H), 4.99 (s, 2H), 3.52 (s, 3H), 3.09 (s, 3H), 2.75 (s, 3H), 2.51 (s, 6H), 2.33 (s, 3H)

Reference Example 108

4-(Methoxymethyl)-3-methyl-7-pivaloylbenzo[b]thiophene-2-carboxylic acid

[Formula 111]

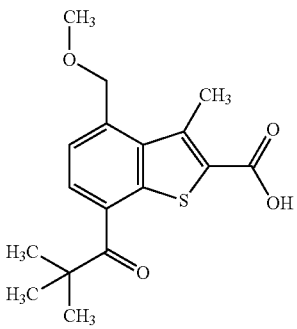

A solution of the compound (306 mg) obtained in Reference Example 73 and methyl iodide (498 μL) in DMSO (3 mL) was heated to 50° C. Potassium hydroxide (1122 mg) and DMSO (3 mL) were added thereto, and the mixture was stirred at the same temperature as above for 1.5 hours. To the reaction mixture, methyl iodide (498 μL) was added, and the mixture was stirred for 30 minutes. The reaction mixture was poured into a mixture of 1 N hydrochloric acid and dichloromethane. The organic layer was dried over anhydrous sodium sulfate and concentrated. The residue was purified by silica gel column chromatography (hexane:dichloromethane=30:70-0:100). To the obtained compound, THF (2 mL), methanol (1 mL), and a 2 N aqueous sodium hydroxide solution (1 mL) were added, and the mixture was stirred at room temperature for 2 hours. To the reaction mixture, 1 N hydrochloric acid was added, followed by extraction with dichloromethane. The organic layer was dried over anhydrous sodium sulfate and concentrated to obtain the title compound (81 mg).

MS (ESI+) m/z: 321 [M+H]+

Reference Example 109

7-Isobutyryl-4-(methoxymethyl)-3-methylbenzo[b]thiophene-2-carboxylic acid

[Formula 112]

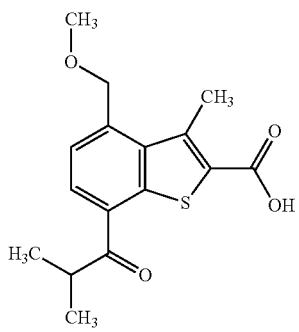

To a mixture of potassium hydroxide (2244 mg) and DMSO (10 mL), the compound (612 mg) obtained in Reference Example 73 and methyl iodide (996 μL) were added, and the mixture was stirred at room temperature for 30 minutes. The reaction mixture was poured into a mixture of 1 N hydrochloric acid and dichloromethane. The organic layer was dried over anhydrous sodium sulfate and concentrated. To the residue, THF (8 mL), methanol (4 mL), and a 2 N aqueous sodium hydroxide solution (4 mL) were added, and the mixture was stirred at room temperature for 1 hour. To the reaction mixture, 1 N hydrochloric acid was added, followed by extraction with dichloromethane. The organic layer was dried over anhydrous sodium sulfate and concentrated, and the obtained solid was washed with a hexane-ethyl acetate (1:1) mixed solution to obtain the title compound (344 mg).

MS (ESI$^+$) m/z: 307 [M+H]$^+$

Reference Example 110

Methyl 2-chloroquinoline-5-carboxylate

[Formula 113]

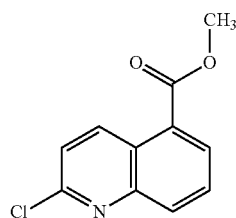

To a suspension of 2-chloroquinoline-5-carboxylic acid (8.00 g) and potassium carbonate (15.98 g) in DMF (20 mL), a solution of methyl iodide (8.20 g) in DMF (20 mL) was added, and the mixture was stirred at room temperature for 3 hours. To the reaction mixture, saturated aqueous sodium chloride and water were added, followed by extraction with chloroform. The organic layer was dried over anhydrous magnesium sulfate and concentrated to obtain the title compound (8.28 g).

$^1$H NMR (CDCl$_3$, 400 MHz): δ (ppm) 9.35 (dd, J=9.3, 0.8 Hz, 1H), 8.31 (dd, J=7.5, 1.3 Hz, 1H), 8.22 (dt, J=8.5, 1.0 Hz, 1H), 7.77 (dd, J=8.4, 7.4 Hz, 1H), 7.51 (d, J=9.3 Hz, 1H), 4.01 (s, 3H)

MS (ESI$^+$) m/z: 222 [M+H]$^+$

Reference Example 111

(2-Chloroquinolin-5-yl)methanol

[Formula 114]

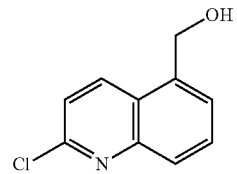

To a solution of the compound (5.000 g) obtained in Reference Example 110 in THF (67 mL), sodium borohydride (3.414 g) was added, then methanol (22 mL) was added dropwise, and the mixture was stirred at 55° C. for 30 minutes. The reaction mixture was cooled to room temperature, and water (125 mL) was added thereto, followed by extraction with ethyl acetate. The organic layer was washed with saturated aqueous sodium chloride, dried over anhydrous magnesium sulfate, and concentrated to obtain the title compound (4.355 g).

$^1$H NMR (CDCl$_3$, 400 MHz): δ (ppm) 8.49 (dd, J=8.8, 0.8 Hz, 1H), 7.99 (d, J=8.5 Hz, 1H), 7.70 (dd, J=8.5, 7.0 Hz, 1H), 7.57 (dd, J=7.0, 1.0 Hz, 1H), 7.45 (d, J=9.0 Hz, 1H), 5.13 (br. s., 2H), 1.82 (br. s., 1H)

MS (ESI$^+$) m/z: 194 [M+H]$^+$

Reference Example 112

(2-Chloroquinolin-5-yl)methyl methanesulfonate

[Formula 115]

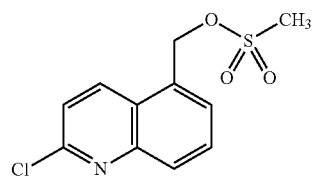

A solution of the compound (465 mg) obtained in Reference Example 111 and triethylamine (502 μL) in dichloromethane (15 mL) was cooled to 0° C. Methanesulfonyl chloride (232 μL) was added thereto, and the mixture was stirred at the same temperature as above for 2 hours. To the reaction mixture, water was added, followed by extraction with dichloromethane. The organic layer was dried over anhydrous sodium sulfate and concentrated. The residue was purified by silica gel column chromatography (hexane:ethyl acetate=2:1-1:2) to obtain the title compound (577 mg).

$^1$H NMR (CDCl$_3$, 400 MHz): δ (ppm) 8.42 (d, J=8.9 Hz, 1H), 8.11 (d, J=8.5 Hz, 1H), 7.72-7.79 (m, 1H), 7.66 (d, J=6.9 Hz, 1H), 7.52 (d, J=8.9 Hz, 1H), 5.66 (s, 2H), 2.92 (s, 3H)

MS (ESI$^+$) m/z: 272 [M+H]$^+$

Reference Example 113

(R)-2-Chloro-5-((3-fluoropyrrolidin-1-yl)methyl) quinoline

[Formula 116]

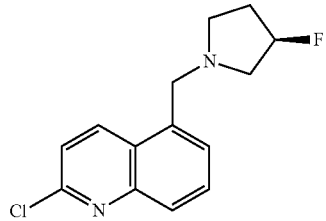

A solution of the compound (500 mg) obtained in Reference Example 112, (R)-3-fluoropyrrolidine hydrochloride (277 mg), and triethylamine (465 mg) in N,N-dimethylacetamide (5 mL) was stirred at 70° C. for 2 hours. The reaction mixture was diluted with ethyl acetate, washed with water, saturated sodium bicarbonate, and saturated aqueous sodium chloride in this order, then dried over anhydrous magnesium sulfate, and concentrated. The residue was purified by silica gel column chromatography (hexane:ethyl acetate=1:1) to obtain the title compound (484 mg).

$^1$H NMR (CDCl$_3$, 400 MHz): δ (ppm) 8.66 (d, J=8.9 Hz, 1H), 7.95 (d, J=8.5 Hz, 1H), 7.65 (t, J=8.5 Hz, 1H), 7.48 (d, J=6.9 Hz, 1H), 7.40 (d, J=8.8 Hz, 1H), 5.06-5.27 (m, 1H), 3.97-4.10 (m, 2H), 2.70-2.92 (m, 3H), 2.42-2.51 (m, 1H), 1.94-2.23 (m, 2H)

Reference Example 114

4-((2-Chloroquinolin-5-yl)methyl) morpholine

[Formula 117]

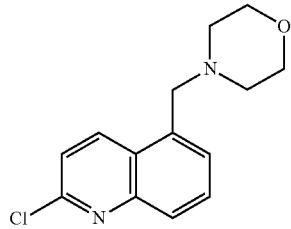

The title compound (261 mg) was obtained in the same way as in Reference Example 113 using the compound (300 mg) obtained in Reference Example 112, morpholine (116 mg), triethylamine (146 mg), and THF (5 mL).

$^1$H NMR (CDCl$_3$, 400 MHz): δ (ppm) 8.69 (d, J=9.1 Hz, 1H), 7.95 (d, J=8.5 Hz, 1H), 7.64 (dd, J=7.2, 8.5 Hz, 1H), 7.45 (d, J=8.0 Hz, 1H), 7.41 (d, J=8.8 Hz, 1H), 3.87 (s, 2H), 3.60-3.70 (m, 4H), 2.41-2.50 (m, 4H)

Reference Example 115

1-(2-Chloroquinolin-5-yl)-N,N-dimethylmethanamine

[Formula 118]

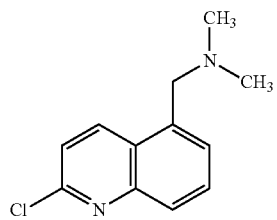

A solution of the compound (108 mg) obtained in Reference Example 112 and dimethylamine (2 M solution in THF, 0.8 mL) in THF (1 mL) was stirred overnight at room temperature. Dimethylamine (2 M solution in THF, 0.8 mL) was added thereto, and the mixture was stirred at 60° C. for 1 hour. Dimethylamine (2 M solution in THF, 0.8 mL) was added thereto, and the mixture was stirred at 60° C. for 2 hours. The reaction mixture was diluted with ethyl acetate, washed with a saturated aqueous solution of sodium bicarbonate and saturated aqueous sodium chloride, then dried over anhydrous magnesium sulfate, and concentrated. The residue was purified by silica gel column chromatography (hexane:ethyl acetate:methanol=10:10:1) to obtain the title compound (53 mg).

$^1$H NMR (CDCl$_3$, 400 MHz): δ (ppm) 8.63-8.66 (m, 1H), 7.96 (d, J=8.5 Hz, 1H), 7.65 (dd, J=7.2, 8.5 Hz, 1H), 7.41-7.47 (m, 1H), 7.40 (d, J=8.8 Hz, 1H), 3.80 (s, 2H), 2.27 (s, 6H)

Reference Example 116

(S)-1-((2-Chloroquinolin-5-yl)methyl) pyrrolidin-3-ol

[Formula 119]

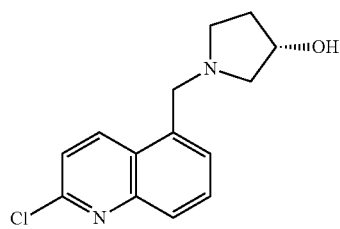

A solution of the compound (140 mg) obtained in Reference Example 112, (S)-3-hydroxypyrrolidine (54 mg), and triethylamine (79 mg) in THF (5 mL) was refluxed overnight. The reaction mixture was diluted with ethyl acetate, washed with saturated sodium bicarbonate and saturated aqueous sodium chloride in this order, then dried over anhydrous magnesium sulfate, and concentrated. The residue was purified by silica gel column chromatography (hexane:ethyl acetate:methanol=10:10:1) to obtain the title compound (129 mg).

$^1$H NMR (CDCl$_3$, 400 MHz): δ (ppm) 8.62-8.64 (m, 1H), 7.95 (d, J=8.5 Hz, 1H), 7.65 (dd, J=7.1, 8.4 Hz, 1H), 7.47 (d, J=8.9 Hz, 1H), 7.40 (d, J=8.8 Hz, 1H), 4.30-4.36 (m, 1H), 3.98-4.06 (m, 2H), 2.80-2.90 (m, 1H), 2.64-2.70 (m, 1H), 2.54-2.61 (m, 1H), 2.30-2.40 (m, 1H), 2.13-2.22 (m, 1H), 1.69-1.84 (m, 2H), Reference Example 117

(R)-1-((2-Chloroquinolin-5-yl)methyl) pyrrolidin-3-ol

[Formula 120]

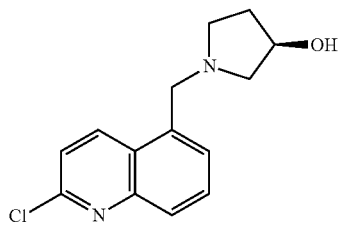

To a solution of the compound (2.943 g) obtained in Reference Example 112 in chloroform (40 mL), triethylamine (2.19 mL) was added, and the mixture was cooled to 0° C. Then, a solution of (R)-3-hydroxypyrrolidine (1.175 g) in chloroform (5 mL) was added thereto, and the mixture was stirred at room temperature for 20 hours. To the reaction mixture, a saturated aqueous solution of sodium bicarbonate was added, followed by extraction with chloroform. The organic layer was dried over anhydrous sodium sulfate and concentrated. The residue was purified by silica gel column chromatography (dichloromethane:methanol=100:1-90:10) to obtain the title compound (2.544 g).

$^1$H NMR (CDCl$_3$, 400 MHz): δ (ppm) 8.62-8.69 (m, 1H), 7.95 (d, J=8.5 Hz, 1H), 7.65 (dd, J=8.5, 7.3 Hz, 1H), 7.47 (d, J=6.5 Hz, 1H), 7.40 (d, J=8.9 Hz, 1H), 4.29-4.37 (m, 1H), 4.01 (s, 2H), 2.80-2.88 (m, 1H), 2.63-2.68 (m, 1H), 2.55-2.61 (m, 1H), 2.29-2.43 (m, 1H), 2.14-2.24 (m, 1H), 1.69-1.77 (m, 1H)

Reference Example 118

(R)-1-((2-((4-Methoxybenzyl)amino)quinolin-5-yl)methyl)pyrrolidin-3-ol

[Formula 121]

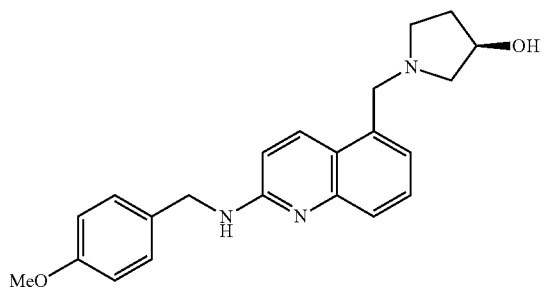

A mixture of the compound (2.45 g) obtained in Reference Example 117 and 4-methoxybenzylamine (7.31 mL) was stirred at 140° C. for 8 hours. The reaction mixture was cooled to room temperature and diluted with dichloromethane, and dry ice was added thereto. The precipitated solid was collected by filtration, and the filtrate was concentrated. The residue was purified by silica gel column chromatography (dichloromethane:methanol=97:3-84:16) to obtain the title compound (2.744 g).

$^1$H NMR (CDCl$_3$, 400 MHz): δ (ppm) 8.30 (d, J=9.7 Hz, 1H), 7.62-7.66 (m, 1H), 7.44 (dd, J=8.5, 7.3 Hz, 1H), 7.31-7.36 (m, 2H), 7.11-7.15 (m, 1H), 6.85-6.90 (m, 2H), 6.63 (d, J=9.3 Hz, 1H), 4.94 (br. s., 1H), 4.64 (d, J=5.7 Hz, 2H), 4.29 (br. s., 1H), 3.90-3.93 (m, 2H), 3.80 (s, 3H), 2.81-2.88 (m, 1H), 2.64-2.69 (m, 1H), 2.53 (dd, J=10.1, 4.9 Hz, 1H), 2.27-2.35 (m, 1H), 2.11-2.21 (m, 1H), 1.66-1.76 (m, 1H)

MS (ESI$^+$) m/z: 364 [M+H]$^+$

Reference Example 119

(R)-1-((2-Aminoquinolin-5-yl)methyl)pyrrolidin-3-ol

[Formula 122]

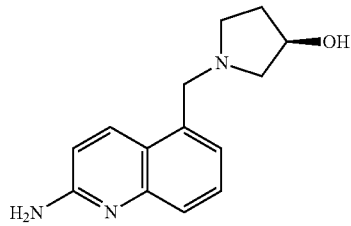

A mixture of the compound (2.744 g) obtained in Reference Example 118 and TFA (11.6 mL) was stirred at 70° C. for 10 hours. The reaction mixture was cooled to room temperature and concentrated. To the residue, chloroform and a 2 N aqueous sodium hydroxide solution were added, followed by extraction with chloroform. The organic layer was dried over anhydrous sodium sulfate and concentrated. The residue was purified by silica gel column chromatography (dichloromethane:methanol=98.5:1.5-93:7) to obtain the title compound (1.411 g).

$^1$H NMR (CDCl$_3$, 400 MHz): δ (ppm) 8.38 (d, J=9.7 Hz, 1H), 7.59 (d, J=8.5 Hz, 1H), 7.46 (dd, J=8.5, 6.9 Hz, 1H), 7.15-7.19 (m, 1H), 6.73 (d, J=9.3 Hz, 1H), 4.71 (br. s., 2H), 4.26-4.33 (m, 1H), 3.89-3.97 (m, 2H), 2.82-2.88 (m, 1H), 2.64-2.69 (m, 1H), 2.54 (dd, J=9.9, 5.1 Hz, 1H), 2.29-2.36 (m, 1H), 2.12-2.22 (m, 1H), 1.68-1.76 (m, 1H)

Reference Example 120

(2-((4-Methoxybenzyl)amino)quinolin-5-yl)methanol

[Formula 123]

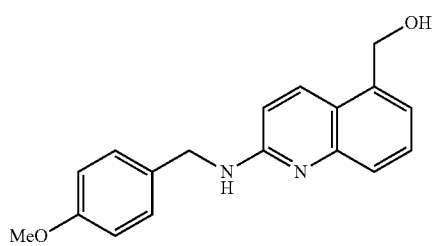

A mixture of the compound (700 mg) obtained in Reference Example 111 and 4-methoxybenzylamine (2.83 mL) was stirred at 140° C. for 4 hours. The reaction mixture was cooled to room temperature and diluted with dichloromethane, and dry ice was added thereto. The precipitated solid was collected by filtration, and the filtrate was concentrated. The residue was purified by silica gel column chromatography (dichloromethane:methanol=97:3-91:9) to obtain the title compound (910 mg).

$^1$H NMR (CDCl$_3$, 400 MHz): δ (ppm) 8.19 (d, J=9.7 Hz, 1H), 7.66-7.69 (m, 1H), 7.42-7.52 (m, 1H), 7.30-7.35 (m, 2H), 7.19-7.24 (m, 1H), 6.85-6.90 (m, 2H), 6.67 (d, J=8.9 Hz, 1H), 5.01 (s, 2H), 4.97 (br. s., 1H), 4.62-4.66 (m, 2H), 3.80 (s, 3H)

MS (ESI$^+$) m/z: 295 [M+H]$^+$

Reference Example 121

(2-Aminoquinolin-5-yl)methanol

[Formula 124]

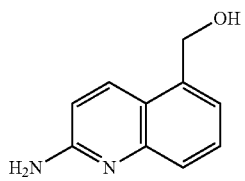

A mixture of the compound (910 mg) obtained in Reference Example 120, TFA (4.8 mL), and dichloromethane (2 mL) was stirred overnight at room temperature and then stirred at 60° C. for 3 hours. The reaction mixture was cooled to room temperature and concentrated. To the residue, a 2 N aqueous sodium hydroxide solution and methanol were added, and the mixture was refluxed for 30 minutes. The reaction mixture was cooled to room temperature, followed by extraction with chloroform. The organic layer was dried over anhydrous sodium sulfate and concentrated. The residue was washed with an ethyl acetate-hexane (2:1) mixed solution to obtain the title compound (214 mg).

$^1$H NMR (CDCl$_3$, 400 MHz): δ (ppm) 8.27 (d, J=9.3 Hz, 1H), 7.61-7.66 (m, 1H), 7.49-7.55 (m, 1H), 7.26-7.27 (m, 1H), 6.78 (d, J=8.9 Hz, 1H), 5.04 (s, 2H), 4.75 (br. s., 2H)

MS (ESI$^+$) m/z: 175 [M+H]$^+$

Reference Example 122

5-(Chloromethyl)quinolin-2-amine

[Formula 125]

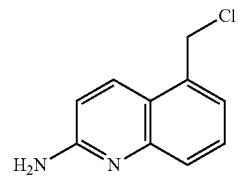

A mixture of the compound (214 mg) obtained in Reference Example 121, thionyl chloride (107.5 μL), acetonitrile (5 mL), and chloroform (2.5 mL) was stirred at 50° C. for 3 hours. The reaction mixture was cooled to room temperature, and a saturated aqueous solution of sodium bicarbonate was added thereto, followed by extraction with chloroform. The organic layer was dried over anhydrous sodium sulfate and concentrated to obtain the title compound (223 mg).

$^1$H NMR (CDCl$_3$, 400 MHz): δ (ppm) 8.23 (d, J=8.9 Hz, 1H), 7.65-7.69 (m, 1H), 7.47-7.53 (m, 1H), 7.27-7.30 (m, 1H), 6.82 (d, J=9.3 Hz, 1H), 4.93 (s, 2H), 4.80 (br. s., 2H)

MS (ESI$^+$) m/z: 193 [M+H]$^+$

Reference Example 123

1-((2-Aminoquinolin-5-yl)methyl)azetidin-3-ol

[Formula 126]

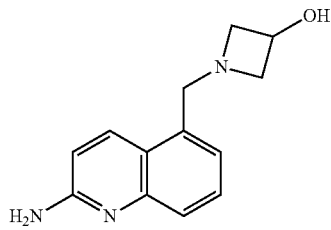

A mixture of the compound (120 mg) obtained in Reference Example 122, 3-hydroxyazetidine hydrochloride (82 mg), acetonitrile (3 mL), water (0.75 mL), and triethylamine (0.75 mL) was stirred at 45° C. for 12 hours. The reaction mixture was cooled to room temperature, and a saturated aqueous solution of sodium bicarbonate was added thereto, followed by extraction with chloroform. The organic layer was dried over anhydrous sodium sulfate and concentrated to obtain the title compound (99 mg).

$^1$H NMR (DMSO, 400 MHz): δ (ppm) 8.13 (d, J=8.9 Hz, 1H), 7.33-7.37 (m, 2H), 7.02-7.05 (m, 1H), 6.74 (d, J=8.9 Hz, 1H), 6.35 (s, 2H), 5.28 (d, J=6.5 Hz, 1H), 4.12-4.20 (m, 1H), 3.82 (s, 2H), 3.42-3.47 (m, 2H), 2.75-2.81 (m, 2H)

MS (ESI$^+$) m/z: 230 [M+H]$^+$

Reference Example 124

5-((3-Methoxyazetidin-1-yl)methyl)quinolin-2-amine

[Formula 127]

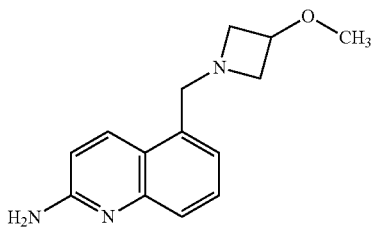

A mixture of the compound (105 mg) obtained in Reference Example 122, 3-methoxyazetidine hydrochloride (81 mg), acetonitrile (3 mL), water (0.75 mL), and triethylamine (0.75 mL) was stirred at 45° C. for 2 hours. The reaction mixture was cooled to room temperature, and a saturated aqueous solution of sodium bicarbonate was added thereto, followed by extraction with chloroform. The organic layer was dried over anhydrous sodium sulfate and concentrated. The residue was purified by silica gel column chromatography (dichloromethane:methanol=99:1-95:5) to obtain the title compound (95 mg).

$^1$H NMR (CDCl$_3$, 400 MHz): δ (ppm) 8.27-8.31 (m, 1H), 7.57-7.61 (m, 1H), 7.45-7.49 (m, 1H), 7.15-7.18 (m, 1H), 6.74 (d, J=8.9 Hz, 1H), 4.71 (br. s., 2H), 4.00-4.08 (m, 1H), 3.94 (s, 2H), 3.56-3.61 (m, 2H), 3.24 (s, 3H), 2.95-3.00 (m, 2H)

MS (ESI$^+$) m/z: 244 [M+H]$^+$

Reference Example 125

2-Chloro-5-(methoxymethyl)quinoline

[Formula 128]

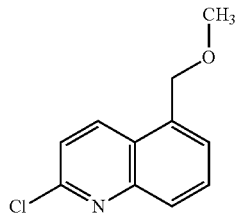

To a solution of the compound (4.348 g) obtained in Reference Example 111 in DMSO (13 mL), methyl iodide (3.36 mL) was added, then potassium hydroxide (2.90 g) was added, and the mixture was stirred at room temperature for 30 minutes. The reaction mixture was cooled to 0° C., and water (21.3 mL) was added dropwise thereto. The precipitated solid was collected by filtration, washed with water (52 mL), and then dried to obtain the title compound (4.439 g).

$^1$H NMR (CDCl$_3$, 400 MHz): δ (ppm) 8.44 (dd, J=8.8, 0.8 Hz, 1H), 7.99 (d, J=8.5 Hz, 1H), 7.68 (dd, J=8.5, 7.0 Hz, 1H), 7.53 (dd, J=7.0, 1.0 Hz, 1H), 7.43 (d, J=8.8 Hz, 1H), 4.86 (s, 2H), 3.42 (s, 3H)

MS (ESI$^+$) m/z: 208 [M+H]$^+$

Reference Example 126

2-Hydrazinyl-5-(methoxymethyl)quinoline

[Formula 129]

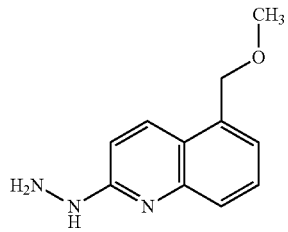

To the compound (4.438 g) obtained in Reference Example 125, hydrazine monohydrate (22 mL) and 1,4-dioxane (22 mL) were added, and the mixture was stirred at 80° C. for 66 hours. The reaction mixture was cooled to room temperature. Water (45 mL) was added thereto, and the mixture was cooled to 0° C. The precipitated solid was collected by filtration, washed with water, and then dried to obtain the title compound (3.644 g).

$^1$H NMR (CDCl$_3$, 400 MHz): δ (ppm) 8.20 (d, J=9.0 Hz, 1H), 7.72 (d, J=8.3 Hz, 1H), 7.47-7.55 (m, 1H), 7.21-7.28 (m, 1H), 6.82 (d, J=9.0 Hz, 1H), 5.95 (br. s., 1H), 4.79 (s, 2H), 4.11 (br. s., 2H), 3.40 (s, 3H)

MS (ESI$^+$) m/z: 204 [M+H]$^+$

Reference Example 127

5-(Methoxymethyl)quinolin-2-amine

[Formula 130]

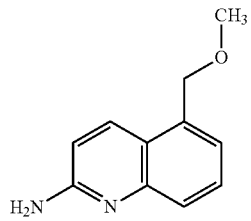

To the compound (3.643 g) obtained in Reference Example 126, Raney nickel (R-200 manufactured by Nikko Rica Corp., 4.6 mL) and methanol (92 mL) were added, and the mixture was stirred at room temperature for 40.5 hours under a hydrogen atmosphere. The reaction mixture was filtered, and the filtrate was concentrated to obtain the title compound (3.292 g).

$^1$H NMR (CDCl$_3$, 400 MHz): δ (ppm) 8.22 (d, J=9.0 Hz, 1H), 7.64 (d, J=8.3 Hz, 1H), 7.50 (dd, J=8.5, 7.0 Hz, 1H), 7.21-7.25 (m, 1H), 6.76 (d, J=9.0 Hz, 1H), 4.79 (s, 2H), 4.72 (br. s., 2H), 3.40 (s, 3H)

MS (ESI$^+$) m/z: 189 [M+H]$^+$

Reference Example 128

5-(Ethoxymethyl)quinolin-2-amine

[Formula 131]

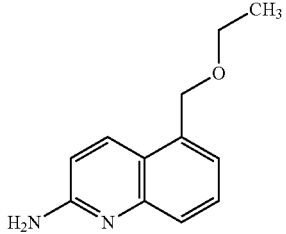

To a solution of the compound (387 mg) obtained in Reference Example 111 in DMSO (2 mL), ethyl iodide (0.386 mL) was added, then potassium hydroxide (258 mg) was added, and the mixture was stirred at room temperature for 30 minutes. To the reaction mixture, water was added, followed by extraction with dichloromethane. The organic layer was dried over anhydrous sodium sulfate and concentrated. To the residue, 1,4-dioxane (2 mL), water (1 mL), and hydrazine monohydrate (1.94 mL) were added, and the mixture was stirred at 70° C. for 3 days and stirred at 80° C. for 2 days. To the reaction mixture, water was added, followed by extraction with dichloromethane. The organic layer was dried over anhydrous sodium sulfate and concentrated. To the residue, methanol (10 mL) and Raney nickel (Raney 2400 manufactured by W.R. Grace and Co., 1 mL) were added, and the mixture was stirred at room temperature for 20 hours under a hydrogen atmosphere. The reaction mixture was filtered, and the filtrate was concentrated to obtain the title compound (289 mg).

$^1$H NMR (CDCl$_3$, 400 MHz): δ (ppm) 8.25 (dd, J=9.0, 0.8 Hz, 1H), 7.63 (d, J=8.3 Hz, 1H), 7.47-7.52 (m, 1H), 7.24 (dd, J=7.0, 1.0 Hz, 1H), 6.76 (d, J=9.0 Hz, 1H), 4.83 (s, 2H), 4.75 (br. s., 2H), 3.57 (q, J=7.0 Hz, 2H), 1.24 (t, J=7.0 Hz, 3H)

MS (ESI$^+$) m/z: 203 [M+H]$^+$

Reference Example 129

2-Chloro-5-((2-methoxyethoxy)methyl)quinoline

[Formula 132]

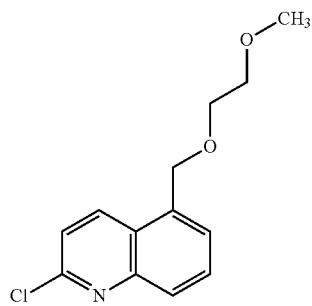

A solution of the compound (97 mg) obtained in Reference Example 111 and 2-methoxyethyl bromide (0.286 mL) in DMF (2 mL) was cooled to 0° C. Sodium hydride (60% oil suspension, 24 mg) was added thereto, and the mixture was stirred at 0° C. for 3 hours and stirred overnight at room temperature. The reaction mixture was cooled to 0° C. Sodium hydride (60% oil suspension, 24 mg) was added thereto, and the mixture was stirred at the same temperature as above for 1 hour. To the reaction mixture, water and a saturated aqueous solution of sodium bicarbonate were added, followed by extraction with dichloromethane. The organic layer was dried over anhydrous sodium sulfate and concentrated. The residue was purified by basic silica gel column chromatography (hexane:ethyl acetate=80:20) to obtain the title compound (97 mg).

$^1$H NMR (CDCl$_3$, 400 MHz): δ (ppm) 8.51 (dd, J=8.8, 0.8 Hz, 1H), 7.99 (d, J=8.5 Hz, 1H), 7.65-7.70 (m, 1H), 7.53 (dd, J=7.0, 1.3 Hz, 1H), 7.43 (d, J=9.0 Hz, 1H), 4.97 (s, 2H), 3.64-3.67 (m, 2H), 3.54-3.57 (m, 2H), 3.38 (s, 3H)

MS (ESI$^+$) m/z: 252 [M+H]$^+$

Reference Example 130

5-((2-Methoxyethoxy)methyl)quinolin-2-amine

[Formula 133]

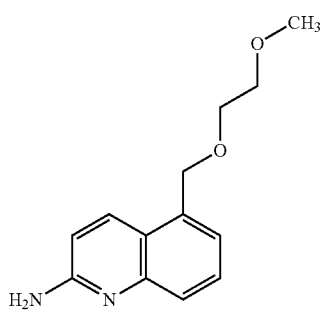

To a solution of the compound (95 mg) obtained in Reference Example 129 in 1,4-dioxane (1.5 mL), hydrazine monohydrate (0.183 mL) was added, and the mixture was stirred overnight at 80° C. To the reaction mixture, hydrazine monohydrate (0.183 mL) was added, and the mixture was stirred overnight at 80° C. The reaction mixture was dried over anhydrous sodium sulfate, diluted with dichloromethane, and then filtered, and the filtrate was concentrated. To the residue, methanol (2 mL) and Raney nickel (Raney 2400 manufactured by W.R. Grace and Co., 0.1 mL) were added, and the mixture was stirred overnight at room temperature under a hydrogen atmosphere. The reaction mixture was filtered, and the filtrate was concentrated. The residue was purified by basic silica gel column chromatography (hexane: ethyl acetate=50:50-10:90) to obtain the title compound (53 mg).

$^1$H NMR (CDCl$_3$, 400 MHz): δ (ppm) 8.29 (dd, J=9.0, 0.8 Hz, 1H), 7.63 (d, J=8.5 Hz, 1H), 7.49 (dd, J=8.5, 7.0 Hz, 1H), 7.23 (dd, J=7.0, 1.3 Hz, 1H), 6.76 (d, J=9.0 Hz, 1H), 4.90 (s, 2H), 4.76 (br. s., 2H), 3.60-3.64 (m, 2H), 3.52-3.56 (m, 2H), 3.38 (s, 3H)

MS (ESI$^+$) m/z: 233 [M+H]$^+$

Reference Example 131

5-((2-((tert-Butyldimethylsilyl)oxy)ethoxy)methyl)-2-chloroquinoline

[Formula 134]

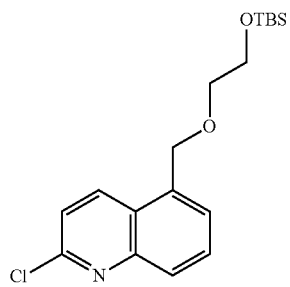

A solution of the compound (194 mg) obtained in Reference Example 111 and (2-bromoethoxy)(tert-butyl)dimethylsilane (0.751 mL) in DMF (4 mL) was cooled to 0° C.

Sodium hydride (60% oil suspension, 60 mg) was added thereto, and the mixture was stirred at 0° C. for 2 hours. To the reaction mixture, water and a saturated aqueous solution of sodium bicarbonate were added, followed by extraction with dichloromethane. The organic layer was dried over anhydrous sodium sulfate and concentrated. The residue was purified by basic silica gel column chromatography (hexane:ethyl acetate=95:5) to obtain the title compound (81 mg).

$^1$H NMR (CDCl$_3$, 400 MHz): δ (ppm) 8.52 (dd, J=8.8, 0.8 Hz, 1H), 7.98 (d, J=8.5 Hz, 1H), 7.67 (dd, J=8.5, 7.0 Hz, 1H), 7.51-7.56 (m, 1H), 7.41 (d, J=9.0 Hz, 1H), 4.97 (s, 2H), 3.78-3.82 (m, 2H), 3.59-3.63 (m, 2H), 0.89 (s, 9H), 0.05 (s, 6H)

MS (ESI$^+$) m/z: 352 [M+H]$^+$

Reference Example 132

5-((2-((tert-Butyldimethylsilyl)oxy)ethoxy)methyl)quinolin-2-amine

[Formula 135]

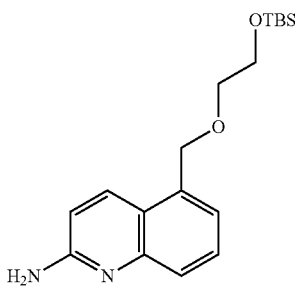

To a solution of the compound (115 mg) obtained in Reference Example 131 in 1,4-dioxane (1.5 mL), hydrazine monohydrate (0.476 mL) was added, and the mixture was stirred overnight at 80° C. To the reaction mixture, hydrazine monohydrate (0.238 mL) was added, and the mixture was stirred overnight at 80° C. The reaction mixture was dried over anhydrous sodium sulfate, diluted with dichloromethane, and then filtered, and the filtrate was concentrated. To the residue, methanol (2 mL) and Raney nickel (Raney 2400 manufactured by W.R. Grace and Co., 0.1 mL) were added, and the mixture was stirred overnight at room temperature under a hydrogen atmosphere. The reaction mixture was filtered, and the filtrate was concentrated. The residue was purified by basic silica gel column chromatography (hexane:ethyl acetate=65:35-30:70) to obtain the title compound (59 mg).

$^1$H NMR (CDCl$_3$, 400 MHz): δ (ppm) 8.29 (d, J=9.0 Hz, 1H), 7.63 (d, J=8.5 Hz, 1H), 7.49 (dd, J=8.5, 7.0 Hz, 1H), 7.22-7.25 (m, 1H), 6.74 (d, J=9.0 Hz, 1H), 4.89 (s, 2H), 4.76 (br. s., 2H), 3.77-3.81 (m, 2H), 3.57-3.60 (m, 2H), 0.89 (s, 9H), 0.05 (s, 6H)

MS (ESI$^+$) m/z: 333 [M+H]$^+$

Reference Example 133

7-Acetyl-N-(5-((2-((tert-butyldimethylsilyl)oxy)ethoxy)methyl)quinolin-2-yl)-4-(methoxymethyl)-3-methylbenzo[b]thiophene-2-carboxamide

[Formula 136]

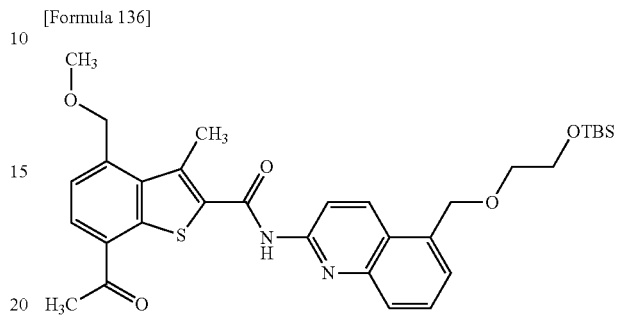

To a mixture of the compound (33.3 mg) obtained in Reference Example 132, the compound (30.6 mg) obtained in Reference Example 74, HBTU (45.5 mg), and dichloromethane (1 mL), triethylamine (0.042 mL) was added, and the mixture was stirred at room temperature for 18 hours. To the reaction mixture, a saturated aqueous solution of sodium bicarbonate was added, followed by extraction with dichloromethane. The organic layer was dried over anhydrous sodium sulfate and concentrated. The residue was purified by basic silica gel column chromatography (hexane:dichloromethane=60:40-40:60) to obtain the title compound (56.4 mg).

$^1$H NMR (CDCl$_3$, 400 MHz): δ (ppm) 8.71 (s, 1H), 8.50-8.61 (m, 2H), 8.09 (d, J=7.8 Hz, 1H), 7.82 (d, J=8.0 Hz, 1H), 7.59-7.66 (m, 2H), 7.46 (d, J=6.8 Hz, 1H), 5.01 (s, 2H), 5.00 (s, 2H), 3.80-3.84 (m, 2H), 3.61-3.65 (m, 2H), 3.52 (s, 3H), 3.00 (s, 3H), 2.79 (s, 3H), 0.91 (s, 9H), 0.07 (s, 6H)

MS (ESI$^+$) m/z: 593 [M+H]$^+$

Reference Example 134

2-Chloro-5-((difluoromethoxy)methyl)quinoline

[Formula 137]

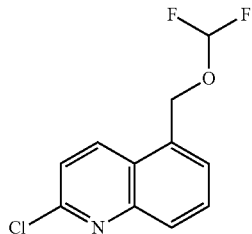

A mixture of the compound (265 mg) obtained in Reference Example 111, anhydrous sodium sulfate (117 mg), 2-(fluorosulfonyl)difluoroacetic acid (488 mg), and acetonitrile (10 mL) was stirred at 50° C. for 2 hours. The reaction mixture was concentrated, and water was added to the residue, followed by extraction with ethyl acetate. The organic layer was washed with a saturated aqueous solution of sodium bicarbonate and saturated aqueous sodium chloride in this order, dried over anhydrous sodium sulfate, and concentrated. The residue was purified by silica gel column chromatography (hexane:ethyl acetate=10:1 to 6:1) to obtain the title compound (32 mg).

$^1$H NMR (CDCl$_3$, 400 MHz): δ (ppm) 8.35-8.37 (m, 1H), 8.06 (d, J=8.8 Hz, 1H), 7.72 (dd, J=7.2, 8.8 Hz, 1H), 7.60 (d, J=7.2 Hz, 1H), 7.48 (d, J=8.5 Hz, 1H), 6.35 (d, J=74.0 Hz, 1H), 5.30 (s, 2H)

Reference Example 135

2-(2-Chloroquinolin-5-yl)propan-2-ol

[Formula 138]

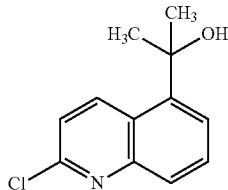

A solution of the compound (600 mg) obtained in Reference Example 110 in THF (10 mL) was cooled to 0° C. Methyl magnesium bromide (1.12 M solution in THF, 5.32 mL) was added dropwise thereto, and the mixture was stirred at the same temperature as above for 40 minutes. To the reaction mixture, water was added, followed by extraction with chloroform. The organic layer was dried over anhydrous sodium sulfate and concentrated. The residue was purified by silica gel column chromatography (chloroform:methanol=100:0-95:5) to obtain the title compound (361 mg).

$^1$H NMR (CDCl$_3$, 400 MHz): δ (ppm) 9.27 (d, J=8.9 Hz, 1H), 7.93-7.97 (m, 1H), 7.61-7.66 (m, 1H), 7.55-7.59 (m, 1H), 7.38 (d, J=8.9 Hz, 1H), 1.83 (s, 6H)

MS (ESI$^+$) m/z: 222 [M+H]$^+$

Reference Example 136

1-(2-Aminoquinolin-5-yl)ethanone

[Formula 139]

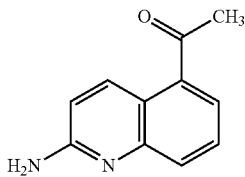

A solution of 5-bromoquinolin-2-amine (1.0 g), dichlorobis(triphenylphosphine)palladium(II) (315 mg), and (1-ethoxyvinyl)tributyltin (3.06 mL) in toluene (30 mL) was refluxed for 2 hours under a nitrogen atmosphere. The reaction mixture was cooled to 0° C. 6 N hydrochloric acid (20 mL) was added thereto, and the mixture was stirred at room temperature for 2 hours. To the reaction mixture, a 2 N aqueous sodium hydroxide solution was added, followed by extraction with ethyl acetate. The organic layer was dried over anhydrous sodium sulfate and concentrated. The residue was purified by basic silica gel column chromatography (dichloromethane:methanol=97.5:2.5) and basic silica gel column chromatography (dichloromethane:methanol=98.75:1.25) to obtain the title compound (468 mg).

$^1$H NMR (CDCl$_3$, 400 MHz): δ (ppm) 8.90-8.94 (m, 1H), 7.82 (dt, J=8.2, 1.0 Hz, 1H), 7.77 (dd, J=7.4, 1.1 Hz, 1H), 7.58 (dd, J=8.4, 7.4 Hz, 1H), 6.82 (d, J=9.3 Hz, 1H), 4.77 (br. s., 2H), 2.72 (s, 3H)

MS (ESI$^+$) m/z: 187 [M+H]$^+$

Reference Example 137

1-(2-Aminoquinolin-5-yl)ethanol

[Formula 140]

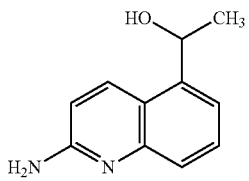

To the compound (326 mg) obtained in Reference Example 136, ethanol (2 mL) and THF (2 mL) were added, and the mixture was cooled to 0° C. Then, sodium borohydride (132 mg) was added thereto, and the mixture was stirred at the same temperature as above for 30 minutes. To the reaction mixture, a saturated aqueous solution of sodium bicarbonate was added, and chloroform and methanol were further added. The organic layer was dried over anhydrous sodium sulfate and concentrated. The residue was purified by basic silica gel column chromatography (chloroform:methanol=98:2) to obtain the title compound (113 mg).

$^1$H NMR (CDCl$_3$, 400 MHz): δ (ppm) 8.29-8.33 (m, 1H), 7.58-7.62 (m, 1H), 7.51-7.56 (m, 1H), 7.37-7.41 (m, 1H), 6.75 (d, J=9.0 Hz, 1H), 5.49 (q, J=6.7 Hz, 1H), 4.72 (br. s., 2H), 1.65 (d, J=6.5 Hz, 3H)

MS (ESI$^+$) m/z: 189 [M+H]$^+$

Reference Example 138

5-(((tert-Butyldimethylsilyl)oxy)methyl)-2-chloroquinoline

[Formula 141]

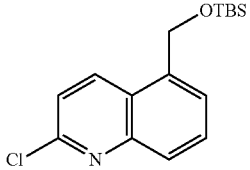

To a solution of the compound (17.54 g) obtained in Reference Example 111 and tert-butyldimethylchlorosilane (20.48 g) in DMF (85 mL), a solution of imidazole (18.50 g) in DMF (20 mL) was added, and the mixture was stirred at room temperature for 5 hours. The reaction mixture was diluted with ethyl acetate, washed with saturated aqueous sodium chloride, water, and saturated aqueous sodium chloride in this order, then dried over anhydrous magnesium sulfate, and concentrated to obtain the title compound (28.42 g).

¹H NMR (CDCl₃, 400 MHz): δ (ppm) 8.41 (dd, J=8.8, 0.8 Hz, 1H), 7.95 (d, J=8.5 Hz, 1H), 7.68 (dd, J=8.4, 7.2 Hz, 1H), 7.56 (dd, J=7.2, 1.1 Hz, 1H), 7.41 (d, J=8.8 Hz, 1H), 5.12 (s, 2H), 0.92 (s, 9H), 0.10 (s, 6H)

MS (ESI⁺) m/z: 308 [M+H]⁺

Reference Example 139

5-(((tert-Butyldimethylsilyl)oxy)methyl)-2-hydrazinylquinoline

[Formula 142]

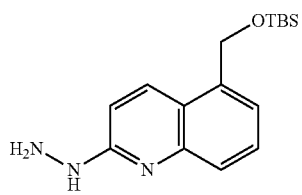

A mixture of the compound (28.42 g) obtained in Reference Example 138, hydrazine monohydrate (134 mL), and 1,4-dioxane (134 mL) was stirred at 80° C. for 48 hours. The reaction mixture was cooled to room temperature, and water was added thereto, followed by extraction with chloroform. The organic layer was washed with water, dried over anhydrous magnesium sulfate, and then concentrated to obtain the title compound (27.27 g).

¹H NMR (CDCl₃, 400 MHz): δ (ppm) 8.19 (dd, J=9.3, 0.8 Hz, 1H), 7.67 (d, J=8.0 Hz, 1H), 7.52 (dd, J=8.3, 7.0 Hz, 1H), 7.29 (dd, J=7.2, 1.1 Hz, 1H), 6.84 (d, J=9.0 Hz, 1H), 5.06 (s, 2H), 0.91 (s, 9H), 0.08 (s, 6H)

MS (ESI⁺) m/z: 304 [M+H]⁺

Reference Example 140

5-(((tert-Butyldimethylsilyl)oxy)methyl)quinolin-2-amine

[Formula 143]

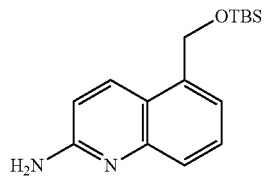

To the compound (27.27 g) obtained in Reference Example 139, Raney nickel (R-200 manufactured by Nikko Rica Corp., 36 mL) and methanol (715 mL) were added, and the mixture was stirred at room temperature for 48 hours under a hydrogen atmosphere. The reaction mixture was filtered through Hyflo Super Cel (manufactured by Nacalai Tesque, Inc.), and the filtrate was concentrated to obtain the title compound (24.92 g).

¹H NMR (CDCl₃, 400 MHz): δ (ppm) 8.20 (d, J=9.0 Hz, 1H), 7.58-7.63 (m, 1H), 7.48-7.54 (m, 1H), 7.26-7.29 (m, 1H), 6.74 (d, J=9.0 Hz, 1H), 5.06 (s, 2H), 4.77 (br. s., 2H), 0.91 (s, 9H), 0.08 (s, 6H)

MS (ESI⁺) m/z: 289 [M+H]⁺

Reference Example 141

7-Acetyl-N-(5-(((tert-butyldimethylsilyl)oxy)methyl)quinolin-2-yl)-4-(methoxymethyl)-3-methylbenzo[b]thiophene-2-carboxamide

[Formula 144]

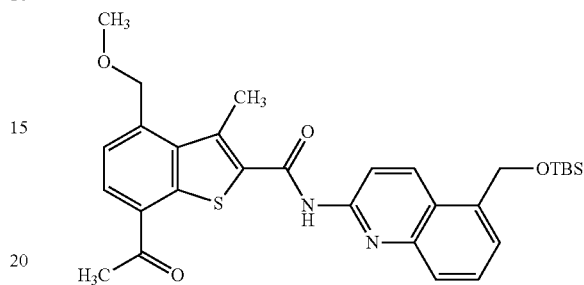

To a suspension of the compound (5.56 g) obtained in Reference Example 74, the compound (5.76 g) obtained in Reference Example 140, and HBTU (11.36 g) in dichloromethane (106 mL) N,N-diisopropylethylamine (10.44 mL) was added, and the mixture was stirred at room temperature for 68.5 hours. To the reaction mixture, water was added, followed by extraction with chloroform. The organic layer was dried over anhydrous magnesium sulfate and concentrated. The residue was purified by silica gel column chromatography (chloroform:ethyl acetate=100:0-90:10), and the obtained solid was washed with 2-propanol to obtain the title compound (8.906 g).

¹H NMR (CDCl₃, 400 MHz): δ (ppm) 8.71 (br. s., 1H), 8.48-8.56 (m, 2H), 8.10 (d, J=7.8 Hz, 1H), 7.77-7.83 (m, 1H), 7.63 (d, J=7.8 Hz, 2H), 7.50 (d, J=7.3 Hz, 1H), 5.16 (s, 2H), 5.01 (s, 2H), 3.53 (s, 3H), 3.01 (s, 3H), 2.79 (s, 3H), 0.94 (s, 9H), 0.12 (s, 6H)

MS (ESI⁺) m/z: 549 [M+H]⁺

Reference Example 142

(S)-(2-(7-Acetyl-4-(methoxymethyl)-3-methylbenzo[b]thiophene-2-carboxamido)quinolin-5-yl)methyl-2-((tert-butoxycarbonyl)amino)-3-methylbutanoate

[Formula 145]

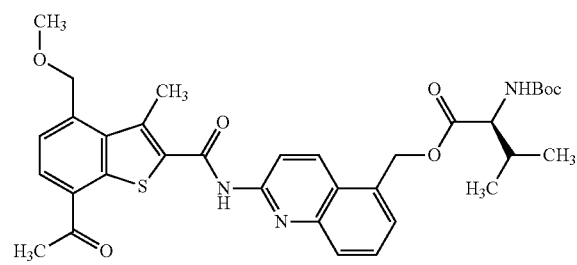

A solution of the compound (150 mg) obtained in Example 79, N-(tert-butoxycarbonyl)-L-valine (90 mg), and N,N-dimethyl-4-aminopyridine (93 mg) in DMF (4 mL) was cooled to 0° C. 1-Ethyl-3-(3-dimethylaminopropyl)carbodiimide hydrochloride (79 mg) was added thereto, and the mixture was stirred overnight at room temperature. The reaction mixture was diluted with ethyl acetate and washed with water. The organic layer was dried over anhydrous sodium sulfate and concentrated. The residue was purified by silica gel column chromatography (hexane:ethyl acetate=70:30-50:50) to obtain the title compound (188 mg).

$^1$H NMR (CDCl$_3$, 400 MHz): δ (ppm) 8.73 (s, 1H), 8.59 (d, J=9.0 Hz, 1H), 8.42 (d, J=9.0 Hz, 1H), 8.10 (d, J=7.8 Hz, 1H), 7.89 (d, J=8.3 Hz, 1H), 7.62-7.68 (m, 2H), 7.51-7.55 (m, 1H), 5.52-5.70 (m, 2H), 5.01 (s, 2H), 3.53 (s, 3H), 3.01 (s, 3H), 2.79 (s, 3H), 2.05-2.15 (m, 1H), 1.55 (s, 9H), 1.44 (s, 6H)

MS (ESI$^+$) m/z: 634 [M+H]$^+$

Reference Example 143

(2-(7-Acetyl-4-(methoxymethyl)-3-methylbenzo[b]thiophene-2-carboxamido)quinolin-5-yl)methyl-2-((tert-butoxycarbonyl)amino)acetate

[Formula 146]

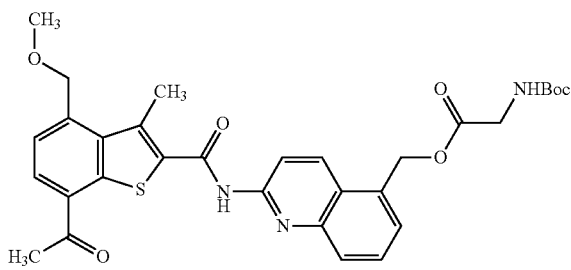

To a solution of the compound (120 mg) obtained in Example 79, N-(tert-butoxycarbonyl)-glycine (58.1 mg), and N,N-dimethyl-4-aminopyridine (74.2 mg) in DMF (4 mL), 1-ethyl-3-(3-dimethylaminopropyl)carbodiimide hydrochloride (63.5 mg) was added, and the mixture was stirred overnight at room temperature. The reaction mixture was diluted with chloroform and washed with water. The organic layer was dried over anhydrous sodium sulfate and concentrated. The residue was purified by silica gel column chromatography (hexane:ethyl acetate=60:40-40:60) to obtain the title compound (151 mg).

$^1$H NMR (CDCl$_3$, 400 MHz): δ (ppm) 8.73 (br. s., 1H), 8.58 (d, J=9.0 Hz, 1H), 8.42 (d, J=9.3 Hz, 1H), 8.10 (d, J=7.8 Hz, 1H), 7.89 (d, J=8.5 Hz, 1H), 7.62-7.68 (m, 2H), 7.53 (d, J=6.8 Hz, 1H), 5.63 (s, 2H), 5.01 (s, 2H), 3.93-3.98 (m, 2H), 3.53 (s, 3H), 3.01 (s, 3H), 2.79 (s, 3H), 1.44 (s, 9H)

MS (ESI$^+$) m/z: 592 [M+H]$^+$

Reference Example 144

(S)-(2-(7-Acetyl-4-(methoxymethyl)-3-methylbenzo[b]thiophene-2-carboxamido)quinolin-5-yl)methyl-2-((tert-butoxycarbonyl)amino)propanoate

[Formula 147]

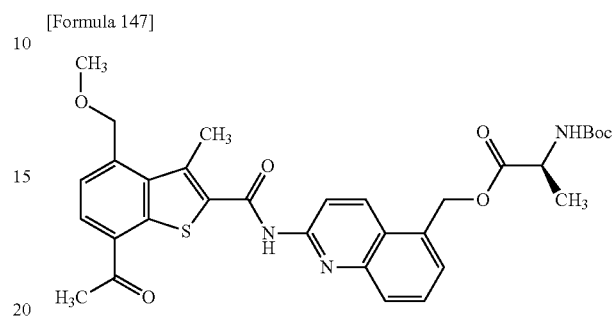

To a solution of the compound (120 mg) obtained in Example 79, N-(tert-butoxycarbonyl)-L-alanine (62.7 mg), and N,N-dimethyl-4-aminopyridine (74.2 mg) in DMF (4 mL), 1-ethyl-3-(3-dimethylaminopropyl)carbodiimide hydrochloride (63.5 mg) was added, and the mixture was stirred overnight at room temperature. The reaction mixture was diluted with ethyl acetate and washed with water. The organic layer was dried over anhydrous sodium sulfate and concentrated. The residue was purified by silica gel column chromatography (hexane:ethyl acetate=55:45-35:65) to obtain the title compound (159 mg).

$^1$H NMR (CDCl$_3$, 400 MHz): δ (ppm) 8.73 (s, 1H), 8.59 (d, J=9.3 Hz, 1H), 8.41 (d, J=9.0 Hz, 1H), 8.10 (d, J=7.5 Hz, 1H), 7.89 (d, J=8.3 Hz, 1H), 7.62-7.68 (m, 2H), 7.53 (d, J=5.5 Hz, 1H), 5.53-5.69 (m, 2H), 5.01 (s, 2H), 4.36 (br. s., 1H), 3.53 (s, 3H), 3.01 (s, 3H), 2.79 (s, 3H), 1.43 (s, 9H), 1.36 (d, J=7.0 Hz, 3H)

MS (ESI$^+$) m/z: 606 [M+H]$^+$

Reference Example 145

(2-(7-Acetyl-4-(methoxymethyl)-3-methylbenzo[b]thiophene-2-carboxamido)quinolin-5-yl)methyl di-tert-butylphosphate

[Formula 148]

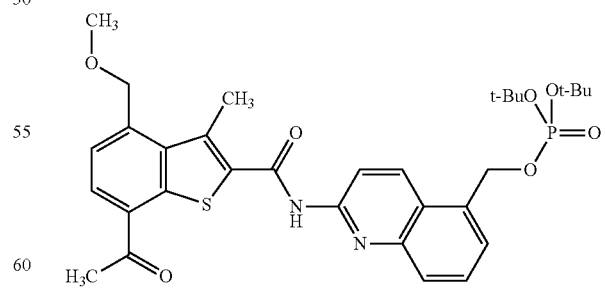

To a solution of the compound (200 mg) obtained in Example 79 in DMF (5 mL), 1H-tetrazole (70.9 mg) and di-tert-butyl N,N-diisopropylphosphoramidite (183 μL) were added, and the mixture was stirred overnight at room temperature. To the reaction mixture, 1H-tetrazole (70.9 mg)

and di-tert-butyl N,N-diisopropylphosphoramidite (183 µL) were added, and the mixture was stirred at room temperature for 2 hours. The reaction mixture was diluted with ethyl acetate and washed with a saturated aqueous solution of sodium bicarbonate. The organic layer was dried over anhydrous sodium sulfate and concentrated. To the residue, chloroform (5 mL) was added, and the mixture was cooled to −40° C. 3-Chloroperbenzoic acid (content: 75%, 138 mg) was added thereto, and the temperature of the mixture was gradually raised to room temperature, followed by stirring overnight. To the reaction mixture, a saturated aqueous solution of sodium bicarbonate was added, followed by extraction with chloroform. The organic layer was dried over anhydrous sodium sulfate and concentrated. The residue was purified by silica gel column chromatography (chloroform:methanol=99.5:0.5-97:3) to obtain the title compound (158 mg).

$^1$H NMR (CDCl$_3$, 400 MHz): δ (ppm) 8.73 (s, 1H), 8.57 (s, 2H), 8.10 (d, J=7.8 Hz, 1H), 7.87 (d, J=8.3 Hz, 1H), 7.61-7.68 (m, 2H), 7.53 (d, J=6.3 Hz, 1H), 5.42 (d, J=7.3 Hz, 2H), 5.01 (s, 2H), 3.53 (s, 3H), 3.01 (s, 3H), 2.79 (s, 3H), 1.47 (s, 18H)

MS (ESI$^+$) m/z: 627 [M+H]$^+$

Reference Example 146

(S)-(2-(7-Acetyl-4-(methoxymethyl)-3-methylbenzo[b]thiophene-2-carboxamido)quinolin-5-yl)methyl-3-(tert-butoxy)-2-((tert-butoxycarbonyl)amino)propanoate

[Formula 149]

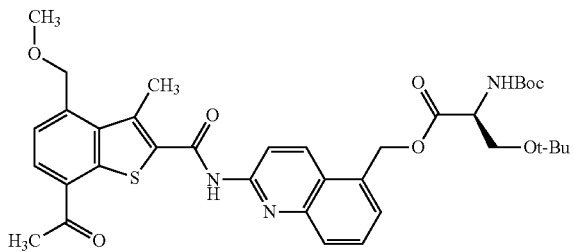

To a solution of the compound (220 mg) obtained in Example 79, N-(tert-butoxycarbonyl)-O-tert-butyl-L-serine (159 mg), and N,N-dimethyl-4-aminopyridine (136 mg) in DMF (5 mL), 1-ethyl-3-(3-dimethylaminopropyl)carbodiimide hydrochloride (116 mg) was added, and the mixture was stirred overnight at room temperature. The reaction mixture was diluted with ethyl acetate and washed with a saturated aqueous solution of sodium bicarbonate and saturated aqueous sodium chloride in this order. The organic layer was dried over anhydrous sodium sulfate and concentrated. The residue was purified by silica gel column chromatography (hexane:ethyl acetate=75:25-20:80) to obtain the title compound (273 mg).

$^1$H NMR (CDCl$_3$, 400 MHz): δ (ppm) 8.71 (s, 1H), 8.58 (d, J=9.3 Hz, 1H), 8.44 (d, J=9.3 Hz, 1H), 8.10 (d, J=7.8 Hz, 1H), 7.88 (d, J=8.5 Hz, 1H), 7.62-7.67 (m, 2H), 7.52-7.55 (m, 1H), 5.65-5.70 (m, 1H), 5.52-5.57 (m, 1H), 5.35-5.39 (m, 1H), 5.01 (s, 2H), 4.40-4.47 (m, 1H), 3.73-3.77 (m, 1H), 3.50-3.56 (m, 1H), 3.53 (s, 3H), 3.01 (s, 3H), 2.79 (s, 3H), 1.44 (s, 9H), 0.95-1.05 (s, 9H)

Reference Example 147

5-(Methoxycarbonyl)quinoline-1-oxide

[Formula 150]

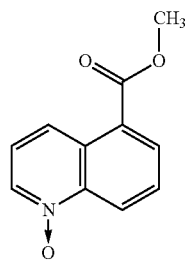

A solution of methyl quinoline-5-carboxylate (21.2 g) in chloroform (200 mL) was cooled to 0° C. 3-Chloroperbenzoic acid (content: 75%, 31.3 g) was added thereto, and the mixture was stirred overnight at room temperature. To the reaction mixture, an aqueous sodium thiosulfate solution and an aqueous potassium carbonate solution were added, followed by extraction with chloroform. The organic layer was dried over anhydrous sodium sulfate and concentrated to obtain the title compound (19.7 g).

$^1$H NMR (CDCl$_3$, 400 MHz): δ (ppm) 9.05 (d, J=8.9 Hz, 1H), 8.93 (d, J=8.9 Hz, 1H), 8.57 (d, J=6.1 Hz, 1H), 8.38 (dd, J=7.3, 1.2 Hz, 1H), 7.80 (dd, J=8.9, 7.3 Hz, 1H), 7.41 (dd, J=8.9, 6.1 Hz, 1H), 4.02 (s, 3H)

MS (ESI$^+$) m/z: 204 [M+H]$^+$

Reference Example 148

Methyl 2-aminoquinoline-5-carboxylate

[Formula 151]

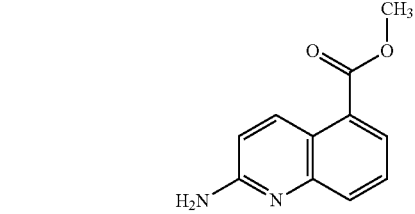

A solution of the compound (2.03 g) obtained in Reference Example 147 in trifluoromethylbenzene/chloroform (30 mL/10 mL) was cooled to 0° C. To the solution, tert-Butylamine (5.25 mL) was added, then p-toluenesulfonic anhydride (6.53 g) was added, and the mixture was stirred at 0° C. for 30 minutes. To the reaction mixture, TFA (20 mL) was added at the same temperature as above, and the mixture was stirred at 85° C. for 2 hours and stirred at 90° C. for 2 hours. The reaction mixture was cooled to room temperature and concentrated. To the residue, a 2 N aqueous sodium hydroxide solution was added, followed by extraction with chloroform. The organic layer was dried over anhydrous sodium sulfate and concentrated. The residue was purified by silica gel column chromatography (dichloromethane:methanol=97:3-90:10) to obtain the title compound (1.26 g).

$^1$H NMR (CDCl$_3$, 400 MHz): δ (ppm) 9.05 (d, J=9.3 Hz, 1H), 7.97 (dd, J=7.3, 1.2 Hz, 1H), 7.84 (dt, J=8.3, 1.1 Hz, 1H), 7.57 (dd, J=8.3, 7.5 Hz, 1H), 6.84 (d, J=9.3 Hz, 1H), 4.80 (br. s., 2H), 3.98 (s, 3H)

MS (ESI$^+$) m/z: 203 [M+H]$^+$

Reference Example 149

(2-Chloroquinolin-5-yl)(morpholino)methanone

[Formula 152]

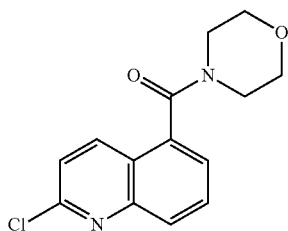

To a solution of 2-chloroquinoline-5-carboxylic acid (150 mg) in chloroform (5 mL), N,N-diisopropylethylamine (252 µL), HBTU (301 mg), and morpholine (69.5 µL) were added, and the mixture was stirred overnight at room temperature. The reaction mixture was diluted with chloroform and washed with a 1 N aqueous sodium hydroxide solution. The organic layer was dried over anhydrous sodium sulfate and concentrated. The residue was purified by silica gel column chromatography (chloroform:methanol=98:2) to obtain the title compound (211 mg).

$^1$H NMR (CDCl$_3$, 400 MHz): δ (ppm) 8.19 (dd, J=8.8, 0.8 Hz, 1H), 8.08 (dt, J=8.5, 1.0 Hz, 1H), 7.76 (dd, J=8.5, 7.0 Hz, 1H), 7.50 (dd, J=7.2, 1.1 Hz, 1H), 7.46 (d, J=9.0 Hz, 1H), 3.81-4.01 (m, 4H), 3.47-3.64 (m, 2H), 3.16-3.34 (m, 2H)

MS (ESI$^+$) m/z: 277 [M+H]$^+$

Reference Example 150

(2-Chloroquinolin-5-yl)(4-methylpiperazin-1-yl)methanone

[Formula 153]

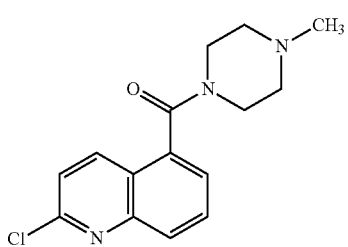

To a solution of 2-chloroquinoline-5-carboxylic acid (150 mg) in chloroform (5 mL), N,N-diisopropylethylamine (252 µL) and HBTU (301 mg) were added, and the mixture was stirred at room temperature for 15 minutes. Then, 1-methylpiperazine (88.2 µL) was added thereto, and the mixture was stirred overnight at room temperature. To the reaction mixture, a 1 N aqueous sodium hydroxide solution was added, followed by extraction with chloroform. The organic layer was dried over anhydrous sodium sulfate and concentrated. The residue was purified by silica gel column chromatography (chloroform:methanol=99:1-95:5) to obtain the title compound (220 mg).

$^1$H NMR (CDCl$_3$, 400 MHz): δ (ppm) 8.18 (dd, J=8.8, 1.0 Hz, 1H), 8.07 (dt, J=8.4, 1.1 Hz, 1H), 7.75 (dd, J=8.5, 7.0 Hz, 1H), 7.49 (dd, J=7.2, 1.1 Hz, 1H), 7.45 (d, J=8.8 Hz, 1H), 3.83-4.04 (m, 2H), 3.15-3.31 (m, 2H), 2.48-2.63 (m, 2H), 2.29-2.34 (m, 1H), 2.32 (s, 3H), 2.21 (br. s., 1H)

MS (ESI$^+$) m/z: 290 [M+H]$^+$

Reference Example 151

2-Chloro-N,N-dimethylquinoline-5-carboxamide

[Formula 154]

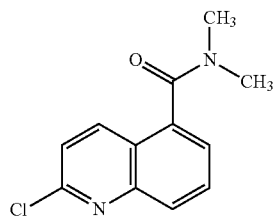

To 2-hydroxyquinoline-5-carboxylic acid (1.51 g), phosphorus oxychloride (5.14 g) was added, and the mixture was stirred at 120° C. for 3 hours. The reaction mixture was concentrated. To the residue, dimethylamine hydrochloride (0.98 g) and chloroform (15 mL) were added at room temperature under an argon atmosphere, and then, triethylamine (12.6 mL) was added dropwise. The reaction mixture was stirred at room temperature for 2 hours. Then, dimethylamine hydrochloride (1.0 g) was added thereto, and the mixture was stirred at room temperature for 14 hours. To the reaction mixture, water was added, followed by extraction with chloroform. The organic layer was dried over anhydrous magnesium sulfate and concentrated. The residue was purified by silica gel column chromatography (chloroform:ethyl acetate=100:0-80:20). To the obtained solid, 2-propanol (8.48 mL) was added, and the mixture was heated to 80° C. and then cooled to 0° C. The precipitated solid was collected by filtration and washed with 2-propanol to obtain the title compound (1.450 g).

$^1$H NMR (CDCl$_3$, 400 MHz): δ (ppm) 8.15 (dd, J=8.8, 1.0 Hz, 1H), 8.06 (dt, J=8.5, 1.0 Hz, 1H), 7.75 (dd, J=8.5, 7.0 Hz, 1H), 7.49-7.53 (m, 1H), 7.43 (d, J=8.8 Hz, 1H), 3.25 (s, 3H), 2.85 (s, 3H)

MS (ESI$^+$) m/z: 235 [M+H]$^+$

Reference Example 152

2-Amino-N,N-dimethylquinoline-5-carboxamide

[Formula 155]

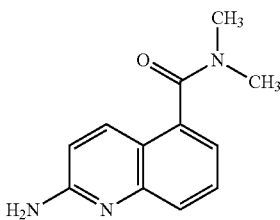

To the compound (1.449 g) obtained in Reference Example 151, hydrazine monohydrate (7.25 mL) and 1,4-dioxane (7.25 mL) were added, and the mixture was stirred at 82° C. for 24 hours. The reaction mixture was cooled to room temperature, and saturated aqueous sodium chloride was added thereto, followed by extraction with chloroform. The organic layer was dried over anhydrous magnesium sulfate and concentrated. To the residue, Raney nickel (R-200 manufactured by Nikko Rica Corp., 1.3 mL) and methanol (25 mL) were added, and the mixture was stirred at room temperature for 51.5 hours under a hydrogen atmosphere. The reaction mixture was filtered through Hyflo Super Cel (manufactured by Nacalai Tesque, Inc.), and the filtrate was concentrated to obtain the title compound (1.268 g).

$^1$H NMR (CDCl$_3$, 400 MHz): δ (ppm) 7.87-7.91 (m, 1H), 7.67 (dt, J=8.3, 1.0 Hz, 1H), 7.55 (dd, J=8.5, 7.0 Hz, 1H), 7.18 (dd, J=7.2, 1.1 Hz, 1H), 6.75 (d, J=8.8 Hz, 1H), 4.79 (br. s., 2H), 3.22 (s, 3H), 2.84 (s, 3H)

MS (ESI$^+$) m/z: 216 [M+H]$^+$

Reference Example 153

2-Chloroquinoline-5-carbonyl chloride

[Formula 156]

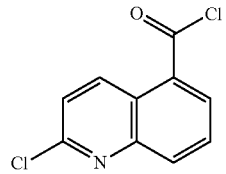

A mixture of 2-chloroquinoline-5-carboxylic acid (2.08 g), thionyl chloride (1.46 mL), and DMF (50 μL) was stirred at 60° C. for 6 hours. The reaction mixture was concentrated to obtain the title compound (2.24 g).

Reference Example 154

Azetidin-1-yl (2-chloroquinolin-5-yl)methanone

[Formula 157]

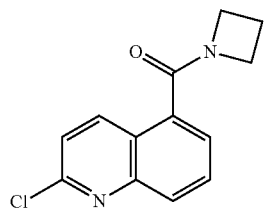

A suspension of the compound (452 mg) obtained in Reference Example 153 in chloroform (5 mL) was cooled to 0° C. Tetrabutylammonium bromide (129 mg), potassium carbonate (553 mg), and azetidine (126 mg) were added thereto, and the mixture was stirred at 0° C. for 1 hour and then stirred at room temperature for 24 hours. To the reaction mixture, water was added, followed by extraction with dichloromethane. The organic layer was dried over anhydrous sodium sulfate and concentrated. The residue was purified by basic silica gel column chromatography (hexane:dichloromethane=60:40-40:60) to obtain the title compound (352 mg).

$^1$H NMR (CDCl$_3$, 400 MHz): δ (ppm) 8.56 (dd, J=8.8, 0.8 Hz, 1H), 8.06-8.10 (m, 1H), 7.73 (dd, J=8.5, 7.0 Hz, 1H), 7.60 (dd, J=7.2, 1.1 Hz, 1H), 7.46 (d, J=8.8 Hz, 1H), 4.32 (t, J=7.8 Hz, 2H), 4.01 (t, J=7.8 Hz, 2H), 2.30-2.41 (m, 2H)

MS (ESI$^+$) m/z: 247 [M+H]$^+$

Reference Example 155

(2-Aminoquinolin-5-yl)(azetidin-1-yl)methanone

[Formula 158]

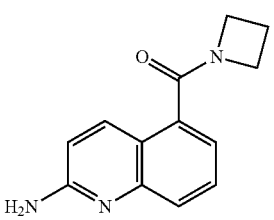

To the compound (345 mg) obtained in Reference Example 154, hydrazine monohydrate (1.36 mL), 1,4-dioxane (2 mL), and water (1 mL) were added, and the mixture was stirred at 70° C. for 18 hours. To the reaction mixture, water was added, followed by extraction with dichloromethane. The organic layer was dried over anhydrous sodium sulfate and concentrated. To the residue, methanol (10 mL) and Raney nickel (Raney 2400 manufactured by W.R. Grace and Co., 0.5 mL) were added, and the mixture was stirred at room temperature for 18 hours under a hydrogen atmosphere. The reaction mixture was filtered, and the filtrate was concentrated to obtain the title compound (245 mg).

$^1$H NMR (CDCl$_3$, 400 MHz): δ (ppm) 8.28 (dd, J=9.0, 0.8 Hz, 1H), 7.68-7.71 (m, 1H), 7.53 (dd, J=8.4, 7.2 Hz, 1H), 7.28 (dd, J=7.2, 1.1 Hz, 1H), 6.78 (d, J=9.3 Hz, 1H), 4.81 (br. s., 2H), 4.29 (t, J=7.9 Hz, 2H), 3.97 (t, J=7.7 Hz, 2H), 2.27-2.36 (m, 2H)

MS (ESI$^+$) m/z: 228 [M+H]$^+$

Reference Example 156

(2-Chloroquinolin-5-yl)(3-fluoroazetidin-1-yl)methanone

[Formula 159]

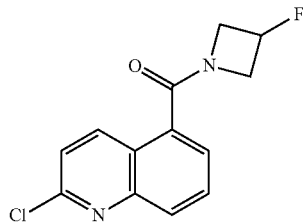

A suspension of the compound (497 mg) obtained in Reference Example 153 in chloroform (6 mL) was cooled to 0° C. Tetrabutylammonium bromide (129 mg), potassium carbonate (829 mg), and 3-fluoroazetidine hydrochloride (223 mg) were added thereto, and the mixture was stirred at 0° C. for 10 minutes and then stirred at room temperature for 39 hours. To the reaction mixture, water was added, followed by extraction with dichloromethane. The organic layer was dried over anhydrous sodium sulfate and concentrated. The residue was purified by basic silica gel column chromatography (hexane:dichloromethane=60:40-50:50) to obtain the title compound (447 mg).

$^1$H NMR (CDCl$_3$, 400 MHz): δ (ppm) 8.58 (dd, J=9.0, 0.8 Hz, 1H), 8.10-8.13 (m, 1H), 7.74 (dd, J=8.4, 7.2 Hz, 1H), 7.62 (dd, J=7.2, 1.1 Hz, 1H), 7.48 (d, J=8.8 Hz, 1H), 5.27-5.48 (m, 1H), 4.49-4.67 (m, 1H), 4.32-4.48 (m, 1H), 4.08-4.31 (m, 2H)

MS (ESI$^+$) m/z: 265 [M+H]$^+$

Reference Example 157

(2-Aminoquinolin-5-yl)(3-fluoroazetidin-1-yl)methanone

[Formula 160]

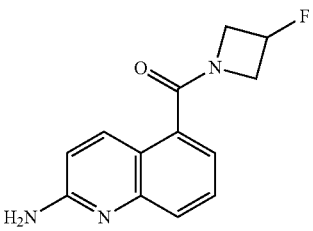

To the compound (440 mg) obtained in Reference Example 156, hydrazine monohydrate (1.62 mL), 1,4-dioxane (2 mL), and water (1 mL) were added, and the mixture was stirred at 60° C. for 36 hours. To the reaction mixture, water was added, followed by extraction with dichloromethane. The organic layer was dried over anhydrous sodium sulfate and concentrated. To the residue, methanol (10 mL) and Raney nickel (Raney 2400 manufactured by W.R. Grace and Co., 0.5 mL) were added, and the mixture was stirred at room temperature for 18 hours under a hydrogen atmosphere. The reaction mixture was filtered, and the filtrate was concentrated to obtain the title compound (140 mg).

$^1$H NMR (CDCl$_3$, 400 MHz): δ (ppm) 8.28 (dd, J=9.0, 0.8 Hz, 1H), 7.73 (dt, J=8.5, 0.9 Hz, 1H), 7.52-7.57 (m, 1H), 7.29 (dd, J=7.3, 1.3 Hz, 1H), 6.79 (d, J=9.3 Hz, 1H), 5.25-5.45 (m, 1H), 4.84 (br. s., 2H), 4.47-4.63 (m, 1H), 4.29-4.45 (m, 1H), 4.04-4.27 (m, 2H)

MS (ESI$^+$) m/z: 246 [M+H]$^+$

Reference Example 158

(2-Chloroquinolin-5-yl)(3,3-difluoroazetidin-1-yl)methanone

[Formula 161]

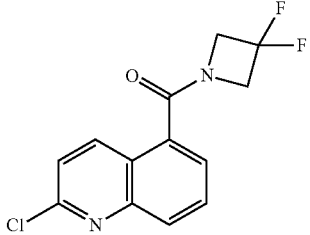

A suspension of the compound (452 mg) obtained in Reference Example 153 in chloroform (6 mL) was cooled to 0° C. Tetrabutylammonium bromide (129 mg), potassium carbonate (829 mg), and 3,3-difluoroazetidine hydrochloride (285 mg) were added thereto, and the mixture was stirred at 0° C. for 30 minutes and then stirred at room temperature for 42 hours. To the reaction mixture, water was added, followed by extraction with dichloromethane. The organic layer was dried over anhydrous sodium sulfate and concentrated. The residue was purified by basic silica gel column chromatography (hexane:dichloromethane=65:35-55:45) to obtain the title compound (477 mg).

$^1$H NMR (CDCl$_3$, 400 MHz): δ (ppm) 8.59 (dd, J=8.8, 0.8 Hz, 1H), 8.13-8.16 (m, 1H), 7.76 (dd, J=8.4, 7.2 Hz, 1H), 7.65 (dd, J=7.3, 1.3 Hz, 1H), 7.50 (d, J=9.0 Hz, 1H), 4.60 (br. s., 2H), 4.34 (br. s., 2H)

MS (ESI$^+$) m/z: 283 [M+H]$^+$

Reference Example 159

(2-Aminoquinolin-5-yl)(3,3-difluoroazetidin-1-yl)methanone

[Formula 162]

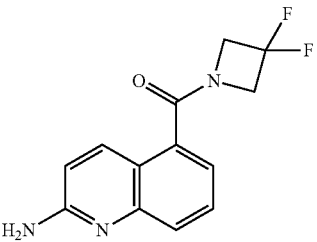

To the compound (470 mg) obtained in Reference Example 158, hydrazine monohydrate (1.62 mL), 1,4-dioxane (2 mL), and water (1 mL) were added, and the mixture was stirred at 50° C. for 60 hours. To the reaction mixture, water was added, followed by extraction with dichloromethane. The organic layer was dried over anhydrous sodium sulfate and concentrated. To the residue, methanol (10 mL) and Raney nickel (Raney 2400 manufactured by W.R. Grace and Co., 0.5 mL) were added, and the mixture was stirred at room temperature for 18 hours under a hydrogen atmosphere. The reaction mixture was filtered, and the filtrate was concentrated to obtain the title compound (357 mg).

$^1$H NMR (CDCl$_3$, 400 MHz): δ (ppm) 8.31 (d, J=9.0 Hz, 1H), 7.76 (d, J=8.3 Hz, 1H), 7.56 (dd, J=8.4, 7.2 Hz, 1H), 7.33 (dd, J=7.3, 1.0 Hz, 1H), 6.82 (d, J=9.0 Hz, 1H), 4.93 (br. s., 2H), 4.57 (br. s., 2H), 4.29 (br. s., 2H)

MS (ESI$^+$) m/z: 264 [M+H]$^+$

Reference Example 160

(2-Chloroquinolin-5-yl)(3-methoxyazetidin-1-yl)methanone

[Formula 163]

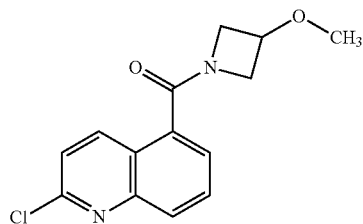

To a mixture of 2-chloroquinoline-5-carboxylic acid (1.84 g), 3-methoxyazetidine hydrochloride (1.20 g), HBTU (3.69 g), and chloroform (80 mL), N,N-diisopropylethylamine (4.64 mL) was added, and the mixture was stirred at room temperature for 24 hours. To the reaction mixture, a 1 N aqueous sodium hydroxide solution was added, followed by extraction with chloroform. The organic layer was dried over anhydrous magnesium sulfate and concentrated. The residue was purified by silica gel column chromatography (chloroform:methanol=100:0-95:5) to obtain the title compound (2.215 g).

$^1$H NMR (CDCl$_3$, 400 MHz): δ (ppm) 8.55 (dd, J=8.9, 0.9 Hz, 1H), 8.07-8.11 (m, 1H), 7.71-7.76 (m, 1H), 7.60 (dd, J=7.0, 1.3 Hz, 1H), 7.46 (d, J=9.0 Hz, 1H), 4.42-4.49 (m, 1H), 4.22-4.28 (m, 1H), 4.07-4.19 (m, 2H), 3.86-3.91 (m, 1H), 3.30 (s, 3H)

MS (ESI$^+$) m/z: 277 [M+H]$^+$

Reference Example 161

(2-Hydrazinylquinolin-5-yl)(3-methoxyazetidin-1-yl)methanone

[Formula 164]

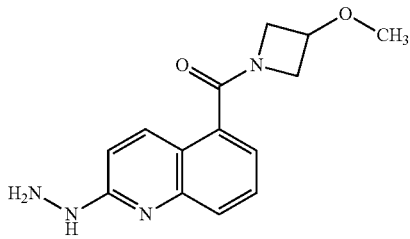

To the compound (2.215 g) obtained in Reference Example 160, 80% hydrazine monohydrate (11 mL) and 1,4-dioxane (11 mL) were added, and the mixture was stirred at 60° C. for 22 hours. To the reaction mixture, water was added, followed by extraction with chloroform. The organic layer was dried over anhydrous magnesium sulfate and concentrated to obtain the title compound (1.82 g).

$^1$H NMR (CDCl$_3$, 400 MHz): δ (ppm) 8.23 (dd, J=9.0, 0.8 Hz, 1H), 7.77-7.81 (m, 1H), 7.52-7.57 (m, 1H), 7.29 (dd, J=7.2, 1.1 Hz, 1H), 6.85 (d, J=9.3 Hz, 1H), 4.40-4.46 (m, 1H), 4.20-4.26 (m, 1H), 4.11-4.16 (m, 1H), 4.04-4.09 (m, 1H), 3.83-3.88 (m, 1H), 3.29 (s, 3H)

MS (ESI$^+$) m/z: 273 [M+H]$^+$

Reference Example 162

(2-Aminoquinolin-5-yl)(3-methoxyazetidin-1-yl)methanone

[Formula 165]

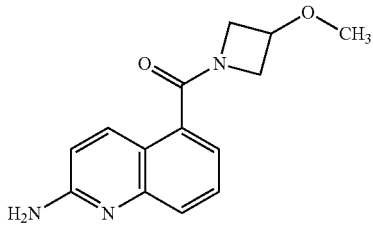

To the compound (1.82 g) obtained in Reference Example 161, methanol (36 mL) and Raney nickel (R-200 manufactured by Nikko Rica Corp., 2 mL) were added, and the mixture was stirred at room temperature for 5 days under a hydrogen atmosphere. The reaction mixture was filtered through Celite, and the filtrate was concentrated to obtain the title compound (1.27 g).

$^1$H NMR (CDCl$_3$, 400 MHz): δ (ppm) 8.26 (d, J=9.0 Hz, 1H), 7.71 (d, J=8.3 Hz, 1H), 7.51-7.56 (m, 1H), 7.29 (dd, J=7.2, 1.1 Hz, 1H), 6.79 (d, J=9.0 Hz, 1H), 4.85 (br. s., 2H), 4.39-4.47 (m, 1H), 4.20-4.27 (m, 1H), 4.04-4.16 (m, 2H), 3.84-3.90 (m, 1H), 3.29 (s, 3H)

MS (ESI$^+$) m/z: 258 [M+H]$^+$

Reference Example 163

5-Methylquinolin-2-amine

[Formula 166]

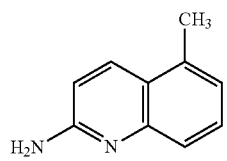

A mixture of the compound (194 mg) obtained in Reference Example 111 and p-methoxybenzylamine (523 µL) was stirred at 160° C. for 1 hour under a nitrogen atmosphere. The reaction mixture was cooled to room temperature and diluted with dichloromethane, and dry ice was then added thereto. The precipitated solid was filtered, and the filtrate was concentrated. To the residue, ethanol (6 mL), 6 N hydrochloric acid (1 mL), and ASCA2 catalyst (manufactured by N.E. Chemcat Corp., 40 mg) were added, and the mixture was stirred at room temperature for 24 hours under a hydrogen atmosphere. The reaction mixture was filtered, and the filtrate was concentrated. To the residue, TFA (3 mL) was added, and the mixture was stirred at room temperature for 45 minutes. The reaction mixture was cooled to 0° C., and water and a 4 N aqueous sodium hydroxide solution were added thereto, followed by extraction with dichloromethane. The organic layer was dried over anhydrous sodium sulfate and concentrated. The residue was purified by basic silica gel column chromatography (hexane:dichloromethane=30:70-10:90) to obtain the title compound (121 mg).

$^1$H NMR (CDCl$_3$, 400 MHz): δ (ppm) 8.08 (dd, J=9.0, 0.8 Hz, 1H), 7.50-7.55 (m, 1H), 7.41-7.47 (m, 1H), 7.08-7.11 (m, 1H), 6.74 (d, J=8.8 Hz, 1H), 4.74 (br. s., 2H), 2.60 (s, 3H)

MS (ESI$^+$) m/z: 159 [M+H]$^+$

Reference Example 164

5-((Methylsulfonyl)methyl)quinolin-2-amine

[Formula 167]

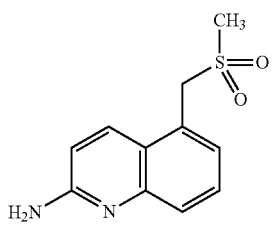

A mixture of the compound (100 mg) obtained in Reference Example 122, sodium methanesulfinate (132 mg), methanol (4 mL), and acetonitrile (4 mL) was stirred at 60° C. for 12 hours. The reaction mixture was cooled to room temperature and concentrated until its volume became approximately ⅓. To the residue, water (6 mL) and chloroform (2 mL) were added, and the mixture was stirred. The precipitated solid was collected by filtration to obtain the title compound (67 mg).

$^1$H NMR (DMSO, 400 MHz): δ (ppm) 8.21 (d, J=9.0 Hz, 1H), 7.45-7.48 (m, 2H), 7.22 (t, J=4.3 Hz, 1H), 6.79 (d, J=9.3 Hz, 1H), 6.45 (s, 2H), 4.87 (s, 2H), 2.98 (s, 3H)

Reference Example 165

Ethyl 7-acetyl-3-methyl-4-(((triisopropylsilyl)oxy)methyl)benzo[b]thiophene-2-carboxylate

[Formula 168]

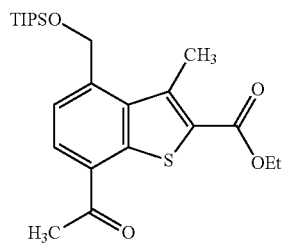

To a solution of the compound (391 mg) obtained in Reference Example 77 in DMF (4 mL), imidazole (182 mg) and triisopropylsilyl chloride (429 µL) were added, and the mixture was stirred overnight at room temperature. The reaction mixture was diluted with ethyl acetate and washed with water and saturated aqueous sodium chloride in this order. The organic layer was dried over anhydrous sodium sulfate and concentrated. The residue was purified by silica gel column chromatography (hexane:ethyl acetate=95:5-90:10) to obtain the title compound (591 mg).

$^1$H NMR (CDCl$_3$, 400 MHz): δ (ppm) 8.12 (d, J=7.8 Hz, 1H), 7.84 (d, J=7.8 Hz, 1H), 5.46 (s, 2H), 4.40 (q, J=7.2 Hz, 2H), 3.00 (s, 3H), 2.75 (s, 3H), 1.42 (t, J=7.0 Hz, 3H), 1.19-1.28 (m, 3H), 1.09-1.15 (m, 18H)

Reference Example 166

7-Acetyl-3-methyl-4-(((triisopropylsilyl)oxy)methyl)benzo[b]thiophene-2-carboxylic acid

[Formula 169]

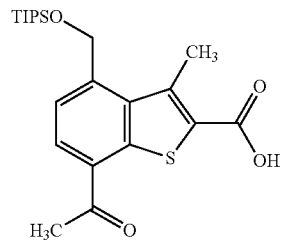

To a suspension of the compound (590 mg) obtained in Reference Example 165 in methanol (10 mL), a 1 N aqueous sodium hydroxide solution (1.97 mL) was added, and the mixture was stirred at room temperature for 3 hours. To the reaction mixture, THF (20 mL) was added, and the mixture was stirred overnight at room temperature. To the reaction mixture, 1 N hydrochloric acid (1.97 mL) was added, and the mixture was concentrated. To the residue, water was added, followed by extraction with chloroform. The organic layer was dried over anhydrous sodium sulfate and concentrated. The residue was purified by silica gel column chromatography (chloroform:methanol=99:1-94:6) to obtain the title compound (424 mg).

$^1$H NMR (CDCl$_3$, 400 MHz): δ (ppm) 8.14 (d, J=7.8 Hz, 1H), 7.85 (d, J=7.8 Hz, 1H), 5.46 (s, 2H), 3.02 (s, 3H), 2.76 (s, 3H), 1.19-1.29 (m, 3H), 1.10-1.15 (m, 18H)

MS (ESI$^+$) m/z: 421 [M+H]$^+$

Reference Example 167

7-Acetyl-N-(5-(methoxymethyl)quinolin-2-yl)-3-methyl-4-(((triisopropylsilyl)oxy)methyl)benzo[b]thiophene-2-carboxamide

[Formula 170]

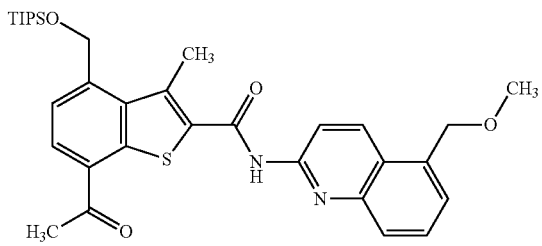

To a suspension of the compound (80 mg) obtained in Reference Example 166, the compound (46.5 mg) obtained in Reference Example 127, and HBTU (75.0 mg) in dichloromethane (5 mL), N,N-diisopropylethylamine (85 μL) was added, and the mixture was stirred at room temperature for 18 hours. To the reaction mixture, water was added, followed by extraction with ethyl acetate. The organic layer was washed with water and saturated aqueous sodium chloride in this order, dried over anhydrous sodium sulfate, and concentrated. The residue was purified by silica gel column chromatography (dichloromethane:methanol=100:0-97:3) to obtain the title compound (82.9 mg).

$^1$H NMR (CDCl$_3$, 400 MHz): δ (ppm) 8.71 (br. s., 1H), 8.53 (s, 2H), 8.15 (d, J=7.8 Hz, 1H), 7.90 (d, J=8.0 Hz, 1H), 7.84 (d, J=8.3 Hz, 1H), 7.63 (dd, J=8.5, 7.0 Hz, 1H), 7.45 (d, J=6.8 Hz, 1H), 5.48 (s, 2H), 4.89 (s, 2H), 3.45 (s, 3H), 2.97 (s, 3H), 2.78 (s, 3H), 1.19-1.31 (m, 3H), 1.11-1.15 (m, 18H)

Reference Example 168

7-Acetyl-N-(5-(((tert-butyldimethylsilyl)oxy)methyl)quinolin-2-yl)-3-methyl-4-(((triisopropylsilyl)oxy)methyl)benzo[b]thiophene-2-carboxamide

[Formula 171]

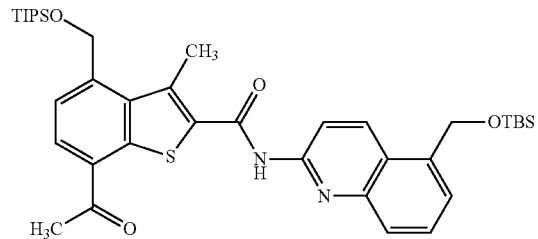

To a suspension of the compound (70 mg) obtained in Reference Example 166, the compound (48 mg) obtained in Reference Example 140, and HBTU (69 mg) in chloroform (4 mL), N,N-diisopropylethylamine (83 μL) was added, and the mixture was stirred at room temperature for 3 days. The reaction mixture was diluted with chloroform and washed with water. The organic layer was dried over anhydrous sodium sulfate and concentrated. The residue was purified by silica gel column chromatography (hexane:ethyl acetate=95:5-75:25) to obtain the title compound (87 mg).

$^1$H NMR (CDCl$_3$, 400 MHz): δ (ppm) 8.71 (br. s., 1H), 8.46-8.54 (m, 2H), 8.15 (d, J=8.0 Hz, 1H), 7.90 (d, J=7.8 Hz, 1H), 7.79 (d, J=8.0 Hz, 1H), 7.64 (dd, J=8.4, 7.2 Hz, 1H), 7.49 (d, J=6.8 Hz, 1H), 5.49 (s, 2H), 5.16 (s, 2H), 2.97 (s, 3H), 2.78 (s, 3H), 1.20-1.31 (m, 3H), 1.11-1.16 (m, 18H), 0.94 (s, 9H), 0.12 (s, 6H)

Reference Example 169

7-Acetyl-N-(5-((3-methoxyazetidin-1-yl)carbonyl)quinolin-2-yl)-3-methyl-4-(((triisopropylsilyl)oxy)methyl)benzo[b]thiophene-2-carboxamide

[Formula 172]

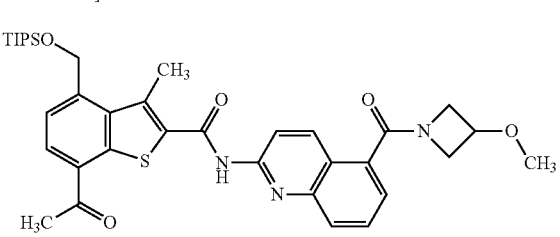

To a solution of the compound (105 mg) obtained in Reference Example 166 in chloroform (10 mL), N,N-diisopropylethylamine (109 μL) and HBTU (114 mg) were added at room temperature, and the mixture was stirred at room temperature for 20 minutes. To the reaction mixture, the compound (64.7 mg) obtained in Reference Example 162 was added, and the mixture was stirred at 50° C. for 2 days. The reaction mixture was cooled to room temperature, and a saturated aqueous solution of sodium bicarbonate was added thereto, followed by extraction with chloroform. The organic layer was dried over anhydrous sodium sulfate and concentrated. The residue was purified by silica gel column chromatography (chloroform:methanol=99.5:0.5-97:3) to obtain the title compound (145 mg).

$^1$H NMR (CDCl$_3$, 400 MHz): δ (ppm) 8.73 (s, 1H), 8.58 (s, 2H), 8.16 (d, J=7.8 Hz, 1H), 7.88-7.95 (m, 2H), 7.67 (dd, J=8.4, 7.2 Hz, 1H), 7.52 (dd, J=7.0, 1.0 Hz, 1H), 5.49 (s, 2H), 4.42-4.51 (m, 1H), 4.22-4.29 (m, 1H), 4.15-4.20 (m, 1H), 4.03-4.10 (m, 1H), 3.84-3.90 (m, 1H), 3.30 (s, 3H), 2.98 (s, 3H), 2.79 (s, 3H), 1.19-1.31 (m, 3H), 1.11-1.18 (m, 18H)

MS (ESI$^+$) m/z: 660 [M+H]$^+$

Reference Example 170

(4-Bromo-3-fluorophenyl)(1,1-²H₂) methanol

[Formula 184]

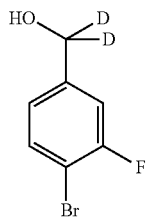

To a solution of methyl 4-bromo-3-fluorobenzoate (13.9 g) in 2-propanol (50 mL), a solution of (²H₄)sodium borohydride (4.96 g) in 2-propanol (50 mL) was added dropwise at room temperature, and the mixture was stirred at 70° C. for 5 hours. The reaction mixture was concentrated, and saturated aqueous sodium chloride was added to the residue, followed by extraction with ethyl acetate. The organic layer was dried over anhydrous sodium sulfate and concentrated. The residue was purified by silica gel column chromatography (hexane:ethyl acetate=100:0-60:40) to obtain the title compound (3.8 g).

$^1$H NMR (CDCl₃, 400 MHz): δ (ppm) 7.52 (dd, J=8.1, 7.3 Hz, 1H), 7.16 (dd, J=9.3, 1.6 Hz, 1H), 7.02 (dd, J=8.1, 2.0 Hz, 1H)

Reference Example 171

1-Bromo-2-fluoro-4-(methoxy(2H₂)methyl)benzene

[Formula 174]

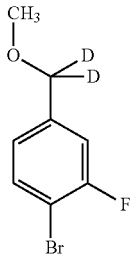

A solution of the compound (3.8 g) obtained in Reference Example 170 in dichloromethane (20 mL) was cooled to 0° C. To the solution, methanesulfonyl chloride (1.573 mL) was added dropwise, then triethylamine (2.81 mL) was added dropwise, and the mixture was stirred at 0° C. for 1 hour. To the reaction mixture, a saturated aqueous solution of sodium bicarbonate was added, followed by extraction with dichloromethane. The organic layer was dried over anhydrous sodium sulfate and concentrated. To the residue, sodium methoxide (1 M solution in methanol, 92 mL) was added dropwise at room temperature, and the mixture was stirred for 2 hours. To the reaction mixture, a saturated aqueous solution of sodium bicarbonate was added, followed by extraction with dichloromethane. The organic layer was washed with saturated aqueous sodium chloride, dried over anhydrous sodium sulfate, and then concentrated to obtain the title compound (3.5 g).

$^1$H NMR (CDCl₃, 400 MHz): δ (ppm) 7.51 (dd, J=8.1, 7.3 Hz, 1H), 7.13 (dd, J=9.1, 1.8 Hz, 1H), 6.99 (dd, J=8.1, 2.4 Hz, 1H), 3.39 (s, 3H)

Reference Example 172

1-(3-Bromo-2-fluoro-6-(methoxy(²H₂)methyl)phenyl)ethanone

[Formula 175]

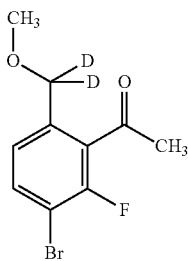

A solution of 2,2,6,6-tetramethylpiperidine (2.68 g) in THF (30 mL) was cooled to -75° C. under an argon stream. n-Butyllithium (1.59 M solution in hexane, 10.95 mL) was added dropwise thereto, and the mixture was stirred at the same temperature as above for 40 minutes. To the reaction mixture, a solution of the compound (3.5 g) obtained in Reference Example 171 in THF (20 mL) was added dropwise, and the mixture was stirred at the same temperature as above for 1 hour. To the reaction mixture, DMF (1.349 mL) was added dropwise, and the mixture was stirred at the same temperature as above for 1 hour. To the reaction mixture, acetic acid (10 mL) and water (50 mL) were added in this order, and the temperature of the mixture was raised to room temperature. The reaction mixture was subjected to extraction with ethyl acetate, and the organic layer was washed with a saturated aqueous solution of sodium bicarbonate and saturated aqueous sodium chloride in this order, then dried over anhydrous sodium sulfate, and concentrated. The residue was dissolved in THF (30 mL). The solution was added dropwise to methyl magnesium bromide (1 M solution in THF, 38.1 mL) cooled to 0° C., and the mixture was stirred at room temperature for 3 hours. To the reaction mixture, a saturated aqueous solution of ammonium chloride and water were added, followed by extraction with ethyl acetate. The organic layer was dried over anhydrous sodium sulfate and concentrated. To the residue, acetonitrile (20 mL), N-methylmorpholine-N-oxide (1.591 g), and tetrapropylammonium perruthenate (0.199 g) were added, and the mixture was stirred at room temperature for 45 minutes. The reaction mixture was washed with 0.1 N hydrochloric acid, dried over anhydrous sodium sulfate, and concentrated. The residue was purified by silica gel column chromatography (hexane:ethyl acetate=2:1) to obtain the title compound (2.4 g).

$^1$H NMR (CDCl₃, 400 MHz): δ (ppm) 7.57 (t, J=7.5 Hz, 1H), 7.11 (d, J=8.1 Hz, 1H), 3.35 (s, 3H), 2.56-2.60 (m, 3H)

Reference Example 173

Ethyl 4-(methoxy($^2H_2$)methyl)-3-methyl-7-((trimethylsilyl)ethynyl)benzo[b]thiophene-2-carboxylate

[Formula 176]

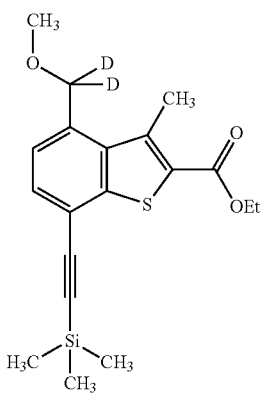

To a solution of the compound (2.4 g) obtained in Reference Example 172 and 1,8-diazabicyclo[5.4.0]-7-undecene (4.12 mL) in DMF (50 mL), ethyl thioglycolate (1.10 mL) was added dropwise, and the mixture was stirred at room temperature for 2 hours. To the reaction mixture, water (400 mL) was added, and the mixture was stirred at 0° C. for 1 hour. The precipitated solid was collected by filtration. The obtained solid was dissolved in ethyl acetate, and the reaction mixture was washed with saturated aqueous sodium chloride. The organic layer was dried over anhydrous sodium sulfate and concentrated. The residue was dissolved in THF (30 mL). To the solution, trimethylsilylacetylene (2.146 mL), tetrakis(triphenylphosphine)palladium(0) (0.221 g), triethylamine (2.66 mL), and copper(I) bromide (0.082 g) were then added, and the mixture was stirred at 80° C. for 12 hours under an argon atmosphere. The reaction mixture was filtered through Celite, and the filtrate was concentrated. The residue was purified by silica gel column chromatography (hexane:ethyl acetate=95:5-50:50) to obtain the title compound (2.8 g).

$^1$H NMR (CDCl$_3$, 400 MHz): δ (ppm) 7.49-7.52 (m, 1H), 7.33 (d, J=7.3 Hz, 1H), 4.41 (q, J=6.9 Hz, 2H), 3.43 (s, 3H), 3.01 (s, 3H), 1.43 (t, J=7.1 Hz, 3H), 0.32 (s, 9H)

Reference Example 174

7-Acetyl-4-(methoxy($^2H_2$)methyl)-3-methylbenzo[b]thiophene-2-carboxylic acid

[Formula 177]

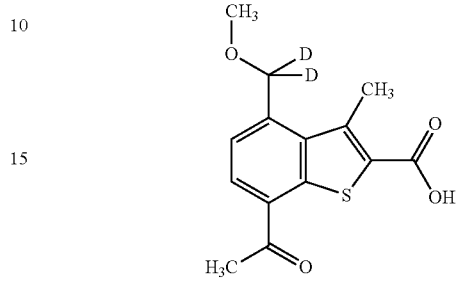

To a solution of the compound (2.8 g) obtained in Reference Example 173 in chloroform (50 mL), p-toluenesulfonic acid monohydrate (8.81 g) was added, and the mixture was stirred at 70° C. for 12 hours. To the reaction mixture, a 2 N aqueous sodium hydroxide solution and a saturated aqueous solution of sodium bicarbonate were added, followed by extraction with chloroform. The organic layer was washed with saturated aqueous sodium chloride, dried over anhydrous sodium sulfate, and concentrated. To the residue, THF (35 mL), ethanol (11.67 mL), and a 4 N aqueous sodium hydroxide solution (5 mL) were added, and the mixture was stirred at room temperature for 24 hours. To the reaction mixture, 4 N hydrochloric acid was added, followed by extraction with ethyl acetate. The organic layer was dried over anhydrous sodium sulfate and concentrated to obtain the title compound (1.4 g).

$^1$H NMR (DMSO, 400 MHz): δ (ppm) 13.40 (br. s., 1H), 8.29 (d, J=7.7 Hz, 1H), 7.63 (d, J=7.7 Hz, 1H), 3.40 (s, 3H), 2.95 (s, 3H), 2.73 (s, 3H)

Reference Example 175

(2-Chloroquinolin-4-yl)(1,1-$^2$H$_2$) methanol

[Formula 178]

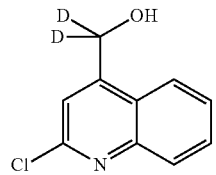

To a solution of methyl 2-chloroquinoline-4-carboxylate (2.1 g) in 2-propanol (30 mL), ($^2$H$_4$)sodium borohydride (0.824 g) was added at 40° C., and the mixture was stirred at 55° C. for 1.5 hours. The reaction mixture was concentrated, and saturated aqueous sodium chloride was added to the residue, followed by extraction with ethyl acetate. The organic layer was dried over anhydrous sodium sulfate and concentrated. To the residue, an ethyl acetate-hexane mixed solution was added, and the mixture was heated and cooled to room temperature. The precipitated solid was collected by filtration to obtain the title compound (1.27 g).

¹H NMR (MeOD, 400 MHz): δ (ppm) 7.95-8.00 (m, 1H), 7.74-7.81 (m, 1H), 7.67 (s, 1H), 7.60-7.65 (m, 2H)
MS (ESI⁺) m/z: 196 [M+H]⁺

Reference Example 176

(R)-1-((2-Aminoquinolin-4-yl)(²H₂)methyl)pyrrolidin-3-ol

[Formula 179]

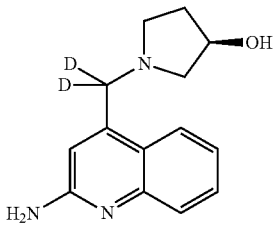

To the compound (1.27 g) obtained in Reference Example 175, dibenzylamine (2.86 mL) was added, and the mixture was stirred at 111° C. for 48 hours. To the reaction mixture, 2 N hydrochloric acid was added, followed by extraction with dichloromethane. The organic layer was filtered, and the filtrate was dried over anhydrous sodium sulfate and then concentrated to obtain 930 mg of a residue. A 510 mg aliquot of the obtained residue was dissolved in dichloromethane (6 mL), and the solution was cooled to 0° C. Triethylamine (0.259 mL) and methanesulfonyl chloride (0.145 mL) were added thereto, and the mixture was stirred at room temperature for 1 hour. The reaction mixture was cooled to 0° C., and a saturated aqueous solution of sodium bicarbonate was added thereto, followed by extraction with dichloromethane. The organic layer was dried over anhydrous sodium sulfate and concentrated. The residue was cooled to 0° C. A solution of (R)-pyrrolidinol (265 mg) and triethylamine (0.399 mL) in THF (10 mL) was added dropwise thereto, and the mixture was stirred at 50° C. for 6 hours. To the reaction mixture, water was added, followed by extraction with ethyl acetate. The organic layer was subjected to extraction with 6 N hydrochloric acid, and the aqueous layer was rendered basic by the addition of an aqueous sodium hydroxide solution, followed by extraction with ethyl acetate. The organic layer was washed with saturated aqueous sodium chloride, dried over anhydrous sodium sulfate, and concentrated. To the residue, dichloromethane (10 mL) and trifluoromethanesulfonic acid (0.746 mL) were added, and the mixture was stirred at 50° C. for 5 hours. The reaction mixture was cooled to 0° C. and rendered basic by the addition of an 8 N aqueous sodium hydroxide solution, followed by extraction with dichloromethane. The organic layer was dried over anhydrous sodium sulfate and concentrated. The residue was purified by silica gel column chromatography (dichloromethane:methanol=100:0-80:20) to obtain the title compound (0.25 g).

¹H NMR (DMSO, 400 MHz): δ (ppm) 7.94 (dd, J=8.5, 1.2 Hz, 1H), 7.65-7.70 (m, 1H), 7.55 (ddd, J=8.3, 6.9, 1.4 Hz, 1H), 7.24-7.30 (m, 1H), 6.81 (s, 1H), 4.73 (br. s., 2H), 4.35-4.41 (m, 1H), 2.94-3.01 (m, 1H), 2.79 (d, J=10.1 Hz, 1H), 2.63 (dd, J=9.9, 5.1 Hz, 1H), 2.38-2.46 (m, 1H), 2.17-2.28 (m, 1H), 1.75-1.84 (m, 1H)
MS (ESI⁺) m/z: 246 [M+H]⁺

Reference Example 177

2-Chloro-5-((²H₃)methoxymethyl)quinoline

[Formula 180]

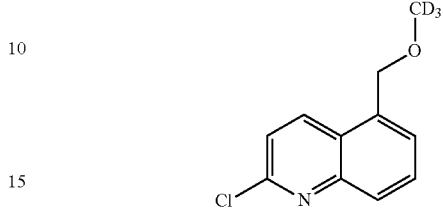

A solution of the compound (480 mg) obtained in Reference Example 111 in DMF (10 mL) was cooled to 0° C. Sodium hydride (60% oil suspension, 119 mg) was added thereto, and the mixture was stirred at room temperature for 20 minutes. Iodo(²H₃)methane (0.079 mL) was added thereto, and the mixture was stirred at room temperature for 2 hours. The reaction mixture was concentrated, and the residue was purified by silica gel column chromatography (chloroform:methanol=10:0-10:1) to obtain the title compound (480 mg).

¹H NMR (CDCl₃, 400 MHz): δ (ppm) 8.44 (dd, J=8.9, 0.9 Hz, 1H), 7.99 (d, J=8.5 Hz, 1H), 7.68 (dd, J=8.5, 7.0 Hz, 1H), 7.51-7.55 (m, 1H), 7.43 (d, J=8.8 Hz, 1H), 4.86 (s, 2H)
MS (ESI⁺) m/z: 211 [M+H]⁺

Reference Example 178

1-Bromo-2-fluoro-4-((²H₃)methoxymethyl)benzene

[Formula 181]

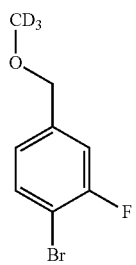

To a solution of the compound (18 g) obtained in Reference Example 65 in DMF (60 mL), sodium hydride (60% oil suspension, 4.92 g) was added at 0° C., and the mixture was stirred at 0° C. for 45 minutes. Iodo(²H₃)methane (7.69 mL) was added thereto, and the mixture was stirred at room temperature for 1 hour. The reaction mixture was concentrated, and water was added to the residue, followed by extraction with ethyl acetate.

The organic layer was dried over anhydrous sodium sulfate and concentrated. The residue was purified by silica gel column chromatography (hexane:ethyl acetate=100:0-80:20) to obtain the title compound (15 g).

¹H NMR (CDCl₃, 400 MHz): δ (ppm) 7.51 (dd, J=8.0, 7.0 Hz, 1H), 7.12 (dd, J=9.3, 1.8 Hz, 1H), 6.97-7.01 (m, 1H), 4.41 (s, 2H)

Reference Example 179

3-Bromo-2-fluoro-6-(($^2$H$_3$)methoxymethyl)benzaldehyde

[Formula 182]

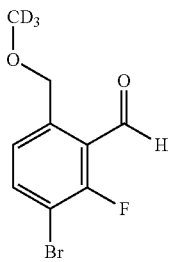

A solution of 2,2,6,6-tetramethylpiperidine (13.76 mL) in THF (30 mL) was cooled to −75° C. under an argon stream. n-Butyllithium (1.59 M solution in hexane, 46.7 mL) was added dropwise thereto, and the mixture was stirred at the same temperature as above for 40 minutes. To the reaction mixture, a solution of the compound (15 g) obtained in Reference Example 178 in THF (110 mL) was added dropwise, and the mixture was stirred at −75° C. for 80 minutes. To the reaction mixture, DMF (5.75 mL) was added dropwise, and the mixture was stirred at −78° C. for 1 hour. To the reaction mixture, acetic acid (10 mL) and water (100 mL) were added in this order, and the temperature of the mixture was raised to room temperature. After extraction with ethyl acetate, the organic layer was washed with a saturated aqueous solution of sodium bicarbonate and saturated aqueous sodium chloride in this order, then dried over anhydrous sodium sulfate, and concentrated. The residue was washed with a diisopropyl ether-hexane (4:1) mixed solution to obtain the title compound (8.8 g).

$^1$H NMR (CDCl$_3$, 400 MHz): δ (ppm) 10.47 (d, J=0.8 Hz, 1H), 7.78 (dd, J=8.5, 7.0 Hz, 1H), 7.44 (dt, J=8.4, 1.1 Hz, 1H), 4.78 (s, 2H)

Reference Example 180

1-(3-Bromo-2-fluoro-6-(($^2$H$_3$)methoxymethyl)phenyl)ethanone

[Formula 183]

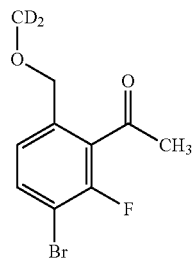

To a solution of the compound (9.3 g) obtained in Reference Example 179 in THF (200 mL), methyl magnesium bromide (1.12 M solution in THF, 83 mL) was added dropwise at 0° C., and the mixture was stirred at room temperature for 3 hours. To the reaction mixture, a saturated aqueous solution of ammonium chloride and water were added, followed by extraction with ethyl acetate. The organic layer was washed with saturated aqueous sodium chloride, dried over anhydrous sodium sulfate, and concentrated. To the residue, acetonitrile (70 mL), N-methylmorpholine-N-oxide (11.23 g), and tetrapropylammonium perruthenate (2.69 g) were added, and the mixture was stirred at room temperature for 6 hours. To the reaction mixture, water was added, followed by extraction with ethyl acetate. The organic layer was dried over anhydrous sodium sulfate and concentrated. The residue was purified by silica gel column chromatography (hexane:ethyl acetate=100:0-3:1) to obtain the title compound (9.3 g).

$^1$H NMR (CDCl$_3$, 400 MHz): δ (ppm) 7.56 (dd, J=8.3, 7.0 Hz, 1H), 7.11 (dq, J=8.3, 0.8 Hz, 1H), 4.43 (s, 2H), 2.57 (d, J=2.8 Hz, 3H)

Reference Example 181

Ethyl 4-(($^2$H$_3$)methoxymethyl)-3-methyl-7-((trimethylsilyl)ethynyl)benzo[b]thiophene-2-carboxylate

[Formula 184]

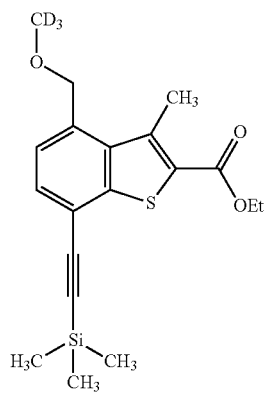

To a solution of the compound (9.3 g) obtained in Reference Example 180 and 1,8-diazabicyclo[5.4.0]-7-undecene (15.92 mL) in DMF (50 mL), ethyl thioglycolate (4.25 mL) was added dropwise, and the mixture was stirred at room temperature for 2 hours. To the reaction mixture, water (400 mL) was added, and the mixture was stirred at 0° C. for 1 hour. The precipitated solid was collected by filtration. The obtained solid was dissolved in ethyl acetate, and the reaction mixture was washed with saturated aqueous sodium chloride. The organic layer was dried over anhydrous sodium sulfate and concentrated. The residue was dissolved in THF (170 mL). To the solution, trimethylsilylacetylene (8.10 mL), tetrakis(triphenylphosphine)palladium(0) (1.001 g), triethylamine (8.05 mL), and copper(I) bromide (0.414 g) were then added, and the mixture was stirred at 80° C. for 12 hours under an argon atmosphere. The reaction mixture was filtered through Celite, and the filtrate was concentrated. The residue was purified by silica gel column chromatography (hexane:ethyl acetate=95:5-50:50) to obtain the title compound (6.0 g).

$^1$H NMR (CDCl$_3$, 400 MHz): δ (ppm) 7.50 (d, J=7.5 Hz, 1H), 7.33 (d, J=7.5 Hz, 1H), 4.85 (s, 2H), 4.41 (q, J=7.3 Hz, 2H), 3.01 (s, 3H), 1.43 (t, J=7.2 Hz, 3H), 0.32 (s, 9H)

Reference Example 182

Ethyl 7-acetyl-4-(($^2$H$_3$)methoxymethyl)-3-methyl-benzo[b]thiophene-2-carboxylate

[Formula 185]

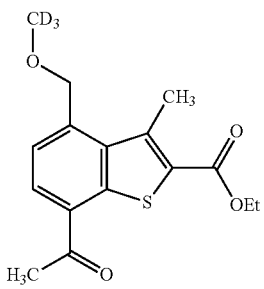

To the compound (6.0 g) obtained in Reference Example 181, p-toluenesulfonic acid monohydrate (9.42 g) and chloroform (80 mL) were added, and the mixture was stirred at 70° C. for 12 hours. The reaction mixture was cooled to room temperature, and a saturated aqueous solution of sodium bicarbonate was added thereto, followed by extraction with chloroform. The organic layer was dried over anhydrous sodium sulfate and concentrated. The residue was purified by basic silica gel column chromatography (chloroform:ethyl acetate=100:0-5:1) to obtain the title compound (4.4 g).

$^1$H NMR (CDCl$_3$, 400 MHz): δ (ppm) 8.07 (d, J=7.8 Hz, 1H), 7.58 (d, J=7.8 Hz, 1H), 4.98 (s, 2H), 4.40 (q, J=7.0 Hz, 2H), 3.03 (s, 3H), 2.75 (s, 3H), 1.43 (t, J=7.2 Hz, 3H)

MS (ESI$^+$) m/z: 310 [M+H]$^+$

Reference Example 183

7-Acetyl-4-(($^2$H$_3$)methoxymethyl)-3-methylbenzo[b]thiophene-2-carboxylic acid

[Formula 186]

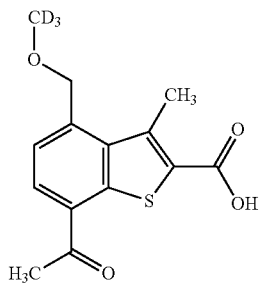

To the compound (4.4 g) obtained in Reference Example 182, ethanol (100 mL) and a 4 N aqueous sodium hydroxide solution (100 mL) were added, and the mixture was stirred at 50° C. for 8 hours. The reaction mixture was cooled to room temperature. Hydrochloric acid was added thereto, and the precipitated solid was collected by filtration to obtain the title compound.

MS (ESI$^+$) m/z: 282 [M+H]$^+$

Reference Example 184

(2-Chloroquinolin-5-yl)(1,1-$^2$H$_2$) methanol

[Formula 187]

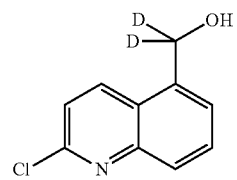

To a solution of the compound (6.9 g) obtained in Reference Example 110 and ($^2$H$_4$)sodium borohydride (4.71 g) in THF (20 mL), methanol (20 mL) was added dropwise at 0° C., and the mixture was stirred at 50° C. for 1 hour. The reaction mixture was concentrated, and, saturated aqueous sodium chloride was added to the residue, followed by extraction with ethyl acetate. The organic layer was dried over anhydrous sodium sulfate and concentrated. To the residue, an ethyl acetate-hexane mixed solution was added, and the mixture was heated and then cooled to 0° C. The precipitated solid was collected by filtration to obtain the title compound (4.5 g).

$^1$H NMR (CDCl$_3$, 400 MHz): δ (ppm) 8.49 (dd, J=8.9, 0.9 Hz, 1H), 7.99 (dt, J=8.5, 1.0 Hz, 1H), 7.70 (dd, J=8.5, 7.0 Hz, 1H), 7.57 (dd, J=7.0, 1.0 Hz, 1H), 7.45 (d, J=8.8 Hz, 1H)

MS (ESI$^+$) m/z: 196 [M+H]$^+$

Reference Example 185

2-Chloro-5-(methoxy($^2$H$_2$)methyl) quinoline

[Formula 188]

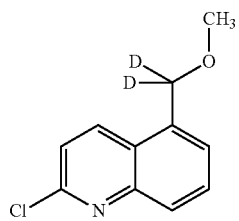

To a solution of the compound (1.0 g) obtained in Reference Example 184 in DMF (10 mL), sodium hydride (60% oil suspension, 245 mg) was added at 0° C., and the mixture was stirred at room temperature for 20 minutes. To the reaction mixture, iodomethane (163 μL) was added, and the mixture was stirred at room temperature for 2 hours. The reaction mixture was concentrated, and the residue was purified by silica gel column chromatography (chloroform:methanol=10:0-10:1) to obtain the title compound (1.1 g).

MS (ESI$^+$) m/z: 210 [M+H]$^+$

Reference Example 186

(2-((4-Methoxybenzyl)amino)quinolin-5-yl)(1,1-²H₂)methanol

[Formula 189]

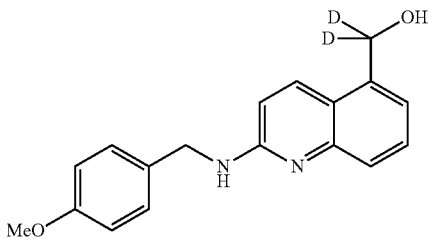

The title compound was obtained by the same operation as in Reference Example 120 using the compound obtained in Reference Example 184 instead of the compound obtained in Reference Example 111 as a starting material for Reference Example 120.

¹H NMR (CDCl₃, 400 MHz): δ (ppm) 8.19 (dd, J=9.0, 0.8 Hz, 1H), 7.66-7.70 (m, 1H), 7.49 (dd, J=8.4, 7.2 Hz, 1H), 7.31-7.36 (m, 2H), 7.19-7.25 (m, 1H), 6.84-6.90 (m, 2H), 6.67 (d, J=9.0 Hz, 1H), 4.62-4.69 (m, 2H), 3.80 (d, J=0.8 Hz, 3H)

MS (ESI⁺) m/z: 297 [M+H]⁺

Reference Example 187

(2-Aminoquinolin-5-yl)(1,1-²H₂) methanol

[Formula 190]

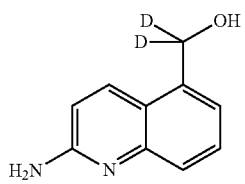

The title compound was obtained by the same operation as in Reference Example 121 using the compound obtained in Reference Example 186 instead of the compound obtained in Reference Example 120 as a starting material for Reference Example 121.

¹H NMR (CDCl₃, 400 MHz): δ (ppm) 8.22 (dd, J=9.0, 0.8 Hz, 1H), 7.62-7.66 (m, 1H), 7.50 (dd, J=8.5, 7.0 Hz, 1H), 7.21-7.25 (m, 1H), 6.76 (d, J=9.0 Hz, 1H), 4.74-4.80 (m, 2H)

MS (ESI⁺) m/z: 177 [M+H]⁺

Reference Example 188

7-Acetyl-4-((²H₃)methoxymethyl)-3-methylbenzo[b]thiophene-2-carboxamide

[Formula 191]

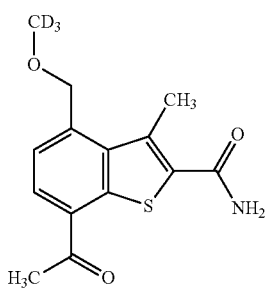

The title compound was obtained by the same operation as in Reference Example 102 using the compound obtained in Reference Example 183 instead of the compound obtained in Reference Example 74 as a starting material for Reference Example 102.

¹H NMR (DMSO, 400 MHz): δ (ppm) 8.25 (d, J=7.8 Hz, 1H), 7.86 (br. s., 1H), 7.60-7.69 (m, 2H), 4.96 (s, 2H), 2.77 (s, 3H), 2.74 (s, 3H)

MS (ESI⁺) m/z: 281 [M+H]⁺

Reference Example 189

Benzyl 3-hydroxyazetidine-1-carboxylate

[Formula 192]

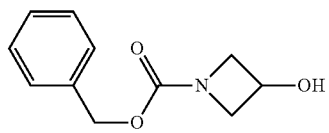

To 3-hydroxyazetidine hydrochloride (500 mg), water (5 mL), methanol (5 mL), and sodium carbonate (1161 mg) were added, and the mixture was cooled to 0° C. Benzyloxycarbonyl chloride (782 µL) was added thereto, and the mixture was stirred at 0° C. for 1 hour and then stirred at room temperature for 4 hours. To the reaction mixture, water was added, followed by extraction with chloroform. The organic layer was dried over anhydrous sodium sulfate and concentrated. The residue was purified by silica gel column chromatography (chloroform:methanol=99:1-92:8) to obtain the title compound (900 mg).

¹H NMR (CDCl₃, 400 MHz): δ (ppm) 7.28-7.38 (m, 5H), 5.09 (s, 2H), 4.57-4.65 (m, 1H), 4.20-4.26 (m, 2H), 3.85-3.91 (m, 2H), 2.50 (dd, J=6.1, 1.4 Hz, 1H)

Reference Example 190

Benzyl 3-($^2$H$_3$)methoxyazetidine-1-carboxylate

[Formula 193]

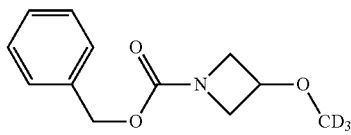

To a solution of the compound (900 mg) obtained in Reference Example 189 in DMF (4 mL), sodium hydride (60% oil suspension, 208 mg) was added at 0° C., and the mixture was stirred for 20 minutes. To the reaction mixture, iodo($^2$H$_3$)methane (405 µL) was added, and the mixture was stirred at 0° C. for 30 minutes and then stirred at room temperature for 2 hours. The reaction mixture was diluted with ethyl acetate and washed with water and saturated aqueous sodium chloride in this order. The organic layer was dried over anhydrous sodium sulfate and concentrated. The residue was purified by silica gel column chromatography (chloroform:methanol=100:0-98:2) to obtain the title compound (798 mg).

$^1$H NMR (CDCl$_3$, 400 MHz): δ (ppm) 7.28-7.38 (m, 5H), 5.10 (s, 2H), 4.12-4.20 (m, 3H), 3.87-3.95 (m, 2H)

MS (ESI$^+$) m/z: 225 [M+H]$^+$

Reference Example 191

3-($^2$H$_3$)Methoxyazetidine hydrochloride

[Formula 194]

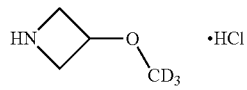

To a solution of the compound (768 mg) obtained in Reference Example 190 in methanol (6 mL), 6 N hydrochloric acid (685 µL) and 10% palladium/carbon (manufactured by Nacalai Tesque, Inc., 60 mg) were added, and the mixture was stirred at room temperature for 1 hour under a hydrogen atmosphere. The reaction mixture was filtered, and the filtrate was concentrated to obtain the title compound (419 mg).

$^1$H NMR (DMSO, 400 MHz): δ (ppm) 9.08 (br. s., 2H), 4.20-4.28 (m, 1H), 4.04-4.15 (m, 2H), 3.72-3.82 (m, 2H)

Reference Example 192

(2-Chloroquinolin-5-yl)(3-($^2$H$_3$) methoxyazetidin-1-yl) methanone

[Formula 195]

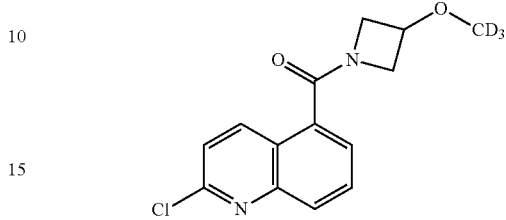

To a solution of 2-chloroquinoline-5-carboxylic acid (345 mg) in chloroform (10 mL), N,N-diisopropylethylamine (1.01 µL) and HBTU (694 mg) were added at room temperature, and the mixture was stirred at room temperature for 30 minutes. To the reaction mixture, the compound (210 mg) obtained in Reference Example 191 was added, and the mixture was stirred overnight at room temperature. N,N-Diisopropylethylamine (129 mg), HBTU (76 mg), and the compound (63 mg) obtained in Reference Example 191 were added thereto, and the mixture was stirred at room temperature for 2 hours. To the reaction mixture, a 1 N aqueous sodium hydroxide solution was added, followed by extraction with chloroform. The organic layer was dried over anhydrous sodium sulfate and concentrated. The residue was purified by silica gel column chromatography (chloroform:methanol=99.5:0.5-97:3) to obtain the title compound (423 mg).

$^1$H NMR (CDCl$_3$, 400 MHz): δ (ppm) 8.55 (dd, J=9.0, 0.8 Hz, 1H), 8.09 (dt, J=8.5, 0.9 Hz, 1H), 7.73 (dd, J=8.4, 7.2 Hz, 1H), 7.60 (dd, J=7.3, 1.3 Hz, 1H), 7.46 (d, J=9.0 Hz, 1H), 4.42-4.49 (m, 1H), 4.22-4.28 (m, 1H), 4.07-4.18 (m, 2H), 3.86-3.91 (m, 1H)

MS (ESI$^+$) m/z: 280 [M+H]$^+$

Reference Example 193

(2-Aminoquinolin-5-yl)(3-($^2$H$_3$)methoxyazetidin-1-yl)methanone

[Formula 196]

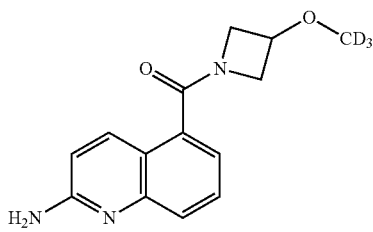

To the compound (423 mg) obtained in Reference Example 192, 80% hydrazine monohydrate (2.0 mL) and 1,4-dioxane (2.0 mL) were added, and the mixture was stirred at 80° C. for 11 hours. The reaction mixture was cooled to room temperature, and saturated aqueous sodium chloride was added thereto, followed by extraction with chloroform. The organic layer was dried over anhydrous sodium sulfate and concentrated. To the residue, methanol (10 mL) and Raney nickel (R-200 manufactured by Nikko Rica Corp., 2.0 mL) were added, and the mixture was stirred at room temperature for 20 hours under a hydrogen atmosphere. The reaction mixture was filtered, and the filtrate was concentrated, followed by extraction with chloroform. The organic layer was dried over anhydrous sodium sulfate and concentrated. The residue was purified by silica gel column chromatography (chloroform:methanol=98:2-91:9) to obtain the title compound (204 mg).

$^1$H NMR (CDCl$_3$, 400 MHz): δ (ppm) 8.26 (d, J=8.5 Hz, 1H), 7.69-7.73 (m, 1H), 7.53 (dd, J=8.4, 7.2 Hz, 1H), 7.28 (dd, J=7.2, 1.1 Hz, 1H), 6.78 (d, J=9.0 Hz, 1H), 4.79 (s, 2H), 4.40-4.46 (m, 1H), 4.20-4.26 (m, 1H), 4.03-4.16 (m, 2H), 3.83-3.89 (m, 1H)

MS (ESI$^+$) m/z: 261 [M+H]$^+$

Example 1

4,7-Diacetyl-3-methyl-N-(quinolin-2-yl)benzo[b]thiophene-2-carboxamide

[Formula 197]

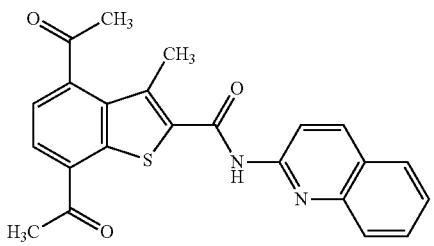

To a solution of the compound (50 mg) obtained in Reference Example 5 in dimethylformamide (5 mL), 2-aminoquinoline (26 mg), 1-ethyl-3-(3-dimethylaminopropyl)carbodiimide hydrochloride (52 mg), and N,N-dimethyl-4-aminopyridine (40 mg) were added at room temperature, and the mixture was stirred at 40° C. for 15 hours. To the reaction mixture, water was added, followed by extraction with dichloromethane. The obtained organic layer was dried over anhydrous sodium sulfate and concentrated. The residue was purified by silica gel column chromatography (dichloromethane:methanol=100:0-89:11) to obtain the title compound (7.5 mg).

$^1$H NMR (DMSO, 400 MHz): δ (ppm) 8.49 (br. s., 1H), 8.27 (d, J=8.9 Hz, 1H), 8.11-8.16 (m, 1H), 8.00-8.04 (m, 1H), 7.90 (d, J=8.5 Hz, 1H), 7.83 (d, J=8.1 Hz, 1H), 7.69-7.75 (m, 1H), 7.46-7.54 (m, 2H), 2.81 (s, 3H), 2.75 (s, 3H), 2.68 (s, 3H)

MS (ESI$^+$) m/z: 403 [M+H]$^+$

Example 2

4,7-Diacetyl-N-(4-(2-hydroxypropan-2-yl)quinolin-2-yl)-3-methylbenzo[b]thiophene-2-carboxamide

[Formula 198]

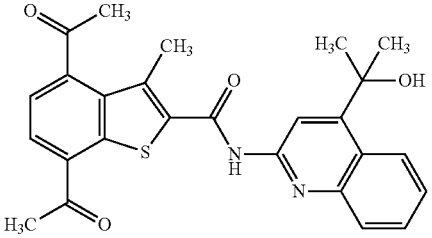

To a suspension of the compound (0.500 g) obtained in Reference Example 5, the compound (0.366 g) obtained in Reference Example 8, and PyBOP (0.942 g) in dichloromethane (18 mL), N,N-diisopropylethylamine (630 μL) was added, and the mixture was stirred at room temperature for 70 hours. To the reaction mixture, the compound (0.366 g) obtained in Reference Example 8 and N,N-diisopropylethylamine (315 μL) were added, and the mixture was stirred at 32° C. for 48 hours. To the reaction mixture, chloroform (50 mL) and water (50 mL) were added, and the obtained organic layer was dried over anhydrous magnesium sulfate and concentrated. To the residue, 2-propanol (3.0 mL) was added, and the mixture was heated to 85° C. and then cooled to room temperature. The precipitated solid was collected by filtration and washed with 2-propanol to obtain the title compound (0.665 g).

$^1$H NMR (CDCl$_3$, 400 MHz): δ (ppm) 8.84 (br. s., 1H), 8.68-8.72 (m, 1H), 8.59 (br. s., 1H), 8.12 (d, J=7.7 Hz, 1H), 7.85 (d, J=8.1 Hz, 1H), 7.62 (ddd, J=8.3, 6.9, 1.4 Hz, 1H), 7.41-7.50 (m, 2H), 2.81 (s, 3H), 2.74 (s, 3H), 2.64 (s, 3H), 2.29 (br. s., 1H), 1.91 (s, 6H)

MS (ESI$^+$) m/z: 461 [M+H]$^+$

Example 3

4,7-Diacetyl-N-(4-(2-hydroxypropan-2-yl)quinolin-2-yl)-3-methylbenzo[b]thiophene-2-carboxamide hydrochloride

[Formula 199]

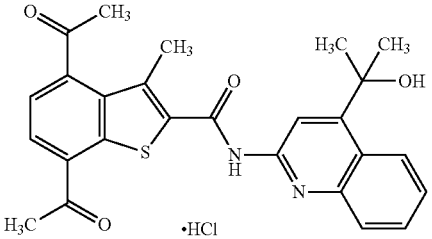

To the compound (46.1 mg) obtained in Example 2, 2-propanol (2 mL) and hydrogen chloride (4 N solution in 1,4-dioxane, 200 μL) were added, and the mixture was then concentrated. To the residue, 2-propanol (1 mL) was added, and the mixture was heated to 60° C. and then cooled to room temperature. The precipitated solid was collected by filtration to obtain the title compound (31.7 mg).

$^1$H NMR (CDCl$_3$, 400 MHz): δ (ppm) 9.04 (s, 1H), 8.86-8.91 (m, 1H), 8.12-8.19 (m, 2H), 7.86-7.92 (m, 1H), 7.67-7.74 (m, 1H), 7.46 (d, J=7.7 Hz, 1H), 3.71 (s, 1H), 2.79 (s, 3H), 2.76 (s, 3H), 2.74 (s, 3H), 1.96 (s, 6H)

MS (ESI$^+$) m/z: 461 [M+H]$^+$

Example 4

4,7-Diacetyl-N-(4-(2-hydroxypropan-2-yl)quinolin-2-yl)-3-methylbenzo[b]thiophene-2-carboxamide hydrobromide

[Formula 200]

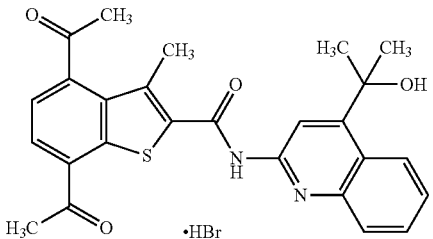

·HBr

To the compound (46.1 mg) obtained in Example 2, 2-propanol (2 mL) and 47% hydrobromic acid (50 µL) were added, and the mixture was then concentrated. To the residue, 2-propanol (1 mL) was added, and the mixture was heated to 60° C. and then cooled to room temperature. The precipitated solid was collected by filtration to obtain the title compound (34.4 mg).

$^1$H NMR (CDCl$_3$, 400 MHz): δ (ppm) 9.06 (s, 1H), 8.87-8.92 (m, 1H), 8.19-8.24 (m, 1H), 8.14 (d, J=7.3 Hz, 1H), 7.91 (t, J=7.7 Hz, 1H), 7.69-7.75 (m, 1H), 7.46 (d, J=7.3 Hz, 1H), 2.79 (s, 3H), 2.77 (s, 3H), 2.76 (s, 3H), 2.52 (s, 1H), 1.96 (s, 6H)

MS (ESI$^+$) m/z: 461 [M+H]$^+$

Example 5

4,7-Diacetyl-N-(4-(2-hydroxypropan-2-yl)quinolin-2-yl)-3-methylbenzo[b]thiophene-2-carboxamide semisulfate

[Formula 201]

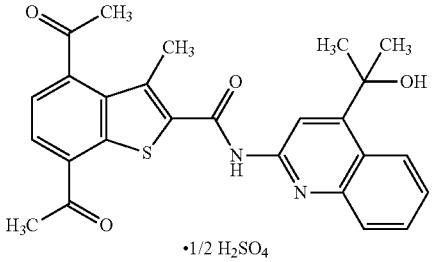

·1/2 H$_2$SO$_4$

To the compound (46.1 mg) obtained in Example 2, 2-propanol (2 mL) and concentrated sulfuric acid (20 µL) were added, and the mixture was then concentrated. To the residue, 2-propanol (1 mL) was added, and then, hexane (1 mL) was added. The precipitated solid was collected by filtration to obtain the title compound (35.5 mg).

$^1$H NMR (CDCl$_3$, 400 MHz): δ (ppm) 8.88 (s, 1H), 8.78-8.82 (m, 1H), 8.17-8.22 (m, 1H), 8.14 (d, J=7.7 Hz, 1H), 7.86-7.93 (m, 1H), 7.69-7.75 (m, 1H), 7.45 (d, J=7.7 Hz, 1H), 2.79 (s, 3H), 2.76 (s, 3H), 2.67 (s, 3H), 1.94 (s, 6H)

MS (ESI$^+$) m/z: 461 [M+H]$^+$

Example 6

4,7-Diacetyl-N-(4-(2-hydroxypropan-2-yl)quinolin-2-yl)-3-methylbenzo[b]thiophene-2-carboxamide methanesulfonate

[Formula 202]

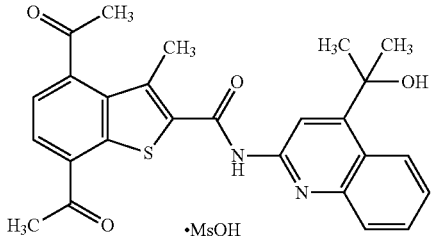

·MsOH

To the compound (46.1 mg) obtained in Example 2, 2-propanol (2 mL) and methanesulfonic acid (40 µL) were added, and the mixture was then concentrated. To the residue, 2-propanol (1 mL) was added, and then, hexane (1 mL) was added. The precipitated solid was collected by filtration to obtain the title compound (40 mg).

$^1$H NMR (CDCl$_3$, 400 MHz): δ (ppm) 8.78-8.82 (m, 2H), 8.11-8.18 (m, 2H), 7.91 (t, J=7.7 Hz, 1H), 7.72 (t, J=7.9 Hz, 1H), 7.48 (d, J=7.7 Hz, 1H), 2.91 (s, 6H), 2.80 (s, 3H), 2.77 (s, 3H), 2.66 (s, 3H)

MS (ESI$^+$) m/z: 461 [M+H]$^+$

Example 7

4,7-Diacetyl-3-ethyl-N-(4-(2-hydroxypropan-2-yl)quinolin-2-yl)benzo[b]thiophene-2-carboxamide

[Formula 203]

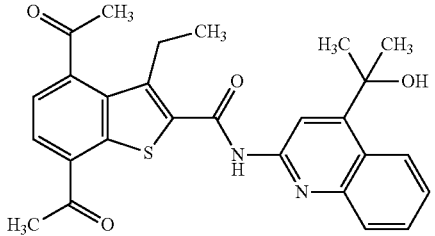

To a suspension of the compound (290 mg) obtained in Reference Example 13, the compound (202 mg) obtained in Reference Example 8, and PyBOP (572 mg) in dichloromethane (5 mL), N,N-diisopropylethylamine (344 µL) were added, and the mixture was stirred at room temperature for 108 hours. To the reaction mixture, dichloromethane and water were added, and the obtained organic layer was dried over anhydrous sodium sulfate and concentrated. The residue was purified by silica gel column chromatography (hexane:ethyl acetate=70:30-20:80) to obtain the title compound (313 mg).

¹H NMR (CDCl₃, 400 MHz): δ (ppm) 8.66-8.74 (m, 2H), 8.54-8.66 (m, 1H), 8.14 (d, J=7.7 Hz, 1H), 7.82-7.94 (m, 1H), 7.62-7.69 (m, 1H), 7.43-7.51 (m, 2H), 3.13-3.24 (m, 2H), 2.81 (s, 3H), 2.77 (s, 3H), 2.17 (br. s., 1H), 1.91 (s, 6H), 1.19-1.25 (m, 3H)

MS (ESI⁺) m/z: 475 [M+H]⁺

Example 8

4,7-Diacetyl-N-(4-(2-hydroxypropan-2-yl)quinolin-2-yl)benzo[b]thiophene-2-carboxamide

[Formula 204]

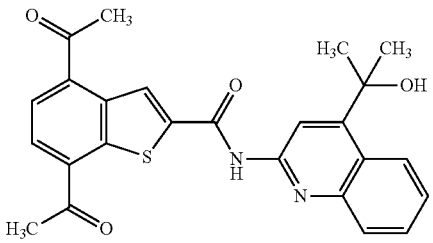

The title compound (57 mg) was obtained in the same way as in Example 7 using the compound (52 mg) obtained in Reference Example 16, the compound (40 mg) obtained in Reference Example 8, PyBOP (115 mg), dichloromethane (2 mL), and N,N-diisopropylethylamine (69 µL).

¹H NMR (CDCl₃, 400 MHz): δ (ppm) 8.93-9.04 (m, 2H), 8.60-8.77 (m, 2H), 8.16-8.21 (m, 1H), 8.07-8.11 (m, 1H), 7.85-7.95 (m, 1H), 7.67 (ddd, J=8.3, 6.9, 1.4 Hz, 1H), 7.48 (ddd, J=8.5, 6.9, 1.2 Hz, 1H), 2.83 (s, 3H), 2.82 (s, 3H), 2.21 (s, 1H), 1.91 (s, 6H)

MS (ESI⁺) m/z: 447 [M+H]⁺

Example 9

7-Acetyl-4-(1-hydroxyethyl)-N-(4-(2-hydroxypropan-2-yl)quinolin-2-yl)-3-methylbenzo[b]thiophene-2-carboxamide

[Formula 205]

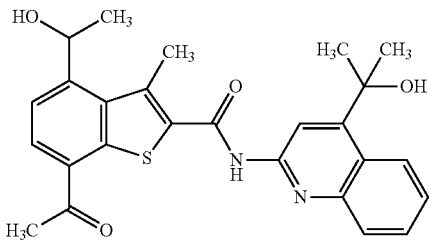

A solution of the compound (20 mg) obtained in Reference Example 24, the compound (14 mg) obtained in Reference Example 8, 1-ethyl-3-(3-dimethylaminopropyl)carbodiimide hydrochloride (19 mg), and 1-hydroxy-7-azabenzotriazole (13 mg) in DMF (10 mL) was stirred at room temperature for 10 hours. The reaction mixture was concentrated, and the residue was purified by silica gel column chromatography (dichloromethane:methanol=100:0-90:10), basic silica gel column chromatography (hexane:ethyl acetate=60:40-0:100), and silica gel column chromatography (ethyl acetate-hexane (1:1) mixed solution: methanol=100:0-93:7) in this order to obtain the title compound (19.4 mg).

¹H NMR (CDCl₃, 400 MHz): δ (ppm) 8.68-8.73 (m, 1H), 8.59 (br. s., 1H), 8.13 (d, J=8.1 Hz, 1H), 7.95 (d, J=8.1 Hz, 1H), 7.88 (d, J=8.1 Hz, 1H), 7.61-7.68 (m, 1H), 7.44-7.51 (m, 1H), 5.98-6.06 (m, 1H), 2.95 (s, 3H), 2.77 (s, 3H), 1.89-1.95 (m, 6H), 1.62 (d, J=6.5 Hz, 3H)

MS (ESI⁺) m/z: 463 [M+H]⁺

Example 10

7-Acetyl-N-(4-(2-hydroxypropan-2-yl)quinolin-2-yl)-3-methyl-4-propionylbenzo[b]thiophene-2-carboxamide

[Formula 206]

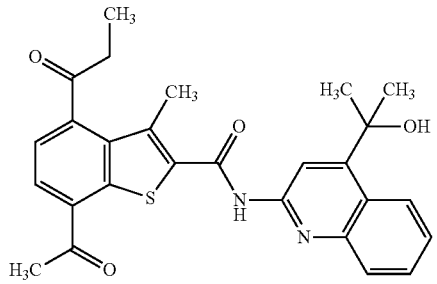

The title compound (21.9 mg) was obtained in the same way as in Example 9 using the compound (87 mg) obtained in Reference Example 28, the compound (45 mg) obtained in Reference Example 8, 1-ethyl-3-(3-dimethylaminopropyl)carbodiimide hydrochloride (86 mg), 1-hydroxy-7-azabenzotriazole (61 mg), and DMF (20 mL).

¹H NMR (CDCl₃, 400 MHz): δ (ppm) 9.09 (br. s., 1H), 8.65 (dd, J=8.7, 1.0 Hz, 1H), 8.50 (br. s., 1H), 8.06 (d, J=7.7 Hz, 1H), 7.78 (d, J=8.1 Hz, 1H), 7.50-7.58 (m, 1H), 7.32-7.39 (m, 2H), 2.92-3.02 (m, 2H), 2.78 (s, 3H), 2.53 (s, 3H), 1.89 (s, 6H), 1.29 (t, J=7.3 Hz, 3H)

MS (ESI⁺) m/z: 475 [M+H]⁺

Example 11

4,7-Diacetyl-3-methyl-N-(4-methylquinolin-2-yl)benzo[b]thiophene-2-carboxamide

[Formula 207]

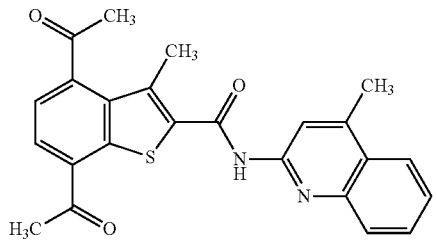

The title compound (16.5 mg) was obtained in the same way as in Example 7 using the compound (100 mg) obtained in Reference Example 5,4-methylquinolin-2-amine (58 mg), PyBOP (281 mg), dichloromethane (30 mL), and N,N-diisopropylethylamine (97 μL).

$^1$H NMR (CDCl$_3$, 400 MHz): δ (ppm) 8.77 (br. s., 1H), 8.33 (br. s., 1H), 8.13 (d, J=7.7 Hz, 1H), 7.96 (d, J=8.1 Hz, 1H), 7.81-7.89 (m, 1H), 7.63-7.72 (m, 1H), 7.42-7.53 (m, 2H), 2.81 (s, 3H), 2.77 (s, 3H), 2.75 (s, 3H), 2.67 (s, 3H)

MS (ESI$^+$) m/z: 417 [M+H]$^+$

Example 12

4,7-Diacetyl-N-(4-methoxyquinolin-2-yl)-3-methyl-benzo[b]thiophene-2-carboxamide

[Formula 208]

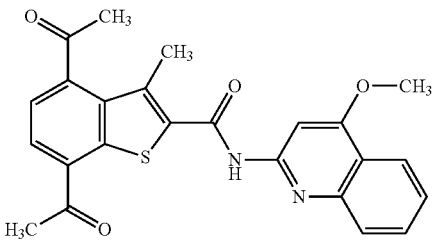

The title compound (35 mg) was obtained in the same way as in Example 9 using the compound (40 mg) obtained in Reference Example 5, the compound (26 mg) obtained in Reference Example 29, 1-ethyl-3-(3-dimethylaminopropyl)carbodiimide hydrochloride (42 mg), 1-hydroxy-7-azabenzotriazole (30 mg), and DMF (15 mL).

$^1$H NMR (CDCl$_3$, 400 MHz): δ (ppm) 8.74 (br. s., 1H), 8.09-8.14 (m, 2H), 7.69-7.75 (m, 1H), 7.62-7.68 (m, 1H), 7.47 (d, J=7.7 Hz, 1H), 7.41 (t, J=7.5 Hz, 1H), 4.15 (s, 3H), 2.81 (s, 3H), 2.75 (s, 3H), 2.69 (s, 3H)

MS (ESI$^+$) m/z: 433 [M+H]$^+$

Example 13

4,7-Diacetyl-N-(4-(1-hydroxyethyl)quinolin-2-yl)-3-methylbenzo[b]thiophene-2-carboxamide

[Formula 209]

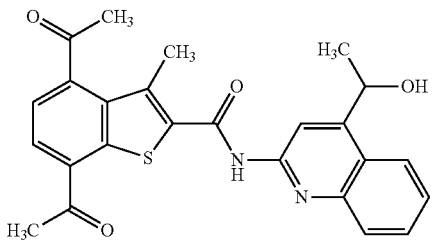

The title compound (54 mg) was obtained in the same way as in Example 9 using the compound (97 mg) obtained in Reference Example 5, the compound (60 mg) obtained in Reference Example 37, 1-ethyl-3-(3-dimethylaminopropyl)carbodiimide hydrochloride (102 mg), 1-hydroxy-7-azabenzotriazole (73 mg), and DMF (15 mL).

$^1$H NMR (CDCl$_3$, 400 MHz): δ (ppm) 8.64 (br. s., 1H), 8.13 (d, J=7.7 Hz, 1H), 8.03 (d, J=8.5 Hz, 1H), 7.89 (d, J=7.7 Hz, 1H), 7.64-7.72 (m, 1H), 7.43-7.54 (m, 2H), 5.59-5.70 (m, 1H), 2.80 (s, 3H), 2.75 (s, 3H), 2.67 (s, 3H), 1.72 (d, J=6.5 Hz, 3H)

MS (ESI$^+$) m/z: 447 [M+H]$^+$

Example 14

4,7-Diacetyl-N-(4-(hydroxymethyl)quinolin-2-yl)-3-methylbenzo[b]thiophene-2-carboxamide

[Formula 210]

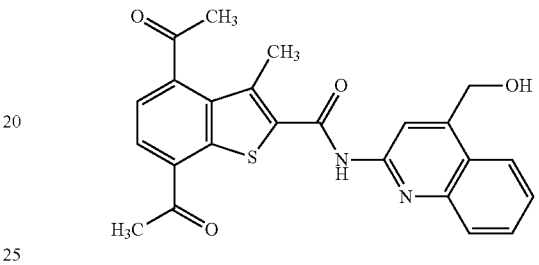

The title compound (17.1 mg) was obtained in the same way as in Example 7 using the compound (108 mg) obtained in Reference Example 5, the compound (62 mg) obtained in Reference Example 39, PyBOP (270 mg), dichloromethane (30 mL), and N,N-diisopropylethylamine (92 mg).

$^1$H NMR (MeOD, 400 MHz): δ (ppm) 8.52 (br. s., 1H), 8.22 (d, J=7.7 Hz, 1H), 7.97 (d, J=8.1 Hz, 1H), 7.88 (d, J=8.1 Hz, 1H), 7.68-7.75 (m, 1H), 7.50-7.60 (m, 2H), 5.19 (s, 2H), 2.83 (s, 3H), 2.79 (s, 3H), 2.64 (s, 3H)

MS (ESI$^+$) m/z: 433 [M+H]$^+$

Example 15

4,7-Diacetyl-3-methyl-N-(4-((N-methylacetamido)methyl)quinolin-2-yl)benzo[b]thiophene-2-carboxamide

[Formula 211]

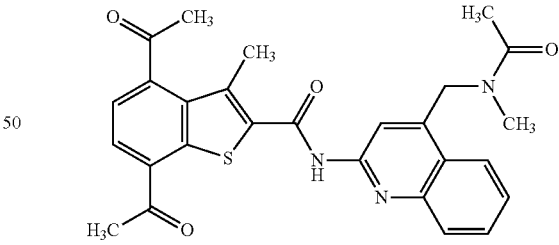

The title compound (69 mg) was obtained in the same way as in Example 9 using the compound (48 mg) obtained in Reference Example 5, the compound (41 mg) obtained in Reference Example 40, 1-ethyl-3-(3-dimethylaminopropyl)carbodiimide hydrochloride (52 mg), 1-hydroxy-7-azabenzotriazole (37 mg), and DMF (5 mL).

$^1$H NMR (CDCl$_3$, 400 MHz): δ (ppm) 8.74 (br. s., 1H), 8.37 (br. s., 1H), 8.14 (d, J=7.7 Hz, 1H), 8.03 (d, J=8.1 Hz, 1H), 7.84-7.90 (m, 1H), 7.66-7.72 (m, 1H), 7.46-7.53 (m, 2H), 5.11 (s, 2H), 3.06 (s, 3H), 2.81 (s, 3H), 2.75 (s, 3H), 2.67 (s, 3H), 2.26 (s, 3H)

MS (ESI$^+$) m/z: 488 [M+H]$^+$

Example 16

N-(4-(2-Hydroxypropan-2-yl)quinolin-2-yl)-3-methyl-7-propionylbenzo[b]thiophene-2-carboxamide

[Formula 212]

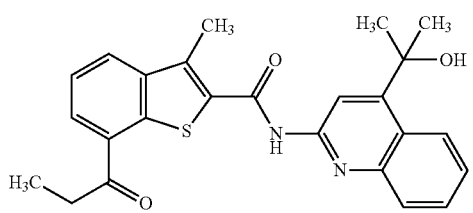

The title compound (62 mg) was obtained in the same way as in Example 7 using the compound (62 mg) obtained in Reference Example 46, the compound (51 mg) obtained in Reference Example 8, PyBOP (143 mg), dichloromethane (2.5 mL), and N,N-diisopropylethylamine (86 μL).

$^1$H NMR (CDCl$_3$, 400 MHz): δ (ppm) 8.67-8.75 (m, 2H), 8.64 (br. s., 1H), 8.19 (d, J=6.9 Hz, 1H), 8.12 (dd, J=8.1, 0.8 Hz, 1H), 7.85-7.93 (m, 1H), 7.59-7.69 (m, 2H), 7.44-7.50 (m, 1H), 3.21 (q, J=7.3 Hz, 2H), 2.86 (s, 3H), 2.17 (s, 1H), 1.92 (s, 6H), 1.35 (t, J=7.3 Hz, 3H)

MS (ESI$^+$) m/z: 433 [M+H]$^+$

Example 17

7-Butyryl-N-(4-(2-hydroxypropan-2-yl)quinolin-2-yl)-3-methylbenzo[b]thiophene-2-carboxamide

[Formula 213]

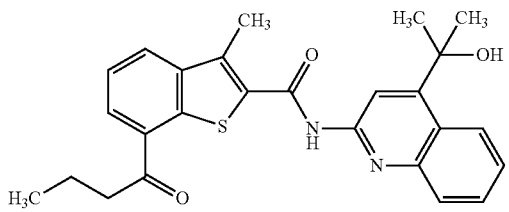

The title compound (22 mg) was obtained in the same way as in Example 7 using the compound (78.7 mg) obtained in Reference Example 48, the compound (60.7 mg) obtained in Reference Example 8, PyBOP (172 mg), dichloromethane (2 mL), and N,N-diisopropylethylamine (103 μL).

$^1$H NMR (CDCl$_3$, 400 MHz): δ (ppm) 8.68-8.75 (m, 2H), 8.64 (br. s., 1H), 8.19 (d, J=6.9 Hz, 1H), 8.11 (dd, J=8.1, 0.8 Hz, 1H), 7.85-7.93 (m, 1H), 7.59-7.69 (m, 2H), 7.44-7.50 (m, 1H), 3.15 (t, J=7.3 Hz, 2H), 2.86 (s, 3H), 2.18 (br. s., 1H), 1.83-1.96 (m, 8H), 1.04-1.11 (m, 3H)

MS (ESI$^+$) m/z: 447 [M+H]$^+$

Example 18

N-(4-(2-Hydroxypropan-2-yl)quinolin-2-yl)-7-isobutyryl-3-methylbenzo[b]thiophene-2-carboxamide

[Formula 214]

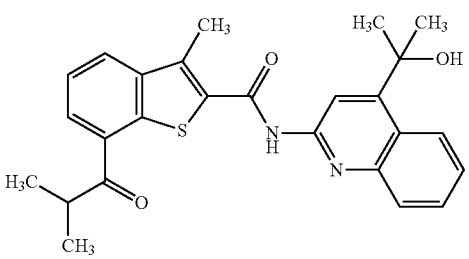

The title compound (89 mg) was obtained in the same way as in Example 7 using the compound (78.7 mg) obtained in Reference Example 50, the compound (60.7 mg) obtained in Reference Example 8, PyBOP (172 mg), dichloromethane (2 mL), and N,N-diisopropylethylamine (103 μL).

$^1$H NMR (CDCl$_3$, 400 MHz): δ (ppm) 8.67-8.77 (m, 2H), 8.63 (br. s., 1H), 8.21 (d, J=7.3 Hz, 1H), 8.12 (dd, J=7.9, 1.0 Hz, 1H), 7.84-7.92 (m, 1H), 7.60-7.68 (m, 2H), 7.43-7.49 (m, 1H), 3.73-3.84 (m, 1H), 2.86 (s, 3H), 2.23 (br. s., 1H), 1.91 (s, 6H), 1.34 (d, J=6.9 Hz, 6H)

MS (ESI$^+$) m/z: 447 [M+H]$^+$

Example 19

7-(Cyclopropylcarbonyl)-N-(4-(2-hydroxypropan-2-yl)quinolin-2-yl)-3-methylbenzo[b]thiophene-2-carboxamide

[Formula 215]

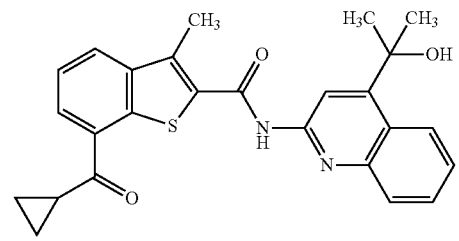

The title compound (84 mg) was obtained in the same way as in Example 7 using the compound (78.1 mg) obtained in Reference Example 52, the compound (60.7 mg) obtained in Reference Example 8, PyBOP (172 mg), dichloromethane (2 mL), and N,N-diisopropylethylamine (103 μL).

$^1$H NMR (CDCl$_3$, 400 MHz): δ (ppm) 8.67-8.74 (m, 2H), 8.63 (br. s., 1H), 8.37 (d, J=7.3 Hz, 1H), 8.13 (d, J=8.1 Hz, 1H), 7.83-7.92 (m, 1H), 7.61-7.69 (m, 2H), 7.43-7.49 (m, 1H), 2.84-2.93 (m, 4H), 2.19 (br. s., 1H), 1.91 (s, 6H), 1.37-1.43 (m, 2H), 1.13-1.19 (m, 2H)

MS (ESI$^+$) m/z: 445 [M+H]$^+$

Example 20

N-(4-(2-Hydroxypropan-2-yl)quinolin-2-yl)-3-methyl-7-pentanoylbenzo[b]thiophene-2-carboxamide

[Formula 216]

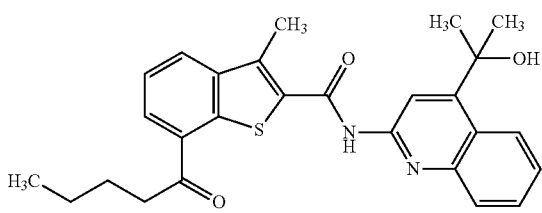

The title compound (88 mg) was obtained in the same way as in Example 7 using the compound (82.9 mg) obtained in Reference Example 54, the compound (60.7 mg) obtained in Reference Example 8, PyBOP (172 mg), dichloromethane (2 mL), and N,N-diisopropylethylamine (103 μL).

$^1$H NMR (CDCl$_3$, 400 MHz): δ (ppm) 8.68-8.74 (m, 2H), 8.64 (br. s., 1H), 8.19 (d, J=7.7 Hz, 1H), 8.12 (d, J=8.1 Hz, 1H), 7.86-7.94 (m, 1H), 7.59-7.69 (m, 2H), 7.44-7.50 (m, 1H), 3.17 (t, J=7.5 Hz, 2H), 2.86 (s, 3H), 2.13 (s, 1H), 1.92 (s, 6H), 1.79-1.89 (m, 2H), 1.42-1.54 (m, 2H), 1.00 (t, J=7.3 Hz, 3H)

MS (ESI$^+$) m/z: 461 [M+H]$^+$

Example 21

7-(Cyclobutylcarbonyl)-N-(4-(2-hydroxypropan-2-yl)quinolin-2-yl)-3-methylbenzo[b]thiophene-2-carboxamide

[Formula 217]

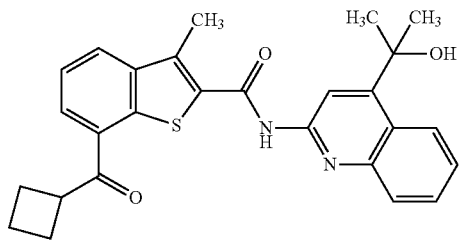

The title compound (65 mg) was obtained in the same way as in Example 7 using the compound (82.3 mg) obtained in Reference Example 56, the compound (60.7 mg) obtained in Reference Example 8, PyBOP (172 mg), dichloromethane (2 mL), and N,N-diisopropylethylamine (103 μL).

$^1$H NMR (CDCl$_3$, 400 MHz): δ (ppm) 8.69-8.75 (m, 2H), 8.65 (br. s., 1H), 8.11 (d, J=8.1 Hz, 1H), 8.03 (d, J=7.3 Hz, 1H), 7.86-7.95 (m, 1H), 7.64-7.70 (m, 1H), 7.57-7.62 (m, 1H), 7.45-7.51 (m, 1H), 4.16-4.27 (m, 1H), 2.86 (s, 3H), 2.50-2.63 (m, 2H), 2.35-2.47 (m, 2H), 2.13-2.24 (m, 2H), 1.96-2.06 (m, 1H), 1.92 (s, 6H)

MS (ESI$^+$) m/z: 459 [M+H]$^+$

Example 22

N-(4-(2-Hydroxypropan-2-yl)quinolin-2-yl)-3-methyl-7-pivaloylbenzo[b]thiophene-2-carboxamide

[Formula 218]

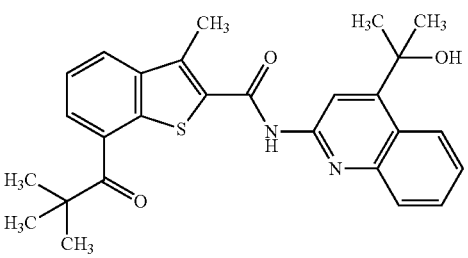

The title compound (48 mg) was obtained in the same way as in Example 7 using the compound (82.9 mg) obtained in Reference Example 58, the compound (60.7 mg) obtained in Reference Example 8, PyBOP (258 mg), dichloromethane (2 mL), and N,N-diisopropylethylamine (103 μL).

$^1$H NMR (CDCl$_3$, 400 MHz): δ (ppm) 8.68-8.74 (m, 2H), 8.65 (br. s., 1H), 8.36 (d, J=7.3 Hz, 1H), 8.08 (d, J=7.7 Hz, 1H), 7.90 (d, J=8.1 Hz, 1H), 7.63-7.69 (m, 1H), 7.55-7.61 (m, 1H), 7.43-7.50 (m, 1H), 2.86 (s, 3H), 2.12 (s, 1H), 1.92 (s, 6H), 1.54 (s, 9H)

MS (ESI$^+$) m/z: 461 [M+H]$^+$

Example 23

N-(4-(2-Hydroxypropan-2-yl)quinolin-2-yl)-3-methyl-7-(3-methylbutanoyl)benzo[b]thiophene-2-carboxamide

[Formula 219]

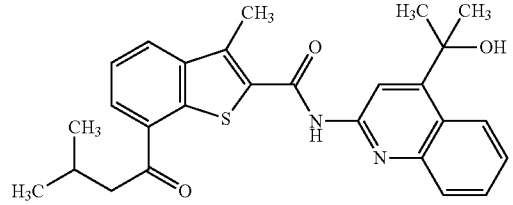

The title compound (63 mg) was obtained in the same way as in Example 7 using the compound (82.9 mg) obtained in Reference Example 60, the compound (60.7 mg) obtained in Reference Example 8, PyBOP (172 mg), dichloromethane (2 mL), and N,N-diisopropylethylamine (103 μL).

$^1$H NMR (CDCl$_3$, 400 MHz): δ(ppm) 8.69-8.74 (m, 2H), 8.65 (br. s., 1H), 8.18 (d, J=7.7 Hz, 1H), 8.12 (d, J=8.1 Hz, 1H), 7.86-7.95 (m, 1H), 7.59-7.69 (m, 2H), 7.44-7.51 (m, 1H), 3.04 (d, J=6.9 Hz, 2H), 2.86 (s, 3H), 2.36-2.48 (m, 1H), 2.13 (br. s., 1H), 1.92 (s, 6H), 1.07 (d, J=6.5 Hz, 6H)

MS (ESI$^+$) m/z: 461 [M+H]$^+$

Example 24

7-(2-Ethylbutanoyl)-N-(4-(2-hydroxypropan-2-yl)quinolin-2-yl)-3-methylbenzo[b]thiophene-2-carboxamide

[Formula 220]

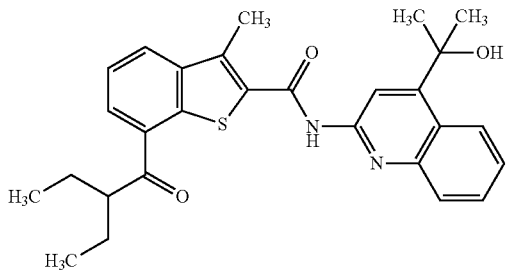

The title compound (55 mg) was obtained in the same way as in Example 7 using the compound (87.1 mg) obtained in Reference Example 62, the compound (60.7 mg) obtained in Reference Example 8, PyBOP (172 mg), dichloromethane (2 mL), and N,N-diisopropylethylamine (103 μL).

$^1$H NMR (CDCl$_3$, 400 MHz): δ (ppm) 8.68-8.76 (m, 2H), 8.65 (s, 1H), 8.22 (d, J=7.7 Hz, 1H), 8.14 (d, J=7.7 Hz, 1H), 7.87-7.93 (m, 1H), 7.61-7.69 (m, 2H), 7.44-7.50 (m, 1H), 3.48-3.55 (m, 1H), 2.87 (s, 3H), 2.12 (s, 1H), 1.86-1.98 (m, 8H), 1.63-1.74 (m, 2H), 0.92 (t, J=7.5 Hz, 6H)

MS (ESI$^+$) m/z: 475 [M+H]$^+$

Example 25

7-(Cyclopentylcarbonyl)-N-(4-(2-hydroxypropan-2-yl)quinolin-2-yl)-3-methylbenzo[b]thiophene-2-carboxamide

[Formula 221]

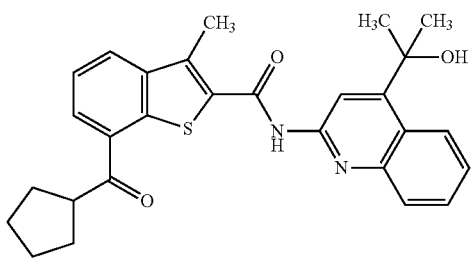

The title compound (71 mg) was obtained in the same way as in Example 7 using the compound (86.5 mg) obtained in Reference Example 64, the compound (60.7 mg) obtained in Reference Example 8, PyBOP (258 mg), dichloromethane (2 mL), and N,N-diisopropylethylamine (103 μL).

$^1$H NMR (CDCl$_3$, 400 MHz): δ (ppm) 8.68-8.75 (m, 2H), 8.64 (br. s., 1H), 8.22 (d, J=7.3 Hz, 1H), 8.12 (d, J=7.7 Hz, 1H), 7.85-7.94 (m, 1H), 7.59-7.69 (m, 2H), 7.43-7.50 (m, 1H), 3.88-3.99 (m, 1H), 2.86 (s, 3H), 2.13 (s, 1H), 2.00-2.09 (m, 4H), 1.91 (s, 6H), 1.67-1.87 (m, 4H)

MS (ESI$^+$) m/z: 473 [M+H]$^+$

Example 26

7-Acetyl-N-(4-(2-hydroxypropan-2-yl)quinolin-2-yl)-4-(methoxymethyl)-3-methylbenzo[b]thiophene-2-carboxamide

[Formula 222]

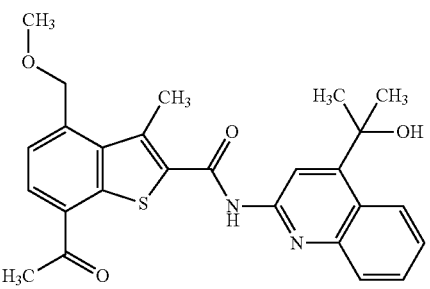

To a suspension of the compound (55.7 mg) obtained in Reference Example 74, the compound (40.5 mg) obtained in Reference Example 8, and PyBOP (114 mg) in dichloromethane (2 mL), N,N-diisopropylethylamine (68.8 μL) was added, and the mixture was stirred at room temperature for 3 days. To the reaction mixture, water was added, followed by extraction with ethyl acetate. The organic layer was dried over anhydrous sodium sulfate and concentrated. The residue was purified by basic silica gel column chromatography (hexane:dichloromethane=30:70-0:100) and silica gel column chromatography (hexane:ethyl acetate=70:30-20:80) in this order to obtain the title compound (49 mg).

$^1$H NMR (CDCl$_3$, 400 MHz): δ (ppm) 8.68-8.78 (m, 2H), 8.62 (br. s., 1H), 8.09 (d, J=7.7 Hz, 1H), 7.88 (d, J=8.1 Hz, 1H), 7.60-7.68 (m, 2H), 7.43-7.49 (m, 1H), 5.00 (s, 2H), 3.53 (s, 3H), 2.99 (s, 3H), 2.78 (s, 3H), 2.22 (br. s., 1H), 1.91 (s, 6H)

MS (ESI$^+$) m/z: 463 [M+H]$^+$

Example 27

7-Acetyl-N-(4-(2-hydroxypropan-2-yl)quinolin-2-yl)-4-(methoxymethyl)-3-methylbenzo[b]thiophene-2-carboxamide hydrochloride

[Formula 223]

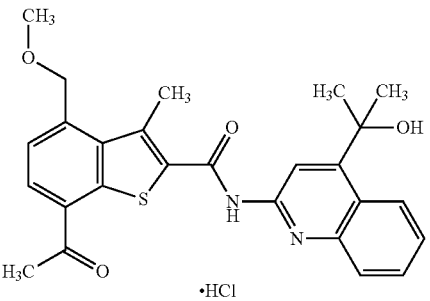

To a solution of the compound (30 mg) obtained in Example 26 in 2-propanol (5 mL), hydrogen chloride (4 N solution in 1,4-dioxane, 0.016 mL) was added. The mixture was concentrated. To the obtained residue, a 2-propanolhexane mixed solution was added, and the mixture was heated and then cooled to room temperature. The precipitated solid was collected by filtration to obtain the title compound (30.1 mg).

$^1$H NMR (CDCl$_3$, 400 MHz): δ (ppm) 9.05 (s, 1H), 8.88 (d, J=8.5 Hz, 1H), 8.17 (d, J=8.5 Hz, 1H), 8.08 (d, J=7.7 Hz, 1H), 7.84-7.90 (m, 1H), 7.65-7.72 (m, 1H), 7.62 (d, J=7.3 Hz, 1H), 5.00 (s, 2H), 3.52 (s, 3H), 3.06 (s, 3H), 2.76 (s, 3H), 1.95 (s, 6H)

MS (ESI$^+$) m/z: 463 [M+H]$^+$

Example 28

7-Acetyl-N-(4-(2-hydroxypropan-2-yl)quinolin-2-yl)-4-(methoxymethyl)-3-methylbenzo[b]thiophene-2-carboxamide hydrobromide

[Formula 224]

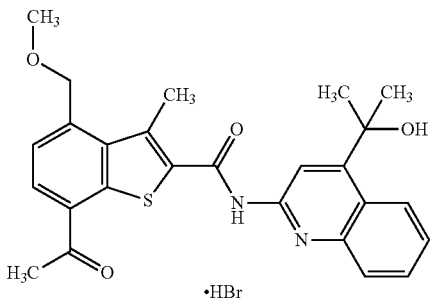

·HBr

To a solution of the compound (30 mg) obtained in Example 26 in 2-propanol (5 mL), 47% hydrobromic acid (3.52 μL) was added. The mixture was concentrated. To the obtained residue, a 2-propanol-hexane mixed solution was added, and the mixture was heated and then cooled to room temperature. The precipitated solid was collected by filtration to obtain the title compound (32 mg).

$^1$H NMR (CDCl$_3$, 400 MHz): δ (ppm) 12.19 (br. s., 1H), 9.08 (s, 1H), 8.88 (d, J=8.1 Hz, 1H), 8.25 (d, J=8.1 Hz, 1H), 8.09 (d, J=7.7 Hz, 1H), 7.87-7.93 (m, 1H), 7.68-7.74 (m, 1H), 7.63 (d, J=7.7 Hz, 1H), 5.00 (s, 2H), 3.52 (s, 3H), 3.09 (s, 3H), 2.76 (s, 3H), 2.58 (s, 1H), 1.95 (s, 6H)

MS (ESI$^+$) m/z: 463 [M+H]$^+$

Example 29

7-Acetyl-4-(ethoxymethyl)-N-(4-(2-hydroxypropan-2-yl)quinolin-2-yl)-3-methylbenzo[b]thiophene-2-carboxamide

[Formula 225]

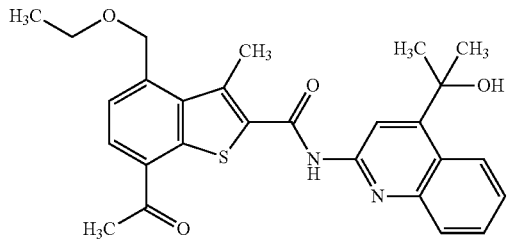

To a suspension of the compound (58 mg) obtained in Reference Example 78, the compound (44 mg) obtained in Reference Example 8, and PyBOP (114 mg) in dichloromethane (2 mL), N,N-diisopropylethylamine (69 μL) was added, and the mixture was stirred at room temperature for 2.5 days. To the reaction mixture, water was added, followed by extraction with dichloromethane. The organic layer was dried over anhydrous sodium sulfate and concentrated. The residue was purified by basic silica gel column chromatography (hexane:dichloromethane=30:70-0:100) and silica gel column chromatography (hexane:ethyl acetate=70:30-20:80) in this order to obtain the title compound (55 mg).

$^1$H NMR (CDCl$_3$, 400 MHz): δ (ppm) 8.82 (br. s., 1H), 8.69 (d, J=8.1 Hz, 1H), 8.58 (br. s., 1H), 8.06 (d, J=7.7 Hz, 1H), 7.84 (d, J=8.5 Hz, 1H), 7.58-7.66 (m, 2H), 7.40-7.47 (m, 1H), 5.01 (s, 2H), 3.69 (q, J=6.9 Hz, 2H), 2.97 (s, 3H), 2.77 (s, 3H), 2.05 (s, 1H), 1.90 (s, 6H), 1.32 (t, J=6.9 Hz, 3H)

MS (ESI$^+$) m/z: 477 [M+H]$^+$

Example 30

7-Acetyl-N-(4-(2-hydroxypropan-2-yl)quinolin-2-yl)-3-methyl-4-(propoxymethyl)benzo[b]thiophene-2-carboxamide

[Formula 226]

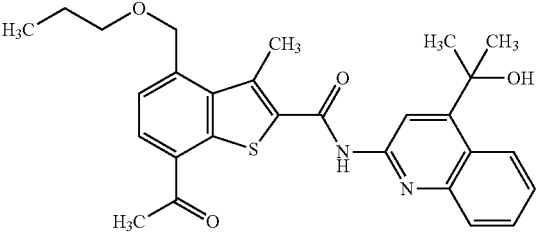

To a suspension of the compound (61 mg) obtained in Reference Example 79, the compound (44 mg) obtained in Reference Example 8, and PyBOP (114 mg) in dichloromethane (2 mL), N,N-diisopropylethylamine (69 μL) was added, and the mixture was stirred at room temperature for 22 hours. To the reaction mixture, water was added, followed by extraction with dichloromethane. The organic layer was dried over anhydrous sodium sulfate and concentrated. The residue was purified by silica gel column chromatography (hexane:ethyl acetate=70:30-20:80) to obtain the title compound (60 mg).

$^1$H NMR (CDCl$_3$, 400 MHz): δ (ppm) 8.83 (br. s., 1H), 8.69 (d, J=8.1 Hz, 1H), 8.58 (br. s., 1H), 8.07 (d, J=7.7 Hz, 1H), 7.84 (d, J=8.5 Hz, 1H), 7.58-7.66 (m, 2H), 7.39-7.47 (m, 1H), 5.01 (s, 2H), 3.58 (t, J=6.7 Hz, 2H), 2.98 (s, 3H), 2.77 (s, 3H), 2.42 (br. s., 1H), 1.90 (s, 6H), 1.66-1.75 (m, 2H), 0.98 (t, J=7.5 Hz, 3H)

MS (ESI$^+$) m/z: 491 [M+H]$^+$

Example 31

7-Acetyl-N-(4-(2-hydroxypropan-2-yl)quinolin-2-yl)-4-(isopropoxymethyl)-3-methylbenzo[b]thiophene-2-carboxamide

[Formula 227]

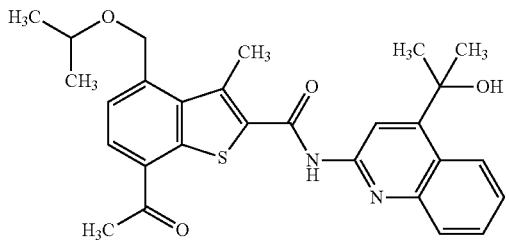

To a suspension of the compound (153 mg) obtained in Reference Example 80, the compound (111 mg) obtained in Reference Example 8, and PyBOP (286 mg) in dichloromethane (5 mL), N,N-diisopropylethylamine (172 µL) was added, and the mixture was stirred at room temperature for 20 hours. To the reaction mixture, water was added, followed by extraction with dichloromethane. The organic layer was dried over anhydrous sodium sulfate and concentrated. The residue was purified by silica gel column chromatography (hexane:ethyl acetate=70:30-20:80) to obtain the title compound (56 mg).

$^1$H NMR (CDCl$_3$, 400 MHz): δ (ppm) 8.65-9.03 (m, 2H), 8.58 (br. s., 1H), 8.07 (d, J=7.7 Hz, 1H), 7.85 (d, J=8.1 Hz, 1H), 7.59-7.68 (m, 2H), 7.41-7.48 (m, 1H), 5.03 (s, 2H), 3.78-3.88 (m, 1H), 3.00 (s, 3H), 2.77 (s, 3H), 2.39 (br. s., 1H), 1.91 (s, 6H), 1.30 (d, J=6.1 Hz, 6H)

MS (ESI$^+$) m/z: 491 [M+H]$^+$

Example 32

7-Acetyl-N-(4-(2-hydroxypropan-2-yl)quinolin-2-yl)-4-(1-methoxyethyl)-3-methylbenzo[b]thiophene-2-carboxamide

[Formula 228]

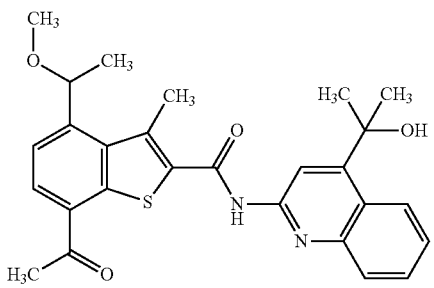

The title compound (16.3 mg) was obtained in the same way as in Example 31 using the compound (35 mg) obtained in Reference Example 83, the compound (25 mg) obtained in Reference Example 8, PyBOP (94 mg), dichloromethane (20 mL), and N,N-diisopropylethylamine (32 µL).

$^1$H NMR (CDCl$_3$, 400 MHz): δ (ppm) 8.73-8.81 (m, 1H), 8.71 (d, J=8.5 Hz, 1H), 8.62 (br. s., 1H), 8.17 (d, J=8.1 Hz, 1H), 7.89 (d, J=8.9 Hz, 1H), 7.84 (d, J=8.1 Hz, 1H), 7.66 (t, J=7.5 Hz, 1H), 7.45-7.51 (m, 1H), 5.45-5.53 (m, 1H), 3.33 (s, 3H), 2.98 (s, 3H), 2.79 (s, 3H), 1.92 (s, 6H), 1.54-1.60 (m, 3H)

MS (ESI$^+$) m/z: 477 [M+H]$^+$

Example 33

7-Acetyl-N-(4-(1-hydroxyethyl)quinolin-2-yl)-4-(methoxymethyl)-3-methylbenzo[b]thiophene-2-carboxamide hydrochloride

[Formula 229]

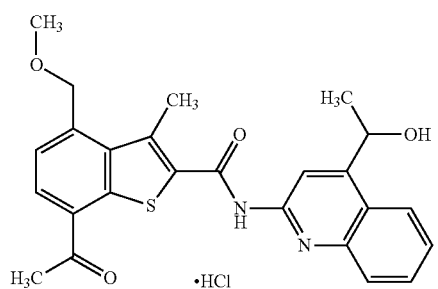

The free base of the title compound was obtained in the same way as in Example 31 using the compound (100 mg) obtained in Reference Example 74, the compound (68 mg) obtained in Reference Example 37, PyBOP (206 mg), dichloromethane (2 mL, and N,N-diisopropylethylamine (102 µL). Then, hydrogen chloride (4 N solution in ethyl acetate) was added thereto, and the mixture was concentrated to obtain the title compound (28.2 mg).

$^1$H NMR (MeOD, 400 MHz): δ (ppm) 8.33-8.37 (m, 2H), 8.22-8.26 (m, 1H), 8.10 (s, 1H), 8.05 (td, J=7.7, 1.2 Hz, 1H), 7.84 (ddd, J=8.4, 7.2, 1.0 Hz, 1H), 7.74 (d, J=7.7 Hz, 1H), 5.74 (q, J=6.4 Hz, 1H), 5.04 (s, 2H), 3.50 (s, 3H), 3.02 (s, 3H), 2.79 (s, 3H), 1.65 (d, J=6.5 Hz, 3H)

MS (ESI$^+$) m/z: 449 [M+H]$^+$

Example 34

7-Acetyl-N-(4-(((2-hydroxyethyl)(methyl)amino)methyl)quinolin-2-yl)-4-(methoxymethyl)-3-methylbenzo[b]thiophene-2-carboxamide dihydrochloride

[Formula 230]

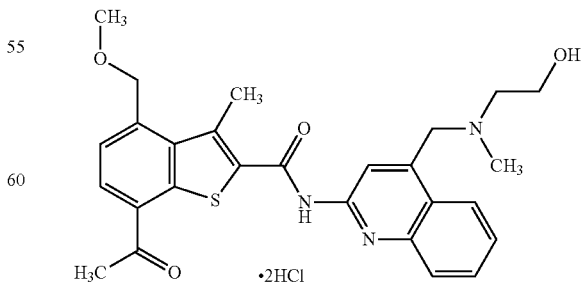

The free base of the title compound was obtained in the same way as in Example 31 using the compound (35 mg)

obtained in Reference Example 74, the compound (32 mg) obtained in Reference Example 85, PyBOP (72 mg), dichloromethane (1 mL), and N,N-diisopropylethylamine (18 mg). Then, hydrogen chloride (4 N solution in ethyl acetate) was added thereto, and the mixture was concentrated to obtain the title compound (38 mg).

$^1$H NMR (MeOD, 400 MHz): δ (ppm) 8.57 (s, 1H), 8.29-8.34 (m, 2H), 8.07-8.11 (m, 1H), 7.87-7.92 (m, 1H), 7.69-7.77 (m, 2H), 5.03 (s, 2H), 3.97-4.10 (m, 2H), 3.49-3.54 (m, 5H), 3.00 (s, 3H), 2.96 (s, 3H), 2.78 (s, 3H)

MS (ESI$^+$) m/z: 492 [M+H]$^+$

Example 35

7-Acetyl-N-(4-((3-hydroxypyrrolidin-1-yl)methyl) quinolin-2-yl)-4-(methoxymethyl)-3-methylbenzo[b] thiophene-2-carboxamide

[Formula 231]

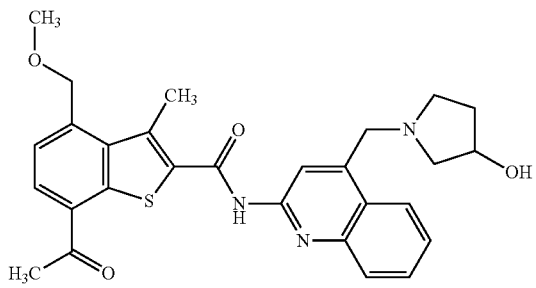

To a suspension of the compound (70.0 mg) obtained in Reference Example 74, the compound (67.4 mg) obtained in Reference Example 86, and PyBOP (144 mg) in dichloromethane (2 mL), N,N-diisopropylethylamine (86.7 μL) was added, and the mixture was stirred at room temperature for 20 hours. To the reaction mixture, water was added, followed by extraction with dichloromethane. The organic layer was dried over anhydrous sodium sulfate and concentrated. The residue was purified by basic silica gel column chromatography (dichloromethane:methanol=100:0-95:5) and basic silica gel column chromatography (hexane:ethyl acetate=50:50-0:100) in this order to obtain the title compound (75 mg).

$^1$H NMR (CDCl$_3$, 400 MHz): δ (ppm) 8.74 (br. s., 1H), 8.52 (br. s., 1H), 8.19 (d, J=8.1 Hz, 1H), 8.09 (d, J=7.7 Hz, 1H), 7.87 (d, J=8.1 Hz, 1H), 7.65-7.70 (m, 1H), 7.63 (d, J=7.7 Hz, 1H), 7.45-7.51 (m, 1H), 5.00 (s, 2H), 4.35-4.40 (m, 1H), 4.12 (s, 2H), 3.53 (s, 3H), 2.98-3.05 (m, 4H), 2.83 (d, J=10.1 Hz, 1H), 2.79 (s, 3H), 2.68 (dd, J=10.1, 4.9 Hz, 1H), 2.44-2.51 (m, 1H), 2.19-2.29 (m, 1H), 1.77-1.85 (m, 1H), 1H)

MS (ESI$^+$) m/z: 504 [M+H]$^+$

Example 36

7-Acetyl-N-(4-((4-hydroxypiperidin-1-yl)methyl) quinolin-2-yl)-4-(methoxymethyl)-3-methylbenzo[b] thiophene-2-carboxamide

[Formula 232]

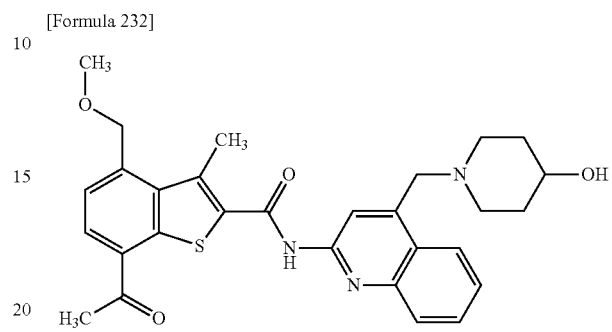

To a suspension of the compound (83 mg) obtained in Reference Example 74, the compound (77 mg) obtained in Reference Example 87, and PyBOP (172 mg) in dichloromethane (3 mL), N,N-diisopropylethylamine (103 μL) was added, and the mixture was stirred at room temperature for 1.5 days. To the reaction mixture, water was added, followed by extraction with dichloromethane. The organic layer was dried over anhydrous sodium sulfate and concentrated. The residue was purified by basic silica gel column chromatography (hexane:ethyl acetate=50:50-0:100) to obtain the title compound (35 mg).

$^1$H NMR (CDCl$_3$, 400 MHz): δ (ppm) 8.69 (s, 1H), 8.51 (br. s., 1H), 8.25 (d, J=7.7 Hz, 1H), 8.10 (d, J=7.7 Hz, 1H), 7.87 (d, J=8.5 Hz, 1H), 7.61-7.71 (m, 2H), 7.45-7.51 (m, 1H), 5.01 (s, 2H), 3.95 (s, 2H), 3.71-3.81 (m, 1H), 3.53 (s, 3H), 3.01 (s, 3H), 2.84-2.92 (m, 2H), 2.79 (s, 3H), 2.27-2.37 (m, 2H), 1.90-1.98 (m, 2H), 1.59-1.71 (m, 2H)

MS (ESI$^+$) m/z: 518 [M+H]$^+$

Example 37

7-Acetyl-N-(4-((3-hydroxypiperidin-1-yl)methyl) quinolin-2-yl)-4-(methoxymethyl)-3-methylbenzo[b] thiophene-2-carboxamide

[Formula 233]

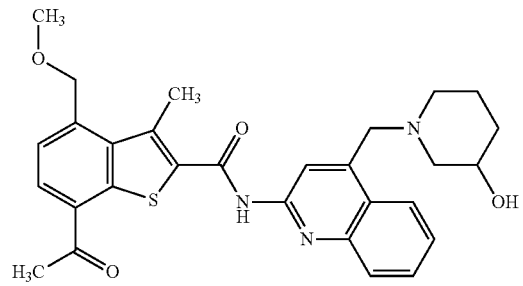

To a suspension of the compound (83 mg) obtained in Reference Example 74, the compound (77 mg) obtained in Reference Example 88, and PyBOP (172 mg) in dichloromethane (3 mL), N,N-diisopropylethylamine (155 μL)

was added, and the mixture was stirred at room temperature for 4.5 days. To the reaction mixture, water was added, followed by extraction with dichloromethane. The organic layer was dried over anhydrous sodium sulfate and concentrated. The residue was purified by basic silica gel column chromatography (hexane:ethyl acetate=50:50-0:100) to obtain the title compound (70 mg).

$^1$H NMR (CDCl$_3$, 400 MHz): δ (ppm) 8.71 (s, 1H), 8.51 (br. s., 1H), 8.18 (d, J=8.5 Hz, 1H), 8.10 (d, J=7.7 Hz, 1H), 7.88 (d, J=7.7 Hz, 1H), 7.61-7.71 (m, 2H), 7.46-7.52 (m, 1H), 5.01 (s, 2H), 3.96 (s, 2H), 3.84-3.91 (m, 1H), 3.53 (s, 3H), 3.01 (s, 3H), 2.79 (s, 3H), 2.37-2.74 (m, 4H), 1.78-1.91 (m, 1H), 1.53-1.71 (m, 3H)

MS (ESI$^+$) m/z: 518 [M+H]$^+$

Example 38

(S)-7-Acetyl-N-(4-((3-hydroxypyrrolidin-1-yl)methyl)quinolin-2-yl)-4-(methoxymethyl)-3-methyl-benzo[b]thiophene-2-carboxamide

[Formula 234]

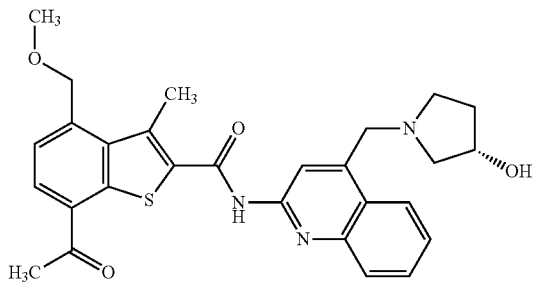

To a suspension of the compound (83 mg) obtained in Reference Example 74, the compound (73 mg) obtained in Reference Example 89, and PyBOP (172 mg) in dichloromethane (3 mL), N,N-diisopropylethylamine (155 μL) was added, and the mixture was stirred at room temperature for 16 hours. To the reaction mixture, water was added, followed by extraction with dichloromethane. The organic layer was dried over anhydrous sodium sulfate and concentrated. The residue was purified by basic silica gel column chromatography (hexane:ethyl acetate=50:50-0:100) to obtain the title compound (55 mg).

$^1$H NMR (CDCl$_3$, 400 MHz): δ (ppm) 8.74 (br. s., 1H), 8.51 (br. s., 1H), 8.18 (d, J=8.5 Hz, 1H), 8.08 (d, J=7.7 Hz, 1H), 7.83-7.90 (m, 1H), 7.60-7.70 (m, 2H), 7.43-7.51 (m, 1H), 4.99 (s, 2H), 4.33-4.42 (m, 1H), 4.11 (s, 2H), 3.52 (s, 3H), 2.97-3.06 (m, 1H), 2.99 (s, 3H), 2.80-2.85 (m, 1H), 2.78 (s, 3H), 2.68 (dd, J=10.1, 4.9 Hz, 1H), 2.44-2.52 (m, 1H), 2.18-2.29 (m, 1H), 1.75-1.86 (m, 1H)

MS (ESI$^+$) m/z: 504 [M+H]$^+$

Example 39

(R)-7-Acetyl-N-(4-((3-hydroxypyrrolidin-1-yl)methyl)quinolin-2-yl)-4-(methoxymethyl)-3-methyl-benzo[b]thiophene-2-carboxamide

[Formula 235]

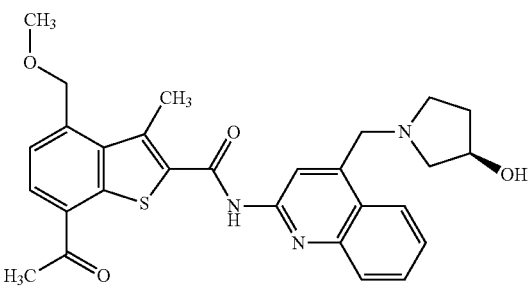

To a suspension of the compound (83 mg) obtained in Reference Example 74, the compound (73 mg) obtained in Reference Example 90, and PyBOP (172 mg) in dichloromethane (3 mL), N,N-diisopropylethylamine (155 μL) was added, and the mixture was stirred at room temperature for 16 hours. To the reaction mixture, water was added, followed by extraction with dichloromethane. The organic layer was dried over anhydrous sodium sulfate and concentrated. The residue was purified by basic silica gel column chromatography (hexane:ethyl acetate=50:50-0:100) and silica gel column chromatography (hexane:ethyl acetate=40:60-0:100) in this order to obtain the title compound (57 mg).

$^1$H NMR (CDCl$_3$, 400 MHz): δ (ppm) 8.71 (s, 1H), 8.53 (br. s., 1H), 8.19 (d, J=8.1 Hz, 1H), 8.10 (d, J=7.7 Hz, 1H), 7.88 (d, J=7.3 Hz, 1H), 7.61-7.71 (m, 2H), 7.46-7.52 (m, 1H), 5.01 (s, 2H), 4.34-4.41 (m, 1H), 4.12 (s, 2H), 3.53 (s, 3H), 2.97-3.06 (m, 4H), 2.83 (d, J=9.7 Hz, 1H), 2.79 (s, 3H), 2.67 (dd, J=9.7, 4.9 Hz, 1H), 2.43-2.51 (m, 1H), 2.19-2.29 (m, 1H), 2.00-2.05 (m, 1H), 1.76-1.86 (m, 1H)

MS (ESI$^+$) m/z: 504 [M+H]$^+$

Example 40

(R)-7-Acetyl-N-(4-((3-hydroxypyrrolidin-1-yl)methyl)quinolin-2-yl)-4-(methoxymethyl)-3-methyl-benzo[b]thiophene-2-carboxamide hydrochloride

[Formula 236]

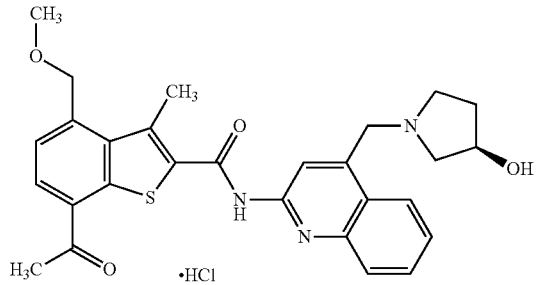

A mixture of the compound (572 mg) obtained in Example 39, 2 N hydrochloric acid (0.625 mL), and a 2-propanol-water (8:2) mixed solution (17.2 mL) was refluxed and cooled to room temperature, and the precipitated solid was collected by filtration to obtain the title compound (400 mg).

$^1$H NMR (CDCl$_3$, 400 MHz): δ (ppm) 11.48 (s, 1H), 10.84 (br. s., 1H), 8.56-8.64 (m, 1H), 8.34 (d, J=7.7 Hz, 2H), 7.95 (d, J=8.5 Hz, 1H), 7.79-7.87 (m, 1H), 7.63-7.72 (m, 2H), 5.50-5.70 (m, 1H), 5.03-5.11 (m, 1H), 5.02 (s, 2H), 4.39-4.55 (m, 1H), 3.59-3.76 (m, 2H), 3.42 (s, 3H), 3.18 (d, J=9.7 Hz, 1H), 2.85 (s, 3H), 2.78 (s, 3H), 2.29-2.45 (m, 1H), 1.76-2.17 (m, 2H)

MS (ESI$^+$) m/z: 504 [M+H]$^+$

Example 41

(R)-7-Acetyl-N-(4-((3-hydroxypyrrolidin-1-yl)methyl)quinolin-2-yl)-4-(methoxymethyl)-3-methyl-benzo[b]thiophene-2-carboxamide p-toluenesulfonate

[Formula 237]

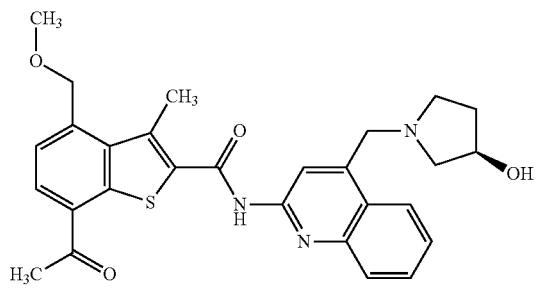

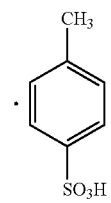

A mixture of the compound (360 mg) obtained in Example 39, p-toluenesulfonic acid monohydrate (138 mg), methanol (1.62), and water (167 μL) was refluxed and cooled to 0° C., and the precipitated solid was collected by filtration to obtain the title compound (346 mg).

$^1$H NMR (DMSO, 400 MHz): δ (ppm) 11.43-11.51 (m, 1H), 10.59 (br. s., 1H), 10.07 (br. s., 1H), 8.55-8.65 (m, 1H), 8.28-8.36 (m, 2H), 7.92-7.99 (m, 1H), 7.79-7.88 (m, 1H), 7.63-7.73 (m, 2H), 7.47 (d, J=8.1 Hz, 2H), 7.11 (d, J=7.7 Hz, 2H), 5.43-5.62 (m, 1H), 5.05-5.10 (m, 1H), 5.01 (s, 2H), 4.40-4.55 (m, 1H), 3.68 (br. s., 2H), 3.47-3.56 (m, 1H), 3.42 (s, 3H), 3.38 (br. s., 1H), 3.17 (s, 2H), 3.14-3.24 (m, 1H), 2.85 (s, 3H), 2.77 (s, 3H), 2.28 (s, 3H), 1.84-2.14 (m, 1H)

MS (ESI$^+$) m/z: 504 [M+H]$^+$

Example 42

(R)-7-Acetyl-3-ethyl-N-(4-((3-hydroxypyrrolidin-1-yl)methyl)quinolin-2-yl)-4-(methoxymethyl)benzo[b]thiophene-2-carboxamide

[Formula 238]

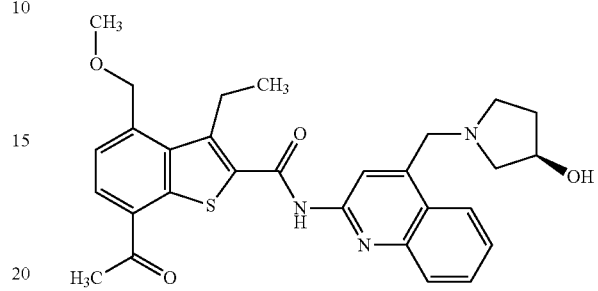

To a solution of the compound (38 mg) obtained in Reference Example 96 and HBTU (67.1 mg) in dichloromethane (5 mL), N,N-diisopropylethylamine (0.057 mL) was added dropwise, and the mixture was stirred at room temperature for 30 minutes. To the reaction mixture, the compound (31.6 mg) obtained in Reference Example 90 was added, and the mixture was stirred at room temperature for 12 hours. To the reaction mixture, water was added, followed by extraction with dichloromethane. The organic layer was dried over anhydrous sodium sulfate and concentrated. The residue was purified by silica gel column chromatography (hexane-ethyl acetate (1:1) mixed solution: methanol=100:0-90:10) to obtain the title compound (4.6 mg).

$^1$H NMR (CDCl$_3$, 400 MHz): δ (ppm) 8.75 (br. s., 1H), 8.52 (br. s., 1H), 8.21 (d, J=8.5 Hz, 1H), 8.12 (d, J=7.7 Hz, 1H), 7.88 (d, J=8.5 Hz, 1H), 7.65-7.72 (m, 2H), 7.45-7.53 (m, 1H), 5.02 (s, 2H), 4.37 (d, J=2.0 Hz, 1H), 4.13 (s, 2H), 3.53 (s, 3H), 3.39-3.48 (m, 2H), 2.97-3.06 (m, 1H), 2.82-2.86 (m, 1H), 2.80 (s, 3H), 2.67 (dd, J=10.1, 5.3 Hz, 1H), 2.42-2.52 (m, 1H), 2.19-2.30 (m, 1H), 1.76-1.87 (m, 1H), 1.40 (t, J=7.5 Hz, 3H)

Example 43

7-Acetyl-4-(methoxymethyl)-3-methyl-N-(4-(pyrrolidin-1-ylmethyl)quinolin-2-yl)benzo[b]thiophene-2-carboxamide

[Formula 239]

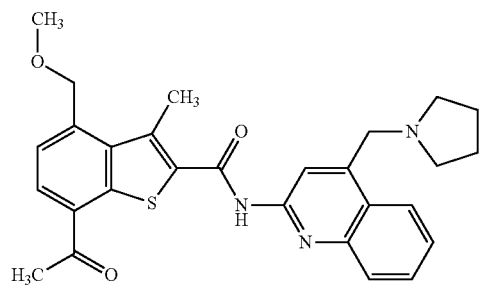

The title compound (135 mg) was obtained in the same way as in Example 39 using the compound (139 mg) obtained in Reference Example 74, the compound (114 mg) obtained in Reference Example 97, PyBOP (312 mg), dichloromethane (2.5 mL), and N,N-diisopropylethylamine (174 μL).

¹H NMR (DMSO, 400 MHz): δ (ppm) 11.21 (br. s., 1H), 8.29-8.39 (m, 2H), 8.24 (d, J=7.7 Hz, 1H), 7.88 (d, J=7.7 Hz, 1H), 7.71-7.79 (m, 1H), 7.69 (d, J=7.7 Hz, 1H), 7.52-7.61 (m, 1H), 5.01 (s, 2H), 3.42 (s, 3H), 2.83 (s, 3H), 2.77 (s, 3H), 2.51-2.72 (m, 4H), 1.68-1.89 (m, 4H)

MS (ESI⁺) m/z: 488 [M+H]⁺

Example 44

7-Acetyl-4-(methoxymethyl)-3-methyl-N-(4-(morpholinomethyl)quinolin-2-yl)benzo[b]thiophene-2-carboxamide

[Formula 240]

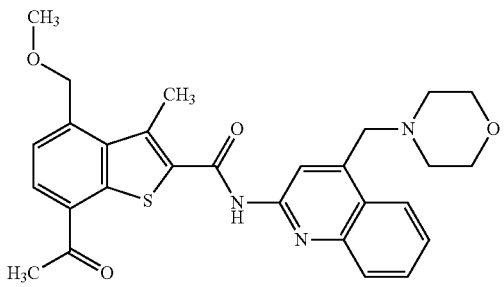

The title compound (25 mg) was obtained in the same way as in Example 39 using the compound (139 mg) obtained in Reference Example 74, the compound (122 mg) obtained in Reference Example 98, PyBOP (312 mg), dichloromethane (2.5 mL), and N,N-diisopropylethylamine (174 μL).

¹H NMR (CDCl₃, 400 MHz): δ (ppm) 8.69 (br. s., 1H), 8.52 (br. s., 1H), 8.24 (d, J=8.1 Hz, 1H), 8.09 (d, J=7.7 Hz, 1H), 7.87 (d, J=7.7 Hz, 1H), 7.65-7.71 (m, 1H), 7.63 (d, J=7.7 Hz, 1H), 7.46-7.52 (m, 1H), 5.01 (s, 2H), 3.96 (s, 2H), 3.73-3.77 (m, 4H), 3.53 (s, 3H), 3.01 (s, 3H), 2.78 (s, 3H), 2.57-2.62 (m, 4H)

MS (ESI⁺) m/z: 504 [M+H]⁺

Example 45

(R)-7-Acetyl-N-(4-((3-fluoropyrrolidin-1-yl)methyl)quinolin-2-yl)-4-(methoxymethyl)-3-methylbenzo[b]thiophene-2-carboxamide

[Formula 241]

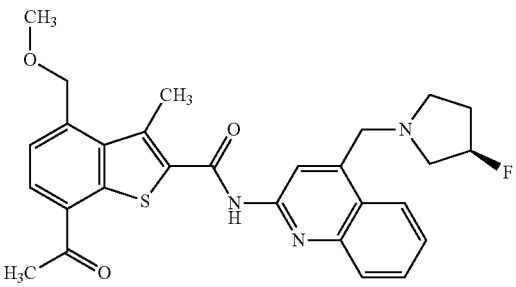

To a solution of the compound (100 mg) obtained in Reference Example 74 and HBTU (186 mg) in dichloromethane (5 mL), N,N-diisopropylethylamine (0.251 mL) was added dropwise, and the mixture was stirred at room temperature for 30 minutes. To the reaction mixture, the compound (88 mg) obtained in Reference Example 99 was added, and the mixture was stirred at room temperature for 12 hours. To the reaction mixture, water was added, followed by extraction with dichloromethane. The organic layer was dried over anhydrous sodium sulfate and concentrated. The residue was purified by silica gel column chromatography (hexane-ethyl acetate (1:1) mixed solution: methanol=100:0-90:10) to obtain the title compound (125 mg).

¹H NMR (CDCl₃, 400 MHz): δ (ppm) 8.75 (br. s., 1H), 8.48 (br. s., 1H), 8.20 (d, J=8.5 Hz, 1H), 8.06 (d, J=7.7 Hz, 1H), 7.85 (d, J=8.1 Hz, 1H), 7.63-7.68 (m, 1H), 7.60 (d, J=7.7 Hz, 1H), 7.43-7.50 (m, 1H), 5.10-5.29 (m, 1H), 4.98 (s, 2H), 4.07-4.19 (m, 2H), 3.51 (s, 3H), 2.98 (s, 3H), 2.87-3.06 (m, 3H), 2.77 (s, 3H), 2.62-2.70 (m, 1H), 2.03-2.26 (m, 2H)

MS (ESI⁺) m/z: 506 [M+H]⁺

Example 46

7-Acetyl-N-(4-((4-fluoropiperidin-1-yl)methyl)quinolin-2-yl)-4-(methoxymethyl)-3-methylbenzo[b]thiophene-2-carboxamide

[Formula 242]

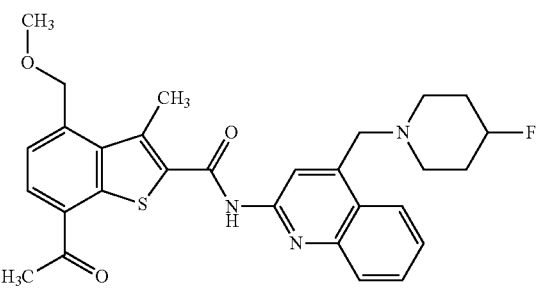

A mixture of the compound (56 mg) obtained in Reference Example 74, the compound (52 mg) obtained in Reference Example 100, HBTU (91 mg), dichloromethane (4 mL), and N,N-diisopropylethylamine (87 μL) was stirred at room temperature for 4 days. To the reaction mixture, a saturated aqueous solution of sodium bicarbonate was added, followed by extraction with dichloromethane. The organic layer was dried over anhydrous sodium sulfate and concentrated. The residue was purified by basic silica gel column chromatography (dichloromethane:methanol=100:0-95:5), and the obtained solid was washed with diethyl ether to obtain the title compound (30 mg).

¹H NMR (CDCl₃, 400 MHz): δ (ppm) 8.69 (br. s., 1H), 8.53 (br. s., 1H), 8.22 (d, J=8.5 Hz, 1H), 8.09 (d, J=7.7 Hz, 1H), 7.87 (d, J=6.9 Hz, 1H), 7.65-7.71 (m, 1H), 7.63 (d, J=7.7 Hz, 1H), 7.45-7.51 (m, 1H), 5.01 (s, 2H), 4.62-4.83 (m, 1H), 3.96 (s, 2H), 3.52 (s, 3H), 3.01 (s, 3H), 2.78 (s, 3H), 2.69-2.77 (m, 2H), 2.49-2.57 (m, 2H), 1.87-2.04 (m, 4H)

MS (ESI⁺) m/z: 520 [M+H]⁺

Example 47

7-Acetyl-N-(4-((3-hydroxyazetidin-1-yl)methyl)quinolin-2-yl)-4-(methoxymethyl)-3-methylbenzo[b]thiophene-2-carboxamide dihydrochloride

[Formula 243]

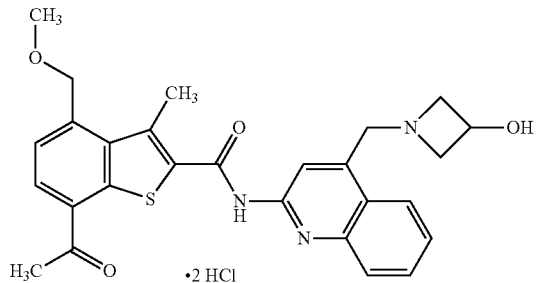

The free base of the title compound was obtained in the same way as in Example 39 using the compound (27.8 mg) obtained in Reference Example 74, the compound (22.9 mg) obtained in Reference Example 101, PyBOP (62.4 mg), dichloromethane (1.0 mL), and N,N-diisopropylethylamine (34.8 μL). To the obtained free base, hydrogen chloride (4 N solution in ethyl acetate) was added, and the mixture was then concentrated to obtain the title compound (10 mg).
$^1$H NMR (MeOD, 400 MHz): δ (ppm) 8.28-8.34 (m, 2H), 8.20-8.25 (m, 1H), 8.11 (d, J=7.7 Hz, 1H), 7.90-7.96 (m, 1H), 7.74-7.80 (m, 1H), 7.72 (d, J=7.7 Hz, 1H), 5.17 (s, 2H), 5.04 (s, 2H), 4.54-4.90 (m, 4H), 4.15-4.36 (m, 1H), 3.50 (s, 3H), 2.98 (s, 3H), 2.79 (s, 3H)
MS (ESI$^+$) m/z: 490 [M+H]$^+$

Example 48

7-Acetyl-N-(4-((3,3-difluoropyrrolidin-1-yl)methyl)quinolin-2-yl)-4-(methoxymethyl)-3-methylbenzo[b]thiophene-2-carboxamide

[Formula 244]

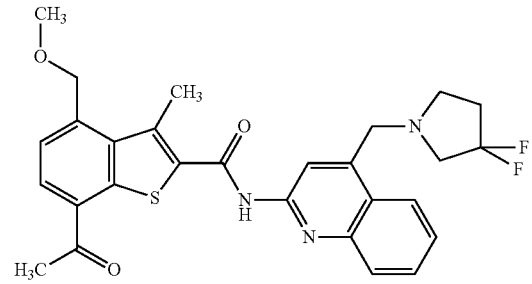

A mixture of the compound (60 mg) obtained in Reference Example 102, the compound (61.2 mg) obtained in Reference Example 103, 4,5-bis(diphenylphosphino)-9,9-dimethylxanthene (12.5 mg), cesium carbonate (85 mg), tris(dibenzylideneacetone)dipalladium(0) (9.9 mg), and 1,4-dioxane (5 mL) was stirred at 150° C. for 1 hour under an argon atmosphere. The reaction mixture was concentrated, and the residue was purified by silica gel column chromatography (hexane-ethyl acetate (1:1) mixed solution:methanol=100:0-90:10) to obtain the title compound (16.5 mg).
$^1$H NMR (CDCl$_3$, 400 MHz): δ (ppm) 8.71 (br. s., 1H), 8.52 (br. s., 1H), 8.18-8.24 (m, 1H), 8.10 (d, J=7.7 Hz, 1H), 7.89 (d, J=7.7 Hz, 1H), 7.67-7.74 (m, 1H), 7.64 (d, J=7.7 Hz, 1H), 7.47-7.55 (m, 1H), 5.01 (s, 2H), 4.11 (s, 2H), 3.53 (s, 3H), 3.02-3.09 (m, 2H), 3.01 (s, 3H), 2.86 (t, J=6.7 Hz, 2H), 2.79 (s, 3H), 2.25-2.40 (m, 2H)
MS (ESI$^+$) m/z: 524 [M+H]$^+$

Example 49

7-Acetyl-4-(methoxymethyl)-3-methyl-N-(quinolin-2-yl)benzo[b]thiophene-2-carboxamide

[Formula 245]

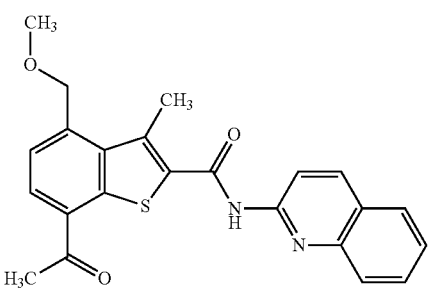

The title compound (9 mg) was obtained in the same way as in Example 48 using the compound (30 mg) obtained in Reference Example 102, 2-chloroquinoline (18 mg), 4,5-bis(diphenylphosphino)-9,9-dimethylxanthene (6 mg), cesium carbonate (42 mg), tris(dibenzylideneacetone)dipalladium (0) (6 mg), and 1,4-dioxane (1 mL).
$^1$H NMR (CDCl$_3$, 400 MHz): δ (ppm) 8.73 (brs, 1H), 8.50-8.54 (m, 1H), 8.24 (d, J=9.0 Hz, 1H), 8.10 (d, J=7.6 Hz, 1H), 7.88 (d, J=6.1 Hz, 1H), 7.82 (d, J=7.7 Hz, 1H), 7.70 (t, J=7.3 Hz, 1H), 7.62-7.64 (m, 1H), 7.49 (t, J=7.4 Hz, 1H), 5.01 (s, 2H), 3.53 (s, 3H), 3.01 (s, 3H), 2.79 (s, 3H)

Example 50

(R)-7-Acetyl-N-(4-((3-hydroxypyrrolidin-1-yl)carbonyl)quinolin-2-yl)-4-(methoxymethyl)-3-methylbenzo[b]thiophene-2-carboxamide

[Formula 246]

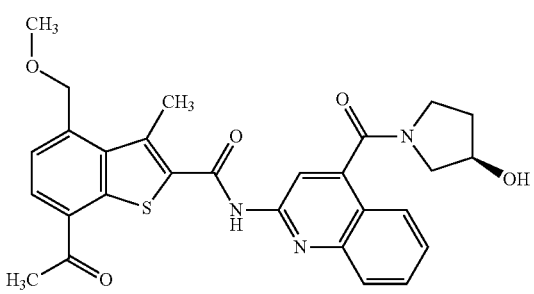

The title compound (14 mg) was obtained in the same way as in Example 39 using the compound (28 mg) obtained in Reference Example 74, the compound (26 mg) obtained in Reference Example 105, PyBOP (62 mg), dichloromethane (5 mL), and N,N-diisopropylethylamine (35 μL).

$^1$H NMR (CDCl$_3$, 400 MHz): δ (ppm) 8.87 (br. s., 1H), 8.55 (d, J=13.8 Hz, 1H), 8.09 (d, J=8.1 Hz, 1H), 7.82-7.94 (m, 2H), 7.67-7.75 (m, 1H), 7.63 (d, J=7.3 Hz, 1H), 7.47-7.54 (m, 1H), 4.99 (d, J=2.0 Hz, 2H), 4.45-4.69 (m, 1H), 3.86-4.01 (m, 2H), 3.46-3.59 (m, 4H), 3.23-3.39 (m, 1H), 2.98 (d, J=3.2 Hz, 3H), 2.78 (s, 3H), 1.93-2.22 (m, 2H)

MS (ESI$^+$) m/z: 518 [M+H]$^+$

Example 51

4,7-Diacetyl-N-(4-((3-hydroxypyrrolidin-1-yl)methyl)quinolin-2-yl)-3-methylbenzo[b]thiophene-2-carboxamide

[Formula 247]

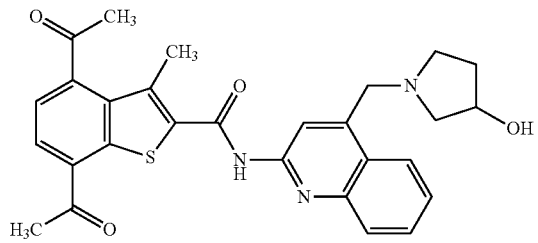

The title compound (30 mg) was obtained in the same way as in Example 9 using the compound (100 mg) obtained in Reference Example 5, the compound (79 mg) obtained in Reference Example 86, 1-ethyl-3-(3-dimethylaminopropyl)carbodiimide hydrochloride (111 mg), 1-hydroxy-7-azabenzotriazole (78 mg), and DMF (6 mL).

$^1$H NMR (CDCl$_3$, 400 MHz): δ (ppm) 8.73 (br. s., 1H), 8.49 (br. s., 1H), 8.18 (d, J=8.1 Hz, 1H), 8.13 (d, J=7.7 Hz, 1H), 7.82-7.89 (m, 1H), 7.64-7.70 (m, 1H), 7.44-7.51 (m, 2H), 4.34-4.41 (m, 1H), 4.11 (s, 2H), 2.97-3.05 (m, 1H), 2.82-2.86 (m, 1H), 2.80 (s, 3H), 2.74 (s, 3H), 2.68-2.71 (m, 1H), 2.67 (s, 2H), 2.44-2.51 (m, 1H), 2.19-2.29 (m, 1H), 1.76-1.85 (m, 1H)

MS (ESI$^+$) m/z: 502 [M+H]$^+$

Example 52

4,7-Diacetyl-N-(4-((3-hydroxyazetidin-1-yl)methyl)quinolin-2-yl)-3-methylbenzo[b]thiophene-2-carboxamide

[Formula 248]

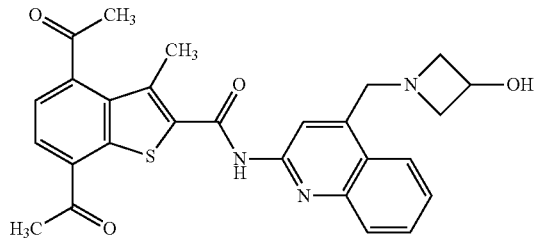

The title compound (14 mg) was obtained in the same way as in Example 9 using the compound (75 mg) obtained in Reference Example 5, the compound (60 mg) obtained in Reference Example 101, 1-ethyl-3-(3-dimethylaminopropyl)carbodiimide hydrochloride (79 mg), 1-hydroxy-7-azabenzotriazole (56 mg), and DMF (5 mL).

$^1$H NMR (CDCl$_3$, 400 MHz): δ (ppm) 8.49 (br. s., 1H), 8.15 (d, J=7.7 Hz, 1H), 8.00 (d, J=8.1 Hz, 1H), 7.87 (d, J=7.7 Hz, 1H), 7.65-7.71 (m, 1H), 7.46-7.53 (m, 2H), 4.66-4.74 (m, 1H), 4.50 (s, 2H), 4.17-4.25 (m, 2H), 3.74-3.82 (m, 2H), 2.81 (s, 3H), 2.76 (s, 3H), 2.65 (s, 3H)

MS (ESI$^+$) m/z: 488 [M+H]$^+$

Example 53

7-Acetyl-N-(4-chloroquinolin-2-yl)-4-(methoxymethyl)-3-methylbenzo[b]thiophene-2-carboxamide

[Formula 249]

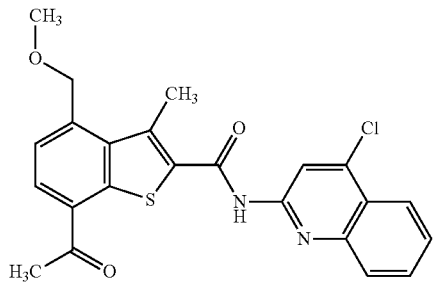

To a solution of the compound (171 mg) obtained in Reference Example 74 in N,N-dimethylacetamide (5 mL), HBTU (276 mg) and N,N-diisopropylethylamine (195 mg) were added under a nitrogen atmosphere, and the mixture was stirred for 30 minutes. To the reaction mixture, 2-amino-4-chloroquinoline (100 mg) was added, and the mixture was stirred at room temperature for 2 hours and stirred overnight 70° C. The reaction mixture was diluted with chloroform and washed with a saturated aqueous solution of sodium bicarbonate and saturated aqueous sodium chloride in this order. The organic layer was dried over anhydrous magnesium sulfate and concentrated. The residue was purified by silica gel column chromatography (hexane:ethyl acetate=4:1). To the obtained partially purified product, an ethyl acetate-heptane mixed solution was added, and the mixture was heated and then cooled to room temperature. The precipitated solid was collected by filtration to obtain the title compound (7 mg).

$^1$H NMR (CDCl$_3$, 400 MHz): δ (ppm) 8.68-8.78 (m, 2H), 8.20 (d, J=7.3 Hz, 1H), 7.88 (d, J=8.5 Hz, 1H), 7.70-7.79 (m, 1H), 7.64 (d, J=7.7 Hz, 1H), 7.54-7.60 (m, 1H), 5.01 (s, 2H), 3.53 (s, 3H), 3.01 (s, 3H), 2.79 (s, 3H)

MS (ESI$^+$) m/z: 439, 441 [M+H]$^+$

Example 54

7-Acetyl-N-(4-aminoquinolin-2-yl)-4-(methoxymethyl)-3-methylbenzo[b]thiophene-2-carboxamide

[Formula 250]

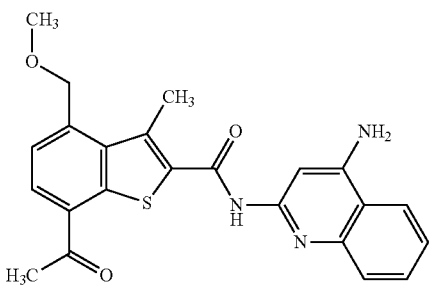

The title compound (15 mg) was obtained in the same way as in Example 53 using the compound (192 mg) obtained in Reference Example 74, N,N-dimethylacetamide (5 mL), HBTU (310 mg), N,N-diisopropylethylamine (219 mg), and 2,4-diaminoquinoline (100 mg).

$^1$H NMR (CDCl$_3$, 400 MHz): δ (ppm) 8.07 (d, J=7.7 Hz, 1H), 7.59-7.79 (m, 5H), 7.35-7.42 (m, 1H), 5.00 (s, 2H), 4.91 (brs, 2H), 3.52 (s, 3H), 2.99 (s, 3H), 2.78 (s, 3H)

MS (ESI$^+$) m/z: 420 [M+H]$^+$

Example 55

7-Acetyl-N-(4-(dimethylamino)quinolin-2-yl)-4-(methoxymethyl)-3-methylbenzo[b]thiophene-2-carboxamide

[Formula 251]

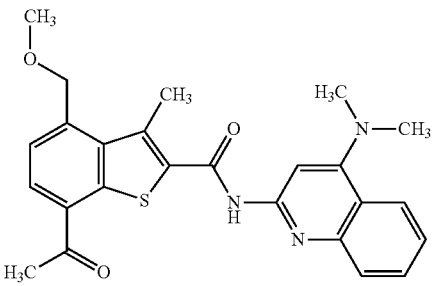

The title compound (10 mg) was obtained in the same way as in Example 53 using the compound (38 mg) obtained in Reference Example 74, N,N-dimethylacetamide (2 mL), HBTU (61 mg), N,N-diisopropylethylamine (40 mg), and the compound (23 mg) obtained in Reference Example 106.

$^1$H NMR (CDCl$_3$, 400 MHz): δ (ppm) 8.07 (d, J=7.7 Hz, 1H), 8.01 (d, J=8.2 Hz, 1H), 7.71-7.80 (m, 1H), 7.57-7.65 (m, 2H), 7.34-7.41 (m, 1H), 7.15-7.29 (m, 1H), 5.01 (s, 2H), 3.52 (s, 3H), 3.14 (brs, 6H), 3.02 (s, 3H), 2.78 (s, 3H)

Example 56

7-Acetyl-4-(methoxymethyl)-3-methyl-N-(4-morpholinoquinolin-2-yl)benzo[b]thiophene-2-carboxamide

[Formula 252]

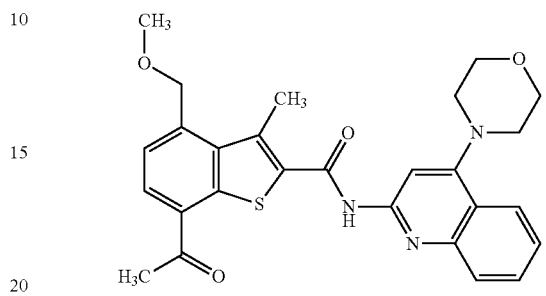

A mixture of 2-amino-4-chloroquinoline (119 mg), morpholine (175 μL), and DMF (7 mL) was stirred overnight at 140° C. To the reaction mixture, saturated sodium bicarbonate was added, followed by extraction with ethyl acetate. The organic layer was washed with saturated sodium bicarbonate, dried over anhydrous sodium sulfate, and concentrated. To the residue, the compound (311 mg) obtained in Reference Example 107, triethylamine (195 μL), acetonitrile (2 mL), and chloroform (2 mL) were added, and the mixture was stirred at 60° C. for 4 hours. To the reaction mixture, a saturated aqueous solution of sodium bicarbonate was added, followed by extraction with dichloromethane. The organic layer was dried over anhydrous sodium sulfate and concentrated. The residue was purified by basic silica gel column chromatography (hexane:ethyl acetate=10:90), and the obtained solid was washed with an ethyl acetate-dichloromethane mixed solution to obtain the title compound (192 mg).

$^1$H NMR (CDCl$_3$, 400 MHz): δ (ppm) 8.67 (br. s., 1H), 8.00-8.16 (m, 2H), 7.96 (d, J=8.1 Hz, 1H), 7.80 (d, J=7.3 Hz, 1H), 7.60-7.66 (m, 2H), 7.38-7.44 (m, 1H), 5.00 (s, 2H), 3.99-4.05 (m, 4H), 3.53 (s, 3H), 3.31-3.37 (m, 4H), 3.01 (s, 3H), 2.78 (s, 3H)

MS (ESI$^+$) m/z: 490 [M+H]$^+$

Example 57

7-Acetyl-4-(methoxymethyl)-3-methyl-N-(4-(4-methylpiperazin-1-yl)quinolin-2-yl)benzo[b]thiophene-2-carboxamide

[Formula 253]

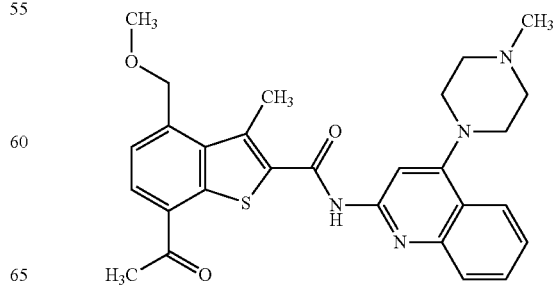

A mixture of 2-amino-4-chloroquinoline (71.4 mg), 1-methylpiperazine (133 μL), and DMF (2 mL) was stirred overnight at 130° C. To the reaction mixture, saturated sodium bicarbonate was added, followed by extraction with ethyl acetate. The organic layer was washed with saturated sodium bicarbonate, dried over anhydrous sodium sulfate, and concentrated. To the residue, the compound (187 mg) obtained in Reference Example 107, triethylamine (117 μL), acetonitrile (2 mL), and chloroform (2 mL) were added, and the mixture was stirred at 60° C. for 3.5 hours. To the reaction mixture, a saturated aqueous solution of sodium bicarbonate was added, followed by extraction with dichloromethane. The organic layer was dried over anhydrous sodium sulfate and concentrated. The residue was purified by basic silica gel column chromatography (dichloromethane:methanol=100:0 to 95:5), and the obtained solid was washed with a hexane-ethyl acetate mixed solution to obtain the title compound (71 mg).

$^1$H NMR (CDCl$_3$, 400 MHz): δ (ppm) 8.64 (br. s., 1H), 8.01-8.12 (m, 2H), 7.95 (d, J=7.7 Hz, 1H), 7.74-7.83 (m, 1H), 7.59-7.65 (m, 2H), 7.36-7.42 (m, 1H), 5.00 (s, 2H), 3.52 (s, 3H), 3.35-3.42 (m, 4H), 3.01 (s, 3H), 2.78 (s, 3H), 2.71-2.76 (m, 4H), 2.43 (s, 3H)

MS (ESI$^+$) m/z: 503 [M+H]$^+$

Example 58

(R)—N-(4-((3-Hydroxypyrrolidin-1-yl)methyl)quinolin-2-yl)-4-(methoxymethyl)-3-methyl-7-pivaloyl-benzo[b]thiophene-2-carboxamide dihydrochloride

[Formula 254]

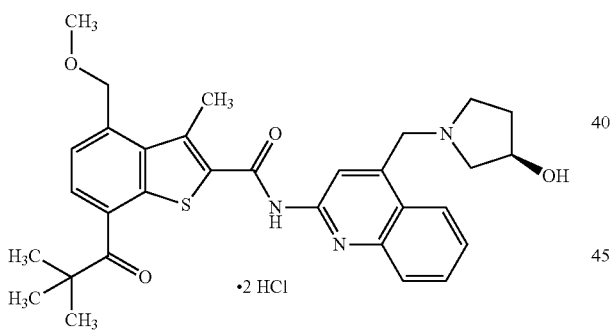

•2 HCl

A mixture of the compound (81 mg) obtained in Reference Example 108, the compound (68 mg) obtained in Reference Example 90, HBTU (115 mg), triethylamine (106 μL), and dichloromethane (5 mL) was stirred overnight at room temperature. To the reaction mixture, a saturated aqueous solution of sodium bicarbonate was added, followed by extraction with dichloromethane. The organic layer was dried over anhydrous sodium sulfate and concentrated. The residue was purified by basic silica gel column chromatography (dichloromethane:methanol=100:0-95:5) and silica gel column chromatography (hexane:ethyl acetate=20:80-0:100) in this order. To the obtained compound, hydrogen chloride (4 N solution in ethyl acetate) was added, and the mixture was concentrated to obtain the title compound (22 mg).

$^1$H NMR (MeOD, 400 MHz): δ (ppm) 8.45 (d, J=7.7 Hz, 1H), 8.39 (d, J=8.1 Hz, 1H), 8.31 (br. s., 1H), 8.24 (d, J=8.5 Hz, 1H), 8.02-8.08 (m, 1H), 7.84-7.91 (m, 1H), 7.69 (d, J=7.7 Hz, 1H), 5.24 (br. s., 2H), 5.02 (s, 2H), 4.63-4.69 (m, 1H), 3.64-4.06 (m, 4H), 3.50 (s, 3H), 3.00 (s, 3H), 2.07-2.61 (m, 2H), 1.49-1.54 (m, 9H)

MS (ESI$^+$) m/z: 546 [M+H]$^+$

Example 59

(R)—N-(4-((3-Hydroxypyrrolidin-1-yl)methyl)quinolin-2-yl)-7-isobutyryl-4-(methoxymethyl)-3-methylbenzo[b]thiophene-2-carboxamide dihydrochloride

[Formula 255]

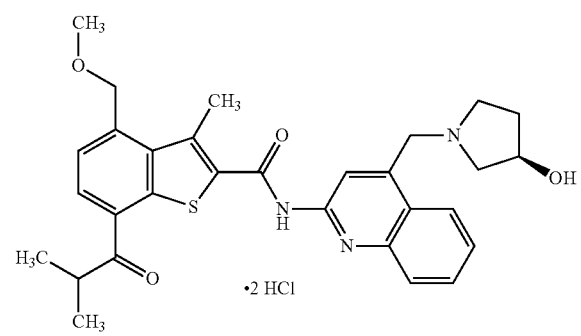

•2 HCl

A mixture of the compound (80 mg) obtained in Reference Example 109, the compound (64 mg) obtained in Reference Example 90, HBTU (119 mg), triethylamine (109 μL), and dichloromethane (4 mL) was stirred overnight at room temperature. To the reaction mixture, a saturated aqueous solution of sodium bicarbonate was added, followed by extraction with dichloromethane. The organic layer was dried over anhydrous sodium sulfate and concentrated. The residue was purified by silica gel column chromatography (hexane:ethyl acetate=20:80-0:100). To the obtained compound, hydrogen chloride (4 N solution in ethyl acetate) was added, and the mixture was concentrated to obtain the title compound (86 mg).

$^1$H NMR (MeOD, 400 MHz): δ (ppm) 8.44 (d, J=8.1 Hz, 1H), 8.40 (d, J=7.7 Hz, 1H), 8.31 (d, J=8.5 Hz, 1H), 8.22 (br. s., 1H), 8.09-8.15 (m, 1H), 7.91-7.96 (m, 1H), 7.75 (d, J=7.7 Hz, 1H), 5.29 (br. s., 2H), 5.05 (s, 2H), 4.64-4.70 (m, 1H), 3.54-4.09 (m, 5H), 3.51 (s, 3H), 3.03 (s, 3H), 2.02-2.63 (m, 2H), 1.28 (d, J=6.5 Hz, 6H)

MS (ESI$^+$) m/z: 532 [M+H]$^+$

Example 60

(R)-7-Acetyl-N-(5-((3-fluoropyrrolidin-1-yl)methyl)quinolin-2-yl)-4-(methoxymethyl)-3-methylbenzo[b]thiophene-2-carboxamide hydrochloride

[Formula 256]

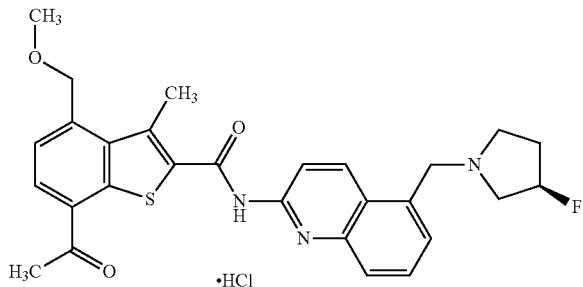

The free base of the title compound (71 mg) was obtained in the same way as in Example 48 using the compound (50 mg) obtained in Reference Example 102, the compound (48 mg) obtained in Reference Example 113, 4,5-bis(diphenylphosphino)-9,9-dimethylxanthene (10 mg), cesium carbonate (70 mg), tris(dibenzylideneacetone)dipalladium(0) (8 mg), and 1,4-dioxane (2 mL). To the obtained compound, hydrogen chloride (4 N solution in 1,4-dioxane, 0.033 mL) was added, further a methanol-ethyl acetate-heptane mixed solution was added, and the mixture was heated and then cooled to room temperature. The precipitated solid was collected by filtration to obtain the title compound (61 mg).

$^1$H NMR (DMSO, 400 MHz): δ (ppm) 11.42 (brs, 1H), 10.87-11.08 (m, 1H), 8.90-8.94 (m, 1H), 8.40 (d, J=9.3 Hz, 1H), 8.33 (d, J=7.7 Hz, 1H), 7.98 (d, J=7.7 Hz, 1H), 7.79-7.92 (m, 2H), 7.69 (d, J=7.7 Hz, 1H), 5.38-5.41 (m, 1H), 5.01 (s, 2H), 4.87-5.10 (m, 2H), 3.70-3.91 (m, 2H), 3.33-3.67 (m, 2H), 3.42 (s, 3H), 2.83 (s, 3H), 2.78 (s, 3H), 2.10-2.40 (m, 2H)

Example 61

7-Acetyl-4-(methoxymethyl)-3-methyl-N-(5-(morpholinomethyl)quinolin-2-yl)benzo[b]thiophene-2-carboxamide hydrochloride

[Formula 257]

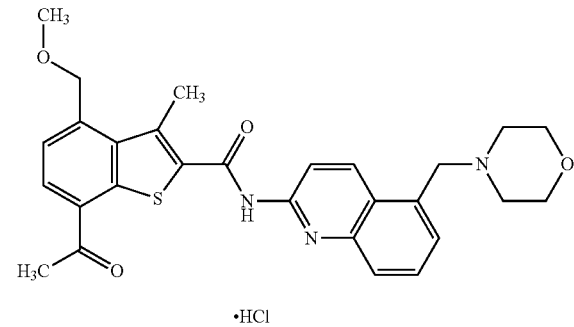

The free base of the title compound (40 mg) was obtained in the same way as in Example 48 using the compound (50 mg) obtained in Reference Example 102, the compound (48 mg) obtained in Reference Example 114, 4,5-bis(diphenylphosphino)-9,9-dimethylxanthene (10 mg), cesium carbonate (70 mg), tris(dibenzylideneacetone)dipalladium(0) (8 mg), and 1,4-dioxane (2 mL). To the obtained compound, hydrogen chloride (4 N solution in 1,4-dioxane, 0.02 mL) was added, further a methanol-ethyl acetate-heptane mixed solution was added, and the mixture was heated and then cooled to room temperature. The precipitated solid was collected by filtration to obtain the title compound (32 mg).

$^1$H NMR (DMSO, 400 MHz): δ (ppm) 11.41 (brs, 1H), 10.35 (brs, 1H), 8.95 (d, J=9.8 Hz, 1H), 8.42 (d, J=9.0 Hz, 1H), 8.33 (d, J=7.6 Hz, 1H), 7.99 (d, J=5.0 Hz, 1H), 7.80-7.88 (m, 2H), 7.69 (d, J=7.7 Hz, 1H), 5.01 (s, 2H), 4.83-4.91 (m, 2H), 3.90-4.00 (m, 2H), 3.57-3.78 (m, 2H), 3.42 (s, 3H), 3.23-3.39 (m, 4H), 2.83 (s, 3H), 2.77 (s, 3H)

Example 62

7-Acetyl-N-(5-((dimethylamino)methyl)quinolin-2-yl)-4-(methoxymethyl)-3-methylbenzo[b]thiophene-2-carboxamide dihydrochloride

[Formula 258]

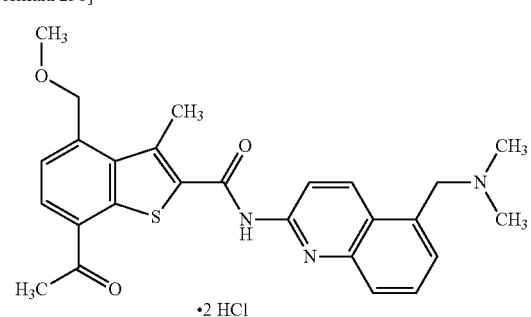

The free base of the title compound (66 mg) was obtained in the same way as in Example 48 using the compound (60 mg) obtained in Reference Example 102, the compound (50 mg) obtained in Reference Example 115, 4,5-bis(diphenylphosphino)-9,9-dimethylxanthene (14 mg), cesium carbonate (90 mg), tris(dibenzylideneacetone)dipalladium(0) (11 mg), and N,N-dimethylacetamide (5 mL). To the obtained compound, hydrogen chloride (4 N solution in 1,4-dioxane, 0.07 mL) was added, further a methanol-ethyl acetate-heptane mixed solution was added, and the mixture was heated and then cooled to room temperature. The precipitated solid was collected by filtration to obtain the title compound (59 mg).

$^1$H NMR (DMSO, 400 MHz): δ (ppm) 11.38 (brs, 1H), 9.98 (brs, 1H), 8.89 (d, J=9.2 Hz, 1H), 8.40 (d, J=9.2 Hz, 1H), 8.33 (d, J=7.7 Hz, 1H), 7.98 (d, J=7.9 Hz, 1H), 7.84 (t, J=7.2 Hz, 1H), 7.78 (d, J=6.6 Hz, 1H), 7.69 (d, J=7.7 Hz, 1H), 5.01 (s, 2H), 4.81 (d, J=5.5 Hz, 2H), 3.42 (s, 3H), 2.83 (s, 3H), 2.82 (s, 3H), 2.80 (s, 3H), 2.77 (s, 3H)

Example 63

(S)-7-Acetyl-N-(5-((3-hydroxypyrrolidin-1-yl)methyl)quinolin-2-yl)-4-(methoxymethyl)-3-methylbenzo[b]thiophene-2-carboxamide dihydrochloride

[Formula 259]

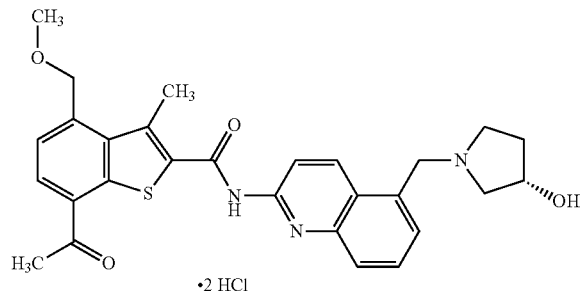

The free base of the title compound (11 mg) was obtained in the same way as in Example 48 using the compound (24 mg) obtained in Reference Example 102, the compound (23 mg) obtained in Reference Example 116, 4,5-bis(diphenylphosphino)-9,9-dimethylxanthene (5 mg), cesium carbonate (34 mg), tris(dibenzylideneacetone)dipalladium(0) (4 mg), and N,N-dimethylacetamide (2 mL). To the obtained compound, hydrogen chloride (4 N solution in 1,4-dioxane, 0.044 mL) was added, further a methanol-ethyl acetate-heptane mixed solution was added, and the mixture was heated and then cooled to room temperature. The precipitated solid was collected by filtration to obtain the title compound (8 mg).

$^1$H NMR (DMSO, 400 MHz): δ (ppm) 11.40 (brs, 1H), 8.82-8.91 (m, 1H), 8.38-8.46 (m, 1H), 8.29-8.35 (m, 1H), 7.94-8.00 (m, 1H), 7.78-7.89 (m, 2H), 7.69 (d, J=7.7 Hz, 1H), 5.01 (s, 2H), 4.85-4.99 (m, 2H), 4.38-4.54 (m, 1H), 3.30-3.63 (m, 2H), 3.42 (s, 3H), 2.87-3.20 (m, 2H), 2.83 (s, 3H), 2.77 (s, 3H), 1.80-2.11 (m, 2H)

MS (ESI$^+$) m/z: 504 [M+H]$^+$

Example 64

(R)-7-Acetyl-N-(5-((3-hydroxypyrrolidin-1-yl)methyl)quinolin-2-yl)-4-(methoxymethyl)-3-methylbenzo[b]thiophene-2-carboxamide dihydrochloride

[Formula 260]

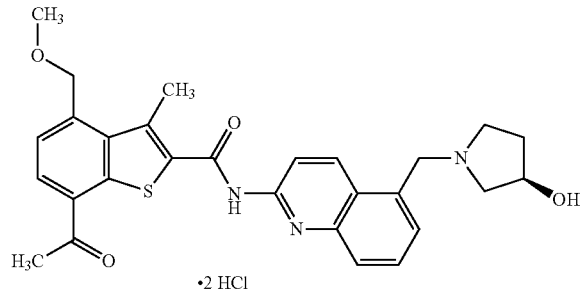

To a suspension of the compound (1.612 g) obtained in Reference Example 74 in chloroform (20 mL), N,N-diisopropylethylamine (2.52 mL) and HBTU (2.745 g) were added, and the mixture was stirred at room temperature for 15 minutes. To the reaction mixture, a solution of the compound (1.409 g) obtained in Reference Example 119 in chloroform (10 mL) was added, and the mixture was stirred overnight at room temperature. To the reaction mixture, a 2 N aqueous sodium hydroxide solution was added, followed by extraction with chloroform. The organic layer was dried over anhydrous sodium sulfate and concentrated. The residue was purified by silica gel column chromatography (dichloromethane:methanol=98:2-90:10) to obtain the free base of the title compound (1.852 g). To a solution of the obtained compound in ethyl acetate/methanol (5 mL/5 mL), hydrogen chloride (4 N solution in ethyl acetate, 2.21 mL) was added, and the mixture was then concentrated. The residue was washed with methanol to obtain the title compound (1.762 g).

$^1$H NMR (DMSO, 400 MHz): δ (ppm) 11.39 (br. s., 1H), 10.56 (br. s., 1H), 8.89 (t, J=9.1 Hz, 1H), 8.38-8.42 (m, 1H), 8.33 (d, J=7.7 Hz, 1H), 7.95-7.99 (m, 1H), 7.80-7.87 (m, 2H), 7.70 (d, J=8.1 Hz, 1H), 5.01 (s, 2H), 4.87-4.99 (m, 2H), 4.38-4.51 (m, 2H), 3.48-3.63 (m, 2H), 3.42 (s, 3H), 3.21-3.35 (m, 2H), 3.06-3.16 (m, 1H), 2.83 (s, 3H), 2.77 (s, 3H)

MS (ESI$^+$) m/z: 504 [M+H]$^+$

Example 65

7-Acetyl-N-(5-((3-hydroxyazetidin-1-yl)methyl)quinolin-2-yl)-4-(methoxymethyl)-3-methylbenzo[b]thiophene-2-carboxamide dihydrochloride

[Formula 261]

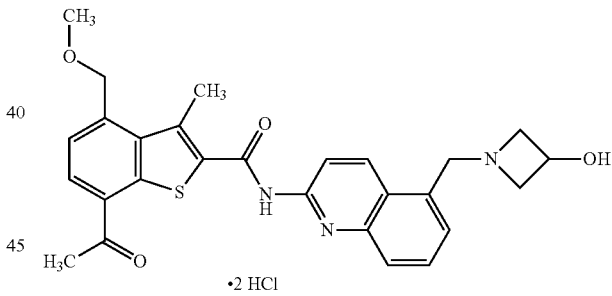

To a suspension of the compound (48.6 mg) obtained in Reference Example 74 in dichloromethane (3 mL), N,N-diisopropylethylamine (76 μL) and HBTU (79 mg) were added, and the mixture was stirred at room temperature for 20 minutes. To the reaction mixture, a solution of the compound (40 mg) obtained in Reference Example 123 in dichloromethane (5 mL) was added, then DMF (2 mL) was added, and the mixture was stirred overnight at room temperature. To the reaction mixture, a 1 N aqueous sodium hydroxide solution was added, followed by extraction with chloroform. The organic layer was dried over anhydrous sodium sulfate and concentrated. The residue was purified by silica gel column chromatography (dichloromethane:methanol=98.5:1.5-89:11) to obtain the free base of the title compound (10 mg). To a solution of the obtained compound in chloroform/methanol (0.25 mL/0.25 mL), hydrogen chloride (4 N solution in 1,4-dioxane, 15 μL) was added, and the mixture was then concentrated to obtain the title compound (11 mg).

¹H NMR (DMSO, 400 MHz): δ (ppm) 11.38 (br. s., 1H), 8.79-8.86 (m, 1H), 8.37-8.42 (m, 1H), 8.33 (d, J=7.7 Hz, 1H), 7.92-7.97 (m, 1H), 7.72-7.83 (m, 2H), 7.70 (d, J=7.7 Hz, 1H), 5.01 (s, 2H), 4.90-4.95 (m, 2H), 4.69-4.78 (m, 1H), 4.41-4.48 (m, 1H), 3.90-4.34 (m, 5H), 3.42 (s, 3H), 2.83 (s, 3H), 2.77 (s, 3H)

MS (ESI⁺) m/z: 490 [M+H]⁺

Example 66

7-Acetyl-N-(5-((3-methoxyazetidin-1-yl)methyl)quinolin-2-yl)-4-(methoxymethyl)-3-methylbenzo[b]thiophene-2-carboxamide

[Formula 262]

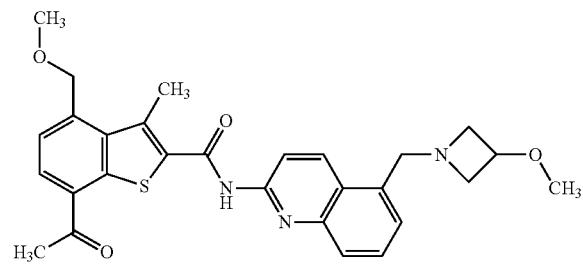

To a suspension of the compound (107.5 mg) obtained in Reference Example 74 in chloroform (3 mL), N,N-diisopropylethylamine (168 μL) and HBTU (161 mg) were added, and the mixture was stirred at room temperature for 20 minutes. To the reaction mixture, a solution of the compound (94 mg) obtained in Reference Example 124 in chloroform (3 mL) was added, and the mixture was stirred at 40° C. for 10 hours. To the reaction mixture, a 1 N aqueous sodium hydroxide solution was added, followed by extraction with chloroform. The organic layer was dried over anhydrous sodium sulfate and concentrated. The residue was purified by silica gel column chromatography (dichloromethane:methanol=98:2) to obtain the title compound (150 mg).

¹H NMR (CDCl₃, 400 MHz): δ (ppm) 8.70 (br. s., 1H), 8.62 (d, J=8.9 Hz, 1H), 8.48-8.55 (m, 1H), 8.09 (d, J=7.7 Hz, 1H), 7.78 (d, J=8.1 Hz, 1H), 7.57-7.66 (m, 2H), 7.38 (d, J=6.9 Hz, 1H), 5.01 (s, 2H), 4.03-4.10 (m, 3H), 3.60-3.66 (m, 2H), 3.52 (s, 3H), 3.26 (s, 3H), 3.00 (s, 3H), 3.01-3.05 (m, 2H), 2.79 (s, 3H)

MS (ESI⁺) m/z: 504 [M+H]⁺

Example 67

7-Acetyl-4-(methoxymethyl)-N-(5-(methoxymethyl)quinolin-2-yl)-3-methylbenzo[b]thiophene-2-carboxamide

[Formula 263]

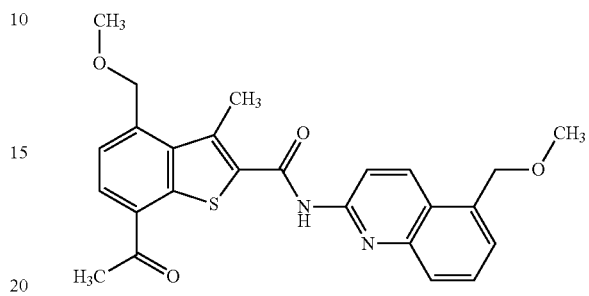

To a suspension of the compound (1.000 g) obtained in Reference Example 127, the compound (1.479 g) obtained in Reference Example 74, and HBTU (3.022 g) in dichloromethane (20 mL) N,N-diisopropylethylamine (2.8 mL) and dichloromethane (8 mL) were added, and the mixture was stirred at room temperature for 72.5 hours. To the reaction mixture, water was added, followed by extraction with chloroform. The organic layer was dried over anhydrous magnesium sulfate and concentrated. The residue was purified by silica gel column chromatography (chloroform:ethyl acetate=90:10-85:15) to obtain the title compound (2.058 g).

¹H NMR (CDCl₃, 400 MHz): δ (ppm) 8.69 (s, 1H), 8.54 (s, 2H), 8.10 (d, J=7.8 Hz, 1H), 7.84 (d, J=8.5 Hz, 1H), 7.60-7.66 (m, 2H), 7.45 (d, J=7.3 Hz, 1H), 5.01 (s, 2H), 4.89 (s, 2H), 3.52 (s, 3H), 3.45 (s, 3H), 3.01 (s, 3H), 2.79 (s, 3H)

MS (ESI⁺) m/z: 449 [M+H]⁺

Example 68

7-Acetyl-4-(methoxymethyl)-N-(5-(methoxymethyl)quinolin-2-yl)-3-methylbenzo[b]thiophene-2-carboxamide hydrochloride

[Formula 264]

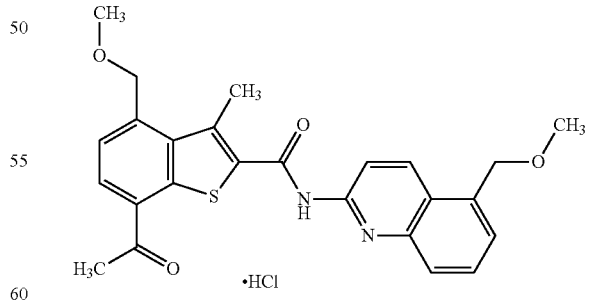

To a solution of the compound (2.057 g) obtained in Example 67 in ethanol (15 mL), hydrogen chloride (4 N solution in ethyl acetate, 1.3 mL) and ethanol (5.6 mL) were added, and the mixture was cooled to 0° C. The precipitated solid was collected by filtration, washed with ethanol, and then dried to obtain the title compound (2.122 g).

¹H NMR (DMSO, 400 MHz): δ (ppm) 11.36 (br. s., 1H), 8.63 (d, J=9.3 Hz, 1H), 8.28-8.34 (m, 2H), 7.88 (d, J=8.3 Hz, 1H), 7.67-7.76 (m, 2H), 7.55 (d, J=7.0 Hz, 1H), 5.01 (s, 2H), 4.88 (s, 2H), 3.42 (s, 3H), 3.38 (s, 3H), 2.84 (s, 3H), 2.77 (s, 3H)

MS (ESI⁺) m/z: 449 [M+H]⁺

Example 69

7-Acetyl-4-(methoxymethyl)-N-(5-(methoxymethyl)quinolin-2-yl)-3-methylbenzo[b]thiophene-2-carboxamide methanesulfonate

[Formula 265]

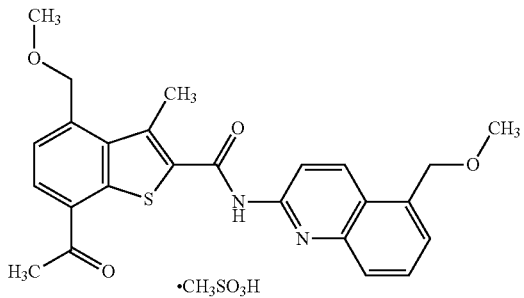

To the compound (270 mg) obtained in Example 67, methanesulfonic acid (58 mg) was added, further a methanol-chloroform-diisopropyl ether mixed solution was added, and the mixture was heated and then cooled to room temperature. The precipitated solid was collected by filtration to obtain the title compound (309 mg).

¹H NMR (DMSO, 400 MHz): δ (ppm) 11.26 (brs, 1H), 8.58 (d, J=9.2 Hz, 1H), 8.31-8.33 (m, 2H), 7.83 (d, J=8.4 Hz, 1H), 7.68-7.72 (m, 2H), 7.53 (d, J=6.0 Hz, 1H), 5.01 (s, 2H), 4.88 (s, 2H), 3.42 (s, 3H), 3.38 (s, 3H), 2.83 (s, 3H), 2.77 (s, 3H), 2.30 (s, 3H)

Example 70

7-Acetyl-N-(5-(ethoxymethyl)quinolin-2-yl)-4-(methoxymethyl)-3-methylbenzo[b]thiophene-2-carboxamide

[Formula 266]

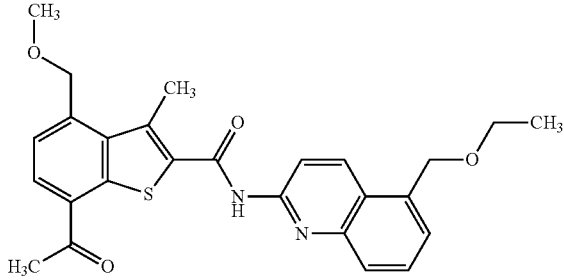

A mixture of the compound (101 mg) obtained in Reference Example 128, the compound (153 mg) obtained in Reference Example 74, HBTU (228 mg), N,N-diisopropylethylamine (0.208 mL), and chloroform (5 mL) was stirred at 50° C. for 24 hours. To the reaction mixture, a saturated aqueous solution of sodium bicarbonate was added, followed by extraction with dichloromethane. The organic layer was dried over anhydrous sodium sulfate and concentrated. The residue was purified by basic silica gel column chromatography (hexane:dichloromethane=60:40-40:60) to obtain the title compound (146 mg).

¹H NMR (CDCl₃, 400 MHz): δ (ppm) 8.71 (br. s., 1H), 8.51-8.59 (m, 2H), 8.09 (d, J=7.8 Hz, 1H), 7.83 (d, J=8.3 Hz, 1H), 7.60-7.66 (m, 2H), 7.44-7.48 (m, 1H), 5.01 (s, 2H), 4.93 (s, 2H), 3.62 (q, J=6.9 Hz, 2H), 3.52 (s, 3H), 3.00 (s, 3H), 2.79 (s, 3H), 1.27 (t, J=7.0 Hz, 3H)

MS (ESI⁺) m/z: 463 [M+H]⁺

Example 71

7-Acetyl-N-(5-((2-methoxyethoxy)methyl)quinolin-2-yl)-4-(methoxymethyl)-3-methylbenzo[b]thiophene-2-carboxamide hydrochloride

[Formula 267]

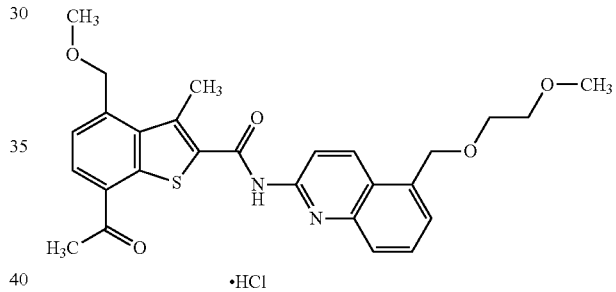

A mixture of the compound (23.2 mg) obtained in Reference Example 130, the compound (30.6 mg) obtained in Reference Example 74, HBTU (45.5 mg), N,N-diisopropylethylamine (0.042 mL), and dichloromethane (1 mL) was stirred at room temperature for 18 hours. To the reaction mixture, a saturated aqueous solution of sodium bicarbonate was added, followed by extraction with dichloromethane. The organic layer was dried over anhydrous sodium sulfate and concentrated. The residue was purified by basic silica gel column chromatography (hexane:dichloromethane=60:40-30:70) to obtain the free base of the title compound (28.6 mg). To a solution of the obtained compound in ethyl acetate (1 mL), hydrogen chloride (4 N solution in ethyl acetate, 58 µL) was added, and the mixture was then concentrated to obtain the title compound (27.0 mg).

¹H NMR (MeOD, 400 MHz): δ (ppm) 9.18 (d, J=9.3 Hz, 1H), 8.32 (d, J=7.5 Hz, 1H), 8.17 (d, J=8.5 Hz, 1H), 7.97-8.03 (m, 1H), 7.80-7.89 (m, 2H), 7.72 (d, J=7.8 Hz, 1H), 5.06 (s, 2H), 5.02 (s, 2H), 3.75-3.79 (m, 2H), 3.60-3.64 (m, 2H), 3.51 (s, 3H), 3.37 (s, 3H), 3.01 (s, 3H), 2.78 (s, 3H)

MS (ESI⁺) m/z: 493 [M+H]⁺

Example 72

7-Acetyl-N-(5-((2-hydroxyethoxy)methyl)quinolin-2-yl)-4-(methoxymethyl)-3-methylbenzo[b]thiophene-2-carboxamide hydrochloride

[Formula 268]

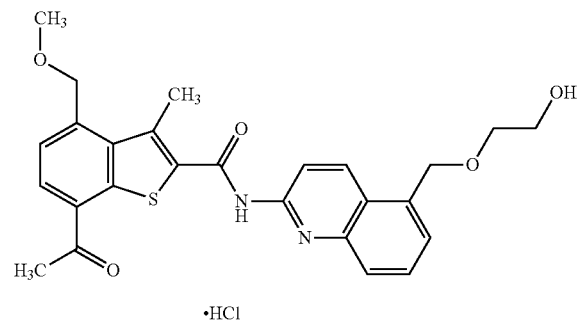

·HCl

To a solution of the compound (53 mg) obtained in Reference Example 133 in ethanol (1 mL), hydrogen chloride (4 N solution in 1,4-dioxane, 0.045 mL) was added, and the mixture was stirred at room temperature for 1 hour. To the reaction mixture, diethyl ether (1 mL) was added, and the mixture was cooled to 0° C. The precipitated solid was collected by filtration and washed with an ethanol-diethyl ether (1:2) mixed solution to obtain the title compound (30.4 mg).

$^1$H NMR (MeOD, 400 MHz): δ (ppm) 9.22 (dd, J=9.5, 0.8 Hz, 1H), 8.35 (d, J=7.5 Hz, 1H), 8.18 (d, J=8.5 Hz, 1H), 7.98-8.03 (m, 1H), 7.89 (d, J=9.5 Hz, 1H), 7.82-7.86 (m, 1H), 7.74 (d, J=7.8 Hz, 1H), 5.08 (s, 2H), 5.04 (s, 2H), 3.73-3.76 (m, 2H), 3.68-3.71 (m, 2H), 3.50 (s, 3H), 3.02 (s, 3H), 2.79 (s, 3H)

MS (ESI$^+$) m/z: 479 [M+H]$^+$

Example 73

7-Acetyl-N-(5-((difluoromethoxy)methyl)quinolin-2-yl)-4-(methoxymethyl)-3-methylbenzo[b]thiophene-2-carboxamide hydrochloride

[Formula 269]

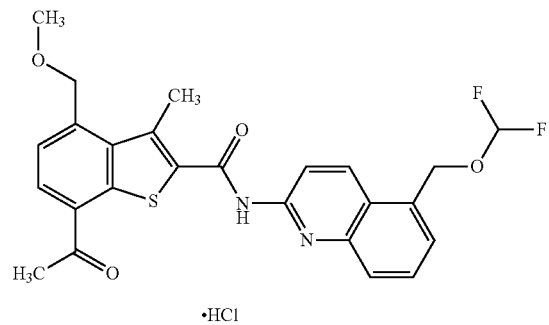

·HCl

A mixture of the compound (53 mg) obtained in Reference Example 102, the compound (47 mg) obtained in Reference Example 134, 4,5-bis(diphenylphosphino)-9,9-dimethylxanthene (11 mg), cesium carbonate (75 mg), tris(dibenzylideneacetone)dipalladium(0) (9 mg), and N,N-dimethylacetamide (4 mL) was stirred at 140° C. for 1 hour. The reaction mixture was diluted with ethyl acetate, washed with water, a saturated aqueous solution of sodium bicarbonate, and saturated aqueous sodium chloride in this order, then dried over anhydrous magnesium sulfate, and concentrated. The residue was purified by silica gel column chromatography (hexane:ethyl acetate=2:1-1:1) to obtain the free base of the title compound (31 mg). To the obtained compound, hydrogen chloride (4 N solution in 1,4-dioxane, 18 µL) was added, then a methanol-diisopropyl ether mixed solution was further added, and the mixture was heated and then cooled to room temperature. The precipitated solid was collected by filtration to obtain the title compound (22 mg).

$^1$H NMR (DMSO, 400 MHz): δ (ppm) 11.29 (brs, 1H), 8.57 (d, J=9.2 Hz, 1H), 8.33-8.38 (m, 2H), 7.90 (d, J=8.8 Hz, 1H), 7.47 (t, J=7.2 Hz, 1H), 7.69 (d, J=7.6 Hz, 1H), 7.62 (d, J=6.8 Hz, 1H), 6.89 (t, J=75.6 Hz, 1H), 5.41 (s, 2H), 5.01 (s, 2H), 2.83 (s, 3H), 2.77 (s, 3H). One peak (s, 3H) might be disappeared because of the overlap with water peak.

MS (ESI$^+$) m/z: 485 [M+H]$^+$

Example 74

7-Acetyl-N-(5-(2-hydroxypropan-2-yl)quinolin-2-yl)-4-(methoxymethyl)-3-methylbenzo[b]thiophene-2-carboxamide

[Formula 270]

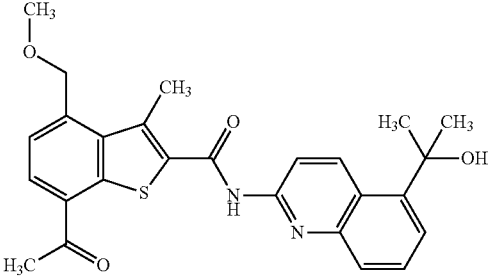

A mixture of the compound (87.7 mg) obtained in Reference Example 102, the compound (77.1 mg) obtained in Reference Example 135, 4,5-bis(diphenylphosphino)-9,9-dimethylxanthene (18.3 mg), cesium carbonate (123 mg), tris(dibenzylideneacetone)dipalladium(0) (14.5 mg), and N-methylpyrrolidone (3 mL) was stirred at 135° C. for 40 minutes. The reaction mixture was diluted with ethyl acetate, washed with water, then dried over anhydrous magnesium sulfate, and concentrated. The residue was purified by silica gel column chromatography (hexane:ethyl acetate=70:30-30:70) to obtain the title compound (45 mg).

$^1$H NMR (DMSO, 400 MHz): δ (ppm) 11.16 (s, 1H), 9.35 (d, J=9.7 Hz, 1H), 8.31 (d, J=7.7 Hz, 1H), 8.25 (d, J=9.3 Hz, 1H), 7.75 (d, J=8.1 Hz, 1H), 7.68 (d, J=7.7 Hz, 1H), 7.63 (t, J=7.7 Hz, 1H), 7.53 (d, J=6.1 Hz, 1H), 5.43 (s, 1H), 5.00 (s, 2H), 3.42 (s, 3H), 2.82 (s, 3H), 2.76 (s, 3H), 1.70 (s, 6H)

MS (ESI$^+$) m/z: 463 [M+H]$^+$

Example 75

7-Acetyl-N-(5-acetylquinolin-2-yl)-4-(methoxymethyl)-3-methylbenzo[b]thiophene-2-carboxamide

[Formula 271]

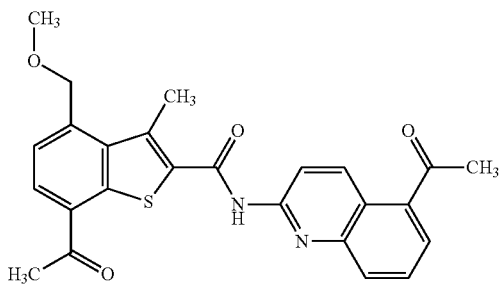

A mixture of the compound (18.6 mg) obtained in Reference Example 136, the compound (30.6 mg) obtained in Reference Example 74, HBTU (45.5 mg), triethylamine (0.042 mL), and chloroform (2 mL) was stirred at 50° C. for 20 hours. To the reaction mixture, a saturated aqueous solution of sodium bicarbonate was added, followed by extraction with dichloromethane. The organic layer was dried over anhydrous sodium sulfate and concentrated. The residue was purified by silica gel column chromatography (chloroform:methanol=99:1-94:6), and the obtained solid was washed with dichloromethane to obtain the title compound (25.5 mg).

$^1$H NMR (CDCl$_3$, 400 MHz): δ (ppm) 9.27 (d, J=9.3 Hz, 1H), 8.72 (s, 1H), 8.61 (d, J=9.3 Hz, 1H), 8.10 (d, J=7.8 Hz, 1H), 8.04 (d, J=8.3 Hz, 1H), 7.98 (dd, J=7.4, 1.1 Hz, 1H), 7.68-7.74 (m, 1H), 7.64 (d, J=7.5 Hz, 1H), 5.01 (s, 2H), 3.53 (s, 3H), 3.01 (s, 3H), 2.79 (s, 3H), 2.77 (s, 3H)

MS (ESI$^+$) m/z: 447 [M+H]$^+$

Example 76

7-Acetyl-N-(5-(1-hydroxyethyl)quinolin-2-yl)-4-(methoxymethyl)-3-methylbenzo[b]thiophene-2-carboxamide

[Formula 272]

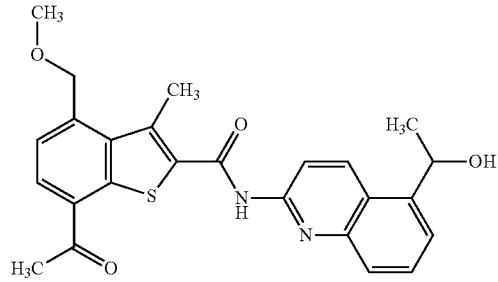

To a solution of the compound (160 mg) obtained in Reference Example 74 in chloroform (5 mL), HBTU (261 mg) and N,N-diisopropylethylamine (250 μL) were added, and the mixture was stirred at room temperature for 20 minutes. To the reaction mixture, the compound (108 mg) obtained in Reference Example 137 in chloroform (5 mL) was added, and the mixture was stirred overnight at room temperature and then stirred at 60° C. for 3 hours. To the reaction mixture, a 1 N aqueous sodium hydroxide solution was added, followed by extraction with chloroform. The organic layer was dried over anhydrous sodium sulfate and concentrated. The residue was purified by silica gel column chromatography (chloroform:methanol=97.5:2.5) to obtain the title compound (200 mg).

$^1$H NMR (CDCl$_3$, 400 MHz): δ (ppm) 8.73 (s, 1H), 8.58-8.63 (m, 1H), 8.49-8.55 (m, 1H), 8.09 (d, J=7.7 Hz, 1H), 7.80 (d, J=8.5 Hz, 1H), 7.59-7.69 (m, 3H), 5.57-5.66 (m, 1H), 5.00 (s, 2H), 3.52 (s, 3H), 3.00 (s, 3H), 2.79 (s, 3H), 1.96-2.01 (m, 1H), 1.69 (d, J=6.4 Hz, 3H)

MS (ESI$^+$) m/z: 449 [M+H]$^+$

Example 77

7-Acetyl-N-(5-(hydroxymethyl)quinolin-2-yl)-4-(methoxymethyl)-3-methylbenzo[b]thiophene-2-carboxamide hydrochloride

[Formula 273]

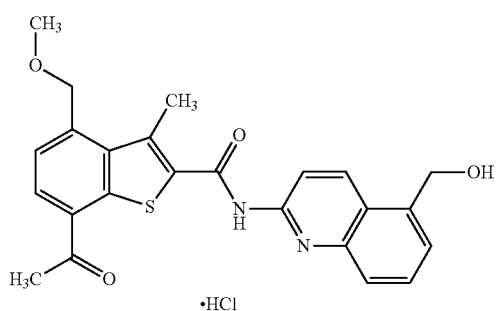

To the compound (8.325 g) obtained in Reference Example 141, ethanol (62.5 mL) and 6 N hydrochloric acid (7.6 mL) were added, and the mixture was stirred at 60° C. for 25 hours. The reaction mixture was cooled to 0° C., and the precipitated solid was collected by filtration and washed with ethanol to obtain the title compound (6.043 g).

$^1$H NMR (DMSO, 400 MHz): δ (ppm) 11.39 (br. s., 1H), 8.68 (d, J=8.5 Hz, 1H), 8.30 (m, 2H), 7.83 (d, J=8.5 Hz, 1H), 7.67-7.77 (m, 2H), 7.58 (d, J=7.3 Hz, 1H), 5.01 (s, 2H), 4.98 (s, 2H), 3.42 (s, 3H), 2.84 (s, 3H), 2.77 (s, 3H)

MS (ESI$^+$) m/z: 435 [M+H]$^+$

Example 78

7-Acetyl-N-(5-(hydroxymethyl)quinolin-2-yl)-4-(methoxymethyl)-3-methylbenzo[b]thiophene-2-carboxamide methanesulfonate

[Formula 274]

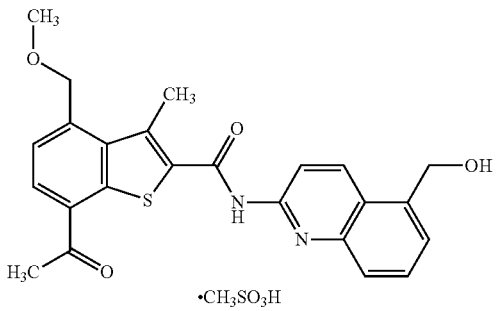

·CH₃SO₃H

To the compound (0.270 g) obtained in Reference Example 141, ethanol (1.35 mL) and methanesulfonic acid (64 µL) were added, and the mixture was stirred at 80° C. for 1 hour. To the reaction mixture, 2-propanol (1.35 mL) was added, and the mixture was stirred at the same temperature as above for 9 hours. The reaction mixture was cooled to 0° C., and the precipitated solid was collected by filtration and washed with 2-propanol to obtain the title compound (0.201 g).

$^1$H NMR (DMSO, 400 MHz): δ (ppm) 11.40 (br. s., 1H), 8.67 (d, J=9.3 Hz, 1H), 8.33 (d, J=7.8 Hz, 1H), 8.26 (d, J=9.0 Hz, 1H), 7.84 (d, J=8.5 Hz, 1H), 7.67-7.77 (m, 2H), 7.58 (d, J=7.0 Hz, 1H), 5.01 (s, 2H), 4.98 (s, 2H), 3.42 (s, 3H), 2.84 (s, 3H), 2.77 (s, 3H), 2.35 (s, 3H)

MS (ESI⁺) m/z: 435 [M+H]⁺

Example 79

7-Acetyl-N-(5-(hydroxymethyl)quinolin-2-yl)-4-(methoxymethyl)-3-methylbenzo[b]thiophene-2-carboxamide

[Formula 275]

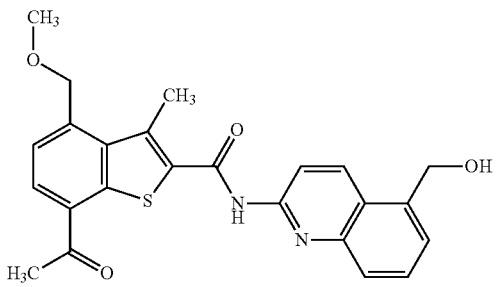

To the compound (6.656 g) obtained in Example 77, potassium carbonate (6.656 g), chloroform (430 mL), water (143 mL), and methanol (43 mL) were added in this order, and the mixture was stirred. The organic layer was dried over anhydrous magnesium sulfate and concentrated. To the residue, DMF was added, and the mixture was heated to 85° C. Water was added thereto, and the mixture was then cooled to 0° C. The precipitated solid was collected by filtration. The obtained solid was washed with a DMF-water (5:3) mixed solution to obtain the title compound (5.607 g).

$^1$H NMR (CDCl₃, 400 MHz): δ (ppm) 8.75 (br. s., 1H), 8.57 (s, 2H), 8.10 (d, J=7.8 Hz, 1H), 7.83 (d, J=8.5 Hz, 1H), 7.61-7.67 (m, 2H), 7.49 (d, J=6.0 Hz, 1H), 5.15 (s, 2H), 5.00 (s, 2H), 3.53 (s, 3H), 3.00 (s, 3H), 2.79 (s, 3H), 1.83 (br. s., 1H)

MS (ESI⁺) m/z: 435 [M+H]⁺

Example 80

7-Acetyl-N-(5-(hydroxymethyl)quinolin-2-yl)-4-(methoxymethyl)-3-methylbenzo[b]thiophene-2-carboxamide hydrobromide

[Formula 276]

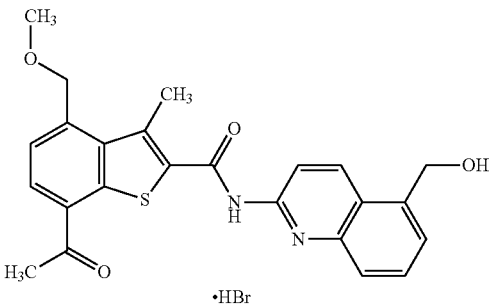

·HBr

To the compound (0.5 g) obtained in Example 79, 8 N hydrobromic acid (158 µL), water (0.72 mL), and acetonitrile (1.68 mL) were added, and the mixture was heated to 100° C. and then cooled to room temperature. The precipitated solid was collected by filtration to obtain the title compound (409 mg).

$^1$H NMR (DMSO, 400 MHz): δ (ppm) 11.26 (br. s., 1H), 8.62 (d, J=8.8 Hz, 1H), 8.27-8.34 (m, 2H), 7.77-7.81 (m, 1H), 7.67-7.73 (m, 2H), 7.55 (d, J=5.8 Hz, 1H), 5.01 (s, 2H), 4.97 (s, 2H), 3.42 (s, 3H), 2.83 (s, 3H), 2.77 (s, 3H)

MS (ESI⁺) m/z: 435 [M+H]⁺

Example 81

7-Acetyl-N-(5-(hydroxymethyl)quinolin-2-yl)-4-(methoxymethyl)-3-methylbenzo[b]thiophene-2-carboxamide p-toluenesulfonate

[Formula 277]

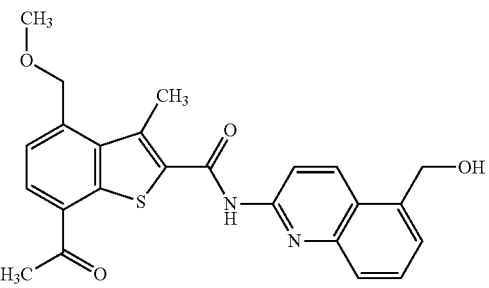

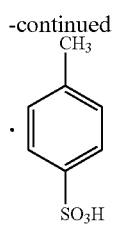

To the compound (6.000 g) obtained in Reference Example 141, p-toluenesulfonic acid monohydrate (6.24 g) and ethanol (60 mL) were added, and the mixture was stirred at 60° C. for 24.5 hours. The reaction mixture was cooled to 0° C., and the precipitated solid was collected by filtration and washed with ethanol to obtain the title compound (6.404 g).

$^1$H NMR (DMSO, 400 MHz): δ (ppm) 11.40 (br. s., 1H), 8.69 (d, J=9.0 Hz, 1H), 8.33 (d, J=7.8 Hz, 1H), 8.25 (d, J=9.3 Hz, 1H), 7.81-7.88 (m, 1H), 7.67-7.78 (m, 2H), 7.58 (d, J=6.8 Hz, 1H), 7.45-7.50 (m, 2H), 7.11 (d, J=8.5 Hz, 2H), 5.01 (s, 2H), 4.98 (s, 2H), 3.42 (s, 3H), 2.85 (s, 3H), 2.77 (s, 3H), 2.29 (s, 3H)

MS (ESI$^+$) m/z: 435 [M+H]$^+$

Example 82

7-Acetyl-N-(5-(hydroxymethyl)quinolin-2-yl)-4-(methoxymethyl)-3-methylbenzo[b]thiophene-2-carboxamide semi-ethane-1,2-disulfonate

[Formula 278]

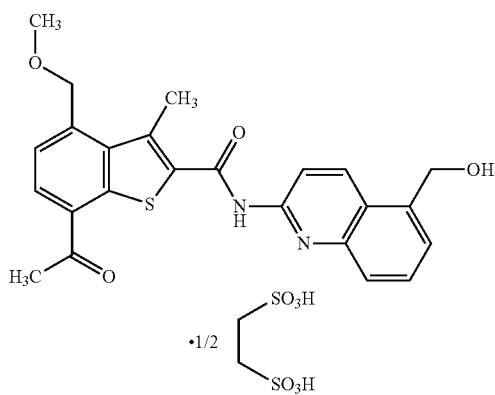

To the compound (1.200 g) obtained in Example 79, ethane-1,2-disulfonic acid dihydrate (0.344 g), water (3 mL), and 2-ethoxyethanol (9 mL) were added, and the mixture was heated to 100° C. and then cooled to 0° C. The precipitated solid was collected by filtration. The obtained solid was washed with 2-ethoxyethanol to obtain the title compound (1.307 g).

$^1$H NMR (DMSO, 400 MHz): δ (ppm) 11.37 (br. s., 1H), 8.67 (d, J=9.3 Hz, 1H), 8.33 (d, J=7.8 Hz, 1H), 8.27 (d, J=9.0 Hz, 1H), 7.83 (d, J=8.3 Hz, 1H), 7.67-7.76 (m, 2H), 7.57 (d, J=7.0 Hz, 1H), 5.01 (s, 2H), 4.98 (s, 2H), 3.42 (s, 3H), 2.84 (s, 3H), 2.77 (s, 3H), 2.67 (s, 2H)

MS (ESI$^+$) m/z: 435 [M+H]$^+$

Example 83

(2-(7-Acetyl-4-(methoxymethyl)-3-methylbenzo[b]thiophene-2-carboxamido)quinolin-5-yl)methylacetate

[Formula 279]

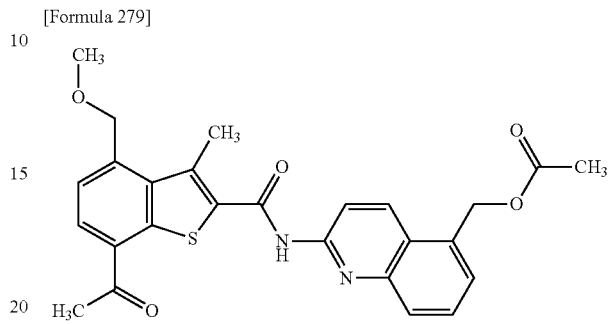

To a solution of the compound (150 mg) obtained in Example 79 in DMF (3 mL), acetic anhydride (36 µL) and pyridine (34 µL) were added, and the mixture was stirred overnight at room temperature and then stirred at 60° C. for 3 hours. To the reaction mixture, acetic anhydride (36 µL) and pyridine (34 µL) were added, and the mixture was stirred overnight at room temperature. To the reaction mixture, water was added, followed by extraction with chloroform. The organic layer was dried over anhydrous sodium sulfate and concentrated. The residue was purified by silica gel column chromatography (chloroform:methanol=99.5:0.5-99:1) to obtain the title compound (50 mg).

$^1$H NMR (CDCl$_3$, 400 MHz): δ (ppm) 8.74 (br. s., 1H), 8.53-8.61 (m, 1H), 8.43 (d, J=9.0 Hz, 1H), 8.10 (d, J=7.5 Hz, 1H), 7.84-7.90 (m, 1H), 7.61-7.69 (m, 2H), 7.50-7.55 (m, 1H), 5.55 (s, 2H), 5.00 (s, 2H), 3.52 (s, 3H), 3.00 (s, 3H), 2.79 (s, 3H), 2.12 (s, 3H)

MS (ESI$^+$) m/z: 477 [M+H]$^+$

Example 84

(S)-(2-(7-Acetyl-4-(methoxymethyl)-3-methylbenzo[b]thiophene-2-carboxamido)quinolin-5-yl)methyl-2-amino-3-methylbutanoate

[Formula 280]

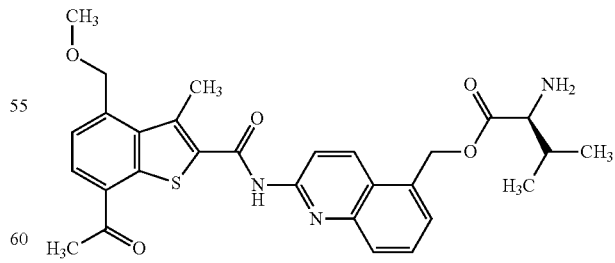

To a solution of the compound (187 mg) obtained in Reference Example 142 in chloroform (4 mL), TFA (1 mL) was added, and the mixture was stirred for 1 hour. The reaction mixture was concentrated, diluted with chloroform, and washed with a saturated aqueous solution of sodium bicarbonate. The organic layer was dried over anhydrous sodium sulfate and concentrated. To the residue, a hexane-ethyl acetate mixed solution was added, and the resulting solid was collected by filtration to obtain the title compound (148 mg).

$^1$H NMR (CDCl$_3$, 400 MHz): δ (ppm) 8.74 (br. s., 1H), 8.55-8.62 (m, 1H), 8.43 (d, J=9.3 Hz, 1H), 8.10 (d, J=7.8 Hz, 1H), 7.88 (d, J=8.5 Hz, 1H), 7.62-7.69 (m, 2H), 7.52-7.56 (m, 1H), 5.54-5.64 (m, 2H), 5.01 (s, 2H), 3.53 (s, 3H), 3.34 (d, J=4.8 Hz, 1H), 3.01 (s, 3H), 2.79 (s, 3H), 1.96-2.06 (m, 1H), 0.94 (d, J=6.8 Hz, 3H), 0.84 (d, J=6.8 Hz, 3H)

MS (ESI$^+$) m/z: 534 [M+H]$^+$

Example 85

(2-(7-Acetyl-4-(methoxymethyl)-3-methylbenzo[b]thiophene-2-carboxamido)quinolin-5-yl)methyl-2-aminoacetate

[Formula 281]

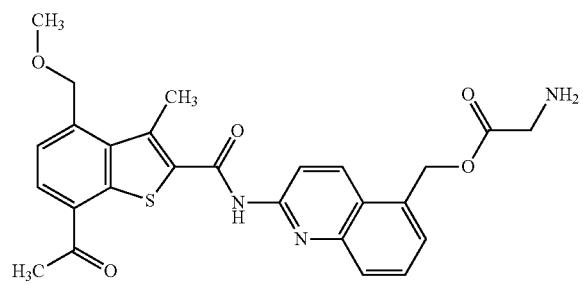

To a solution of the compound (148 mg) obtained in Reference Example 143 in chloroform (4 mL), TFA (1 mL) was added, and the mixture was stirred at room temperature for 1 hour. The reaction mixture was concentrated, and a saturated aqueous solution of sodium bicarbonate was added to the residue, followed by extraction with chloroform. The organic layer was dried over anhydrous sodium sulfate and concentrated to obtain the title compound (110 mg).

$^1$H NMR (CDCl$_3$, 400 MHz): δ (ppm) 8.73 (br. s., 1H), 8.55-8.61 (m, 1H), 8.43 (d, J=8.8 Hz, 1H), 8.10 (d, J=7.8 Hz, 1H), 7.89 (d, J=8.0 Hz, 1H), 7.62-7.69 (m, 2H), 7.51-7.55 (m, 1H), 5.61 (s, 2H), 5.01 (s, 2H), 3.53 (s, 3H), 3.49 (s, 2H), 3.01 (s, 3H), 2.79 (s, 3H)

MS (ESI$^+$) m/z: 492 [M+H]$^+$

Example 86

(S)-(2-(7-Acetyl-4-(methoxymethyl)-3-methylbenzo[b]thiophene-2-carboxamido)quinolin-5-yl)methyl-2-aminopropanoate

[Formula 282]

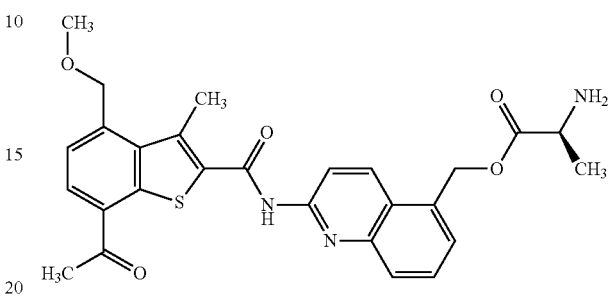

To a solution of the compound (152 mg) obtained in Reference Example 144 in chloroform (4 mL), TFA (1 mL) was added, and the mixture was stirred at room temperature for 1 hour. The reaction mixture was concentrated, and a saturated aqueous solution of sodium bicarbonate was added to the residue, followed by extraction with chloroform. The organic layer was dried over anhydrous sodium sulfate and concentrated to obtain the title compound (118 mg).

$^1$H NMR (CDCl$_3$, 400 MHz): δ (ppm) 8.75 (br. s., 1H), 8.55-8.60 (m, 1H), 8.41 (d, J=9.3 Hz, 1H), 8.10 (d, J=7.8 Hz, 1H), 7.88 (d, J=8.5 Hz, 1H), 7.60-7.68 (m, 23H), 7.50-7.54 (m, 1H), 5.54-5.64 (m, 2H), 5.00 (s, 2H), 3.60 (q, J=7.0 Hz, 1H), 3.53 (s, 3H), 3.00 (s, 3H), 2.79 (s, 3H), 1.33 (d, J=7.0 Hz, 3H)

MS (ESI$^+$) m/z: 506 [M+H]$^+$

Example 87

(2-(7-Acetyl-4-(methoxymethyl)-3-methylbenzo[b]thiophene-2-carboxamido)quinolin-5-yl)methyl dihydrogen phosphate hydrochloride

[Formula 283]

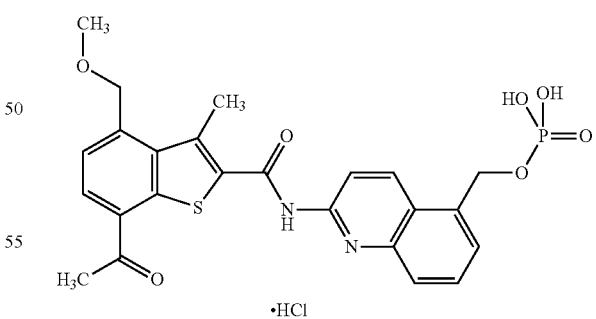

To a solution of the compound (153 mg) obtained in Reference Example 145 in methanol (1.5 mL), 6 N hydrochloric acid (0.5 mL) was added, and the mixture was stirred at room temperature for 3 days. To the reaction mixture, acetonitrile (4 mL) was added dropwise, and the mixture was stirred at room temperature for 3 hours. The precipitated solid was collected by filtration to obtain the title compound (116 mg).

¹H NMR (DMSO, 400 MHz): δ (ppm) 11.30 (br. s., 1H), 8.63 (d, J=9.3 Hz, 1H), 8.30-8.37 (m, 2H), 7.85-7.89 (m, 1H), 7.73 (dd, J=8.5, 7.0 Hz, 1H), 7.69 (d, J=7.8 Hz, 1H), 7.58-7.61 (m, 1H), 5.35 (d, J=6.5 Hz, 2H), 5.01 (s, 2H), 3.42 (s, 3H), 2.83 (s, 3H), 2.77 (s, 3H)

MS (ESI⁺) m/z: 515 [M+H]⁺

Example 88

(2-(7-Acetyl-4-(methoxymethyl)-3-methylbenzo[b]thiophene-2-carboxamido)quinolin-5-yl)methyl phosphate disodium salt

[Formula 284]

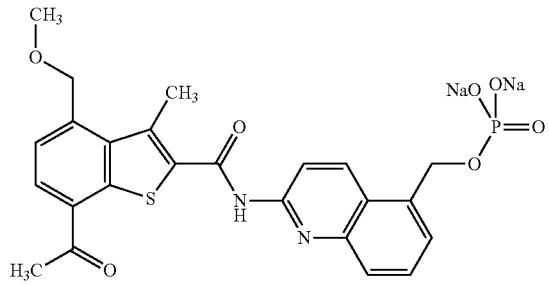

To a suspension of the compound (408 mg) obtained in Example 87 in ethanol (8.88 mL), a 1 N aqueous sodium hydroxide solution (2.22 mL) was added, and the mixture was ultrasonically vibrated. The precipitated solid was collected by filtration and washed with a water-ethanol (1:4) mixed solution to obtain the title compound (360 mg).

¹H NMR (D₂O, 400 MHz): δ (ppm) 8.20 (d, J=8.8 Hz, 1H), 7.85 (d, J=7.8 Hz, 1H), 7.73-7.79 (m, 1H), 7.52-7.66 (m, 3H), 7.35 (d, J=7.8 Hz, 1H), 5.10 (d, J=4.8 Hz, 2H), 4.78-4.80 (m, 2H), 3.51 (s, 3H), 2.77 (s, 3H), 2.53 (s, 3H)

MS (ESI⁺) m/z: 515 [M+H]⁺

Example 89

4-((2-(7-Acetyl-4-(methoxymethyl)-3-methylbenzo[b]thiophene-2-carboxamido)quinolin-5-yl)methoxy)-4-oxobutanoic acid

[Formula 285]

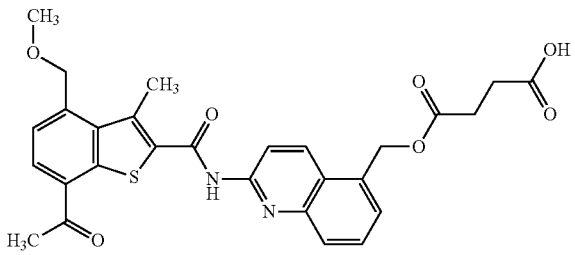

A solution of the compound (700 mg) obtained in Example 79, succinic anhydride (193 mg), triethylamine (0.268 mL), and N,N-dimethyl-4-aminopyridine (9.8 mg) in DMF (12 mL) was stirred at 85° C. for 2.5 hours. The reaction mixture was concentrated, and an aqueous acetic acid solution was added to the residue, followed by extraction with chloroform. The organic layer was dried over anhydrous sodium sulfate and concentrated. The residue was washed with water to obtain the title compound (781 mg).

¹H NMR (DMSO, 400 MHz): δ (ppm) 11.28 (br. s., 1H), 8.55 (d, J=9.0 Hz, 1H), 8.36 (d, J=9.3 Hz, 1H), 8.32 (d, J=7.8 Hz, 1H), 7.85-7.89 (m, 1H), 7.67-7.75 (m, 2H), 7.57-7.60 (m, 1H), 5.57 (s, 2H), 5.01 (s, 2H), 3.42 (s, 3H), 2.83 (s, 3H), 2.77 (s, 3H), 2.57-2.62 (m, 2H), 2.50-2.54 (m, 2H)

MS (ESI⁺) m/z: 535 [M+H]⁺

Example 90

4-((2-(7-Acetyl-4-(methoxymethyl)-3-methylbenzo[b]thiophene-2-carboxamido)quinolin-5-yl)methoxy)-4-oxobutanoic acid sodium salt

[Formula 286]

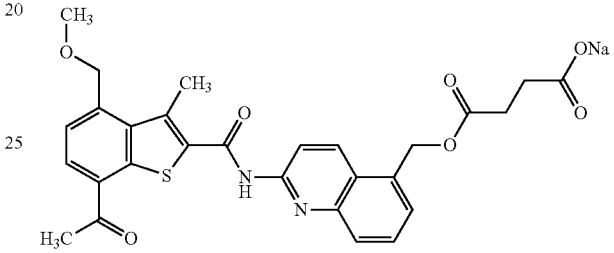

To a suspension of the compound (114 mg) obtained in Example 89 in ethanol (1.12 mL), a 1 N aqueous sodium hydroxide solution (224 μL) was added and dissolved by heating, and the solution was then cooled to room temperature. The precipitated solid was collected by filtration to obtain the title compound (47 mg).

¹H NMR (DMSO, 400 MHz): δ (ppm) 11.29 (br. s., 1H), 8.56 (d, J=9.0 Hz, 1H), 8.29-8.35 (m, 2H), 7.84 (d, J=8.5 Hz, 1H), 7.66-7.72 (m, 2H), 7.55-7.59 (m, 1H), 5.50 (s, 2H), 5.01 (s, 2H), 3.42 (s, 3H), 2.84 (s, 3H), 2.77 (s, 3H), 2.43 (t, J=7.2 Hz, 2H), 2.10-2.16 (m, 2H)

MS (ESI⁺) m/z: 535 [M+H]⁺

Example 91

(S)-(2-(7-Acetyl-4-(methoxymethyl)-3-methylbenzo[b]thiophene-2-carboxamido)quinolin-5-yl)methyl-2-amino-3-hydroxypropanoate

[Formula 287]

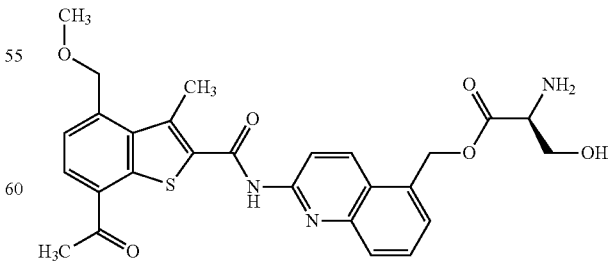

To a solution of the compound (305 mg) obtained in Reference Example 146 in chloroform (3 mL), TFA (3 mL) was added, and the mixture was stirred at room temperature

Example 92

Methyl 2-(7-acetyl-4-(methoxymethyl)-3-methylbenzo[b]thiophene-2-carboxamido)quinoline-5-carboxylate

[Formula 288]

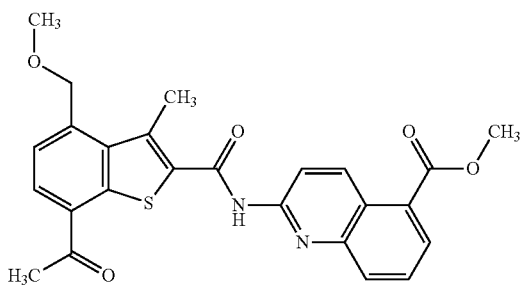

To a suspension of the compound (1.0 g) obtained in Reference Example 74 in chloroform (50 mL), N,N-diisopropylethylamine (1.56 mL) and HBTU (1.635 g) were added, and the mixture was stirred at room temperature for 15 minutes. To the reaction mixture, the compound (726 mg) obtained in Reference Example 148 was added, and the mixture was stirred at 50° C. for 8 hours and stirred at 55° C. for 6 hours. The reaction mixture was cooled to room temperature, and a 1 N aqueous sodium hydroxide solution was added thereto, followed by extraction with chloroform. The organic layer was dried over anhydrous sodium sulfate and concentrated. The residue was purified by silica gel column chromatography (dichloromethane:methanol=99:1-97:3) to obtain the title compound (1.59 g).

$^1$H NMR (CDCl$_3$, 400 MHz): δ (ppm) 9.39 (d, J=9.3 Hz, 1H), 8.72 (s, 1H), 8.62 (d, J=9.3 Hz, 1H), 8.20 (dd, J=7.3, 1.2 Hz, 1H), 8.10 (d, J=7.7 Hz, 1H), 8.06 (d, J=8.5 Hz, 1H), 7.70 (dd, J=8.3, 7.5 Hz, 1H), 7.64 (d, J=7.7 Hz, 1H), 5.01 (s, 2H), 4.03 (s, 3H), 3.53 (s, 3H), 3.01 (s, 3H), 2.80 (s, 3H)

MS (ESI$^+$) m/z: 463 [M+H]$^+$ for 5 hours. The reaction mixture was concentrated, and a saturated aqueous solution of sodium bicarbonate was added to the residue, followed by extraction with chloroform. The organic layer was dried over anhydrous sodium sulfate and concentrated. The residue was purified by silica gel column chromatography (chloroform-ethyl acetate (1:1) mixed solution:methanol=99:1-89:11) to obtain the title compound (171 mg).

$^1$H NMR (CDCl$_3$, 400 MHz): δ (ppm) 8.74 (br. s., 1H), 8.55-8.62 (m, 1H), 8.41 (d, J=9.0 Hz, 1H), 8.10 (d, J=7.8 Hz, 1H), 7.89 (d, J=8.3 Hz, 1H), 7.62-7.69 (m, 2H), 7.53 (d, J=7.0 Hz, 1H), 5.63 (s, 2H), 5.01 (s, 2H), 3.76-3.82 (m, 1H), 3.68-3.73 (m, 1H), 3.63-3.67 (m, 1H), 3.53 (s, 3H), 3.01 (s, 3H), 2.79 (s, 3H)

MS (ESI$^+$) m/z: 522 [M+H]$^+$

Example 93

2-(7-Acetyl-4-(methoxymethyl)-3-methylbenzo[b]thiophene-2-carboxamido)quinoline-5-carboxylic acid

[Formula 289]

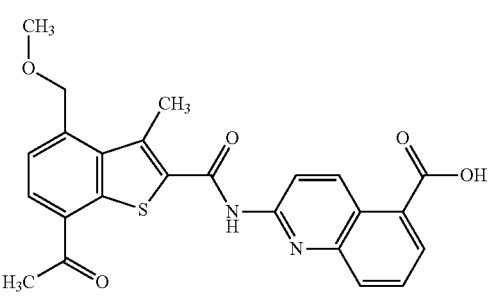

A mixture of the compound (41 mg) obtained in Example 92, lithium chloride (18.8 mg), and pyridine (5 mL) was stirred at 170° C. for 20 minutes and stirred at 190° C. for 1 hour and 20 minutes. The reaction mixture was concentrated, and an aqueous acetic acid solution was added to the residue, followed by extraction with chloroform. The organic layer was dried over anhydrous sodium sulfate and concentrated. The residue was purified by silica gel column chromatography (chloroform:methanol=97:3-90:10) to obtain the title compound (29 mg).

$^1$H NMR (DMSO, 400 MHz): δ (ppm) 11.33 (s, 1H), 9.33 (d, J=9.3 Hz, 1H), 8.42 (d, J=9.5 Hz, 1H), 8.32 (d, J=7.8 Hz, 1H), 8.17 (dd, J=7.3, 1.3 Hz, 1H), 8.03-8.11 (m, 1H), 7.82 (dd, J=8.4, 7.4 Hz, 1H), 7.69 (d, J=7.8 Hz, 1H), 5.01 (s, 2H), 3.42 (s, 3H), 2.83 (s, 3H), 2.77 (s, 3H)

MS (ESI$^+$) m/z: 449 [M+H]$^+$

Example 94

2-(7-Acetyl-4-(methoxymethyl)-3-methylbenzo[b]thiophene-2-carboxamido)-N-(pyrrolidin-1-yl)quinoline-5-carboxamide

[Formula 290]

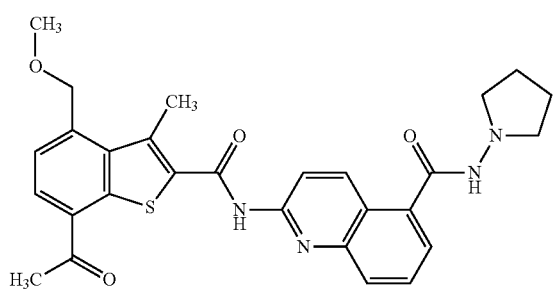

To a solution of 1-ethyl-3-(3-dimethylaminopropyl)carbodiimide hydrochloride (16 mg) and 1-hydroxybenzotriazole (9 mg) in N,N-dimethylacetamide (2 mL), the compound (25 mg) obtained in Example 93 was added under a nitrogen atmosphere, and the mixture was stirred for 1 hour. To the reaction mixture, a solution of triethylamine (17 mg) and pyrrolidin-1-amine hydrochloride (21 mg) in N,N-dimethylacetamide (2 mL) was added, and the mixture was stirred overnight. To the reaction mixture, water was added, followed by extraction with ethyl acetate. The organic layer was washed with a saturated aqueous solution of sodium bicarbonate and saturated aqueous sodium chloride in this order, dried over anhydrous magnesium sulfate, and concentrated. The residue was purified by silica gel column chromatography (hexane:ethyl acetate=1:1) to obtain the title compound (6 mg).

$^1$H NMR (CDCl$_3$, 400 MHz): δ (ppm) 8.78 (d, J=9.3 Hz, 1H), 8.51-8.60 (m, 1H), 8.09 (d, J=7.7 Hz, 1H), 7.94 (d, J=8.0 Hz, 1H), 7.54-7.68 (m, 3H), 5.00 (s, 2H), 3.53 (s, 3H), 3.08-3.19 (m, 4H), 3.00 (s, 3H), 2.79 (s, 3H), 1.95-2.04 (m, 4H)

MS (ESI$^+$) m/z: 517 [M+H]$^+$

Example 95

7-Acetyl-4-(methoxymethyl)-3-methyl-N-(5-((morpholin-4-yl)carbonyl)quinolin-2-yl)benzo[b]thiophene-2-carboxamide

[Formula 291]

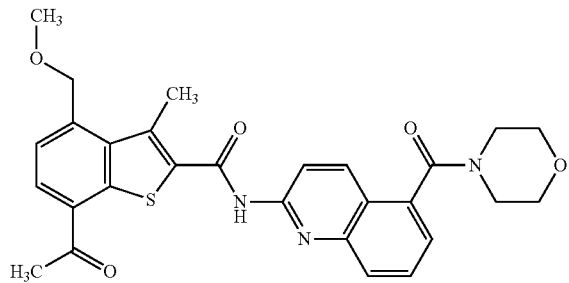

A mixture of the compound (100 mg) obtained in Reference Example 102, the compound (120 mg) obtained in Reference Example 149, 4,5-bis(diphenylphosphino)-9,9-dimethylxanthene (20.9 mg), cesium carbonate (141 mg), tris(dibenzylideneacetone)dipalladium(0) (16.5 mg), and N-methylpyrrolidone (3 mL) was stirred at 135° C. for 40 minutes. The reaction mixture was diluted with ethyl acetate and washed with water and saturated aqueous sodium chloride in this order. The organic layer was dried over anhydrous sodium sulfate and concentrated. The residue was purified by silica gel column chromatography (chloroform:methanol=99:1-97.5:2.5) to obtain the title compound (64 mg).

$^1$H NMR (CDCl$_3$, 400 MHz): δ (ppm) 8.74 (s, 1H), 8.59 (d, J=9.3 Hz, 1H), 8.28 (d, J=9.0 Hz, 1H), 8.11 (d, J=7.8 Hz, 1H), 7.92 (d, J=8.5 Hz, 1H), 7.70 (dd, J=8.4, 7.2 Hz, 1H), 7.64 (d, J=7.5 Hz, 1H), 7.41 (dd, J=7.0, 1.3 Hz, 1H), 5.01 (s, 2H), 3.83-4.04 (m, 4H), 3.51-3.62 (m, 2H), 3.53 (s, 3H), 3.25 (br. s., 2H), 3.01 (s, 3H), 2.79 (s, 3H)

MS (ESI$^+$) m/z: 518 [M+H]$^+$

Example 96

7-Acetyl-4-(methoxymethyl)-3-methyl-N-(5-((4-methylpiperazin-1-yl)carbonyl)quinolin-2-yl)benzo[b]thiophene-2-carboxamide

[Formula 292]

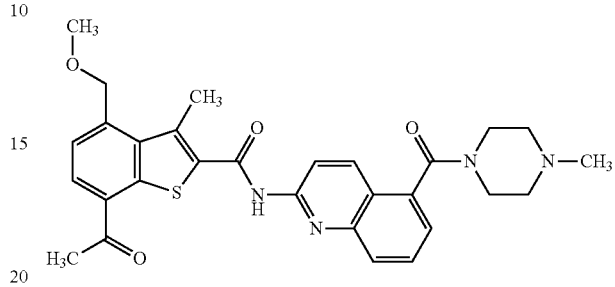

A mixture of the compound (95.7 mg) obtained in Reference Example 102, the compound (100 mg) obtained in Reference Example 150, 4,5-bis(diphenylphosphino)-9,9-dimethylxanthene (20.0 mg), cesium carbonate (135 mg), tris(dibenzylideneacetone)dipalladium(0) (16 mg), and N-methylpyrrolidone (2.5 mL) was stirred at 135° C. for 40 minutes. The reaction mixture was diluted with ethyl acetate and washed with water. The organic layer was dried over anhydrous sodium sulfate and concentrated. The residue was purified by basic silica gel column chromatography (hexane:chloroform=30:70-0:100) to obtain the title compound (21 mg).

$^1$H NMR (CDCl$_3$, 400 MHz): δ (ppm) 8.74 (s, 1H), 8.58 (d, J=9.0 Hz, 1H), 8.27 (d, J=9.0 Hz, 1H), 8.11 (d, J=7.5 Hz, 1H), 7.91 (d, J=8.5 Hz, 1H), 7.69 (dd, J=8.5, 7.0 Hz, 1H), 7.64 (d, J=7.8 Hz, 1H), 7.41 (dd, J=7.0, 1.0 Hz, 1H), 5.01 (s, 2H), 4.08 (br. s., 1H), 3.86 (br. s., 1H), 3.53 (s, 3H), 3.24 (br. s., 2H), 3.01 (s, 3H), 2.79 (s, 3H), 2.51-2.66 (m, 2H), 2.33 (s, 3H), 2.28-2.32 (m, 1H), 2.22 (br. s., 1H)

MS (ESI$^+$) m/z: 533 [M+H]$^+$

Example 97

2-(7-Acetyl-4-(methoxymethyl)-3-methylbenzo[b]thiophene-2-carboxamido)-N,N-dimethylquinoline-5-carboxamide

[Formula 293]

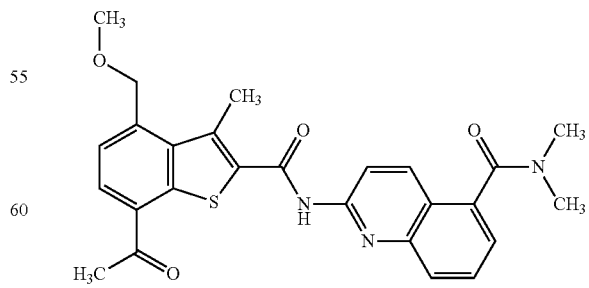

To a suspension of the compound (1.267 g) obtained in Reference Example 152, the compound (1.638 g) obtained in Reference Example 74, and HBTU (3.348 g) in dichloromethane (33.3 mL), N,N-diisopropylethylamine (3.1 mL) was added, and the mixture was stirred for 95 hours. To the reaction mixture, water was added, followed by extraction with chloroform. The organic layer was washed with an aqueous solution of dilute acetic acid and a saturated aqueous solution of sodium bicarbonate in this order, dried over anhydrous magnesium sulfate, and concentrated. The residue was purified by silica gel column chromatography (chloroform:ethyl acetate=90:10-20:80) to obtain a partially purified product. To the obtained partially purified product, ethyl acetate (10.5 mL) was added, and the mixture was heated to 70° C. and then cooled to 0° C. The precipitated solid was collected by filtration. The obtained solid was washed with ethyl acetate to obtain the title compound (2.256 g).

$^1$H NMR (CDCl$_3$, 400 MHz): δ (ppm) 8.73 (s, 1H), 8.56 (d, J=9.3 Hz, 1H), 8.22 (d, J=9.3 Hz, 1H), 8.10 (d, J=7.8 Hz, 1H), 7.90 (d, J=8.3 Hz, 1H), 7.61-7.72 (m, 2H), 7.42 (dd, J=7.2, 1.1 Hz, 1H), 5.01 (s, 2H), 3.53 (s, 3H), 3.27 (s, 3H), 3.01 (s, 3H), 2.85 (s, 3H), 2.79 (s, 3H)

MS (ESI$^+$) m/z: 476 [M+H]$^+$

Example 98

7-Acetyl-N-(5-((azetidin-1-yl)carbonyl)quinolin-2-yl)-4-(methoxymethyl)-3-methylbenzo[b]thiophene-2-carboxamide

[Formula 294]

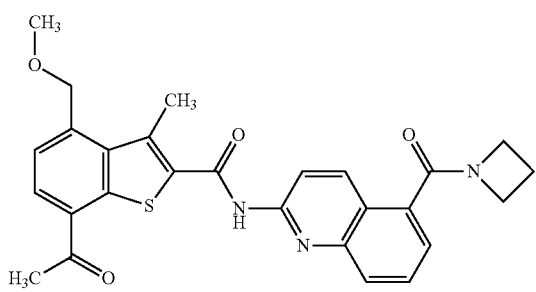

To a suspension of the compound (68.2 mg) obtained in Reference Example 155, the compound (92 mg) obtained in Reference Example 74, and HBTU (137 mg) in chloroform (3 mL), triethylamine (125 μL) was added, and the mixture was stirred at 50° C. for 22 hours. To the reaction mixture, a saturated aqueous solution of sodium bicarbonate was added, followed by extraction with dichloromethane. The organic layer was dried over anhydrous sodium sulfate and concentrated. The residue was purified by silica gel column chromatography (chloroform:methanol=100:0-95:5) to obtain the title compound (119 mg).

$^1$H NMR (CDCl$_3$, 400 MHz): δ (ppm) 8.75 (br. s., 1H), 8.56-8.62 (m, 2H), 8.10 (d, J=7.5 Hz, 1H), 7.92 (d, J=8.5 Hz, 1H), 7.62-7.70 (m, 2H), 7.51 (dd, J=7.2, 1.1 Hz, 1H), 5.01 (s, 2H), 4.34 (t, J=7.8 Hz, 2H), 3.98 (t, J=7.7 Hz, 2H), 3.53 (s, 3H), 3.01 (s, 3H), 2.79 (s, 3H), 2.31-2.40 (m, 2H)

MS (ESI$^+$) m/z: 488 [M+H]$^+$

Example 99

7-Acetyl-N-(5-((3-fluoroazetidin-1-yl)carbonyl)quinolin-2-yl)-4-(methoxymethyl)-3-methylbenzo[b]thiophene-2-carboxamide

[Formula 295]

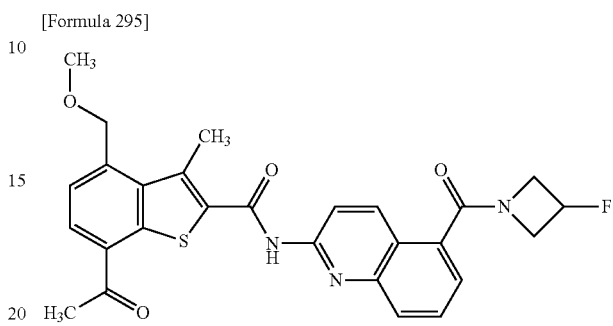

To a suspension of the compound (73.6 mg) obtained in Reference Example 157, the compound (92 mg) obtained in Reference Example 74, and HBTU (137 mg) in chloroform (4.5 mL), triethylamine (125 μL) was added, and the mixture was stirred at 50° C. for 20 hours. To the reaction mixture, a saturated aqueous solution of sodium bicarbonate was added, followed by extraction with dichloromethane. The organic layer was dried over anhydrous sodium sulfate and concentrated. The residue was purified by basic silica gel column chromatography (hexane:dichloromethane=40:60-10:90) to obtain a partially purified product. The obtained partially purified product was dissolved in dichloromethane (6 mL), and hexane (6 mL) was then added to the solution. The precipitated solid was collected by filtration to obtain the title compound (116 mg).

$^1$H NMR (CDCl$_3$, 400 MHz): δ(ppm) 8.74 (s, 1H), 8.60 (s, 2H), 8.11 (d, J=7.8 Hz, 1H), 7.96 (d, J=8.5 Hz, 1H), 7.62-7.71 (m, 2H), 7.53 (dd, J=7.0, 1.0 Hz, 1H), 5.27-5.48 (m, 1H), 5.01 (s, 2H), 4.53-4.68 (m, 1H), 4.34-4.49 (m, 1H), 4.07-4.29 (m, 2H), 3.53 (s, 3H), 3.01 (s, 3H), 2.79 (s, 3H)

MS (ESI$^+$) m/z: 506 [M+H]$^+$

Example 100

7-Acetyl-N-(5-((3,3-difluoroazetidin-1-yl)carbonyl)quinolin-2-yl)-4-(methoxymethyl)-3-methylbenzo[b]thiophene-2-carboxamide

[Formula 296]

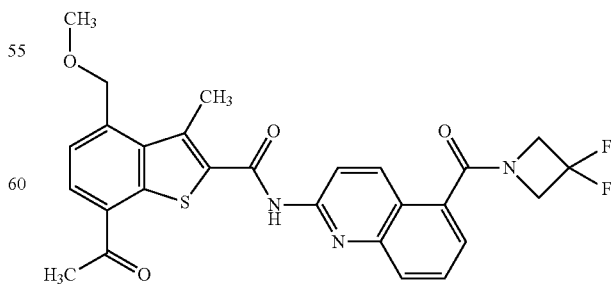

To a suspension of the compound (79 mg) obtained in Reference Example 159, the compound (92 mg) obtained in Reference Example 74, and HBTU (137 mg) in chloroform (4.5 mL), triethylamine (125 μL) was added, and the mixture was stirred at 50° C. for 20 hours. To the reaction mixture, a saturated aqueous solution of sodium bicarbonate was added, followed by extraction with dichloromethane. The organic layer was dried over anhydrous sodium sulfate and concentrated. The residue was purified by silica gel column chromatography (chloroform:methanol=100:0-95:5) and basic silica gel column chromatography (hexane:dichloromethane=40:60-20:75) to obtain the title compound (92 mg).

$^1$H NMR (CDCl$_3$, 400 MHz): δ (ppm) 8.75 (s, 1H), 8.62 (s, 2H), 8.11 (d, J=7.8 Hz, 1H), 7.98 (d, J=8.0 Hz, 1H), 7.63-7.72 (m, 2H), 7.56 (dd, J=7.2, 1.1 Hz, 1H), 5.01 (s, 2H), 4.22-4.73 (m, 4H), 3.53 (s, 3H), 3.01 (s, 3H), 2.79 (s, 3H)

MS (ESI$^+$) m/z: 524 [M+H]$^+$

Example 101

7-Acetyl-N-(5-((3-hydroxyazetidin-1-yl)carbonyl)quinolin-2-yl)-4-(methoxymethyl)-3-methylbenzo[b]thiophene-2-carboxamide

[Formula 297]

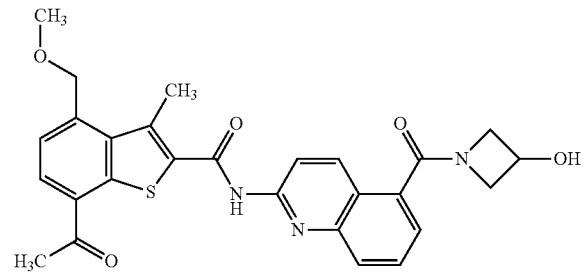

To a suspension of the compound (120 mg) obtained in Example 93 in chloroform (30 mL), N,N-diisopropylethylamine (210 μL) and HBTU (122 mg) were added, and the mixture was stirred at room temperature for 20 minutes. To the reaction mixture, 3-hydroxyazetidine hydrochloride (58.6 mg) was added, and the mixture was stirred overnight at room temperature. The reaction mixture was concentrated, and the residue was purified by silica gel column chromatography (chloroform:methanol=99:1-90:10) to obtain the title compound (78 mg).

$^1$H NMR (CDCl$_3$, 400 MHz): δ (ppm) 8.74 (s, 1H), 8.56-8.62 (m, 2H), 8.10 (d, J=7.5 Hz, 1H), 7.93 (d, J=8.3 Hz, 1H), 7.66 (td, J=8.8, 7.4 Hz, 2H), 7.50-7.54 (m, 1H), 5.01 (s, 2H), 4.76 (d, J=4.8 Hz, 1H), 4.53-4.62 (m, 1H), 4.09-4.20 (m, 2H), 3.87-3.94 (m, 1H), 3.53 (s, 3H), 3.01 (s, 3H), 2.79 (s, 3H), 2.23-2.30 (m, 1H)

MS (ESI$^+$) m/z: 504 [M+H]$^+$

Example 102

7-Acetyl-N-(5-((3-methoxyazetidin-1-yl)carbonyl)quinolin-2-yl)-4-(methoxymethyl)-3-methylbenzo[b]thiophene-2-carboxamide

[Formula 298]

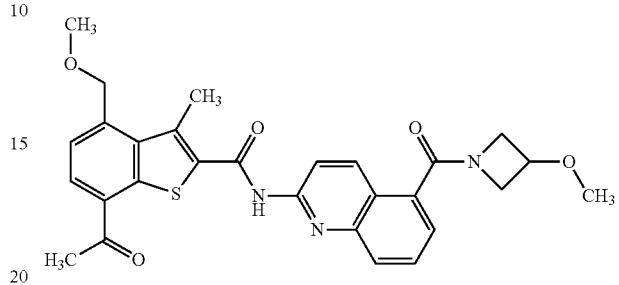

A mixture of the compound (1.27 g) obtained in Reference Example 162, the compound (1.38 g) obtained in Reference Example 74, HBTU (2.82 g), N,N-diisopropylethylamine (2.63 mL), and chloroform (60 mL) was stirred at room temperature for 1.5 hours and then stirred at 40° C. for 17.5 hours. To the reaction mixture, a 1 N aqueous sodium hydroxide solution was added, followed by extraction with chloroform. The organic layer was dried over anhydrous magnesium sulfate and concentrated. The residue was purified by silica gel column chromatography (chloroform:methanol=100:0-95:5), and the obtained solid was washed with ethanol to obtain the title compound (1.78 g).

$^1$H NMR (CDCl$_3$, 400 MHz): δ (ppm) 8.74 (s, 1H), 8.59 (s, 2H), 8.10 (d, J=7.8 Hz, 1H), 7.93 (d, J=8.0 Hz, 1H), 7.62-7.70 (m, 2H), 7.52 (dd, J=7.0, 1.0 Hz, 1H), 5.01 (s, 2H), 4.44-4.51 (m, 1H), 4.23-4.29 (m, 1H), 4.15-4.21 (m, 1H), 4.04-4.10 (m, 1H), 3.85-3.91 (m, 1H), 3.53 (s, 3H), 3.30 (s, 3H), 3.01 (s, 3H), 2.79 (s, 3H)

MS (ESI$^+$) m/z: 518 [M+H]$^+$

Example 103

7-Acetyl-N-(5-((3-methoxyazetidin-1-yl)carbonyl)quinolin-2-yl)-4-(methoxymethyl)-3-methylbenzo[b]thiophene-2-carboxamide hydrochloride

[Formula 299]

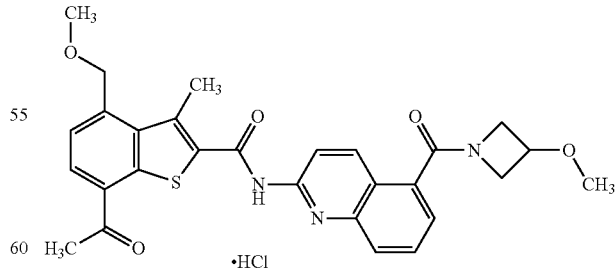

To a suspension of the compound (5.0 g) obtained in Example 102 in methanol (20 mL), hydrogen chloride (4 N solution in 1,4-dioxane, 2.66 mL) was added dropwise at room temperature, and the mixture was stirred at room temperature for 10 minutes and then stirred at 50° C. for 10 minutes. The reaction mixture was cooled to room temperature and stirred overnight. The reaction mixture was cooled to 4° C., and the precipitated solid was collected by filtration to obtain the title compound (2.817 g).

$^1$H NMR (CDCl$_3$, 400 MHz): δ (ppm) 11.97 (br. s., 1H), 9.11 (d, J=9.5 Hz, 1H), 8.91 (d, J=9.5 Hz, 1H), 8.29 (d, J=8.5 Hz, 1H), 8.10 (d, J=7.8 Hz, 1H), 7.91 (dd, J=8.4, 7.4 Hz, 1H), 7.71 (dd, J=7.3, 1.0 Hz, 1H), 7.63 (d, J=7.8 Hz, 1H), 5.00 (s, 2H), 4.45-4.52 (m, 1H), 4.26-4.33 (m, 1H), 4.16-4.23 (m, 2H), 3.96-4.02 (m, 1H), 3.52 (s, 3H), 3.33 (s, 3H), 3.06 (s, 3H), 2.77 (s, 3H)

MS (ESI$^+$) m/z: 518 [M+H]$^+$

Example 104

7-Acetyl-N-(5-((3-methoxyazetidin-1-yl)carbonyl)quinolin-2-yl)-4-(methoxymethyl)-3-methylbenzo[b]thiophene-2-carboxamide benzenesulfonate

[Formula 300]

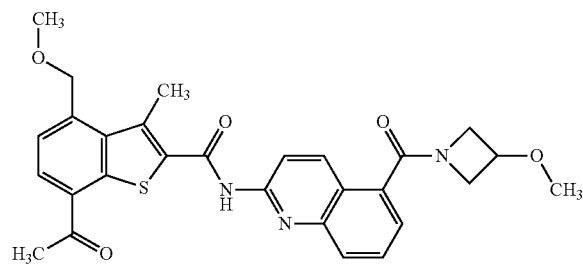 [SMILES: COC1CN(C(=O)c2cccc3nc(NC(=O)c4sc5c(C(C)=O)ccc(CO)c5c4C)ccc23)C1]

To a suspension of the compound (1.10 g) obtained in Example 102 in methanol (5.5 mL), benzenesulfonic acid monohydrate (412 mg) was added at room temperature, and the mixture was heated to 70° C., then cooled to room temperature, and stirred overnight. The reaction mixture was cooled to 4° C., and the precipitated solid was collected by filtration to obtain the title compound (1.176 g).

$^1$H NMR (CDCl$_3$, 400 MHz): δ (ppm) 9.11-9.18 (m, 1H), 8.87 (d, J=9.8 Hz, 1H), 8.43-8.51 (m, 1H), 8.09 (d, J=7.5 Hz, 1H), 7.83-7.93 (m, 3H), 7.69-7.74 (m, 1H), 7.62 (d, J=7.8 Hz, 1H), 7.25-7.35 (m, 5H), 4.95 (s, 2H), 4.44-4.53 (m, 1H), 4.26-4.33 (m, 1H), 4.15-4.22 (m, 2H), 3.94-4.01 (m, 1H), 3.49 (s, 3H), 3.33 (s, 3H), 2.93 (s, 3H), 2.78 (s, 3H)

MS (ESI$^+$) m/z: 518 [M+H]$^+$

Example 105

7-Acetyl-N-(5-((3-methoxyazetidin-1-yl)carbonyl)quinolin-2-yl)-4-(methoxymethyl)-3-methylbenzo[b]thiophene-2-carboxamide methanesulfonate

[Formula 301]

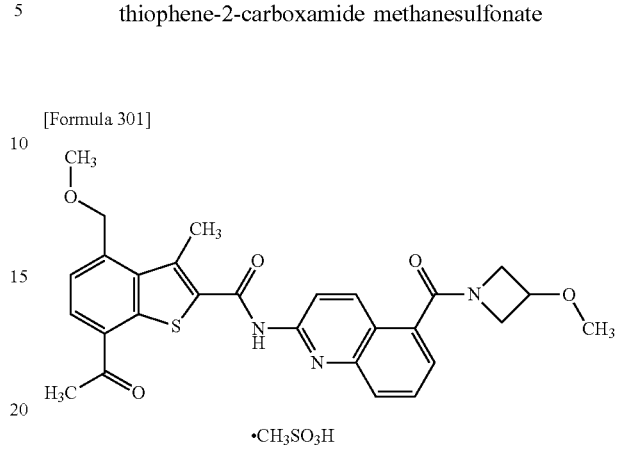

To a suspension of the compound (1.5 g) obtained in Example 102 in acetonitrile (4.5 mL), methanesulfonic acid (207 μL) was added at room temperature, and the mixture was heated to 40° C., then cooled to room temperature, and stirred overnight. The reaction mixture was cooled to 0° C., and the precipitated solid was collected by filtration to obtain the title compound (1.0 g).

$^1$H NMR (CDCl$_3$, 400 MHz): δ (ppm) 12.58 (br. s., 1H), 9.14 (d, J=9.0 Hz, 1H), 8.94 (d, J=9.5 Hz, 1H), 8.48 (d, J=8.8 Hz, 1H), 8.11 (d, J=7.5 Hz, 1H), 7.88-7.94 (m, 1H), 7.69-7.74 (m, 1H), 7.64 (d, J=7.8 Hz, 1H), 5.01 (s, 2H), 4.45-4.52 (m, 1H), 4.26-4.33 (m, 1H), 4.16-4.24 (m, 2H), 3.95-4.01 (m, 1H), 3.51 (s, 3H), 3.33 (s, 3H), 3.00 (s, 3H), 2.98 (s, 3H), 2.76 (s, 3H)

MS (ESI$^+$) m/z: 518 [M+H]$^+$

Example 106

7-Acetyl-N-(5-((3-methoxyazetidin-1-yl)carbonyl)quinolin-2-yl)-4-(methoxymethyl)-3-methylbenzo[b]thiophene-2-carboxamide p-toluenesulfonate

[Formula 302]

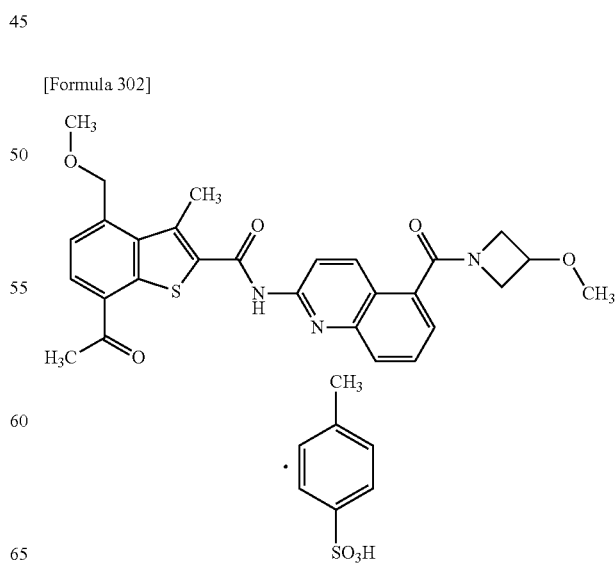

To a suspension of the compound (1.012 g) obtained in Example 102 in ethanol (5.0 mL), p-toluenesulfonic acid monohydrate (409 mg) was added at room temperature, and the mixture was heated to 90° C., then cooled to room temperature, and stirred overnight. The reaction mixture was cooled to 4° C., and the precipitated solid was collected by filtration. The obtained solid was washed with ethanol to obtain the title compound (1.175 g).

$^1$H NMR (CDCl$_3$, 400 MHz): δ (ppm) 12.67 (br. s., 1H), 9.10-9.17 (m, 1H), 8.86 (d, J=9.8 Hz, 1H), 8.43-8.50 (m, 1H), 8.09 (d, J=7.8 Hz, 1H), 7.86-7.93 (m, 1H), 7.69-7.75 (m, 3H), 7.63 (d, J=7.8 Hz, 1H), 7.02-7.07 (m, 2H), 4.95 (s, 2H), 4.44-4.52 (m, 1H), 4.27-4.33 (m, 1H), 4.16-4.23 (m, 2H), 3.97 (d, J=5.8 Hz, 1H), 3.49 (s, 3H), 3.33 (s, 3H), 2.93 (s, 3H), 2.78 (s, 3H), 2.29 (s, 3H)

MS (ESI$^+$) m/z: 518 [M+H]$^+$

Example 107

7-Acetyl-N-(5-((3-methoxyazetidin-1-yl)carbonyl)quinolin-2-yl)-4-(methoxymethyl)-3-methylbenzo[b]thiophene-2-carboxamide hydrobromide

[Formula 303]

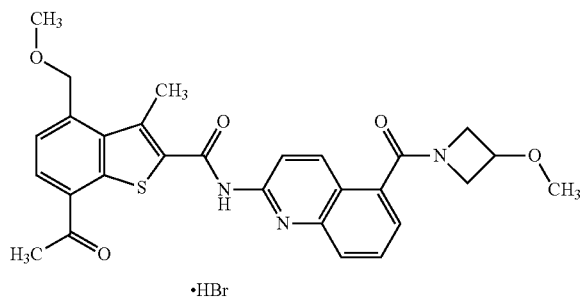

·HBr

To a suspension of the compound (400 mg) obtained in Example 102 in methanol (20 mL), 48% hydrobromic acid (90 μL) was added at room temperature, and the mixture was stirred for 10 minutes. The reaction mixture was concentrated. To the residue, 2-propanol (25 mL) was added, and the mixture was stirred. The reaction mixture was concentrated. To the residue, ethanol (25 mL) was added, and the mixture was stirred for 30 minutes. The reaction mixture was concentrated. To the residue, 2-propanol (25 mL) was added, and the mixture was stirred overnight at room temperature. The precipitated solid was collected by filtration to obtain the title compound (328 mg).

$^1$H NMR (DMSO, 400 MHz): δ (ppm) 8.57 (d, J=9.3 Hz, 1H), 8.31-8.37 (m, 2H), 7.96 (d, J=8.5 Hz, 1H), 7.79-7.75 (m, 1H), 7.69 (d, J=7.5 Hz, 1H), 7.62 (d, J=7.5 Hz, 1H), 5.02 (s, 2H), 4.34-4.38 (m, 1H), 4.24-4.29 (m, 1H), 4.10-4.14 (m, 1H), 3.98-3.95 (m, 1H), 3.79-3.85 (m, 1H), 3.42 (s, 3H), 3.21 (s, 3H), 2.83 (s, 3H), 2.77 (s, 3H)

MS (ESI$^+$) m/z: 518 [M+H]$^+$

Example 108

7-Acetyl-4-(methoxymethyl)-3-methyl-N-(5-methylquinolin-2-yl)benzo[b]thiophene-2-carboxamide

[Formula 304]

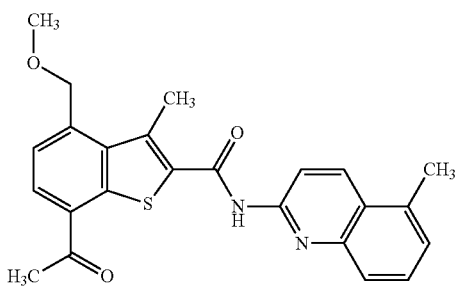

To a suspension of the compound (63.3 mg) obtained in Reference Example 163, the compound (122 mg) obtained in Reference Example 74, and HBTU (182 mg) in chloroform (4 mL), triethylamine (166 μL) was added, and the mixture was stirred at 50° C. for 23 hours. To the reaction mixture, a saturated aqueous solution of sodium bicarbonate was added, followed by extraction with dichloromethane. The organic layer was dried over anhydrous sodium sulfate and concentrated. The residue was purified by basic silica gel column chromatography (hexane:dichloromethane=55:45-40:60), and the obtained solid was washed with ethyl acetate to obtain the title compound (102 mg).

$^1$H NMR (CDCl$_3$, 400 MHz): δ (ppm) 8.72 (br. s., 1H), 8.53 (d, J=8.3 Hz, 1H), 8.40 (d, J=9.3 Hz, 1H), 8.09 (d, J=7.5 Hz, 1H), 7.72 (d, J=8.0 Hz, 1H), 7.63 (d, J=7.8 Hz, 1H), 7.54-7.60 (m, 1H), 7.30 (d, J=7.0 Hz, 1H), 5.01 (s, 2H), 3.52 (s, 3H), 3.01 (s, 3H), 2.78 (s, 3H), 2.70 (s, 3H)

MS (ESI$^+$) m/z: 419 [M+H]$^+$

Example 109

7-Acetyl-4-(methoxymethyl)-3-methyl-N-(5-((methylsulfonyl)methyl)quinolin-2-yl)benzo[b]thiophene-2-carboxamide

[Formula 305]

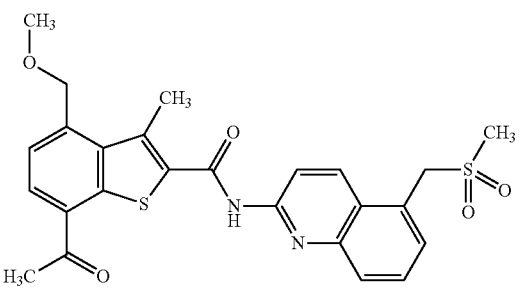

To a suspension of the compound (77.7 mg) obtained in Reference Example 74 in chloroform (2 mL), N,N-diisopropylethylamine (122 μL) and HBTU (116.5 mg) were added, and the mixture was stirred at room temperature for 20 minutes. To the reaction mixture, the compound (66 mg) obtained in Reference Example 164 was added, and the mixture was stirred at 60° C. for 4.5 hours. The reaction mixture was cooled to room temperature, and a 1 N aqueous sodium hydroxide solution was added thereto, followed by extraction with chloroform. The organic layer was dried over anhydrous sodium sulfate and concentrated. The residue was purified by silica gel column chromatography (chloroform:methanol=99:1-97.5:2.5) to obtain the title compound (90 mg).

¹H NMR (DMSO, 400 MHz): δ (ppm) 11.29 (br. s., 1H), 8.76 (d, J=9.3 Hz, 1H), 8.30-8.35 (m, 2H), 7.90 (d, J=8.3 Hz, 1H), 7.77 (dd, J=8.4, 7.2 Hz, 1H), 7.69 (d, J=7.8 Hz, 1H), 7.61 (dd, J=7.3, 1.0 Hz, 1H), 5.09 (s, 2H), 5.01 (s, 2H), 3.42 (s, 3H), 3.05 (s, 3H), 2.83 (s, 3H), 2.77 (s, 3H)

MS (ESI⁺) m/z: 497 [M+H]⁺

Example 110

7-Acetyl-4-(methoxymethyl)-3-methyl-N-(5-((methylsulfonyl)methyl)quinolin-2-yl)benzo[b]thiophene-2-carboxamide hydrochloride

[Formula 306]

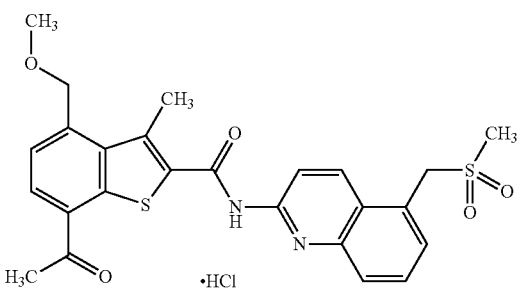

To a suspension of the compound (76 mg) obtained in Example 109 in methanol/ethyl acetate (2 mL/2 mL), hydrogen chloride (4 N solution in ethyl acetate, 77 μL) was added, and the mixture was concentrated. The obtained solid was washed with ethyl acetate to obtain the title compound (78 mg).

¹H NMR (DMSO, 400 MHz): δ (ppm) 11.31 (br. s., 1H), 8.78 (d, J=9.3 Hz, 1H), 8.29-8.34 (m, 2H), 7.91 (d, J=8.8 Hz, 1H), 7.75-7.81 (m, 1H), 7.69 (d, J=7.8 Hz, 1H), 7.62 (d, J=7.3 Hz, 1H), 5.09 (s, 2H), 5.01 (s, 2H), 3.42 (s, 3H), 3.05 (s, 3H), 2.83 (s, 3H), 2.77 (s, 3H)

MS (ESI⁺) m/z: 497[M+H]⁺

Example 111

7-Acetyl-4-(methoxymethyl)-3-methyl-N-(5-((methylsulfonyl)methyl)quinolin-2-yl)benzo[b]thiophene-2-carboxamide methanesulfonate

[Formula 307]

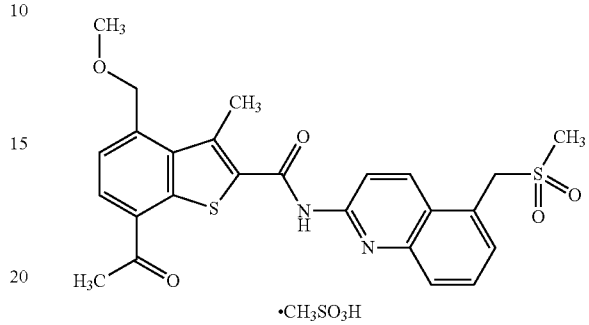

To a suspension of the compound (290 mg) obtained in Example 109 in methanol (10 mL), methanesulfonic acid (39 μL) and dichloromethane (5 mL) were added. To the reaction mixture, diethyl ether (40 mL) was added, and the precipitated solid was collected by filtration and washed with diethyl ether (5 mL) to obtain the title compound (311 mg).

¹H NMR (MeOD, 400 MHz): δ (ppm) 9.20 (d, J=9.5 Hz, 1H), 8.34 (d, J=7.8 Hz, 1H), 8.25 (d, J=8.5 Hz, 1H), 8.05 (dd, J=8.5, 7.5 Hz, 1H), 7.94 (d, J=9.5 Hz, 1H), 7.90 (dd, J=7.3, 0.8 Hz, 1H), 7.73 (d, J=7.5 Hz, 1H), 5.14 (s, 2H), 5.03 (s, 2H), 3.50 (s, 3H), 3.11 (s, 3H), 3.01 (s, 3H), 2.79 (s, 3H), 2.69 (s, 3H)

MS (ESI⁺) m/z: 497 [M+H]⁺

Example 112

7-Acetyl-4-(methoxymethyl)-3-methyl-N-(5-((methylsulfonyl)methyl)quinolin-2-yl)benzo[b]thiophene-2-carboxamide hydrobromide

[Formula 308]

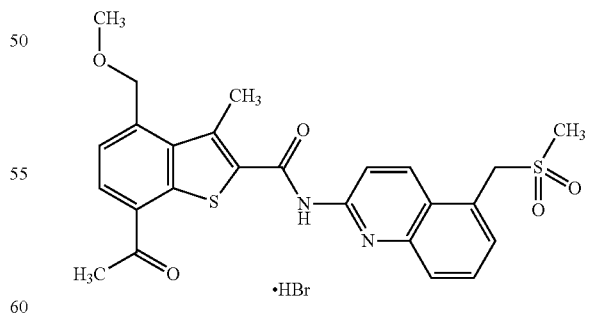

To a solution of the compound (16.64 g) obtained in Example 109 in chloroform (6.4 L), 48% hydrobromic acid (4.26 mL) was added at room temperature, and the mixture was stirred for 1 hour. The reaction mixture was concentrated. To the residue, ethanol (400 mL) was added, and the mixture was stirred at room temperature for 1 hour. The solid was collected by filtration and washed with ethanol (100 mL) to obtain the title compound (18.69 g).

¹H NMR (DMSO, 400 MHz): δ (ppm) 8.81 (d, J=9.3 Hz, 1H), 8.29-8.34 (m, 2H), 7.94 (d, J=8.5 Hz, 1H), 7.82-7.78 (m, 1H), 7.69 (d, J=7.5 Hz, 1H), 7.63 (d, J=7.5 Hz, 1H), 5.10 (s, 2H), 5.01 (s, 2H), 3.42 (s, 3H), 3.06 (s, 3H), 2.85 (s, 3H), 2.77 (s, 3H)

MS (ESI⁺) m/z: 497 [M+H]⁺

Example 113

7-Acetyl-4-(hydroxymethyl)-N-(5-(methoxymethyl) quinolin-2-yl)-3-methylbenzo[b]thiophene-2-carboxamide

[Formula 309]

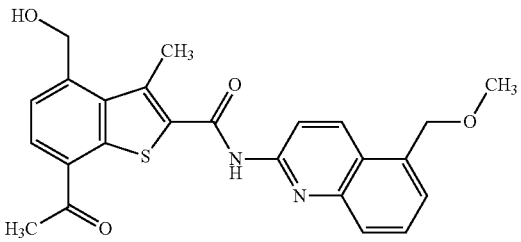

To a solution of the compound (85.0 mg) obtained in Reference Example 167 in THF (6 mL), acetic acid (13 μL) and tetrabutylammonium fluoride (1 M solution in THF, 220 μL) were added, and the mixture was stirred overnight at room temperature. To the reaction mixture, a saturated aqueous solution of sodium bicarbonate was added, followed by extraction with chloroform. The organic layer was dried over anhydrous sodium sulfate and concentrated. To the residue, an ethyl acetate-hexane mixed solution was added, and the mixture was heated and then cooled to room temperature. The precipitated solid was collected by filtration to obtain the title compound (57.0 mg).

¹H NMR (CDCl₃, 400 MHz): δ (ppm) 8.15-8.47 (m, 3H), 7.67-7.82 (m, 2H), 7.54-7.66 (m, 1H), 7.34-7.47 (m, 1H), 5.12-5.16 (m, 1H), 5.14 (s, 2H), 4.81-4.87 (m, 2H), 3.36 (s, 3H), 3.28 (s, 3H), 1.98 (s, 3H)

Example 114

7-Acetyl-4-(hydroxymethyl)-N-(5-(hydroxymethyl) quinolin-2-yl)-3-methylbenzo[b]thiophene-2-carboxamide

[Formula 310]

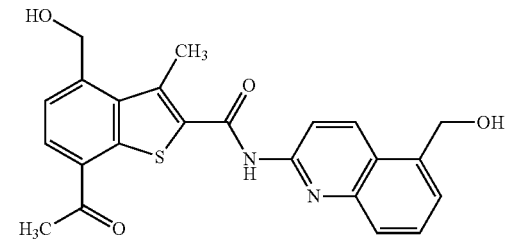

To a solution of the compound (87 mg) obtained in Reference Example 168 in dichloromethane/THF (2 mL/2 mL), acetic acid (18 μL) and tetrabutylammonium fluoride (1 M solution in THF, 315 μL) were added at room temperature, and the mixture was stirred overnight at room temperature. To the reaction mixture, tetrabutylammonium fluoride (1 M solution in THF, 315 μL) was added, and the mixture was stirred at room temperature for 2 hours. The reaction mixture was concentrated, and the residue was purified by silica gel column chromatography (chloroform:methanol=97.5:2.5-90:10) to obtain the title compound (35 mg).

¹H NMR (DMSO, 400 MHz): δ (ppm) 11.18 (br. s., 1H), 8.60 (d, J=9.0 Hz, 1H), 8.28-8.34 (m, 2H), 7.74-7.79 (m, 2H), 7.67-7.72 (m, 1H), 7.52-7.56 (m, 1H), 5.61 (t, J=5.3 Hz, 1H), 5.40 (t, J=5.5 Hz, 1H), 5.13-5.17 (m, 2H), 4.94-4.99 (m, 2H), 2.85 (s, 3H), 2.76 (s, 3H)

MS (ESI⁺) m/z: 421 [M+H]⁺

Example 115

7-Acetyl-4-(hydroxymethyl)-N-(5-((3-methoxyazetidin-1-yl)carbonyl)quinolin-2-yl)-3-methylbenzo[b]thiophene-2-carboxamide

[Formula 311]

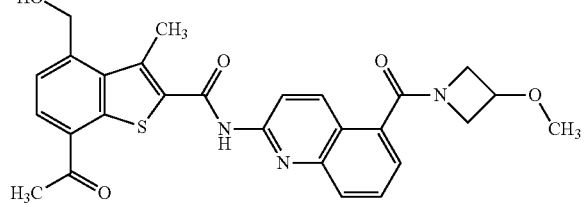

To a solution of the compound (145 mg) obtained in Reference Example 169 in THF (10 mL), acetic acid (18.8 μL) and tetrabutylammonium fluoride (1 M solution in THF, 330 μL) were added, and the mixture was stirred at room temperature for 1 hour. To the reaction mixture, a saturated aqueous solution of sodium bicarbonate was added, followed by extraction with chloroform. The organic layer was dried over anhydrous sodium sulfate and concentrated. The obtained solid was washed with an ethyl acetate-hexane (1:1) mixed solution to obtain the title compound (82 mg).

¹H NMR (DMSO, 400 MHz): δ (ppm) 11.27 (s, 1H), 8.56 (d, J=9.3 Hz, 1H), 8.31-8.40 (m, 2H), 7.94 (d, J=8.3 Hz, 1H), 7.74-7.79 (m, 2H), 7.60-7.63 (m, 1H), 5.61 (t, J=5.4 Hz, 1H), 5.15 (d, J=5.3 Hz, 2H), 4.33-4.39 (m, 1H), 4.23-4.29 (m, 1H), 4.09-4.15 (m, 1H), 3.94-3.99 (m, 1H), 3.79-3.84 (m, 1H), 3.21 (s, 3H), 2.84 (s, 3H), 2.76 (s, 3H)

MS (ESI⁺) m/z: 504 [M+H]⁺

Example 116

(R)-7-Acetyl-N-(4-((3-hydroxypyrrolidin-1-yl)($^2$H$_2$)methyl)quinolin-2-yl)-4-(methoxy($^2$H$_2$)methyl)-3-methylbenzo[b]thiophene-2-carboxamide

[Formula 312]

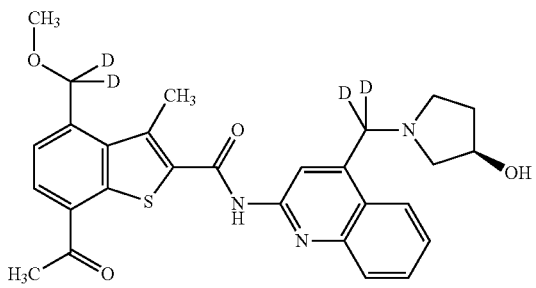

A solution of the compound (286 mg) obtained in Reference Example 174, HBTU (486 mg), and N,N-diisopropylethylamine (0.445 mL) in DMF (10 mL) was stirred for 20 minutes. Then, the compound (250 mg) obtained in Reference Example 176 was added thereto, and the mixture was stirred at room temperature for 24 hours. The reaction mixture was concentrated, and the residue was purified by silica gel column chromatography (dichloromethane:methanol=100:0-90:10) to obtain the title compound (240 mg).

$^1$H NMR (CDCl$_3$, 400 MHz): δ (ppm) 8.77 (br. s., 1H), 8.50 (br. s., 1H), 8.17 (d, J=8.5 Hz, 1H), 8.08 (d, J=7.7 Hz, 1H), 7.86 (d, J=8.5 Hz, 1H), 7.63-7.70 (m, 1H), 7.61 (d, J=7.7 Hz, 1H), 7.44-7.50 (m, 1H), 4.34-4.40 (m, 1H), 3.51 (s, 3H), 2.98 (s, 3H), 2.96-3.05 (m, 1H), 2.83 (d, J=9.7 Hz, 1H), 2.78 (s, 3H), 2.66-2.71 (m, 1H), 2.44-2.52 (m, 1H), 2.19-2.29 (m, 1H), 1.75-1.86 (m, 1H)

MS (ESI$^+$) m/z: 508 [M+H]$^+$

Example 117

7-Acetyl-4-(methoxymethyl)-N-(5-(($^2$H$_3$)methoxymethyl)quinolin-2-yl)-3-methylbenzo[b]thiophene-2-carboxamide

[Formula 313]

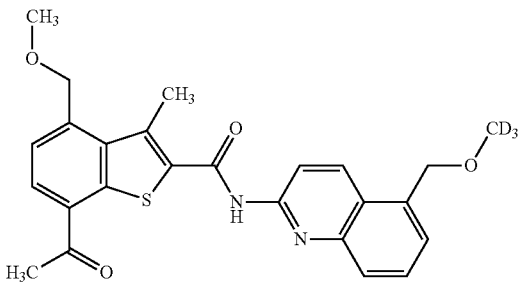

A mixture of the compound (90 mg) obtained in Reference Example 102, the compound (68.4 mg) obtained in Reference Example 177, copper(I) iodide (61.8 mg), potassium carbonate (135 mg), N,N'-dimethylethylenediamine (57.2 mg), and N,N-dimethylacetamide (3 mL) was stirred at 162° C. for 3 hours under an argon atmosphere. The reaction mixture was concentrated, and the residue was purified by silica gel column chromatography (chloroform:methanol=100:0-80:20) to obtain a partially purified product. To the obtained partially purified product, ethyl acetate was added, and the mixture was heated and then cooled to room temperature. The precipitated solid was collected by filtration to obtain the title compound (60 mg).

$^1$H NMR (CDCl$_3$, 400 MHz): δ (ppm) 8.68-8.77 (m, 1H), 8.53 (br. s., 1H), 8.09 (d, J=7.8 Hz, 1H), 7.82-7.86 (m, 1H), 7.60-7.67 (m, 2H), 7.42-7.47 (m, 1H), 7.33-7.38 (m, 1H), 5.00 (s, 2H), 4.88 (s, 2H), 3.52 (s, 3H), 3.00 (s, 3H), 2.78 (s, 3H)

MS (ESI$^+$) m/z: 452 [M+H]$^+$

Example 118

7-Acetyl-4-(($^2$H$_3$)methoxymethyl)-N-(5-(methoxymethyl)quinolin-2-yl)-3-methylbenzo[b]thiophene-2-carboxamide

[Formula 314]

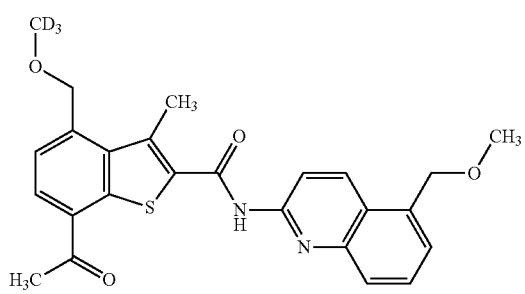

To a solution of the compound (200 mg) obtained in Reference Example 183 in 1,2-dichloroethane (7 mL), triethylamine (258 μL) and HBTU (324 mg) were added at room temperature, and the mixture was stirred at room temperature for 1 hour. To the reaction mixture, the compound (134 mg) obtained in Reference Example 127 was added, and the mixture was stirred at 40° C. for 12 hours. The reaction mixture was concentrated, and the residue was purified by silica gel column chromatography (ethyl acetate-hexane (1:1) mixed solution:methanol=100:0-90:10) to obtain the title compound (140 mg).

$^1$H NMR (CDCl$_3$, 400 MHz): δ (ppm) 8.71 (s, 1H), 8.54 (s, 2H), 8.09 (d, J=7.5 Hz, 1H), 7.84 (d, J=8.3 Hz, 1H), 7.60-7.66 (m, 2H), 7.45 (d, J=6.5 Hz, 1H), 5.01 (s, 2H), 4.89 (s, 2H), 3.45 (s, 3H), 3.00 (s, 3H), 2.79 (s, 3H)

MS (ESI$^+$) m/z: 452 [M+H]$^+$

Example 119

7-Acetyl-N-(5-(hydroxy($^2$H$_2$)methyl)quinolin-2-yl)-4-(methoxymethyl)-3-methylbenzo[b]thiophene-2-carboxamide hydrochloride

[Formula 315]

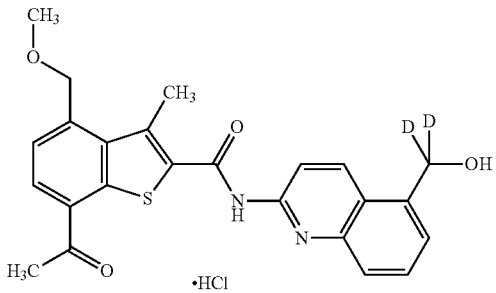

The title compound was obtained by the same operation as in Example 71 using the compound obtained in Reference Example 187 instead of the compound obtained in Reference Example 130 as a starting material for Example 71.

$^1$H NMR (DMSO, 400 MHz): δ (ppm) 11.38 (br. s., 1H), 8.67 (d, J=9.3 Hz, 1H), 8.33 (d, J=7.8 Hz, 1H), 8.28 (d, J=9.3 Hz, 1H), 7.81-7.85 (m, 1H), 7.68-7.76 (m, 2H), 7.55-7.59 (m, 1H), 5.01 (s, 2H), 3.42 (s, 3H), 2.84 (s, 3H), 2.77 (s, 3H)
MS (ESI$^+$) m/z: 437 [M+H]$^+$

Example 120

7-Acetyl-N-(5-(hydroxymethyl)quinolin-2-yl)-4-(($^2$H$_3$)methoxymethyl)-3-methylbenzo[b]thiophene-2-carboxamide

[Formula 316]

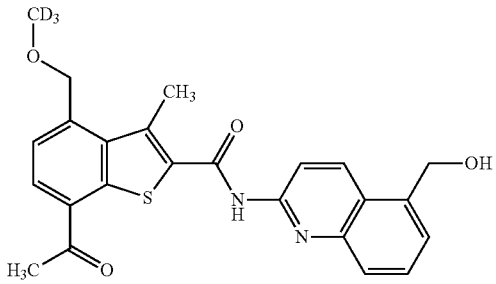

A mixture of the compound (200 mg) obtained in Reference Example 188, the compound (138 mg) obtained in Reference Example 111, copper(I) iodide (136 mg), potassium carbonate (296 mg), N,N'-dimethylethylenediamine (126 mg), and N,N-dimethylacetamide (3 mL) was stirred at 162° C. for 3 hours under an argon atmosphere. The reaction mixture was concentrated, and the residue was purified by silica gel column chromatography (chloroform:methanol=100:0-80:20) to obtain a partially purified product. To the obtained partially purified product, ethyl acetate was added, and the mixture was heated and then cooled to room temperature. The precipitated solid was collected by filtration to obtain the title compound (19 mg).

$^1$H NMR (CDCl$_3$, 400 MHz): δ (ppm) 8.76 (br. s., 1H), 8.56 (s, 2H), 8.09 (d, J=7.8 Hz, 1H), 7.82 (d, J=8.8 Hz, 1H), 7.60-7.66 (m, 2H), 7.48 (d, J=7.0 Hz, 1H), 5.11-5.18 (m, 2H), 5.00 (s, 2H), 2.99 (s, 3H), 2.79 (s, 3H)
MS (ESI$^+$) m/z: 438 [M+H]$^+$

Example 121

7-Acetyl-N-(5-((3-methoxyazetidin-1-yl)carbonyl)quinolin-2-yl)-4-(($^2$H$_3$)methoxymethyl)-3-methylbenzo[b]thiophene-2-carboxamide

[Formula 317]

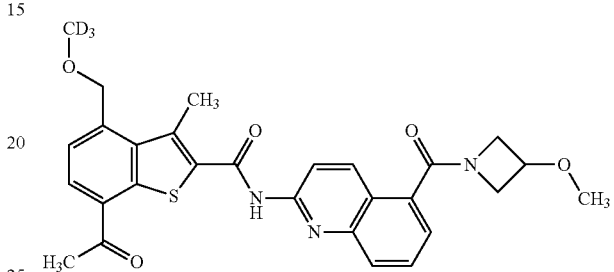

To a solution of the compound (38 mg) obtained in Reference Example 183 in chloroform (3 mL), N,N-diisopropylethylamine (59 μL) and HBTU (61 mg) were added, and the mixture was stirred at room temperature for 20 minutes. To the reaction mixture, the compound (35 mg) obtained in Reference Example 162 was added, and the mixture was stirred overnight at 40° C. The reaction mixture was cooled to room temperature, and a 1 N aqueous sodium hydroxide solution was added thereto, followed by extraction with chloroform. The organic layer was dried over anhydrous sodium sulfate and concentrated. The residue was purified by silica gel column chromatography (chloroform:methanol=99:1-96:4) to obtain the title compound (54 mg).

$^1$H NMR (CDCl$_3$, 400 MHz): δ (ppm) 8.73 (s, 1H), 8.59 (s, 2H), 8.10 (d, J=7.5 Hz, 1H), 7.93 (d, J=7.8 Hz, 1H), 7.62-7.70 (m, 2H), 7.49-7.54 (m, 1H), 5.01 (s, 2H), 4.45-4.51 (m, 1H), 4.23-4.29 (m, 1H), 4.15-4.21 (m, 1H), 4.03-4.10 (m, 1H), 3.85-3.90 (m, 1H), 3.30 (s, 3H), 3.01 (s, 3H), 2.79 (s, 3H)
MS (ESI$^+$) m/z: 521 [M+H]$^+$

Example 122

7-Acetyl-N-(5-((3-($^2$H$_3$)methoxyazetidin-1-yl)carbonyl)quinolin-2-yl)-4-(methoxymethyl)-3-methylbenzo[b]thiophene-2-carboxamide

[Formula 318]

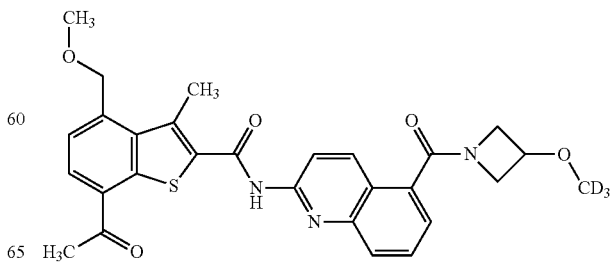

To a solution of the compound (42.8 mg) obtained in Reference Example 74 in chloroform (4 mL), N,N-diisopropylethylamine (67 μL) and HBTU (70 mg) were added at room temperature, and the mixture was stirred at room temperature for 20 minutes. To the reaction mixture, the compound (40 mg) obtained in Reference Example 193 was added, and the mixture was stirred at 60° C. for 12 hours. The reaction mixture was cooled to room temperature, and a 1 N aqueous sodium hydroxide solution was added thereto, followed by extraction with chloroform. The organic layer was dried over anhydrous sodium sulfate and concentrated. The residue was purified by silica gel column chromatography (chloroform:methanol=99.5:0.5-96:4) to obtain the title compound (73 mg).

$^1$H NMR (CDCl$_3$, 400 MHz): δ (ppm) 8.74 (s, 1H), 8.58 (s, 2H), 8.10 (d, J=7.5 Hz, 1H), 7.93 (d, J=8.5 Hz, 1H), 7.62-7.70 (m, 2H), 7.51 (dd, J=7.0, 1.0 Hz, 1H), 5.01 (s, 2H), 4.44-4.52 (m, 1H), 4.22-4.29 (m, 1H), 4.14-4.20 (m, 1H), 4.03-4.10 (m, 1H), 3.84-3.91 (m, 1H), 3.53 (s, 3H), 3.01 (s, 3H), 2.79 (s, 3H)

MS (ESI$^+$) m/z: 521 [M+H]$^+$

Example 123

7-Acetyl-N-(5-((3-($^2$H$_3$) methoxyazetidin-1-yl)carbonyl) quinolin-2-yl)-4-(methoxy($^2$H$_2$)methyl)-3-methylbenzo[b]thiophene-2-carboxamide

[Formula 319]

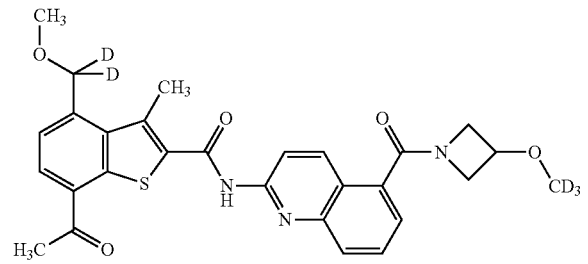

To a solution of the compound (43 mg) obtained in Reference Example 174 in chloroform (4 mL), N,N-diisopropylethylamine (67 μL) and HBTU (70 mg) were added at room temperature, and the mixture was stirred at room temperature for 20 minutes. To the reaction mixture, the compound (40 mg) obtained in Reference Example 193 was added, and the mixture was stirred at 60° C. for 15 hours. The reaction mixture was cooled to room temperature, and a 1 N aqueous sodium hydroxide solution was added thereto, followed by extraction with chloroform. The organic layer was dried over anhydrous sodium sulfate and concentrated. The residue was purified by silica gel column chromatography (chloroform:methanol=99.5:0.5-96:4) to obtain the title compound (69 mg).

$^1$H NMR (CDCl$_3$, 400 MHz): δ (ppm) 8.74 (s, 1H), 8.58 (s, 2H), 8.10 (d, J=7.8 Hz, 1H), 7.93 (d, J=8.5 Hz, 1H), 7.62-7.70 (m, 2H), 7.52 (dd, J=7.2, 1.1 Hz, 1H), 4.44-4.51 (m, 1H), 4.22-4.30 (m, 1H), 4.14-4.20 (m, 1H), 4.03-4.10 (m, 1H), 3.84-3.90 (m, 1H), 3.52 (s, 3H), 3.01 (s, 3H), 2.79 (s, 3H)

MS (ESI$^+$) m/z: 523 [M+H]$^+$

Example 124

7-Acetyl-4-(methoxymethyl)-3-methyl-N-(4-(piperazin-1-ylmethyl)quinolin-2-yl)benzo[b]thiophene-2-carboxamide

[Formula 320]

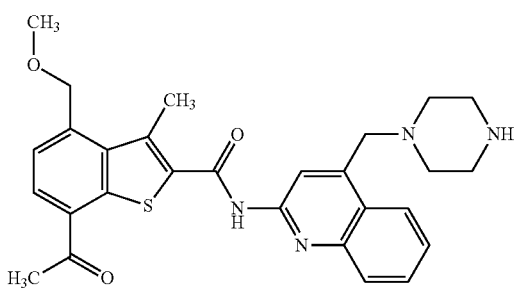

(1) 4-(Piperazin-1-ylmethyl)quinolin-2-amine

[Formula 321]

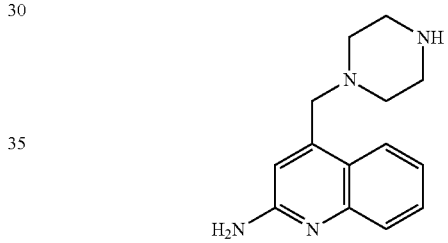

To a solution of 4-(bromomethyl)-2-chloroquinoline (1.28 g) and triethylamine (836 μL) in acetonitrile (10 mL), tert-butyl piperazine-1-carboxylate (931 mg) was added, and the mixture was stirred at room temperature for 3 hours. To the reaction mixture, a saturated aqueous solution of sodium bicarbonate was added, followed by extraction with dichloromethane. The organic layer was dried over anhydrous sodium sulfate and concentrated. To the residue, 4-methoxybenzylamine (3.27 mL) was added, and the mixture was stirred at 100° C. for 20 hours under an argon atmosphere. The reaction mixture was dissolved in dichloromethane. To the solution, dry ice was added. The precipitated solid was collected by filtration, and the filtrate was concentrated. To the residue, toluene (1.62 mL) and methanesulfonic acid (1.62 mL) were added, and the mixture was stirred at 80° C. for 20 hours. To the reaction mixture, 4 N sodium hydroxide was added, followed by extraction with dichloromethane. The organic layer was dried over anhydrous sodium sulfate and concentrated. The residue was washed with ethyl acetate to obtain the title compound (530 mg).

$^1$H NMR (MeOD, 400 MHz): δ (ppm) 8.01 (d, J=8.5 Hz, 1H), 7.46-7.54 (m, 2H), 7.19-7.25 (m, 1H), 6.88 (s, 1H), 3.79 (s, 2H), 3.29-3.32 (m, 4H), 2.82-2.87 (m, 4H), 2.52 (br. s., 4H)

MS (ESI$^+$) m/z: 243 [M+H]$^+$ (2) tert-Butyl4-((2-aminoquinolin-4-yl)methyl)piperazine-1-carboxylate

[Formula 322]

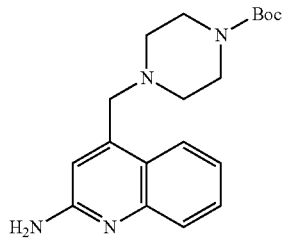

To a solution of the compound (145 mg) obtained in the preceding paragraph (1) and triethylamine (88 µL) in dichloromethane (3 mL), di-tert-butyl dicarbonate (229 mg) was added, and the mixture was stirred at room temperature for 2 hours. To the reaction mixture, a saturated aqueous solution of sodium bicarbonate was added, followed by extraction with dichloromethane. The organic layer was dried over anhydrous sodium sulfate and concentrated to obtain the title compound (253 mg).

MS (ESI$^+$) m/z: 343 [M+H]$^+$ (3) 7-Acetyl-4-(methoxymethyl)-3-methyl-N-(4-(piperazin-1-ylmethyl)quinolin-2-yl)benzo[b]thiophene-2-carboxamide

[Formula 323]

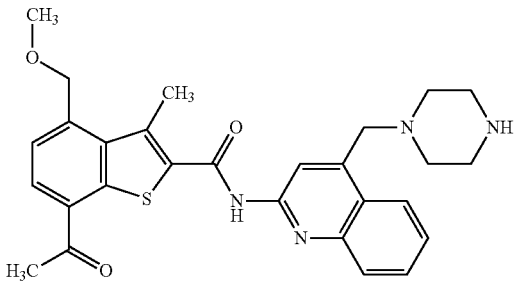

To a suspension of the compound (167 mg) obtained in Reference Example 74, the compound (253 mg) obtained in the preceding paragraph (2), and PyBOP (375 mg) in dichloromethane (3 mL), N,N-diisopropylethylamine (209 µL) was added, and the mixture was stirred at room temperature for 20 hours. To the reaction mixture, TFA (1.5 mL) was added, and the mixture was stirred at room temperature for 6 hours. The reaction mixture was diluted with dichloromethane, followed by extraction with 0.5 N hydrochloric acid. The aqueous layer was rendered basic by the addition of a 4 N aqueous sodium hydroxide solution, followed by extraction with dichloromethane. The organic layer was dried over anhydrous sodium sulfate and concentrated. The residue was washed with a dichloromethane-hexane (1:1) mixed solution to obtain the title compound (113 mg).

$^1$H NMR (CDCl$_3$, 400 MHz): δ (ppm) 8.48 (br. s., 1H), 8.26 (d, J=7.3 Hz, 1H), 8.09 (d, J=7.7 Hz, 1H), 7.86 (d, J=8.1 Hz, 1H), 7.61-7.70 (m, 2H), 7.46-7.51 (m, 1H), 5.01 (s, 2H), 3.94 (s, 2H), 3.53 (s, 3H), 3.01 (s, 3H), 2.93 (t, J=4.9 Hz, 4H), 2.79 (s, 3H), 2.56 (br. s., 4H)

MS (ESI$^+$) m/z: 503 [M+H]$^+$

Example 125

7-Acetyl-4-(methoxymethyl)-3-methyl-N-(4-((4-methylpiperazin-1-yl)methyl)quinolin-2-yl)benzo[b]thiophene-2-carboxamide

[Formula 324]

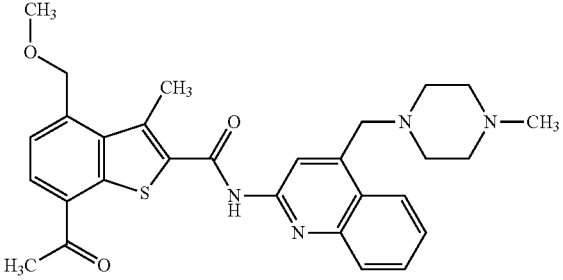

(1) 4-((4-Methylpiperazin-1-yl)methyl)quinolin-2-amine

[Formula 325]

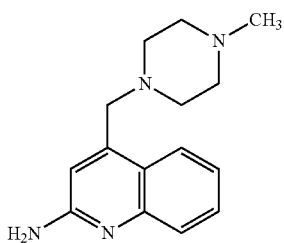

To a solution of 4-(bromomethyl)-2-chloroquinoline (1.28 g) and triethylamine (836 µL) in acetonitrile (10 mL), 1-methylpiperazine (555 µL) was added, and the mixture was stirred at room temperature for 3 hours. To the reaction mixture, a saturated aqueous solution of sodium bicarbonate was added, followed by extraction with dichloromethane. The organic layer was dried over anhydrous sodium sulfate and concentrated. To the residue, 4-methoxybenzylamine (3.27 mL) was added, and the mixture was stirred at 100° C. for 20 hours under an argon atmosphere. The reaction mixture was dissolved in dichloromethane. To the solution, dry ice was added. The precipitated solid was collected by filtration, and the filtrate was concentrated. To the residue, toluene (1.62 mL) and methanesulfonic acid (1.62 mL) were added, and the mixture was stirred at 80° C. for 20 hours. To the reaction mixture, 4 N sodium hydroxide was added, followed by extraction with dichloromethane. The organic layer was dried over anhydrous sodium sulfate and concentrated. The residue was washed with ethyl acetate to obtain the title compound (356 mg).

$^1$H NMR (MeOD, 400 MHz): δ (ppm) 8.01 (d, J=7.7 Hz, 1H), 7.46-7.54 (m, 2H), 7.19-7.25 (m, 1H), 6.86 (s, 1H), 3.82 (d, J=0.8 Hz, 2H), 2.34-2.75 (m, 8H), 2.28 (s, 3H)

MS (ESI$^+$) m/z: 257 [M+H]$^+$ (2) 7-Acetyl-4-(methoxymethyl)-3-methyl-N-(4-((4-methylpiperazin-1-yl)methyl)quinolin-2-yl)benzo[b]thiophene-2-carboxamide

[Formula 326]

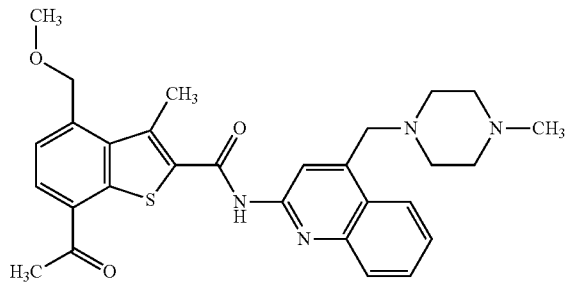

To a suspension of the compound (139 mg) obtained in Reference Example 74, the compound (128 mg) obtained in the preceding paragraph (1), and PyBOP (312 mg) in dichloromethane (2.5 mL), N,N-diisopropylethylamine (174 μL) was added, and the mixture was stirred at room temperature for 20 hours. The reaction mixture was diluted with dichloromethane, followed by extraction with 0.5 N hydrochloric acid. The aqueous layer was rendered basic by the addition of a 4 N aqueous sodium hydroxide solution, followed by extraction with dichloromethane. The organic layer was dried over anhydrous sodium sulfate and concentrated. The residue was purified by basic silica gel column chromatography (dichloromethane:methanol=100:0-90:10) to obtain the title compound (133 mg).

$^1$H NMR (CDCl$_3$, 400 MHz): δ (ppm) 8.68 (br. s., 1H), 8.50 (br. s., 1H), 8.24 (d, J=8.1 Hz, 1H), 8.09 (d, J=7.7 Hz, 1H), 7.86 (d, J=8.1 Hz, 1H), 7.61-7.70 (m, 2H), 7.45-7.50 (m, 1H), 5.00 (s, 2H), 3.97 (s, 2H), 3.52 (s, 3H), 3.01 (s, 3H), 2.78 (s, 3H), 2.63 (br. s, 4H), 2.49 (br. s., 4H), 2.30 (s, 3H)
MS (ESI$^+$) m/z: 517 [M+H]$^+$ Formulation Example 5 g of a compound obtained in any of Examples, 90 g of lactose, 34 g of corn starch, 20 g of crystalline cellulose, and 1 g of magnesium stearate were mixed using a blender and then compressed in a tableting machine to obtain tablets.

Test Example 1

Measurement of PDE10A inhibitory activity-1

To a solution containing 20 mM Tris-HCl (pH 7.5), 1 mM MgCl$_2$, 100 μM EDTA, 330 μg/ml bovine serum albumin, 50 kU/ml 5'-nucleotidase, 0.1 μCi $^3$H-cAMP (64 nM cAMP), and PDE10A (H-PDE10A2, Human Phosphodiesterase 10A2, Scottish Biomedical), a test compound was added, and the mixture was reacted at 25° C. for 2 hours. To the reaction solution, QAE-Sephadex (17-0190-01, GE Healthcare Japan Corp.) suspended in 10 mM HEPES-Na (pH 7.0) (hereinafter, also referred to as a "QAE-Sephadex suspension") was added, and the mixture was shaken for 1 minute and left standing for 5 minutes to obtain a supernatant. To the supernatant, a QAE-Sephadex suspension was further added, and the mixture was shaken for 1 minute and left standing for 5 minutes. Then, the obtained supernatant was transferred to LumaPlate (PerkinElmer, Inc.) and assayed using a radiation counter (TopCount NXT, PerkinElmer, Inc.).

The value of the sample reacted without the addition of both a test compound and PDE10A was defined as 0%, and the value of the sample reacted in the presence of PDE10A without the addition of a test compound was defined as 100%. IC$_{50}$ represents the concentration at which a test compound inhibits 50% of the metabolic activity of PDE10A. The results are shown in Table 1. As is evident, the compound of the present invention has PDE10A inhibitory activity.

TABLE 1

| Example No. | IC$_{50}$ (nM) |
|---|---|
| 3 | 5.9 |
| 4 | 5.8 |
| 5 | 11 |
| 6 | 5.1 |
| 27 | 1.6 |
| 28 | 2.0 |
| 38 | 0.42 |
| 39 | 0.41 |
| 40 | 0.65 |
| 41 | 1.3 |
| 67 | 1.8 |
| 68 | 1.9 |
| 77 | 3.1 |
| 78 | 1.7 |
| 79 | 1.4 |
| 80 | 1.1 |
| 81 | 1.9 |
| 82 | 0.87 |
| 88 | 0.99 |
| 102 | 0.70 |
| 103 | 0.31 |
| 104 | 2.2 |
| 105 | 2.1 |
| 107 | 0.73 |
| 109 | 0.61 |
| 110 | 1.4 |
| 111 | 1.1 |
| 112 | 0.84 |

Test Example 2

Measurement of PDE10A Inhibitory Activity-2

A human acute lymphoblastic lymphoma T cell line MOLT-4 (which can be purchased under ATCC No. CRL-1582 from ATCC) was cultured in an RPMI1640 medium containing 10% fetal bovine serum to obtain 5×10$^8$ MOLT-4 cells. The cells were recovered by centrifugation and suspended in 10 ml of buffer solution A (25 mM Tris-HCl, 5 mM 2-mercaptoethanol, 2 mM benzamidine, 2 mM EDTA, and 0.1 mM 4-(2-aminoethyl)benzenesulfonyl hydrochloride, pH 7.5). The cells were homogenized using a Polytron homogenizer and centrifuged (4° C., 25,000 g, 10 minutes). Then, the supernatant was further ultracentrifuged (4° C., 100,000 g, 60 minutes). The obtained supernatant was filtered through a 0.2 μm filter to obtain a soluble fraction.

HiTrap Q HP column (5 ml×2, GE Healthcare Japan Corp.) equilibrated with buffer solution A was charged with the obtained soluble fraction. Phosphodiesterase was eluted with 300 ml of buffer solution A containing a linear gradient solution of 0 to 0.8 M NaCl to recover sixty 5-ml fractions. Each fraction was tested for cAMP-metabolizing phosphodiesterase activity. In each fraction, a fraction eluted as an active peak centered around 250 mM NaCl was collected from fractions that had cAMP metabolic activity and did not lose the metabolic activity by 10 μM rolipram (PDE4 selective inhibitor) and 10 μM milrinone (PDE3 selective inhibitor).

In order to confirm whether or not PDE10A mRNA was expressed in the MOLT-4 cells, total RNA was prepared from the MOLT-4 cells according to a standard method and analyzed by RT-PCR using PDE10A gene-specific primers (PDE10A sense primer: 5'-TGCTCCATGGTG-GAAGTGGA-3' (SEQ ID NO: 1) and PDE10A antisense primer: 5'-CAACTGGAAGCATGCGGTCA-3' (SEQ ID NO: 2)). As a result, PDE10A mRNA was detected from the total RNA of the MOLT-4 cells. On the other hand, total RNA was prepared from Jurkat cells, one type of human T cell, and similarly subjected to RT-PCR. As a result, PDE10A mRNA was rarely detected. An active peak centered around 250 mM NaCl was not observed in fractions obtained by the treatment of Jurkat cells in the same way as above. Eur J Biochem. 1999, 266 (3), 1118-2 has reported that PDE10A from the rat striatum and testis is eluted as an active peak centered around 250 mM NaCl. As is evident, MOLT-4 expresses PDE10A, and the fraction eluted as an active peak centered around 250 mM NaCl, prepared from MOLT-4, has cAMP-metabolizing phosphodiesterase activity of PDE10A.

For these reasons, this fraction was used as a solution for the evaluation of PDE10A inhibitory activity. The obtained solution was used to calculate the inhibitory activity ($IC_{50}$) of a test compound in the same way as in the aforementioned test. The results are shown in Table 2. As is evident, the compound of the present invention has PDE10A inhibitory activity.

TABLE 2

| Example No. | $IC_{50}$ (nM) |
|---|---|
| 1 | 1.6 |
| 2 | 2.6 |
| 7 | 5.0 |
| 8 | 12 |
| 9 | 7.8 |
| 10 | 20 |
| 11 | 2.2 |
| 12 | 4.4 |
| 13 | 2.0 |
| 14 | 0.89 |
| 15 | 2.3 |
| 16 | 4.8 |
| 17 | 2.6 |
| 18 | 0.47 |
| 19 | 0.92 |
| 20 | 10 |
| 21 | 0.67 |
| 22 | 1.0 |
| 23 | 10 |
| 24 | 25 |
| 25 | 4.0 |
| 26 | 1.8 |
| 29 | 3.0 |
| 30 | 11 |
| 31 | 16 |
| 32 | 9.1 |
| 33 | 0.90 |
| 34 | 0.94 |
| 35 | 0.29 |
| 36 | 0.35 |
| 37 | 0.50 |
| 38 | 0.23 |
| 39 | 0.35 |
| 42 | 0.92 |
| 43 | 6.2 |
| 44 | 2.1 |
| 45 | 0.50 |

TABLE 2-continued

| Example No. | $IC_{50}$ (nM) |
|---|---|
| 46 | 0.44 |
| 47 | 0.49 |
| 48 | 0.85 |
| 49 | 1.1 |
| 50 | 2.6 |
| 51 | 1.5 |
| 52 | 1.2 |
| 53 | 18 |
| 54 | 0.054 |
| 55 | 0.45 |
| 56 | 1.1 |
| 57 | 1.6 |
| 58 | 0.085 |
| 59 | 0.31 |
| 60 | 1.2 |
| 61 | 1.3 |
| 62 | 1.8 |
| 63 | 1.1 |
| 64 | 0.76 |
| 65 | 0.39 |
| 66 | 1.2 |
| 68 | 0.93 |
| 69 | 0.38 |
| 70 | 1.6 |
| 71 | 0.75 |
| 72 | 0.54 |
| 73 | 2.0 |
| 74 | 3.0 |
| 75 | 0.91 |
| 76 | 0.53 |
| 77 | 0.82 |
| 83 | 0.86 |
| 84 | 7.1 |
| 85 | 1.1 |
| 86 | 1.1 |
| 87 | 0.60 |
| 89 | 0.37 |
| 90 | 1.0 |
| 91 | 0.74 |
| 92 | 12 |
| 93 | 0.11 |
| 94 | 1.2 |
| 95 | 0.48 |
| 96 | 0.31 |
| 97 | 0.26 |
| 98 | 0.21 |
| 99 | 0.11 |
| 100 | 0.42 |
| 101 | 0.11 |
| 102 | 0.30 |
| 106 | 0.50 |
| 108 | 1.6 |
| 110 | 0.23 |
| 113 | 0.12 |
| 114 | 2.1 |
| 115 | 0.89 |
| 116 | 0.15 |
| 117 | 0.61 |
| 118 | 0.76 |
| 119 | 0.34 |
| 120 | 0.64 |
| 121 | 0.57 |
| 122 | 0.29 |
| 123 | 0.22 |
| 124 | 2.9 |
| 125 | 0.80 |

Some compounds of the present invention were examined for their inhibitory activity against isozymes other than PDE10A and were found to exhibit little inhibitory activity. As is also evident from this, the cAMP-metabolizing phosphodiesterase activity of the fraction used in this test is based on PDE10A.

Test Example 3

Test on Suppression of Phencyclidine-Induced Hyperlocomotion in Mice

Male C57BL/6 Cr mice (Japan SLC, Inc.) (8 weeks old) were used in the experiment. A test compound was suspended at 1 mg/mL in a 0.5% hydroxypropylcellulose solution to prepare a suspension for administration. The suspension of the test compound or a solvent (0.5% hydroxypropylcellulose solution) was orally administered at a dose of 10 mL/kg to each mouse. After the administration, the mouse was immediately placed in a locomotor activity measurement apparatus (Muromachi Kikai Co., Ltd., locomotor activity measurement system SUPERMEX). Approximately 1 hour later, phencyclidine (5 mg/10 mL/kg) or a solvent (10 mL/kg saline) was subcutaneously administered to the mouse. The locomotor activity was measured from immediately after the subcutaneous administration to 1 hour later.

When the activity of a group that received the oral administration of a solvent (0.5% hydroxypropylcellulose solution) and the subcutaneous administration of a solvent (saline) (solvent administration control group) was defined as 0% and the activity of a group that received the oral administration of a solvent (0.5% hydroxypropylcellulose solution) and the subcutaneous administration of phencyclidine (phencyclidine administration control group) was defined as 100%, Table 3 shows the extent to which the administration of a test compound (10 mg/kg) suppressed the activity as compared with the phencyclidine administration control group. For example, 30% inhibition means that when the activity of the phencyclidine administration control group was defined as 100, the activity of the group given a test compound was 70. Percent inhibition exceeding 100 means that when the activity of the phencyclidine administration control group was defined as 100, the activity of the group given a test compound was lower than that of the solvent administration control group.

TABLE 3

| Example No. | % inhibition |
|---|---|
| 26 | 84 |
| 36 | 69 |
| 38 | 88 |
| 39 | 103 |
| 42 | 85 |
| 44 | 104 |
| 45 | 97 |
| 47 | 73 |
| 49 | 104 |
| 54 | 68 |
| 55 | 127 |
| 57 | 86 |
| 59 | 67 |
| 60 | 107 |
| 61 | 122 |
| 63 | 84 |
| 64 | 109 |
| 65 | 37 |
| 66 | 91 |
| 68 | 121 |
| 69 | 81 |
| 71 | 89 |
| 72 | 83 |
| 76 | 102 |
| 77 | 96 |
| 81 | 122 |
| 84 | 92 |
| 85 | 85 |

TABLE 3-continued

| Example No. | % inhibition |
|---|---|
| 86 | 88 |
| 87 | 92 |
| 96 | 65 |
| 97 | 50 |
| 101 | 35 |
| 102 | 120 |
| 106 | 87 |
| 110 | 76 |
| 112 | 57 |
| 116 | 180 |
| 117 | 57 |
| 118 | 77 |
| 120 | 52 |
| 121 | 59 |
| 125 | 86 |

$ED_{50}$ is further shown in Table 4. When the activity of the solvent administration control group was defined as 0% and the activity of the phencyclidine administration control group was defined as 100%, $ED_{50}$ was calculated by the linear regression method.

TABLE 4

| Example No. | $ED_{50}$ (mg/kg) |
|---|---|
| 38 | 7.0 |
| 39 | 3.1 |
| 61 | 5.7 |
| 64 | 7.2 |
| 68 | 3.6 |
| 69 | 3.0 |
| 81 | 3.3 |
| 106 | 2.2 |

Since the phencyclidine-induced mice used in Test Example 3 are animal models with schizophrenia, the compound of the present invention is useful in the treatment of schizophrenia.

Test Example 4

Test Using Model Animal with Huntington's Disease

The test can be conducted with reference to a method described in, for example, Neurobiology of Disease 34 (2009) 450-456 (Non-patent Literature 2 mentioned above) to confirm whether or not a test compound is useful in the treatment of Huntington's disease.

FREE TEXT OF SEQUENCE LISTING

SEQ ID NO: 1: PCR sense primer for PDE10A

SEQ ID NO: 2: PCR antisense primer for PDE10A

The invention claimed is:

1. A compound represented by the general formula (I):

[Formula 1]

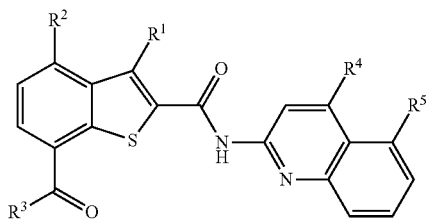

(I)

wherein
R$^1$ represents a hydrogen atom or a C1-C3 alkyl group;
R$^2$ represents a hydrogen atom, a C1-C3 alkylcarbonyl group, a hydroxy-C1-C3 alkyl group, or a C1-C3 alkoxy-C1-C3 alkyl group;
R$^3$ represents a C1-C6 alkyl group or a C3-C6 cycloalkyl group;
R$^4$ and R$^5$ each independently represent a hydrogen atom, a C1-C6 alkyl group optionally substituted by one substituent selected from substituent group α, or an (azetidin-1-yl)carbonyl group optionally substituted by one substituent selected from substituent group α; and
substituent group α is the group consisting of a hydroxy group, a C1-C6 alkoxy group, a methylsulfonyl group, a hydroxypyrrolidine group, and a hydroxypiperidine group, provided that
at least one of R$^4$ and R$^5$ is a hydrogen atom
or a pharmaceutically acceptable salt thereof.

2. The compound or a pharmaceutically acceptable salt thereof according to claim 1, wherein R$^1$ is a hydrogen atom, a methyl group, or an ethyl group.

3. The compound or a pharmaceutically acceptable salt thereof according to claim 1, wherein R$^2$ is a hydrogen atom, an acetyl group, a propionyl group, a hydroxymethyl group, a 1-hydroxyethyl group, a 1-methoxyethyl group, a methoxymethyl group, an ethoxymethyl group, a propoxymethyl group, or an isopropoxymethyl group.

4. The compound or a pharmaceutically acceptable salt thereof according to claim 1, wherein R$^3$ is a methyl group, an ethyl group, a propyl group, an isopropyl group, a butyl group, an isobutyl group, a 1-ethylpropyl group, a tert-butyl group, a cyclopropyl group, a cyclobutyl group, or a cyclopentyl group.

5. The compound or a pharmaceutically acceptable salt thereof according to claim 1, wherein R$^3$ is a methyl group.

6. The compound or a pharmaceutically acceptable salt thereof according to claim 1, wherein R$^4$ is a hydrogen atom, and R$^5$ is a methyl group, a hydroxymethyl group, a 1-hydroxyethyl group, a 2-hydroxypropan-2-yl group, a methoxymethyl group, an ethoxymethyl group, a methylsulfonylmethyl group, a (3-hydroxypyrrolidin-1-yl)methyl group, a (3-hydroxyazetidin-1-yl)carbonyl group, or a (3-methoxyazetidin-1-yl)carbonyl group.

7. The compound or a pharmaceutically acceptable salt thereof according to claim 1, wherein R$^5$ is a hydrogen atom, and R$^4$ is a methyl group, a hydroxymethyl group, a 1-hydroxyethyl group, a 2-hydroxypropan-2-yl group, a (3-hydroxypyrrolidin-1-yl)methyl group, a (3-hydroxypiperidin-1-yl)methyl group, or a (4-hydroxypiperidin-1-yl)methyl group.

8. A compound selected from the group consisting of the following:
  7-acetyl-N-(4-((4-hydroxypiperidin-1-yl)methyl)quinolin-2-yl)-4-(methoxymethyl)-3-methylbenzo[b]thiophene-2-carboxamide;
  7-acetyl-N-(4-((3-hydroxypyrrolidin-1-yl)methyl)quinolin-2-yl)-4-(methoxymethyl)-3-methylbenzo[b]thiophene-2-carboxamide;
  (S)-7-acetyl-N-(4-((3-hydroxypyrrolidin-1-yl)methyl)quinolin-2-yl)-4-(methoxymethyl)-3-methylbenzo[b]thiophene-2-carboxamide;
  (R)-7-acetyl-N-(4-((3-hydroxypyrrolidin-1-yl)methyl)quinolin-2-yl)-4-(methoxymethyl)-3-methylbenzo[b]thiophene-2-carboxamide;
  (R)-7-acetyl-N-(4-((3-hydroxypyrrolidin-1-yl)methyl)quinolin-2-yl)-4-(methoxymethyl)-3-methylbenzo[b]thiophene-2-carboxamide hydrochloride;

(R)-7-acetyl-N-(4-((3-hydroxypyrrolidin-1-yl)methyl) quinolin-2-yl)-4-(methoxymethyl)-3-methylbenzo[b] thiophene-2-carboxamide p-toluenesulfonate;

7-acetyl-N-(5-((3-methoxyazetidin-1-yl)carbonyl)quinolin-2-yl)-4-(methoxymethyl)-3-methylbenzo[b]thiophene-2-carboxamide;

7-acetyl-N-(5-((3-methoxyazetidin-1-yl)carbonyl)quinolin-2-yl)-4-(methoxymethyl)-3-methylbenzo[b]thiophene-2-carboxamide hydrochloride;

7-acetyl-N-(5-((3-methoxyazetidin-1-yl)carbonyl)quinolin-2-yl)-4-(methoxymethyl)-3-methylbenzo[b]thiophene-2-carboxamide benzenesulfonate;

7-acetyl-N-(5-((3-methoxyazetidin-1-yl)carbonyl)quinolin-2-yl)-4-(methoxymethyl)-3-methylbenzo[b]thiophene-2-carboxamide methanesulfonate;

7-acetyl-N-(5-((3-methoxyazetidin-1-yl)carbonyl)quinolin-2-yl)-4-(methoxymethyl)-3-methylbenzo[b]thiophene-2-carboxamide p-toluenesulfonate;

7-acetyl-N-(5-((3-methoxyazetidin-1-yl)carbonyl)quinolin-2-yl)-4-(methoxymethyl)-3-methylbenzo[b]thiophene-2-carboxamide hydrobromide;

7-acetyl-4-(methoxymethyl)-3-methyl-N-(5-((methylsulfonyl)methyl)quinolin-2-yl)benzo[b]thiophene-2-carboxamide;

7-acetyl-4-(methoxymethyl)-3-methyl-N-(5-((methylsulfonyl)methyl)quinolin-2-yl)benzo[b]thiophene-2-carboxamide hydrochloride;

7-acetyl-4-(methoxymethyl)-3-methyl-N-(5-((methylsulfonyl)methyl)quinolin-2-yl)benzo[b]thiophene-2-carboxamide methanesulfonate;

7-acetyl-4-(methoxymethyl)-3-methyl-N-(5-((methylsulfonyl)methyl)quinolin-2-yl)benzo[b]thiophene-2-carboxamide hydrobromide;

7-acetyl-4-(methoxymethyl)-N-(5-(methoxymethyl)quinolin-2-yl)-3-methylbenzo[b]thiophene-2-carboxamide;

7-acetyl-4-(methoxymethyl)-N-(5-(methoxymethyl)quinolin-2-yl)-3-methylbenzo[b]thiophene-2-carboxamide hydrochloride;

7-acetyl-4-(methoxymethyl)-N-(5-(methoxymethyl)quinolin-2-yl)-3-methylbenzo[b]thiophene-2-carboxamide methanesulfonate;

7-acetyl-N-(5-(hydroxymethyl)quinolin-2-yl)-4-(methoxymethyl)-3-methylbenzo[b]thiophene-2-carboxamide;

7-acetyl-N-(5-(hydroxymethyl)quinolin-2-yl)-4-(methoxymethyl)-3-methylbenzo[b]thiophene-2-carboxamide hydrochloride;

7-acetyl-N-(5-(hydroxymethyl)quinolin-2-yl)-4-(methoxymethyl)-3-methylbenzo[b]thiophene-2-carboxamide methanesulfonate;

7-acetyl-N-(5-(hydroxymethyl)quinolin-2-yl)-4-(methoxymethyl)-3-methylbenzo[b]thiophene-2-carboxamide hydrobromide;

7-acetyl-N-(5-(hydroxymethyl)quinolin-2-yl)-4-(methoxymethyl)-3-methylbenzo[b]thiophene-2-carboxamide p-toluenesulfonate;

7-acetyl-N-(5-(hydroxymethyl)quinolin-2-yl)-4-(methoxymethyl)-3-methylbenzo[b]thiophene-2-carboxamide semi-ethane-1,2-disulfonate;

7-acetyl-N-(4-(2-hydroxypropan-2-yl)quinolin-2-yl)-4-(methoxymethyl)-3-methylbenzo[b]thiophene-2-carboxamide;

7-acetyl-N-(4-(2-hydroxypropan-2-yl)quinolin-2-yl)-4-(methoxymethyl)-3-methylbenzo[b]thiophene-2-carboxamide hydrochloride; and 7-acetyl-N-(4-(2-hydroxypropan-2-yl)quinolin-2-yl)-4-(methoxymethyl)-3-methylbenzo[b]thiophene-2-carboxamide hydrobromide.

9. The compound or a pharmaceutically acceptable salt thereof according to claim 1, wherein the compound or pharmaceutically acceptable salt thereof is 7-Acetyl-N-(4-((4-hydroxypiperidin-1-yl)methyl)quinolin-2-yl)-4-(methoxymethyl)-3-methylbenzo [b]thiophene-2-carboxamide or a pharmaceutically acceptable salt thereof.

10. The compound or a pharmaceutically acceptable salt thereof according to claim 1, wherein the compound or pharmaceutically acceptable salt thereof is 7-Acetyl-N-(4-((3-hydroxypyrrolidin-1-yl)methyl)quinolin-2-yl)-4-(methoxymethyl)-3-methylbenzo [b]thiophene-2-carboxamide or a pharmaceutically acceptable salt thereof.

11. The compound or a pharmaceutically acceptable salt thereof according to claim 1, wherein the compound or pharmaceutically acceptable salt thereof is (S)-7-Acetyl-N-(4-((3-hydroxypyrrolidin-1-yl)methyl)quinolin-2-yl)-4-(methoxymethyl)-3-methylbenzo[b]thiophene-2-carboxamide or a pharmaceutically acceptable salt thereof.

12. The compound or a pharmaceutically acceptable salt thereof according to claim 1, wherein the compound or pharmaceutically acceptable salt thereof is (R)-7-Acetyl-N-(4-((3-hydroxypyrrolidin-1-yl)methyl)quinolin-2-yl)-4-(methoxymethyl)-3-methylbenzo [b]thiophene-2-carboxamide or a pharmaceutically acceptable salt thereof.

13. The compound according to claim 8, wherein the compound is (R)-7-Acetyl-N-(4-((3-hydroxypyrrolidin-1-yl)methyl)quinolin-2-y1)-4-(methoxymethyl)-3-methylbenzo [b]thiophene-2-carboxamide hydrochloride.

14. The compound according to claim 8, wherein the compound is (R)-7-Acetyl-N-(4-((3-hydroxypyrrolidin-1-yl)methyl)quinolin-2-yl)-4-(methoxymethyl)-3-methylbenzo [b]thiophene-2-carboxamide p-toluenesulfonate.

15. The compound or a pharmaceutically acceptable salt thereof according to claim 1, wherein the compound or pharmaceutically acceptable salt thereof is 7-Acetyl-N-(5-((3-methoxyazetidin-1-yl)carbonyl)quinolin-2-yl)-4-(methoxymethyl)-3-methylbenzo [b]thiophene-2-carboxamide or a pharmaceutically acceptable salt thereof.

16. The compound according to claim 8, wherein the compound is 7-Acetyl-N-(5-((3-methoxyazetidin-1-yl)carbonyl)quinolin-2-yl)-4-(methoxymethyl)-3-methylbenzo[b]thiophene-2-carboxamide hydrochloride.

17. The compound according to claim 8, wherein the compound is 7-Acetyl-N-(5-((3-methoxyazetidin-1-yl)carbonyl)quinolin-2-yl)-4-(methoxymethyl)-3-methylbenzo[b]thiophene-2-carboxamide benzenesulfonate.

18. The compound according to claim 8, wherein the compound is 7-Acetyl-N-(5-((3-methoxyazetidin-1-yl)carbonyl)quinolin-2-yl)-4-(methoxymethyl)-3-methylbenzo[b]thiophene-2-carboxamide methanesulfonate.

19. The compound according to claim 8, wherein the compound is 7-Acetyl-N-(5-((3-methoxyazetidin-1-yl)carbonyl)quinolin-2-yl)-4-(methoxymethyl)-3-methylbenzo[b]thiophene-2-carboxamide p-toluenesulfonate.

20. The compound according to claim 8, wherein the compound is 7-Acetyl-N-(5-((3-methoxyazetidin-1-yl)carbonyl)quinolin-2-yl)-4-(methoxymethyl)-3-methylbenzo[b]thiophene-2-carboxamide hydrobromide.

21. The compound or a pharmaceutically acceptable salt thereof according to claim 1, wherein the compound or pharmaceutically acceptable salt thereof is 7-Acetyl-4-(methoxymethyl)-3-methyl-N-(5-((methylsulfonyl)methyl)quinolin-2-yl)benzo[b]thiophene-2-carboxamide or a pharmaceutically acceptable salt thereof.

22. The compound according to claim 8, wherein the compound is 7-Acetyl-4-(methoxymethyl)-3-methyl-N-(5-((methylsulfonyl)methyl)quinolin-2-yl)benzo [b]thiophene-2-carboxamide hydrochloride.

23. The compound according to claim 8, wherein the compound is 7-Acetyl-4-(methoxymethyl)-3-methyl-N-(5-((methylsulfonyl)methyl)quinolin-2-yl)benzo[b]thiophene-2-carboxamide methanesulfonate.

24. The compound according to claim 8, wherein the compound is 7-Acetyl-4-(methoxymethyl)-3-methyl-N-(5-((methylsulfonyl)methyl)quinolin-2-yl)benzo [b]thiophene-2-carboxamide hydrobromide.

25. The compound or a pharmaceutically acceptable salt thereof according to claim 1, wherein the compound or pharmaceutically acceptable salt thereof is 7-Acetyl-4-(methoxymethyl)-N-(5-(methoxymethyl)quinolin-2-yl)-3-methylbenzo[b]thiophene-2-carboxamide or a pharmaceutically acceptable salt thereof.

26. The compound according to claim 8, wherein the compound is 7-Acetyl-4-(methoxymethyl)-N-(5-(methoxymethyl)quinolin-2-yl)-3-methylbenzo [b]thiophene-2-carboxamide hydrochloride.

27. The compound according to claim 8, wherein the compound is 7-Acetyl-4-(methoxymethyl)-N-(5-(methoxymethyl)quinolin-2-yl)-3-methylbenzo [b]thiophene-2-carboxamide methanesulfonate.

28. The compound or a pharmaceutically acceptable salt thereof according to claim 1, wherein the compound or pharmaceutically acceptable salt thereof is 7-Acetyl-N-(5-(hydroxymethyl)quinolin-2-yl)-4-(methoxymethyl)-3-methylbenzo[b]thiophene-2-carboxamide or a pharmaceutically acceptable salt thereof.

29. The compound according to claim 8, wherein the compound is 7-Acetyl-N-(5-(hydroxymethyl)quinolin-2-yl)-4-(methoxymethyl)-3-methylbenzo[b]thiophene-2-carboxamide hydrochloride.

30. The compound according to claim 8, wherein the compound is 7-Acetyl-N-(5-(hydroxymethyl)quinolin-2-yl)-4-(methoxymethyl)-3-methylbenzo[b]thiophene-2-carboxamide methanesulfonate.

31. The compound according to claim 8, wherein the compound is 7-Acetyl-N-(5-(hydroxymethyl)quinolin-2-yl)-4-(methoxymethyl)-3-methylbenzo[b]thiophene-2-carboxamide hydrobromide.

32. The compound according to claim 8, wherein the compound is 7-Acetyl-N-(5-(hydroxymethyl)quinolin-2-yl)-4-(methoxymethyl)-3-methylbenzo[b]thiophene-2-carboxamide p-toluenesulfonate.

33. The compound according to claim 8, wherein the compound of is 7-Acetyl-N-(5-(hydroxymethyl)quinolin-2-yl)-4-(methoxymethyl)-3-methylbenzo [b]thiophene-2-carboxamide semi-ethane-1,2-disulfonate.

34. The compound or a pharmaceutically acceptable salt thereof according to claim 1, wherein the compound or pharmaceutically acceptable salt thereof is 7-Acetyl-N-(4-(2-hydroxypropan-2-yl)quinolin-2-yl)-4-(methoxymethyl)-3-methylbenzo[b]thiophene-2-carboxamide or a pharmaceutically acceptable salt thereof.

35. The compound according to claim 8, wherein the compound is 7-Acetyl-N-(4-(2-hydroxypropan-2-yl)quinolin-2-yl)-4-(methoxymethyl)-3-methylbenzo [b]thiophene-2-carboxamide hydrochloride.

36. The compound according to claim 8, wherein the compound is 7-Acetyl-N-(4-(2-hydroxypropan-2-yl)quinolin-2-yl)-4-(methoxymethyl)-3-methylbenzo [b]thiophene-2-carboxamide hydrobromide.

37. A pharmaceutical composition comprising a compound or a pharmaceutically acceptable salt thereof according to claim 1 as an active ingredient.

38. A method for treating schizophrenia, comprising administering a therapeutically effective amount of a compound or a pharmaceutically acceptable salt thereof according to claim 1 to a mammal.

39. The method according to claim 38, wherein the mammal is a human.

40. A method for inhibiting PDE10A in a subject, comprising administering to a subject an amount of a compound or a pharmaceutically acceptable salt thereof according to claim 1 effective to inhibit PDE10A.

41. The method according to claim 40, wherein the mammal is a human.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: PCR sense primer for PDE10A

<400> SEQUENCE: 1
tgctccatgg tggaagtgga                                               20

<210> SEQ ID NO 2
<211> LENGTH: 20
<212> TYPE: DNA
<213> ORGANISM: Artificial Sequence
<220> FEATURE:
<223> OTHER INFORMATION: PCR antisense primer for PDE10A

<400> SEQUENCE: 2
caactggaag catgcggtca                                               20